US012702694B2

(12) United States Patent
Spiegelman et al.

(10) Patent No.: US 12,702,694 B2
(45) Date of Patent: Aug. 11, 2026

(54) METHODS FOR IDENTIFICATION, ASSESSMENT, PREVENTION, AND TREATMENT OF METABOLIC DISORDERS USING SLIT2

(71) Applicant: Dana-Farber Cancer Institute, Inc., Boston, MA (US)

(72) Inventors: Bruce M. Spiegelman, Waban, MA (US); Katrin J. Svensson, Palo Alto, CA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 17/682,454

(22) Filed: Feb. 28, 2022

(65) Prior Publication Data

US 2022/0193193 A1 Jun. 23, 2022

Related U.S. Application Data

(62) Division of application No. 15/741,326, filed as application No. PCT/US2016/042543 on Jul. 15, 2016, now Pat. No. 11,291,706.

(60) Provisional application No. 62/193,359, filed on Jul. 16, 2015.

(51) Int. Cl.

| | |
|---|---|
| ***G01N 33/50*** | (2006.01) |
| ***A61K 9/00*** | (2006.01) |
| ***A61K 38/17*** | (2006.01) |
| ***C07K 14/47*** | (2006.01) |
| ***C07K 14/705*** | (2006.01) |

(52) U.S. Cl.

CPC ........ *A61K 38/1709* (2013.01); *A61K 9/0019* (2013.01); *C07K 14/4702* (2013.01); *C07K 14/705* (2013.01); *G01N 33/5023* (2013.01); *G01N 2333/4703* (2013.01); *G01N 2500/04* (2013.01); *G01N 2500/10* (2013.01)

(58) Field of Classification Search

CPC ....................... A61K 38/1709; G01N 2500/04

See application file for complete search history.

(56) References Cited

U.S. PATENT DOCUMENTS

| | | | | |
|---|---|---|---|---|
| 11,291,706 | B2 | 4/2022 | Spiegelman et al. | |
| 2010/0055688 | A1 * | 3/2010 | Chinnaiyan .......... | C12Q 1/6886 435/6.14 |
| 2013/0074199 | A1 | 3/2013 | Spiegelman et al. | |
| 2018/0193416 | A1 | 7/2018 | Spiegelman et al. | |
| 2022/0193193 | A1 | 6/2022 | Spiegelman et al. | |

FOREIGN PATENT DOCUMENTS

| | | | | |
|---|---|---|---|---|
| WO | WO-2006007400 | A2 * | 1/2006 | ................ A61P 3/04 |
| WO | WO-2007/128884 | A1 | 11/2007 | |
| WO | WO-2008/06330 | A2 | 1/2008 | |
| WO | WO-2014/194402 | A1 | 12/2014 | |

OTHER PUBLICATIONS

Fredriksson et al. ("Analysis of inhibition by H89 of UCP1 gene expression and thermogenesis indicates protein kinase A mediation of Beta3-adrenergic signalling rather than Beta3-andrenoceptor antagonism by H89", Biochimica et Biophysica Acta, 2001, pp. 206-217 (Year: 2001).*

Kozak et al. , "UCP1: its involvement and utility in obesity", Int H Obes, 2008, S32-S38 (Year: 2008).*

Buechler et al., "Adipose tissue fibrosis," World Journal of Diabetes, 6(4): 548-553 (2015).

Cohen et al., "Brown and beige fat: molecular parts of a thermogenic machine," Diabetes, 64(7):2346-2351 (2015).

Extended European Search Report for EP Application No. 16825258.3 mailed Jan. 21, 2019.

Fredholm et al., "The Effect of Alkylxanthines and Other Phosphodiesterase Inhibitors on Adenosine-Receptor Mediated Decrease in Lipolysis and Cyclic AMP Accumulation in Rat Fat Cells," Acta Pharmacologica et Toxicologica, 54(1): 64-71 (1984).

Fredriksson et al., "Analysis of inhibition by H89 of UCP1 gene expression and thermogenesis indicates protein kinase A mediation of 3-adrenergic signalling rather than β3-andrenoceptor antagonism by H89," Biochimica et Biophysica Acta 1538:206-217 (2001).

GenBank: AAD25539.1, SLIT2 [*Homo sapiens*], 1999 (Year: 1999).

Ghiglotti et al., "Adipose Tissue Immune Response: Novel Triggers and Consequences for Chronic Inflammatory Conditions," Inflammation, 37(4): 1337-1353 (2014).

Harms et al., "Brown and beige fat: development, function and therapeutic potential," Nature Medicine, 19(10):1252-1263 (2013).

International Search Report and Written Opinion for International Application No. PCT/US16/42543 dated Sep. 28, 2016.

Lim et al., "Slit2 Exerts Anti-Inflammatory Actions in Human Placenta and is Decreased with Maternal Obesity," American Journal of Reproductive Immunology, 73(1):66-78 (2014).

Svensson et al. "A Secreted Slit2 Fragment Regulates Adipose Tissue Thermogenesis and Metabolic Function," Cell Metabolism, 23(3):454-466 (2016).

The Human Protein Atlas, "ROBO1," www.proteinatlas.org/ENSC00000169855-ROBO1, 2015 (Year: 2015).

Zhang et al., "Slit2/Robo4 Signaling Modulates HIV-1 gp120-Induced Lymphatic Hyperpermeability," PLOS Pathogens 8(1):1-13 (2012).

Zhao et al., "Isoflurane post-conditioning protects primary cultures of cortical neurons against oxygen and glucose deprivation injury via upregulation of Slit2/Robo1," Brain Research, 1537:283-289 (2013).

Zhou et al., "The role of SLIT-ROBO signaling in proliferative diabetic retinopathy and retinal pigment epithelial cells," Molecular Vision, 17:1526-1536 (2011).

* cited by examiner

*Primary Examiner* — Catherine S Hibbert

(74) *Attorney, Agent, or Firm* — Foley Hoag LLP; DeAnn F. Smith

(57) ABSTRACT

The present invention relates to methods for identifying, assessing, preventing, and treating metabolic disorders and modulating metabolic processes using Slit2.

10 Claims, 35 Drawing Sheets

Specification includes a Sequence Listing.

FIG. 2A

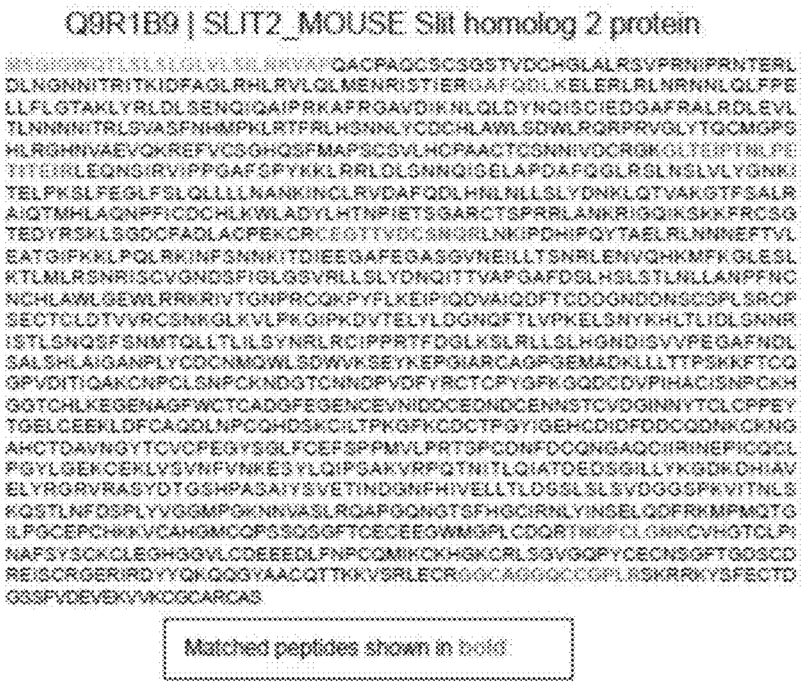

(SEQ ID NO: 125)

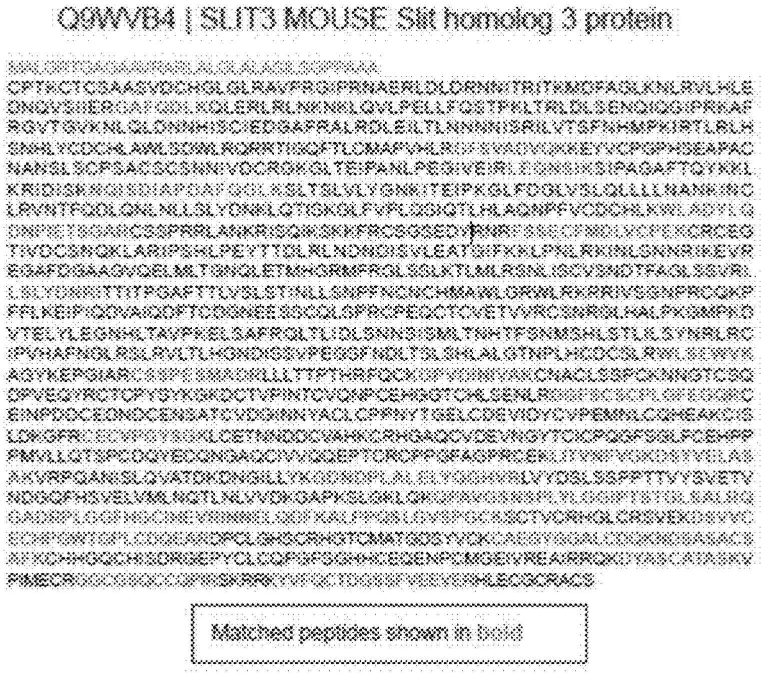

(SEQ ID NO: 126)

Q9R1B9 | SLIT2_MOUSE Slit homolog 2 protein

[illegible]QACPAQCSCSGSTVDCHGLALRSVPRNIPRNTERL
DLNGNNITRITKIDFAGLRHLRVLQLMENRISTIERGAFQDLKELERLRLNRNNLQLFPE
LLFLGTAKLYRLDLSENQIQAIPRKAFRGAVDIKNLQLDYNQISCIEDGAFRALRDLEVL
TLNNNNITRLSVASFNHMPKLRTFRLHSNNLYCDCHLAWLSDWLRQRPRVGLYTQCMGPS
HLRGHNVAEVQKREFVCSGHQSFMAPSCSVLHCPAACTCSNNIVDCRGKGLTEIPTNLPE
TITEIRLEQNSIRVIPPGAFSPYKKLRRLDLSNNQISELAPDAFQGLRSLNSLVLYGNKI
TELPKSLFEGLFSLQLLLLNANKINCLRVDAFQDLHNLNLLSLYDNKLQTVAKGTFSALR
AIQTMHLAQNPFICDCHLKWLADYLHTNPIETSGARCTSPRRLANKRIGQIKSKKFRCSG
TEDYRSKLSGDCFADLACPEKCRCEGTTVDCSNQKLNKIPDHIPQYTAELRLNNNEFTVL
EATGIFKKLPQLRKINFSNNKITDIEEGAFEGASGVNEILLTSNRLENVQHKMFKGLESL
KTLMLRSNRISCVGNDSFIGLSSVRLLSLYDNQITTVAPGAFDSLHSLSTLNLLANPFNC
NCHLAWLGEWLRKKRIVTGNPRCQKPYFLKEIPIQDVAIQDFTCDDGNDDNSCSPLSRCP
SECTCLDTVVRCSNKGLKVLPKGIPKDVTELYLDGNQFTLVPKELSNYKHLTLIDLSNNR
ISTLSNQSFSNMTQLLTLILSYNRLRCIPPRTFDGLKSLRLLSLHGNDISVVPEGAFNDL
SALSHLAIGANPLYCDCNMQWLSDWVKSEYKEPGIARCAGPGEMADKLLLTTPSKKFTCQ
GPVDITIQAKCNPCLSNPCKNDGTCNNDPVDFYRCTCPYGFKGQDCDVPIHACISNPCKH
GGTCHLKEGENAGFWCTCADGFEGENCEVNIDDCEDNDCENNSTCVDGINNYTCLCPPEY
TGELCEEKLDFCAQDLNPCQHDSKCILTPKGFKCDCTPGYIGEHCDIDFDDCQDNKCKNG
AHCTDAVNGYTCVCPEGYSGLFCEFSPPMVLPRTSPCDNFDCQNGAQCIIRINEPICQCL
PGYLGEKCEKLVSVNFVNKESYLQIPSAKVRPQTNITLQIATDEDSGILLYKGDKDHIAV
ELYRGRVRASYDTGSHPASAIYSVETINDGNFHIVELLTLDSSLSLSVDGGSPKVITNLS
KQSTLNFDSPLYVGGMPGKNNVASLRQAPGQNGTSFHGCIRNLYINSELQDFRKMPMQTG
ILPGCEPCHKKVCAHGMCQPSSQSGFTCECEEGWMGPLCDQRTNDPCLGNKCVHGTCLPI
NAFSYSCKCLEGHGGVLCDEEEDLFNPCQMIKCKHGKCRLSGVGQPYCECNSGFTGDSCD
REISCRGERIRDYYQKQQGYAACQTTKKVSRLECRGGCAGGQCCGPLRSKRRKYSFECTD
GSSFVDEVEKVVKCGCARCAS (SEQ ID NO: 125)

Matched peptides shown in bold

Q9WVB4 | SLIT3 MOUSE Slit homolog 3 protein

[illegible]
CPTKCTCSAASVDCHGLGLRAVPRGIPRNAERLDLDRNNITRITKMDFAGLKNLRVLHLE
DNQVSIIERGAFQDLKQLERLRLNKNKLQVLPELLFQSTPKLTRLDLSENQIQGIPRKAF
RGVTGVKNLQLDNNHISCIEDGAFRALRDLEILTLNNNNISRILVTSFNHMPKIRTLRLH
SNHLYCDCHLAWLSDWLRQRRTIGQFTLCMAPVHLRGFSVADVQKKEYVCPGPHSEAPAC
NANSLSCPSACSCSNNIVDCRGKGLTEIPANLPEGIVEIRLEQNSIKSIPAGAFTQYKKL
KRIDISKNQISDIAPDAFQGLKSLTSLVLYGNKITEIPKGLFDGLVSLQLLLLNANKINC
LRVNTFQDLQNLNLLSLYDNKLQTISKGLFVPLQSIQTLHLAQNPFVCDCHLKWLADYLQ
DNPIETSGARCSSPRRLANKRISQIKSKKFRCSGSEDYRNRFSSECFMDLVCPEKCRCEG
TIVDCSNQKLARIPSHLPEYTTDLRLNDNDISVLEATGIFKKLPNLRKINLSNNRIKEVR
EGAFDGAAGVQELMLTGNQLETMHGRMFRGLSSLKTLMLRSNLISCVSNDTFAGLSSVRL
LSLYDNRITTITPGAFTTLVSLSTINLLSNPFNCNCHMAWLGRWLRKRRIVSGNPRCQKP
FFLKEIPIQDVAIQDFTCDGNEESSCQLSPRCPEQCTCVETVVRCSNRGLHALPKGMPKD
VTELYLEGNHLTAVPKELSAFRQLTLIDLSNNSISMLTNHTFSNMSHLSTLILSYNRLRC
IPVHAFNGLRSLRVLTLHGNDISSVPEGSFNDLTSLSHLALGTNPLHCDCSLRWLSEWVK
AGYKEPGIARCSSPESMADRLLLTTPTHRFQCKGPVDINIVAKCNACLSSPCKNNGTCSQ
DPVEQYRCTCPYSYKGKDCTVPINTCVQNPCEHGGTCHLSENLRDGFSCSCPLGFEGQRC
EINPDDCEDNDCENSATCVDGINNYACLCPPNYTGELCDEVIDYCVPEMNLCQHEAKCIS
LDKGFRCECVPGYSGKLCETNNDDCVAHKCRHGAQCVDEVNGYTCICPQGFSGLFCEHPP
PMVLLQTSPCDQYECQNGAQCIVVQQEPTCRCPPGFAGPRCEKLITVNFVGKDSYVELAS
AKVRPQANISLQVATDKDNGILLYKGDNDPLALELYQGHVRLVYDSLSSPPTTVYSVETV
NDGQFHSVELVMLNQTLNLVVDKGAPKSLGKLQKQPAVGINSPLYLGGIPTSTGLSALRQ
GADRPLGGFHGCIHEVRINNELQDFKALPPQSLGVSPGCKSCTVCKHGLCRSVEKDSVVC
ECHPGWTGPLCDQEARDPCLGHSCRHGTCMATGDSYVCKCAEGYGGALCDQKNDSASACS
AFKCHHGQCHISDRGEPYCLCQPGFSGHHCEQENPCMGEIVREAIRRQKDYASCATASKV
PIMECRGGCGSQCCQPIRSKRRKYVFQCTDGSSFVEEVERHLECGCRACS (SEQ ID NO: 126)

Matched peptides shown in bold

Secreted
Slit2-C-terminal FLAG
150
100
75
51
α-Slit2
α-FLAG (SEQ ID NO: 125)
(amino acid residues 1114 to 1521 of SEQ ID NO: 125)
Matched peptides shown in bold Slit2-FL
Slit2-N
Slit2-C
SP
LRR1
LRR2
LRR3
LRR4
EGF
Laminin G
CK
V5

LacZ
Slit2-N
Slit2-C
250
Cells
Liver
Plasma

Day 5-7
Oxygen consumption (ml/kg/h)
3000
2000
1000
0
LacZ
Slit2-C
*
Tissue wet weight (g)
BAT
LacZ
Slit2-C
**
0.12
0.10
0.08
0.06
0.04
0.02
0.00
iWAT
*
0.20
0.18
0.16
0.14
0.12
0.10
0.08
0.06
0.04
0.02
0.00
eWAT
ns
0.30
0.25
0.20
0.15

FLAG peptide Nuclei
PM20D1 Nuclei
S2-C protein treatment
0 1 5 10 50 100 (nM)
150
100
75
51
37
phospho-PKA substrate (RRXpS/pT)
PKA substrate phosphorylation
Quantification of PKA substrate phosphorylated relative time point 0
#1
#2
#3
#4
#5
0
1
2
3
4
0 5 15 30 60 90
Time (min)

Vascular and neuronal markers

BAT
LacZ
Slit2-FL
relative mRNA expression
2.0
1.5
1.0
0.5
0.0
Tie2
VE cadherin
CD31
CD34
tyrosine hydroxylase
IWAT
LacZ
Slit2-FL
relative mRNA expression
1.5
1.0
0.5
0.0
Tie2
VE cadherin
CD31
CD34
tyrosine hydroxylase
Quadriceps
LacZ
Slit2-FL
relative mRNA expression
2.0
1.5
1.0
0.5
0.0
Tie2
VE cadherin
CD31
CD34
tyrosine hydroxylase

SEQUENCE LISTING

<160> NUMBER OF SEQ ID NOS: 127

<210> SEQ ID NO 1
<211> LENGTH: 4590
<212> TYPE: DNA
<213> ORGANISM: Homo sapiens

<400> SEQUENCE: 1
atgcgcggcg ttggctggca gatgctgtcc ctgtcgctgg ggttagtgct ggcgatcctg 60
aacaaggtgg caccgcaggc gtgcccggcg cagtgctctt gctcgggcag cacagtggac 120
tgtcacgggc tggcgctgcg cagcgtgccc aggaatatcc cccgcaacac cgagagactg 180
gatttaaatg gaaataacat cacaagaatt acgaagacag attttgctgg tcttagacat 240
ctaagagttc ttcagcttat ggagaataag attagcacca ttgaaagagg agcattccag 300
gatcttaaag aactagagag actgcgttta aacagaaatc accttcagct gtttcctgag 360
ttgctgtttc ttgggactgc gaagctatac aggcttgatc tcagtgaaaa ccaaattcag 420
gcaatcccaa ggaaagcttt ccgtggggca gttgacataa aaaatttgca actggattac 480
aaccagatca gctgtattga agatggggca ttcagggctc tccgggacct ggaagtgctc 540
actctcaaca ataacaacat tactagactt tctgtggcaa gtttcaacca tatgcctaaa 600
cttaggactt ttcgactgca ttcaaacaac ctgtattgtg actgccacct ggcctggctc 660
tccgactggc ttcgccaaag gcctcgggtt ggtctgtaca ctcagtgtat gggcccctcc 720
cacctgagag gccataatgt agccgaggtt caaaaacgag aatttgtctg cagtggtcac 780
cagtcattta tggctccttc ttgtagtgtt ttgcactgcc ctgccgcctg tacctgtagc 840
aacaatatcg tagactgtcg tgggaaaggt ctcactgaga tccccacaaa tcttccagag 900
accatcacag aaatacgttt ggaacagaac acaatcaaag tcatccctcc tggagctttc 960
tcaccatata aaaagcttag acgaattgac ctgagcaata atcagatctc tgaacttgca 1020
ccagatgctt tccaaggact acgctctctg aattcacttg tcctctatgg aaataaaatc 1080
acagaactcc ccaaaagttt atttgaagga ctgttttcct tacagctcct attattgaat 1140
gccaacaaga taaactgcct tcgggtagat gcttttcagg atctccacaa cttgaacctt 1200
ctctccctat atgacaacaa gcttcagacc atcgccaagg ggaccttttc acctcttcgg 1260
gccattcaaa ctatgcattt ggcccagaac ccctttattt gtgactgcca tctcaagtgg 1320
ctagcggatt atctccatac caacccgatt gagaccagtg gtgcccgttg caccagcccc 1380
cgccgcctgg caaacaaaag aattggacag atcaaaagca agaaattccg ttgttcagct 1440
aaagaacagt atttcattcc aggtacagaa gattatcgat caaaattaag tggagactgc 1500
tttgcggatc tggcttgccc tgaaaagtgt cgctgtgaag gaaccacagt agattgctct 1560
aatcaaaagc tcaacaaaat cccggagcac attccccagt acactgcaga gttgcgtctc 1620
aataataatg aatttaccgt gttggaagcc acaggaatct ttaagaaact tcctcaatta 1680
cgtaaaataa actttagcaa caataagatc acagatattg aggagggagc atttgaagga 1740
gcatctggtg taaatgaaat acttcttacg agtaatcgtt tggaaaatgt gcagcataag 1800
atgttcaagg gattggaaag cctcaaaact ttgatgttga gaagcaatcg aataacctgt 1860
gtggggaatg acagtttcat aggactcagt tctgtgcgtt tgctttcttt gtatgataat 1920
caaattacta cagttgcacc aggggcattt gatactctcc attctttatc tactctaaac 1980
ctcttggcca atccttttaa ctgtaactgc tacctggctt ggttgggaga gtggctgaga 2040
aagaagagaa ttgtcacggg aaatcctaga tgtcaaaaac catacttcct gaaagaaata 2100

-continued

```
cccatccagg atgtggccat tcaggacttc acttgtgatg acggaaatga tgacaatagt   2160
tgctccccac tttctcgctg tcctactgaa tgtacttgct tggatacagt cgtccgatgt   2220
agcaacaagg gtttgaaggt cttgccgaaa ggtattccaa gagatgtcac agagttgtat   2280
ctggatggaa accaatttac actggttccc aaggaactct ccaactacaa acatttaaca   2340
cttatagact taagtaacaa cagaataagc acgctttcta atcagagctt cagcaacatg   2400
acccagctcc tcaccttaat tcttagttac aaccgtctga gatgtattcc tcctcgcacc   2460
tttgatggat taaagtctct tcgattactt tctctacatg gaaatgacat ttctgttgtg   2520
cctgaaggtg ctttcaatga tctttctgca ttatcacatc tagcaattgg agccaaccct   2580
ctttactgtg attgtaacat gcagtggtta tccgactggg tgaagtcgga atataaggag   2640
cctggaattg ctcgttgtgc tggtcctgga gaaatggcag ataaactttt actcacaact   2700
ccctccaaaa aatttacctg tcaaggtcct gtggatgtca atattctagc taagtgtaac   2760
ccctgcctat caaatccgtg taaaaatgat ggcacatgta atagtgatcc agttgacttt   2820
taccgatgca cctgtccata tggtttcaag gggcaggact gtgatgtccc aattcatgcc   2880
tgcatcagta acccatgtaa acatggagga acttgccact taaaggaagg agaagaagat   2940
ggattctggt gtatttgtgc tgatggattt gaaggagaaa attgtgaagt caacgttgat   3000
gattgtgaag ataatgactg tgaaaataat tctacatgtg tcgatggcat taataactac   3060
acatgccttt gcccacctga gtatacaggt gagttgtgtg aggagaagct ggacttctgt   3120
gcccaggacc tgaacccctg ccagcacgat tcaaagtgca tcctaactcc aaagggattc   3180
aaatgtgact gcacaccagg gtacgtaggt gaacactgcg acatcgattt tgacgactgc   3240
caagacaaca agtgtaaaaa cggagcccac tgcacagatg cagtgaacgg ctatacgtgc   3300
atatgccccg aaggttacag tggcttgttc tgtgagtttt ctccacccat ggtcctccct   3360
cgtaccagcc cctgtgataa ttttgattgt cagaatggag ctcagtgtat cgtcagaata   3420
aatgagccaa tatgtcagtg tttgcctggc tatcagggag aaaagtgtga aaaattggtt   3480
agtgtgaatt ttataaacaa agagtcttat cttcagattc cttcagccaa ggttcggcct   3540
cagacgaaca taacacttca gattgccaca gatgaagaca gcggaatcct cctgtataag   3600
ggtgacaaag accatatcgc ggtagaactc tatcgggggc gtgttcgtgc cagctatgac   3660
accggctctc atccagcttc tgccatttac agtgtggaga caatcaatga tggaaacttc   3720
cacattgtgg aactacttgc cttggatcag agtctctctt tgtccgtgga tggtgggaac   3780
cccaaaatca tcactaactt gtcaaagcag tccactctga attttgactc tccactctat   3840
gtaggaggca tgccagggaa gagtaacgtg gcatctctgc gccaggcccc tgggcagaac   3900
ggaaccagct tccacggctg catccggaac ctttacatca acagtgagct gcaggacttc   3960
cagaaggtgc cgatgcaaac aggcattttg cctggctgtg agccatgcca caagaaggtg   4020
tgtgcccatg gcacatgcca gcccagcagc caggcaggct tcacctgcga gtgccaggaa   4080
ggatggatgg ggcccctctg tgaccaacgg accaatgacc cttgccttgg aaataaatgc   4140
gtacatggca cctgcttgcc catcaatgcg ttctcctaca gctgtaagtg cttggagggc   4200
catggaggtg tcctctgtga tgaagaggag gatctgttta acccatgcca ggcgatcaag   4260
tgcaagcatg ggaagtgcag gctttcaggt ctggggcagc cctactgtga atgcagcagt   4320
ggatacacgg gggacagctg tgatcgagaa atctcttgtc gaggggaaag gataagagat   4380
tattaccaaa agcagcaggg ctatgctgct tgccaaacaa ccaagaaggt gtcccgatta   4440
```

-continued

```
gagtgcagag gtgggtgtgc aggagggcag tgctgtggac cgctgaggag caagcggcgg   4500

aaatactctt tcgaatgcac tgacggctcc tcctttgtgg acgaggttga gaaagtggtg   4560

aagtgcggct gtacgaggtg tgtgtcctaa                                    4590


<210> SEQ ID NO 2
<211> LENGTH: 1529
<212> TYPE: PRT
<213> ORGANISM: Homo sapiens

<400> SEQUENCE: 2

Met Arg Gly Val Gly Trp Gln Met Leu Ser Leu Ser Leu Gly Leu Val
1               5                   10                  15

Leu Ala Ile Leu Asn Lys Val Ala Pro Gln Ala Cys Pro Ala Gln Cys
            20                  25                  30

Ser Cys Ser Gly Ser Thr Val Asp Cys His Gly Leu Ala Leu Arg Ser
        35                  40                  45

Val Pro Arg Asn Ile Pro Arg Asn Thr Glu Arg Leu Asp Leu Asn Gly
    50                  55                  60

Asn Asn Ile Thr Arg Ile Thr Lys Thr Asp Phe Ala Gly Leu Arg His
65                  70                  75                  80

Leu Arg Val Leu Gln Leu Met Glu Asn Lys Ile Ser Thr Ile Glu Arg
                85                  90                  95

Gly Ala Phe Gln Asp Leu Lys Glu Leu Glu Arg Leu Arg Leu Asn Arg
            100                 105                 110

Asn His Leu Gln Leu Phe Pro Glu Leu Leu Phe Leu Gly Thr Ala Lys
        115                 120                 125

Leu Tyr Arg Leu Asp Leu Ser Glu Asn Gln Ile Gln Ala Ile Pro Arg
    130                 135                 140

Lys Ala Phe Arg Gly Ala Val Asp Ile Lys Asn Leu Gln Leu Asp Tyr
145                 150                 155                 160

Asn Gln Ile Ser Cys Ile Glu Asp Gly Ala Phe Arg Ala Leu Arg Asp
                165                 170                 175

Leu Glu Val Leu Thr Leu Asn Asn Asn Asn Ile Thr Arg Leu Ser Val
            180                 185                 190

Ala Ser Phe Asn His Met Pro Lys Leu Arg Thr Phe Arg Leu His Ser
        195                 200                 205

Asn Asn Leu Tyr Cys Asp Cys His Leu Ala Trp Leu Ser Asp Trp Leu
    210                 215                 220

Arg Gln Arg Pro Arg Val Gly Leu Tyr Thr Gln Cys Met Gly Pro Ser
225                 230                 235                 240

His Leu Arg Gly His Asn Val Ala Glu Val Gln Lys Arg Glu Phe Val
                245                 250                 255

Cys Ser Gly His Gln Ser Phe Met Ala Pro Ser Cys Ser Val Leu His
            260                 265                 270

Cys Pro Ala Ala Cys Thr Cys Ser Asn Asn Ile Val Asp Cys Arg Gly
        275                 280                 285

Lys Gly Leu Thr Glu Ile Pro Thr Asn Leu Pro Glu Thr Ile Thr Glu
    290                 295                 300

Ile Arg Leu Glu Gln Asn Thr Ile Lys Val Ile Pro Pro Gly Ala Phe
305                 310                 315                 320

Ser Pro Tyr Lys Lys Leu Arg Arg Ile Asp Leu Ser Asn Asn Gln Ile
                325                 330                 335

Ser Glu Leu Ala Pro Asp Ala Phe Gln Gly Leu Arg Ser Leu Asn Ser
            340                 345                 350
```

```
Leu Val Leu Tyr Gly Asn Lys Ile Thr Glu Leu Pro Lys Ser Leu Phe
        355                 360                 365

Glu Gly Leu Phe Ser Leu Gln Leu Leu Leu Leu Asn Ala Asn Lys Ile
    370                 375                 380

Asn Cys Leu Arg Val Asp Ala Phe Gln Asp Leu His Asn Leu Asn Leu
385                 390                 395                 400

Leu Ser Leu Tyr Asp Asn Lys Leu Gln Thr Ile Ala Lys Gly Thr Phe
                405                 410                 415

Ser Pro Leu Arg Ala Ile Gln Thr Met His Leu Ala Gln Asn Pro Phe
            420                 425                 430

Ile Cys Asp Cys His Leu Lys Trp Leu Ala Asp Tyr Leu His Thr Asn
        435                 440                 445

Pro Ile Glu Thr Ser Gly Ala Arg Cys Thr Ser Pro Arg Arg Leu Ala
    450                 455                 460

Asn Lys Arg Ile Gly Gln Ile Lys Ser Lys Lys Phe Arg Cys Ser Ala
465                 470                 475                 480

Lys Glu Gln Tyr Phe Ile Pro Gly Thr Glu Asp Tyr Arg Ser Lys Leu
                485                 490                 495

Ser Gly Asp Cys Phe Ala Asp Leu Ala Cys Pro Glu Lys Cys Arg Cys
            500                 505                 510

Glu Gly Thr Thr Val Asp Cys Ser Asn Gln Lys Leu Asn Lys Ile Pro
        515                 520                 525

Glu His Ile Pro Gln Tyr Thr Ala Glu Leu Arg Leu Asn Asn Asn Glu
    530                 535                 540

Phe Thr Val Leu Glu Ala Thr Gly Ile Phe Lys Lys Leu Pro Gln Leu
545                 550                 555                 560

Arg Lys Ile Asn Phe Ser Asn Asn Lys Ile Thr Asp Ile Glu Glu Gly
                565                 570                 575

Ala Phe Glu Gly Ala Ser Gly Val Asn Glu Ile Leu Leu Thr Ser Asn
            580                 585                 590

Arg Leu Glu Asn Val Gln His Lys Met Phe Lys Gly Leu Glu Ser Leu
        595                 600                 605

Lys Thr Leu Met Leu Arg Ser Asn Arg Ile Thr Cys Val Gly Asn Asp
    610                 615                 620

Ser Phe Ile Gly Leu Ser Ser Val Arg Leu Leu Ser Leu Tyr Asp Asn
625                 630                 635                 640

Gln Ile Thr Thr Val Ala Pro Gly Ala Phe Asp Thr Leu His Ser Leu
                645                 650                 655

Ser Thr Leu Asn Leu Leu Ala Asn Pro Phe Asn Cys Asn Cys Tyr Leu
            660                 665                 670

Ala Trp Leu Gly Glu Trp Leu Arg Lys Lys Arg Ile Val Thr Gly Asn
        675                 680                 685

Pro Arg Cys Gln Lys Pro Tyr Phe Leu Lys Glu Ile Pro Ile Gln Asp
    690                 695                 700

Val Ala Ile Gln Asp Phe Thr Cys Asp Asp Gly Asn Asp Asp Asn Ser
705                 710                 715                 720

Cys Ser Pro Leu Ser Arg Cys Pro Thr Glu Cys Thr Cys Leu Asp Thr
                725                 730                 735

Val Val Arg Cys Ser Asn Lys Gly Leu Lys Val Leu Pro Lys Gly Ile
            740                 745                 750

Pro Arg Asp Val Thr Glu Leu Tyr Leu Asp Gly Asn Gln Phe Thr Leu
        755                 760                 765
```

```
Val Pro Lys Glu Leu Ser Asn Tyr Lys His Leu Thr Leu Ile Asp Leu
    770                 775                 780

Ser Asn Asn Arg Ile Ser Thr Leu Ser Asn Gln Ser Phe Ser Asn Met
785                 790                 795                 800

Thr Gln Leu Leu Thr Leu Ile Leu Ser Tyr Asn Arg Leu Arg Cys Ile
                805                 810                 815

Pro Pro Arg Thr Phe Asp Gly Leu Lys Ser Leu Arg Leu Leu Ser Leu
            820                 825                 830

His Gly Asn Asp Ile Ser Val Val Pro Glu Gly Ala Phe Asn Asp Leu
        835                 840                 845

Ser Ala Leu Ser His Leu Ala Ile Gly Ala Asn Pro Leu Tyr Cys Asp
    850                 855                 860

Cys Asn Met Gln Trp Leu Ser Asp Trp Val Lys Ser Glu Tyr Lys Glu
865                 870                 875                 880

Pro Gly Ile Ala Arg Cys Ala Gly Pro Gly Glu Met Ala Asp Lys Leu
                885                 890                 895

Leu Leu Thr Thr Pro Ser Lys Lys Phe Thr Cys Gln Gly Pro Val Asp
            900                 905                 910

Val Asn Ile Leu Ala Lys Cys Asn Pro Cys Leu Ser Asn Pro Cys Lys
        915                 920                 925

Asn Asp Gly Thr Cys Asn Ser Asp Pro Val Asp Phe Tyr Arg Cys Thr
    930                 935                 940

Cys Pro Tyr Gly Phe Lys Gly Gln Asp Cys Asp Val Pro Ile His Ala
945                 950                 955                 960

Cys Ile Ser Asn Pro Cys Lys His Gly Gly Thr Cys His Leu Lys Glu
                965                 970                 975

Gly Glu Glu Asp Gly Phe Trp Cys Ile Cys Ala Asp Gly Phe Glu Gly
            980                 985                 990

Glu Asn Cys Glu Val Asn Val Asp  Asp Cys Glu Asp Asn  Asp Cys Glu
        995                 1000                1005

Asn Asn  Ser Thr Cys Val Asp  Gly Ile Asn Asn Tyr  Thr Cys Leu
    1010                 1015                 1020

Cys Pro  Pro Glu Tyr Thr Gly  Glu Leu Cys Glu Glu  Lys Leu Asp
    1025                 1030                 1035

Phe Cys  Ala Gln Asp Leu Asn  Pro Cys Gln His Asp  Ser Lys Cys
    1040                 1045                 1050

Ile Leu  Thr Pro Lys Gly Phe  Lys Cys Asp Cys Thr  Pro Gly Tyr
    1055                 1060                 1065

Val Gly  Glu His Cys Asp Ile  Asp Phe Asp Asp Cys  Gln Asp Asn
    1070                 1075                 1080

Lys Cys  Lys Asn Gly Ala His  Cys Thr Asp Ala Val  Asn Gly Tyr
    1085                 1090                 1095

Thr Cys  Ile Cys Pro Glu Gly  Tyr Ser Gly Leu Phe  Cys Glu Phe
    1100                 1105                 1110

Ser Pro  Pro Met Val Leu Pro  Arg Thr Ser Pro Cys  Asp Asn Phe
    1115                 1120                 1125

Asp Cys  Gln Asn Gly Ala Gln  Cys Ile Val Arg Ile  Asn Glu Pro
    1130                 1135                 1140

Ile Cys  Gln Cys Leu Pro Gly  Tyr Gln Gly Glu Lys  Cys Glu Lys
    1145                 1150                 1155

Leu Val  Ser Val Asn Phe Ile  Asn Lys Glu Ser Tyr  Leu Gln Ile
    1160                 1165                 1170

Pro Ser  Ala Lys Val Arg Pro  Gln Thr Asn Ile Thr  Leu Gln Ile
```

```
    1175                1180                1185

Ala Thr  Asp Glu Asp Ser Gly  Ile Leu Leu Tyr Lys  Gly Asp Lys
    1190                1195                1200

Asp His  Ile Ala Val Glu Leu  Tyr Arg Gly Arg Val  Arg Ala Ser
    1205                1210                1215

Tyr Asp  Thr Gly Ser His Pro  Ala Ser Ala Ile Tyr  Ser Val Glu
    1220                1225                1230

Thr Ile  Asn Asp Gly Asn Phe  His Ile Val Glu Leu  Leu Ala Leu
    1235                1240                1245

Asp Gln  Ser Leu Ser Leu Ser  Val Asp Gly Gly Asn  Pro Lys Ile
    1250                1255                1260

Ile Thr  Asn Leu Ser Lys Gln  Ser Thr Leu Asn Phe  Asp Ser Pro
    1265                1270                1275

Leu Tyr  Val Gly Gly Met Pro  Gly Lys Ser Asn Val  Ala Ser Leu
    1280                1285                1290

Arg Gln  Ala Pro Gly Gln Asn  Gly Thr Ser Phe His  Gly Cys Ile
    1295                1300                1305

Arg Asn  Leu Tyr Ile Asn Ser  Glu Leu Gln Asp Phe  Gln Lys Val
    1310                1315                1320

Pro Met  Gln Thr Gly Ile Leu  Pro Gly Cys Glu Pro  Cys His Lys
    1325                1330                1335

Lys Val  Cys Ala His Gly Thr  Cys Gln Pro Ser Ser  Gln Ala Gly
    1340                1345                1350

Phe Thr  Cys Glu Cys Gln Glu  Gly Trp Met Gly Pro  Leu Cys Asp
    1355                1360                1365

Gln Arg  Thr Asn Asp Pro Cys  Leu Gly Asn Lys Cys  Val His Gly
    1370                1375                1380

Thr Cys  Leu Pro Ile Asn Ala  Phe Ser Tyr Ser Cys  Lys Cys Leu
    1385                1390                1395

Glu Gly  His Gly Gly Val Leu  Cys Asp Glu Glu Glu  Asp Leu Phe
    1400                1405                1410

Asn Pro  Cys Gln Ala Ile Lys  Cys Lys His Gly Lys  Cys Arg Leu
    1415                1420                1425

Ser Gly  Leu Gly Gln Pro Tyr  Cys Glu Cys Ser Ser  Gly Tyr Thr
    1430                1435                1440

Gly Asp  Ser Cys Asp Arg Glu  Ile Ser Cys Arg Gly  Glu Arg Ile
    1445                1450                1455

Arg Asp  Tyr Tyr Gln Lys Gln  Gln Gly Tyr Ala Ala  Cys Gln Thr
    1460                1465                1470

Thr Lys  Lys Val Ser Arg Leu  Glu Cys Arg Gly Gly  Cys Ala Gly
    1475                1480                1485

Gly Gln  Cys Cys Gly Pro Leu  Arg Ser Lys Arg Arg  Lys Tyr Ser
    1490                1495                1500

Phe Glu  Cys Thr Asp Gly Ser  Ser Phe Val Asp Glu  Val Glu Lys
    1505                1510                1515

Val Val  Lys Cys Gly Cys Thr  Arg Cys Val Ser
    1520                1525
```

<210> SEQ ID NO 3
<211> LENGTH: 4578
<212> TYPE: DNA
<213> ORGANISM: Homo sapiens

<400> SEQUENCE: 3

-continued

```
atgcgcggcg ttggctggca gatgctgtcc ctgtcgctgg ggttagtgct ggcgatcctg     60
aacaaggtgg caccgcaggc gtgcccggcg cagtgctctt gctcgggcag cacagtggac    120
tgtcacgggc tggcgctgcg cagcgtgccc aggaatatcc cccgcaacac cgagagactg    180
gatttaaatg gaaataacat cacaagaatt acgaagacag attttgctgg tcttagacat    240
ctaagagttc ttcagcttat ggagaataag attagcacca ttgaaagagg agcattccag    300
gatcttaaag aactagagag actgcgttta aacagaaatc accttcagct gtttcctgag    360
ttgctgtttc ttgggactgc gaagctatac aggcttgatc tcagtgaaaa ccaaattcag    420
gcaatcccaa ggaaagcttt ccgtggggca gttgacataa aaaatttgca actggattac    480
aaccagatca gctgtattga agatggggca ttcagggctc tccgggacct ggaagtgctc    540
actctcaaca ataacaacat tactagactt tctgtggcaa gtttcaacca tatgcctaaa    600
cttaggactt ttcgactgca ttcaaacaac ctgtattgtg actgccacct ggcctggctc    660
tccgactggc ttcgccaaag gcctcgggtt ggtctgtaca ctcagtgtat gggcccctcc    720
cacctgagag gccataatgt agccgaggtt caaaaacgag aatttgtctg cagtgatgag    780
gaagaaggtc accagtcatt tatggctcct tcttgtagtg ttttgcactg ccctgccgcc    840
tgtacctgta gcaacaatat cgtagactgt cgtgggaaag gtctcactga gatccccaca    900
aatcttccag agaccatcac agaaatacgt ttggaacaga acacaatcaa agtcatccct    960
cctggagctt tctcaccata taaaaagctt agacgaattg acctgagcaa taatcagatc   1020
tctgaacttg caccagatgc tttccaagga ctacgctctc tgaattcact tgtcctctat   1080
ggaaataaaa tcacagaact ccccaaaagt ttatttgaag gactgttttc cttacagctc   1140
ctattattga atgccaacaa gataaactgc cttcgggtag atgcttttca ggatctccac   1200
aacttgaacc ttctctccct atatgacaac aagcttcaga ccatcgccaa ggggaccttt   1260
tcacctcttc gggccattca aactatgcat ttggcccaga acccctttat ttgtgactgc   1320
catctcaagt ggctagcgga ttatctccat accaacccga ttgagaccag tggtgcccgt   1380
tgcaccagcc cccgccgcct ggcaaacaaa agaattggac agatcaaaag caagaaattc   1440
cgttgttcag gtacagaaga ttatcgatca aaattaagtg gagactgctt tgcggatctg   1500
gcttgccctg aaaagtgtcg ctgtgaagga accacagtag attgctctaa tcaaaagctc   1560
aacaaaatcc cggagcacat tccccagtac actgcagagt tgcgtctcaa taataatgaa   1620
tttaccgtgt tggaagccac aggaatcttt aagaaacttc ctcaattacg taaaataaac   1680
tttagcaaca ataagatcac agatattgag gagggagcat ttgaaggagc atctggtgta   1740
aatgaaatac ttcttacgag taatcgtttg gaaaatgtgc agcataagat gttcaaggga   1800
ttggaaagcc tcaaaacttt gatgttgaga agcaatcgaa taacctgtgt ggggaatgac   1860
agtttcatag gactcagttc tgtgcgtttg ctttctttgt atgataatca aattactaca   1920
gttgcaccag gggcatttga tactctccat tctttatcta ctctaaacct cttggccaat   1980
ccttttaact gtaactgcta cctggcttgg ttgggagagt ggctgagaaa gaagagaatt   2040
gtcacgggaa atcctagatg tcaaaaacca tacttcctga aagaaatacc catccaggat   2100
gtggccattc aggacttcac ttgtgatgac ggaaatgatg acaatagttg ctccccactt   2160
tctcgctgtc ctactgaatg tacttgcttg gatacagtcg tccgatgtag caacaagggt   2220
ttgaaggtct tgccgaaagg tattccaaga gatgtcacag agttgtatct ggatggaaac   2280
caatttacac tggttcccaa ggaactctcc aactacaaac atttaacact tatagactta   2340
agtaacaaca gaataagcac gctttctaat cagagcttca gcaacatgac ccagctcctc   2400
```

-continued

```
accttaattc ttagttacaa ccgtctgaga tgtattcctc ctcgcacctt tgatggatta   2460
aagtctcttc gattactttc tctacatgga aatgacattt ctgttgtgcc tgaaggtgct   2520
ttcaatgatc tttctgcatt atcacatcta gcaattggag ccaaccctct ttactgtgat   2580
tgtaacatgc agtggttatc cgactgggtg aagtcggaat ataaggagcc tggaattgct   2640
cgttgtgctg gtcctggaga aatggcagat aaactttac tcacaactcc ctccaaaaaa   2700
tttacctgtc aaggtcctgt ggatgtcaat attctagcta agtgtaaccc ctgcctatca   2760
aatccgtgta aaaatgatgg cacatgtaat agtgatccag ttgactttta ccgatgcacc   2820
tgtccatatg gtttcaaggg gcaggactgt gatgtcccaa ttcatgcctg catcagtaac   2880
ccatgtaaac atggaggaac ttgccactta aaggaaggag aagaagatgg attctggtgt   2940
atttgtgctg atggatttga aggagaaaat tgtgaagtca acgttgatga ttgtgaagat   3000
aatgactgtg aaaataattc tacatgtgtc gatggcatta ataactacac atgcctttgc   3060
ccacctgagt atacaggtga gttgtgtgag gagaagctgg acttctgtgc ccaggacctg   3120
aacccctgcc agcacgattc aaagtgcatc ctaactccaa agggattcaa atgtgactgc   3180
acaccagggt acgtaggtga acactgcgac atcgattttg acgactgcca agacaacaag   3240
tgtaaaaacg gagcccactg cacagatgca gtgaacggct atacgtgcat atgccccgaa   3300
ggttacagtg gcttgttctg tgagttttct ccacccatgg tcctccctcg taccagcccc   3360
tgtgataatt ttgattgtca gaatggagct cagtgtatcg tcagaataaa tgagccaata   3420
tgtcagtgtt tgcctggcta tcagggagaa aagtgtgaaa aattggttag tgtgaatttt   3480
ataaacaaag agtcttatct tcagattcct tcagccaagg ttcggcctca gacgaacata   3540
acacttcaga ttgccacaga tgaagacagc ggaatcctcc tgtataaggg tgacaaagac   3600
catatcgcgg tagaactcta tcgggggcgt gttcgtgcca gctatgacac cggctctcat   3660
ccagcttctg ccatttacag tgtggagaca atcaatgatg gaaacttcca cattgtggaa   3720
ctacttgcct tggatcagag tctctctttg tccgtggatg gtgggaaccc caaaatcatc   3780
actaacttgt caaagcagtc cactctgaat tttgactctc cactctatgt aggaggcatg   3840
ccagggaaga gtaacgtggc atctctgcgc caggcccctg ggcagaacgg aaccagcttc   3900
cacggctgca tccggaacct ttacatcaac agtgagctgc aggacttcca gaaggtgccg   3960
atgcaaacag gcattttgcc tggctgtgag ccatgccaca agaaggtgtg tgcccatggc   4020
acatgccagc ccagcagcca ggcaggcttc acctgcgagt gccaggaagg atggatgggg   4080
cccctctgtg accaacggac caatgaccct tgccttggaa ataaatgcgt acatggcacc   4140
tgcttgccca tcaatgcgtt ctcctacagc tgtaagtgct tggagggcca tggaggtgtc   4200
ctctgtgatg aagaggagga tctgtttaac ccatgccagg cgatcaagtg caagcatggg   4260
aagtgcaggc tttcaggtct ggggcagccc tactgtgaat gcagcagtgg atacacgggg   4320
gacagctgtg atcgagaaat ctcttgtcga ggggaaagga taagagatta ttaccaaaag   4380
cagcagggct atgctgcttg ccaaacaacc aagaaggtgt cccgattaga gtgcagaggt   4440
gggtgtgcag gagggcagtg ctgtggaccg ctgaggagca agcggcggaa atactctttc   4500
gaatgcactg acggctcctc ctttgtggac gaggttgaga aagtggtgaa gtgcggctgt   4560
acgaggtgtg tgtcctaa                                                 4578
```

<210> SEQ ID NO 4
<211> LENGTH: 1525
<212> TYPE: PRT

<213> ORGANISM: Homo sapiens

<400> SEQUENCE: 4

Met Arg Gly Val Gly Trp Gln Met Leu Ser Leu Ser Leu Gly Leu Val
1 5 10 15

Leu Ala Ile Leu Asn Lys Val Ala Pro Gln Ala Cys Pro Ala Gln Cys
20 25 30

Ser Cys Ser Gly Ser Thr Val Asp Cys His Gly Leu Ala Leu Arg Ser
35 40 45

Val Pro Arg Asn Ile Pro Arg Asn Thr Glu Arg Leu Asp Leu Asn Gly
50 55 60

Asn Asn Ile Thr Arg Ile Thr Lys Thr Asp Phe Ala Gly Leu Arg His
65 70 75 80

Leu Arg Val Leu Gln Leu Met Glu Asn Lys Ile Ser Thr Ile Glu Arg
85 90 95

Gly Ala Phe Gln Asp Leu Lys Glu Leu Glu Arg Leu Arg Leu Asn Arg
100 105 110

Asn His Leu Gln Leu Phe Pro Glu Leu Leu Phe Leu Gly Thr Ala Lys
115 120 125

Leu Tyr Arg Leu Asp Leu Ser Glu Asn Gln Ile Gln Ala Ile Pro Arg
130 135 140

Lys Ala Phe Arg Gly Ala Val Asp Ile Lys Asn Leu Gln Leu Asp Tyr
145 150 155 160

Asn Gln Ile Ser Cys Ile Glu Asp Gly Ala Phe Arg Ala Leu Arg Asp
165 170 175

Leu Glu Val Leu Thr Leu Asn Asn Asn Asn Ile Thr Arg Leu Ser Val
180 185 190

Ala Ser Phe Asn His Met Pro Lys Leu Arg Thr Phe Arg Leu His Ser
195 200 205

Asn Asn Leu Tyr Cys Asp Cys His Leu Ala Trp Leu Ser Asp Trp Leu
210 215 220

Arg Gln Arg Pro Arg Val Gly Leu Tyr Thr Gln Cys Met Gly Pro Ser
225 230 235 240

His Leu Arg Gly His Asn Val Ala Glu Val Gln Lys Arg Glu Phe Val
245 250 255

Cys Ser Asp Glu Glu Glu Gly His Gln Ser Phe Met Ala Pro Ser Cys
260 265 270

Ser Val Leu His Cys Pro Ala Ala Cys Thr Cys Ser Asn Asn Ile Val
275 280 285

Asp Cys Arg Gly Lys Gly Leu Thr Glu Ile Pro Thr Asn Leu Pro Glu
290 295 300

Thr Ile Thr Glu Ile Arg Leu Glu Gln Asn Thr Ile Lys Val Ile Pro
305 310 315 320

Pro Gly Ala Phe Ser Pro Tyr Lys Lys Leu Arg Arg Ile Asp Leu Ser
325 330 335

Asn Asn Gln Ile Ser Glu Leu Ala Pro Asp Ala Phe Gln Gly Leu Arg
340 345 350

Ser Leu Asn Ser Leu Val Leu Tyr Gly Asn Lys Ile Thr Glu Leu Pro
355 360 365

Lys Ser Leu Phe Glu Gly Leu Phe Ser Leu Gln Leu Leu Leu Leu Asn
370 375 380

Ala Asn Lys Ile Asn Cys Leu Arg Val Asp Ala Phe Gln Asp Leu His
385 390 395 400

-continued

```
Asn Leu Asn Leu Leu Ser Leu Tyr Asp Asn Lys Leu Gln Thr Ile Ala
                405                 410                 415

Lys Gly Thr Phe Ser Pro Leu Arg Ala Ile Gln Thr Met His Leu Ala
            420                 425                 430

Gln Asn Pro Phe Ile Cys Asp Cys His Leu Lys Trp Leu Ala Asp Tyr
        435                 440                 445

Leu His Thr Asn Pro Ile Glu Thr Ser Gly Ala Arg Cys Thr Ser Pro
    450                 455                 460

Arg Arg Leu Ala Asn Lys Arg Ile Gly Gln Ile Lys Ser Lys Lys Phe
465                 470                 475                 480

Arg Cys Ser Gly Thr Glu Asp Tyr Arg Ser Lys Leu Ser Gly Asp Cys
                485                 490                 495

Phe Ala Asp Leu Ala Cys Pro Glu Lys Cys Arg Cys Glu Gly Thr Thr
            500                 505                 510

Val Asp Cys Ser Asn Gln Lys Leu Asn Lys Ile Pro Glu His Ile Pro
        515                 520                 525

Gln Tyr Thr Ala Glu Leu Arg Leu Asn Asn Asn Glu Phe Thr Val Leu
    530                 535                 540

Glu Ala Thr Gly Ile Phe Lys Lys Leu Pro Gln Leu Arg Lys Ile Asn
545                 550                 555                 560

Phe Ser Asn Asn Lys Ile Thr Asp Ile Glu Glu Gly Ala Phe Glu Gly
                565                 570                 575

Ala Ser Gly Val Asn Glu Ile Leu Leu Thr Ser Asn Arg Leu Glu Asn
            580                 585                 590

Val Gln His Lys Met Phe Lys Gly Leu Glu Ser Leu Lys Thr Leu Met
        595                 600                 605

Leu Arg Ser Asn Arg Ile Thr Cys Val Gly Asn Asp Ser Phe Ile Gly
    610                 615                 620

Leu Ser Ser Val Arg Leu Leu Ser Leu Tyr Asp Asn Gln Ile Thr Thr
625                 630                 635                 640

Val Ala Pro Gly Ala Phe Asp Thr Leu His Ser Leu Ser Thr Leu Asn
                645                 650                 655

Leu Leu Ala Asn Pro Phe Asn Cys Asn Cys Tyr Leu Ala Trp Leu Gly
            660                 665                 670

Glu Trp Leu Arg Lys Lys Arg Ile Val Thr Gly Asn Pro Arg Cys Gln
        675                 680                 685

Lys Pro Tyr Phe Leu Lys Glu Ile Pro Ile Gln Asp Val Ala Ile Gln
    690                 695                 700

Asp Phe Thr Cys Asp Asp Gly Asn Asp Asp Asn Ser Cys Ser Pro Leu
705                 710                 715                 720

Ser Arg Cys Pro Thr Glu Cys Thr Cys Leu Asp Thr Val Val Arg Cys
                725                 730                 735

Ser Asn Lys Gly Leu Lys Val Leu Pro Lys Gly Ile Pro Arg Asp Val
            740                 745                 750

Thr Glu Leu Tyr Leu Asp Gly Asn Gln Phe Thr Leu Val Pro Lys Glu
        755                 760                 765

Leu Ser Asn Tyr Lys His Leu Thr Leu Ile Asp Leu Ser Asn Asn Arg
    770                 775                 780

Ile Ser Thr Leu Ser Asn Gln Ser Phe Ser Asn Met Thr Gln Leu Leu
785                 790                 795                 800

Thr Leu Ile Leu Ser Tyr Asn Arg Leu Arg Cys Ile Pro Pro Arg Thr
                805                 810                 815

Phe Asp Gly Leu Lys Ser Leu Arg Leu Leu Ser Leu His Gly Asn Asp
```

-continued

```
            820                 825                 830

Ile Ser Val Val Pro Glu Gly Ala Phe Asn Asp Leu Ser Ala Leu Ser
        835                 840                 845

His Leu Ala Ile Gly Ala Asn Pro Leu Tyr Cys Asp Cys Asn Met Gln
    850                 855                 860

Trp Leu Ser Asp Trp Val Lys Ser Glu Tyr Lys Glu Pro Gly Ile Ala
865                 870                 875                 880

Arg Cys Ala Gly Pro Gly Glu Met Ala Asp Lys Leu Leu Leu Thr Thr
                885                 890                 895

Pro Ser Lys Lys Phe Thr Cys Gln Gly Pro Val Asp Val Asn Ile Leu
            900                 905                 910

Ala Lys Cys Asn Pro Cys Leu Ser Asn Pro Cys Lys Asn Asp Gly Thr
        915                 920                 925

Cys Asn Ser Asp Pro Val Asp Phe Tyr Arg Cys Thr Cys Pro Tyr Gly
    930                 935                 940

Phe Lys Gly Gln Asp Cys Asp Val Pro Ile His Ala Cys Ile Ser Asn
945                 950                 955                 960

Pro Cys Lys His Gly Gly Thr Cys His Leu Lys Glu Gly Glu Glu Asp
                965                 970                 975

Gly Phe Trp Cys Ile Cys Ala Asp Gly Phe Glu Gly Glu Asn Cys Glu
            980                 985                 990

Val Asn Val Asp Asp Cys Glu Asp  Asn Asp Cys Glu Asn  Asn Ser Thr
        995                 1000                1005

Cys Val  Asp Gly Ile Asn Asn  Tyr Thr Cys Leu Cys  Pro Pro Glu
    1010                1015                1020

Tyr Thr  Gly Glu Leu Cys Glu  Glu Lys Leu Asp Phe  Cys Ala Gln
    1025                1030                1035

Asp Leu  Asn Pro Cys Gln His  Asp Ser Lys Cys Ile  Leu Thr Pro
    1040                1045                1050

Lys Gly  Phe Lys Cys Asp Cys  Thr Pro Gly Tyr Val  Gly Glu His
    1055                1060                1065

Cys Asp  Ile Asp Phe Asp Asp  Cys Gln Asp Asn Lys  Cys Lys Asn
    1070                1075                1080

Gly Ala  His Cys Thr Asp Ala  Val Asn Gly Tyr Thr  Cys Ile Cys
    1085                1090                1095

Pro Glu  Gly Tyr Ser Gly Leu  Phe Cys Glu Phe Ser  Pro Pro Met
    1100                1105                1110

Val Leu  Pro Arg Thr Ser Pro  Cys Asp Asn Phe Asp  Cys Gln Asn
    1115                1120                1125

Gly Ala  Gln Cys Ile Val Arg  Ile Asn Glu Pro Ile  Cys Gln Cys
    1130                1135                1140

Leu Pro  Gly Tyr Gln Gly Glu  Lys Cys Glu Lys Leu  Val Ser Val
    1145                1150                1155

Asn Phe  Ile Asn Lys Glu Ser  Tyr Leu Gln Ile Pro  Ser Ala Lys
    1160                1165                1170

Val Arg  Pro Gln Thr Asn Ile  Thr Leu Gln Ile Ala  Thr Asp Glu
    1175                1180                1185

Asp Ser  Gly Ile Leu Leu Tyr  Lys Gly Asp Lys Asp  His Ile Ala
    1190                1195                1200

Val Glu  Leu Tyr Arg Gly Arg  Val Arg Ala Ser Tyr  Asp Thr Gly
    1205                1210                1215

Ser His  Pro Ala Ser Ala Ile  Tyr Ser Val Glu Thr  Ile Asn Asp
    1220                1225                1230
```

```
Gly Asn  Phe His Ile Val Glu  Leu Leu Ala Leu Asp  Gln Ser Leu
    1235                 1240                 1245

Ser Leu  Ser Val Asp Gly Gly  Asn Pro Lys Ile Ile  Thr Asn Leu
    1250                 1255                 1260

Ser Lys  Gln Ser Thr Leu Asn  Phe Asp Ser Pro Leu  Tyr Val Gly
    1265                 1270                 1275

Gly Met  Pro Gly Lys Ser Asn  Val Ala Ser Leu Arg  Gln Ala Pro
    1280                 1285                 1290

Gly Gln  Asn Gly Thr Ser Phe  His Gly Cys Ile Arg  Asn Leu Tyr
    1295                 1300                 1305

Ile Asn  Ser Glu Leu Gln Asp  Phe Gln Lys Val Pro  Met Gln Thr
    1310                 1315                 1320

Gly Ile  Leu Pro Gly Cys Glu  Pro Cys His Lys Lys  Val Cys Ala
    1325                 1330                 1335

His Gly  Thr Cys Gln Pro Ser  Ser Gln Ala Gly Phe  Thr Cys Glu
    1340                 1345                 1350

Cys Gln  Glu Gly Trp Met Gly  Pro Leu Cys Asp Gln  Arg Thr Asn
    1355                 1360                 1365

Asp Pro  Cys Leu Gly Asn Lys  Cys Val His Gly Thr  Cys Leu Pro
    1370                 1375                 1380

Ile Asn  Ala Phe Ser Tyr Ser  Cys Lys Cys Leu Glu  Gly His Gly
    1385                 1390                 1395

Gly Val  Leu Cys Asp Glu Glu  Glu Asp Leu Phe Asn  Pro Cys Gln
    1400                 1405                 1410

Ala Ile  Lys Cys Lys His Gly  Lys Cys Arg Leu Ser  Gly Leu Gly
    1415                 1420                 1425

Gln Pro  Tyr Cys Glu Cys Ser  Ser Gly Tyr Thr Gly  Asp Ser Cys
    1430                 1435                 1440

Asp Arg  Glu Ile Ser Cys Arg  Gly Glu Arg Ile Arg  Asp Tyr Tyr
    1445                 1450                 1455

Gln Lys  Gln Gln Gly Tyr Ala  Ala Cys Gln Thr Thr  Lys Lys Val
    1460                 1465                 1470

Ser Arg  Leu Glu Cys Arg Gly  Gly Cys Ala Gly Gly  Gln Cys Cys
    1475                 1480                 1485

Gly Pro  Leu Arg Ser Lys Arg  Arg Lys Tyr Ser Phe  Glu Cys Thr
    1490                 1495                 1500

Asp Gly  Ser Ser Phe Val Asp  Glu Val Glu Lys Val  Val Lys Cys
    1505                 1510                 1515

Gly Cys  Thr Arg Cys Val Ser
    1520                 1525
```

<210> SEQ ID NO 5
<211> LENGTH: 4566
<212> TYPE: DNA
<213> ORGANISM: Homo sapiens

<400> SEQUENCE: 5

```
atgcgcggcg ttggctggca gatgctgtcc ctgtcgctgg ggttagtgct ggcgatcctg     60

aacaaggtgg caccgcaggc gtgcccggcg cagtgctctt gctcgggcag cacagtggac    120

tgtcacgggc tggcgctgcg cagcgtgccc aggaatatcc cccgcaacac cgagagactg    180

gatttaaatg gaaataacat cacaagaatt acgaagacag attttgctgg tcttagacat    240

ctaagagttc ttcagcttat ggagaataag attagcacca ttgaaagagg agcattccag    300
```

-continued

```
gatcttaaag aactagagag actgcgttta aacagaaatc accttcagct gtttcctgag    360
ttgctgtttc ttgggactgc gaagctatac aggcttgatc tcagtgaaaa ccaaattcag    420
gcaatcccaa ggaaagcttt ccgtggggca gttgacataa aaaatttgca actggattac    480
aaccagatca gctgtattga agatggggca ttcagggctc tccgggacct ggaagtgctc    540
actctcaaca ataacaacat tactagactt tctgtggcaa gtttcaacca tatgcctaaa    600
cttaggactt ttcgactgca ttcaaacaac ctgtattgtg actgccacct ggcctggctc    660
tccgactggc ttcgccaaag gcctcgggtt ggtctgtaca ctcagtgtat gggcccctcc    720
cacctgagag gccataatgt agccgaggtt caaaaacgag aatttgtctg cagtggtcac    780
cagtcattta tggctccttc ttgtagtgtt ttgcactgcc ctgccgcctg tacctgtagc    840
aacaatatcg tagactgtcg tgggaaaggt ctcactgaga tccccacaaa tcttccagag    900
accatcacag aaatacgttt ggaacagaac acaatcaaag tcatccctcc tggagctttc    960
tcaccatata aaaagcttag acgaattgac ctgagcaata atcagatctc tgaacttgca   1020
ccagatgctt tccaaggact acgctctctg aattcacttg tcctctatgg aaataaaatc   1080
acagaactcc ccaaaagttt atttgaagga ctgttttcct tacagctcct attattgaat   1140
gccaacaaga taaactgcct tcgggtagat gcttttcagg atctccacaa cttgaacctt   1200
ctctccctat atgacaacaa gcttcagacc atcgccaagg ggaccttttc acctcttcgg   1260
gccattcaaa ctatgcattt ggcccagaac ccctttattt gtgactgcca tctcaagtgg   1320
ctagcggatt atctccatac caacccgatt gagaccagtg gtgcccgttg caccagcccc   1380
cgccgcctgg caaacaaaag aattggacag atcaaaagca agaaattccg ttgttcaggt   1440
acagaagatt atcgatcaaa attaagtgga gactgctttg cggatctggc ttgccctgaa   1500
aagtgtcgct gtgaaggaac cacagtagat tgctctaatc aaaagctcaa caaaatcccg   1560
gagcacattc cccagtacac tgcagagttg cgtctcaata ataatgaatt taccgtgttg   1620
gaagccacag gaatctttaa gaaacttcct caattacgta aaataaactt tagcaacaat   1680
aagatcacag atattgagga gggagcattt gaaggagcat ctggtgtaaa tgaaatactt   1740
cttacgagta atcgtttgga aaatgtgcag cataagatgt tcaagggatt ggaaagcctc   1800
aaaactttga tgttgagaag caatcgaata acctgtgtgg ggaatgacag tttcatagga   1860
ctcagttctg tgcgtttgct ttctttgtat gataatcaaa ttactacagt tgcaccaggg   1920
gcatttgata ctctccattc tttatctact ctaaacctct tggccaatcc ttttaactgt   1980
aactgctacc tggcttggtt gggagagtgg ctgagaaaga agagaattgt cacgggaaat   2040
cctagatgtc aaaaaccata cttcctgaaa gaaataccca tccaggatgt ggccattcag   2100
gacttcactt gtgatgacgg aaatgatgac aatagttgct ccccactttc tcgctgtcct   2160
actgaatgta cttgcttgga tacagtcgtc cgatgtagca acaagggttt gaaggtcttg   2220
ccgaaaggta ttccaagaga tgtcacagag ttgtatctgg atggaaacca atttacactg   2280
gttcccaagg aactctccaa ctacaaacat ttaacactta tagacttaag taacaacaga   2340
ataagcacgc tttctaatca gagcttcagc aacatgaccc agctcctcac cttaattctt   2400
agttacaacc gtctgagatg tattcctcct cgcacctttg atggattaaa gtctcttcga   2460
ttactttctc tacatggaaa tgacatttct gttgtgcctg aaggtgcttt caatgatctt   2520
tctgcattat cacatctagc aattggagcc aaccctcttt actgtgattg taacatgcag   2580
tggttatccg actgggtgaa gtcggaatat aaggagcctg gaattgctcg ttgtgctggt   2640
cctggagaaa tggcagataa acttttactc acaactccct ccaaaaaatt tacctgtcaa   2700
```

-continued

```
ggtcctgtgg atgtcaatat tctagctaag tgtaacccct gcctatcaaa tccgtgtaaa   2760

aatgatggca catgtaatag tgatccagtt gacttttacc gatgcacctg tccatatggt   2820

ttcaaggggc aggactgtga tgtcccaatt catgcctgca tcagtaaccc atgtaaacat   2880

ggaggaactt gccacttaaa ggaaggagaa gaagatggat tctggtgtat ttgtgctgat   2940

ggatttgaag gagaaaattg tgaagtcaac gttgatgatt gtgaagataa tgactgtgaa   3000

aataattcta catgtgtcga tggcattaat aactacacat gcctttgccc acctgagtat   3060

acaggtgagt tgtgtgagga gaagctggac ttctgtgccc aggacctgaa cccctgccag   3120

cacgattcaa agtgcatcct aactccaaag ggattcaaat gtgactgcac accagggtac   3180

gtaggtgaac actgcgacat cgattttgac gactgccaag acaacaagtg taaaaacgga   3240

gcccactgca cagatgcagt gaacggctat acgtgcatat gccccgaagg ttacagtggc   3300

ttgttctgtg agttttctcc acccatggtc ctccctcgta ccagcccctg tgataatttt   3360

gattgtcaga atggagctca gtgtatcgtc agaataaatg agccaatatg tcagtgtttg   3420

cctggctatc agggagaaaa gtgtgaaaaa ttggttagtg tgaattttat aaacaaagag   3480

tcttatcttc agattccttc agccaaggtt cggcctcaga cgaacataac acttcagatt   3540

gccacagatg aagacagcgg aatcctcctg tataagggtg acaaagacca tatcgcggta   3600

gaactctatc gggggcgtgt tcgtgccagc tatgacaccg gctctcatcc agcttctgcc   3660

atttacagtg tggagacaat caatgatgga aacttccaca ttgtggaact acttgccttg   3720

gatcagagtc tctctttgtc cgtggatggt gggaacccca aaatcatcac taacttgtca   3780

aagcagtcca ctctgaattt tgactctcca ctctatgtag gaggcatgcc agggaagagt   3840

aacgtggcat ctctgcgcca ggcccctggg cagaacggaa ccagcttcca cggctgcatc   3900

cggaaccttt acatcaacag tgagctgcag gacttccaga aggtgccgat gcaaacaggc   3960

attttgcctg gctgtgagcc atgccacaag aaggtgtgtg cccatggcac atgccagccc   4020

agcagccagg caggcttcac ctgcgagtgc caggaaggat ggatggggcc cctctgtgac   4080

caacggacca atgacccttg ccttggaaat aaatgcgtac atggcacctg cttgcccatc   4140

aatgcgttct cctacagctg taagtgcttg gagggccatg gaggtgtcct ctgtgatgaa   4200

gaggaggatc tgtttaaccc atgccaggcg atcaagtgca agcatgggaa gtgcaggctt   4260

tcaggtctgg ggcagcccta ctgtgaatgc agcagtggat acacggggga cagctgtgat   4320

cgagaaatct cttgtcgagg ggaaaggata agagattatt accaaaagca gcagggctat   4380

gctgcttgcc aaacaaccaa gaaggtgtcc cgattagagt gcagaggtgg gtgtgcagga   4440

gggcagtgct gtggaccgct gaggagcaag cggcggaaat actctttcga atgcactgac   4500

ggctcctcct ttgtggacga ggttgagaaa gtggtgaagt gcggctgtac gaggtgtgtg   4560

tcctaa                                                              4566
```

<210> SEQ ID NO 6
<211> LENGTH: 1521
<212> TYPE: PRT
<213> ORGANISM: Homo sapiens

<400> SEQUENCE: 6

```
Met Arg Gly Val Gly Trp Gln Met Leu Ser Leu Ser Leu Gly Leu Val
1               5                   10                  15

Leu Ala Ile Leu Asn Lys Val Ala Pro Gln Ala Cys Pro Ala Gln Cys
            20                  25                  30
```

```
Ser Cys Ser Gly Ser Thr Val Asp Cys His Gly Leu Ala Leu Arg Ser
        35                  40                  45

Val Pro Arg Asn Ile Pro Arg Asn Thr Glu Arg Leu Asp Leu Asn Gly
    50                  55                  60

Asn Asn Ile Thr Arg Ile Thr Lys Thr Asp Phe Ala Gly Leu Arg His
65                  70                  75                  80

Leu Arg Val Leu Gln Leu Met Glu Asn Lys Ile Ser Thr Ile Glu Arg
                85                  90                  95

Gly Ala Phe Gln Asp Leu Lys Glu Leu Glu Arg Leu Arg Leu Asn Arg
            100                 105                 110

Asn His Leu Gln Leu Phe Pro Glu Leu Leu Phe Leu Gly Thr Ala Lys
        115                 120                 125

Leu Tyr Arg Leu Asp Leu Ser Glu Asn Gln Ile Gln Ala Ile Pro Arg
    130                 135                 140

Lys Ala Phe Arg Gly Ala Val Asp Ile Lys Asn Leu Gln Leu Asp Tyr
145                 150                 155                 160

Asn Gln Ile Ser Cys Ile Glu Asp Gly Ala Phe Arg Ala Leu Arg Asp
                165                 170                 175

Leu Glu Val Leu Thr Leu Asn Asn Asn Asn Ile Thr Arg Leu Ser Val
            180                 185                 190

Ala Ser Phe Asn His Met Pro Lys Leu Arg Thr Phe Arg Leu His Ser
        195                 200                 205

Asn Asn Leu Tyr Cys Asp Cys His Leu Ala Trp Leu Ser Asp Trp Leu
    210                 215                 220

Arg Gln Arg Pro Arg Val Gly Leu Tyr Thr Gln Cys Met Gly Pro Ser
225                 230                 235                 240

His Leu Arg Gly His Asn Val Ala Glu Val Gln Lys Arg Glu Phe Val
                245                 250                 255

Cys Ser Gly His Gln Ser Phe Met Ala Pro Ser Cys Ser Val Leu His
            260                 265                 270

Cys Pro Ala Ala Cys Thr Cys Ser Asn Asn Ile Val Asp Cys Arg Gly
        275                 280                 285

Lys Gly Leu Thr Glu Ile Pro Thr Asn Leu Pro Glu Thr Ile Thr Glu
    290                 295                 300

Ile Arg Leu Glu Gln Asn Thr Ile Lys Val Ile Pro Pro Gly Ala Phe
305                 310                 315                 320

Ser Pro Tyr Lys Lys Leu Arg Arg Ile Asp Leu Ser Asn Asn Gln Ile
                325                 330                 335

Ser Glu Leu Ala Pro Asp Ala Phe Gln Gly Leu Arg Ser Leu Asn Ser
            340                 345                 350

Leu Val Leu Tyr Gly Asn Lys Ile Thr Glu Leu Pro Lys Ser Leu Phe
        355                 360                 365

Glu Gly Leu Phe Ser Leu Gln Leu Leu Leu Leu Asn Ala Asn Lys Ile
    370                 375                 380

Asn Cys Leu Arg Val Asp Ala Phe Gln Asp Leu His Asn Leu Asn Leu
385                 390                 395                 400

Leu Ser Leu Tyr Asp Asn Lys Leu Gln Thr Ile Ala Lys Gly Thr Phe
                405                 410                 415

Ser Pro Leu Arg Ala Ile Gln Thr Met His Leu Ala Gln Asn Pro Phe
            420                 425                 430

Ile Cys Asp Cys His Leu Lys Trp Leu Ala Asp Tyr Leu His Thr Asn
        435                 440                 445

Pro Ile Glu Thr Ser Gly Ala Arg Cys Thr Ser Pro Arg Arg Leu Ala
```

```
    450                 455                 460

Asn Lys Arg Ile Gly Gln Ile Lys Ser Lys Lys Phe Arg Cys Ser Gly
465                 470                 475                 480

Thr Glu Asp Tyr Arg Ser Lys Leu Ser Gly Asp Cys Phe Ala Asp Leu
                485                 490                 495

Ala Cys Pro Glu Lys Cys Arg Cys Glu Gly Thr Thr Val Asp Cys Ser
            500                 505                 510

Asn Gln Lys Leu Asn Lys Ile Pro Glu His Ile Pro Gln Tyr Thr Ala
        515                 520                 525

Glu Leu Arg Leu Asn Asn Asn Glu Phe Thr Val Leu Glu Ala Thr Gly
    530                 535                 540

Ile Phe Lys Lys Leu Pro Gln Leu Arg Lys Ile Asn Phe Ser Asn Asn
545                 550                 555                 560

Lys Ile Thr Asp Ile Glu Glu Gly Ala Phe Glu Gly Ala Ser Gly Val
                565                 570                 575

Asn Glu Ile Leu Leu Thr Ser Asn Arg Leu Glu Asn Val Gln His Lys
            580                 585                 590

Met Phe Lys Gly Leu Glu Ser Leu Lys Thr Leu Met Leu Arg Ser Asn
        595                 600                 605

Arg Ile Thr Cys Val Gly Asn Asp Ser Phe Ile Gly Leu Ser Ser Val
    610                 615                 620

Arg Leu Leu Ser Leu Tyr Asp Asn Gln Ile Thr Thr Val Ala Pro Gly
625                 630                 635                 640

Ala Phe Asp Thr Leu His Ser Leu Ser Thr Leu Asn Leu Leu Ala Asn
                645                 650                 655

Pro Phe Asn Cys Asn Cys Tyr Leu Ala Trp Leu Gly Glu Trp Leu Arg
            660                 665                 670

Lys Lys Arg Ile Val Thr Gly Asn Pro Arg Cys Gln Lys Pro Tyr Phe
        675                 680                 685

Leu Lys Glu Ile Pro Ile Gln Asp Val Ala Ile Gln Asp Phe Thr Cys
    690                 695                 700

Asp Asp Gly Asn Asp Asp Asn Ser Cys Ser Pro Leu Ser Arg Cys Pro
705                 710                 715                 720

Thr Glu Cys Thr Cys Leu Asp Thr Val Val Arg Cys Ser Asn Lys Gly
                725                 730                 735

Leu Lys Val Leu Pro Lys Gly Ile Pro Arg Asp Val Thr Glu Leu Tyr
            740                 745                 750

Leu Asp Gly Asn Gln Phe Thr Leu Val Pro Lys Glu Leu Ser Asn Tyr
        755                 760                 765

Lys His Leu Thr Leu Ile Asp Leu Ser Asn Asn Arg Ile Ser Thr Leu
    770                 775                 780

Ser Asn Gln Ser Phe Ser Asn Met Thr Gln Leu Leu Thr Leu Ile Leu
785                 790                 795                 800

Ser Tyr Asn Arg Leu Arg Cys Ile Pro Pro Arg Thr Phe Asp Gly Leu
                805                 810                 815

Lys Ser Leu Arg Leu Leu Ser Leu His Gly Asn Asp Ile Ser Val Val
            820                 825                 830

Pro Glu Gly Ala Phe Asn Asp Leu Ser Ala Leu Ser His Leu Ala Ile
        835                 840                 845

Gly Ala Asn Pro Leu Tyr Cys Asp Cys Asn Met Gln Trp Leu Ser Asp
    850                 855                 860

Trp Val Lys Ser Glu Tyr Lys Glu Pro Gly Ile Ala Arg Cys Ala Gly
865                 870                 875                 880
```

-continued

```
Pro Gly Glu Met Ala Asp Lys Leu Leu Leu Thr Thr Pro Ser Lys Lys
                885                 890                 895

Phe Thr Cys Gln Gly Pro Val Asp Val Asn Ile Leu Ala Lys Cys Asn
            900                 905                 910

Pro Cys Leu Ser Asn Pro Cys Lys Asn Asp Gly Thr Cys Asn Ser Asp
        915                 920                 925

Pro Val Asp Phe Tyr Arg Cys Thr Cys Pro Tyr Gly Phe Lys Gly Gln
    930                 935                 940

Asp Cys Asp Val Pro Ile His Ala Cys Ile Ser Asn Pro Cys Lys His
945                 950                 955                 960

Gly Gly Thr Cys His Leu Lys Glu Gly Glu Glu Asp Gly Phe Trp Cys
                965                 970                 975

Ile Cys Ala Asp Gly Phe Glu Gly Glu Asn Cys Glu Val Asn Val Asp
            980                 985                 990

Asp Cys Glu Asp Asn Asp Cys Glu  Asn Asn Ser Thr Cys  Val Asp Gly
        995                 1000                1005

Ile Asn  Asn Tyr Thr Cys Leu  Cys Pro Pro Glu Tyr  Thr Gly Glu
    1010                1015                1020

Leu Cys  Glu Glu Lys Leu Asp  Phe Cys Ala Gln Asp  Leu Asn Pro
    1025                1030                1035

Cys Gln  His Asp Ser Lys Cys  Ile Leu Thr Pro Lys  Gly Phe Lys
    1040                1045                1050

Cys Asp  Cys Thr Pro Gly Tyr  Val Gly Glu His Cys  Asp Ile Asp
    1055                1060                1065

Phe Asp  Asp Cys Gln Asp Asn  Lys Cys Lys Asn Gly  Ala His Cys
    1070                1075                1080

Thr Asp  Ala Val Asn Gly Tyr  Thr Cys Ile Cys Pro  Glu Gly Tyr
    1085                1090                1095

Ser Gly  Leu Phe Cys Glu Phe  Ser Pro Pro Met Val  Leu Pro Arg
    1100                1105                1110

Thr Ser  Pro Cys Asp Asn Phe  Asp Cys Gln Asn Gly  Ala Gln Cys
    1115                1120                1125

Ile Val  Arg Ile Asn Glu Pro  Ile Cys Gln Cys Leu  Pro Gly Tyr
    1130                1135                1140

Gln Gly  Glu Lys Cys Glu Lys  Leu Val Ser Val Asn  Phe Ile Asn
    1145                1150                1155

Lys Glu  Ser Tyr Leu Gln Ile  Pro Ser Ala Lys Val  Arg Pro Gln
    1160                1165                1170

Thr Asn  Ile Thr Leu Gln Ile  Ala Thr Asp Glu Asp  Ser Gly Ile
    1175                1180                1185

Leu Leu  Tyr Lys Gly Asp Lys  Asp His Ile Ala Val  Glu Leu Tyr
    1190                1195                1200

Arg Gly  Arg Val Arg Ala Ser  Tyr Asp Thr Gly Ser  His Pro Ala
    1205                1210                1215

Ser Ala  Ile Tyr Ser Val Glu  Thr Ile Asn Asp Gly  Asn Phe His
    1220                1225                1230

Ile Val  Glu Leu Leu Ala Leu  Asp Gln Ser Leu Ser  Leu Ser Val
    1235                1240                1245

Asp Gly  Gly Asn Pro Lys Ile  Ile Thr Asn Leu Ser  Lys Gln Ser
    1250                1255                1260

Thr Leu  Asn Phe Asp Ser Pro  Leu Tyr Val Gly Gly  Met Pro Gly
    1265                1270                1275
```

```
Lys Ser  Asn Val Ala Ser Leu  Arg Gln Ala Pro Gly  Gln Asn Gly
    1280                 1285                 1290

Thr Ser  Phe His Gly Cys Ile  Arg Asn Leu Tyr Ile  Asn Ser Glu
    1295                 1300                 1305

Leu Gln  Asp Phe Gln Lys Val  Pro Met Gln Thr Gly  Ile Leu Pro
    1310                 1315                 1320

Gly Cys  Glu Pro Cys His Lys  Lys Val Cys Ala His  Gly Thr Cys
    1325                 1330                 1335

Gln Pro  Ser Ser Gln Ala Gly  Phe Thr Cys Glu Cys  Gln Glu Gly
    1340                 1345                 1350

Trp Met  Gly Pro Leu Cys Asp  Gln Arg Thr Asn Asp  Pro Cys Leu
    1355                 1360                 1365

Gly Asn  Lys Cys Val His Gly  Thr Cys Leu Pro Ile  Asn Ala Phe
    1370                 1375                 1380

Ser Tyr  Ser Cys Lys Cys Leu  Glu Gly His Gly Gly  Val Leu Cys
    1385                 1390                 1395

Asp Glu  Glu Glu Asp Leu Phe  Asn Pro Cys Gln Ala  Ile Lys Cys
    1400                 1405                 1410

Lys His  Gly Lys Cys Arg Leu  Ser Gly Leu Gly Gln  Pro Tyr Cys
    1415                 1420                 1425

Glu Cys  Ser Ser Gly Tyr Thr  Gly Asp Ser Cys Asp  Arg Glu Ile
    1430                 1435                 1440

Ser Cys  Arg Gly Glu Arg Ile  Arg Asp Tyr Tyr Gln  Lys Gln Gln
    1445                 1450                 1455

Gly Tyr  Ala Ala Cys Gln Thr  Thr Lys Lys Val Ser  Arg Leu Glu
    1460                 1465                 1470

Cys Arg  Gly Gly Cys Ala Gly  Gly Gln Cys Cys Gly  Pro Leu Arg
    1475                 1480                 1485

Ser Lys  Arg Arg Lys Tyr Ser  Phe Glu Cys Thr Asp  Gly Ser Ser
    1490                 1495                 1500

Phe Val  Asp Glu Val Glu Lys  Val Val Lys Cys Gly  Cys Thr Arg
    1505                 1510                 1515

Cys Val  Ser
    1520
```

<210> SEQ ID NO 7
<211> LENGTH: 4629
<212> TYPE: DNA
<213> ORGANISM: Mus musculus

<400> SEQUENCE: 7

```
atgagtggca ttggctggca gacactgtcc ctatcgctgg ggttagtgtt gtcgatcttg     60

aacaaggtgg cgccgcaggc gtgcccggcc cagtgctcct gttcaggcag cacggtggac    120

tgtcatgggc tggcactgcg cagtgtgccc aggaatatcc cccgcaacac cgagagactg    180

gatttgaatg gaaataacat cacgaggatc acgaagatag attttgctgg tctcaggcac    240

ctcagagttc ttcagctcat ggagaacaga atcagcacca tcgagagggg agcattccag    300

gatcttaagg agctggaaag actgcgttta aacagaaata accttcagtt gtttcctgag    360

ctgctgtttc tcgggactgc gaagctctac cggcttgatc tcagtgaaaa tcaaattcaa    420

gcaattccaa ggaaggcttt ccgtggggca gttgacatta aaaacctgca actggattac    480

aaccagatca gctgcattga agatggggcg ttcagagctc tacgagatct ggaagtgctc    540

actctgaaca ataacaatat tactagactt tcagtggcaa gtttcaacca tatgcctaaa    600
```

-continued

```
cttaggacat ttcgactcca ctcgaacaac ttgtactgcg actgccacct agcctggctc    660
tcagactggc ttcgccaaag gccacgggtg ggcttgtaca ctcagtgtat gggcccatcc    720
cacctgaggg gccacaatgt agcagaggtt caaaaacgag agtttgtctg cagtgatgag    780
gaagaaggtc accagtcatt catggctccc tcctgcagtg tgctgcactg ccccgctgct    840
tgtacctgta gcaacaacat tgtagactgc cgagggaaag gtctcactga gatccccaca    900
aatctgcctg agaccatcac agaaatacgt ttggaacaga actccatcag ggtcatccct    960
ccaggagcct tctcaccata caaaaagctt agacgactag acctgagcaa caaccagatc   1020
tctgaacttg caccagatgc cttccaagga ctgcgctctc tgaattcact tgtcctgtat   1080
ggaaataaaa tcacagaact cccaaaaagt ttattcgaag gactattttc cttgcagcta   1140
ctattattga atgccaacaa gataaactgc cttcgggtag atgcttttca ggacctgcac   1200
aacttgaacc ttctctcctt atatgacaat aagcttcaga cggttgccaa gggcaccttc   1260
tcagccctca gagccatcca aactatgcat ttggcccaga atcctttcat ttgtgactgc   1320
catctcaagt ggctagcgga ttatctccac accaacccaa ttgagaccag cggtgcccgt   1380
tgcaccagcc cccgccgcct ggcaaacaaa agaattggac agatcaaaag caagaaattc   1440
cgttgttcag ctaaagaaca gtatttcatt ccaggtacag aagattatcg atcaaaatta   1500
agtggagact gctttgcaga cttggcttgt cctgagaagt gtcgctgtga agggaccaca   1560
gtagactgct ccaatcaaag actcaacaaa atccctgacc atattcccca gtacacagca   1620
gagctgcgtc tcaataataa tgaattcaca gtgttagaag ccacgggaat atttaagaaa   1680
cttcctcagt tacgtaaaat caactttagc aacaataaga tcacggatat cgaggagggt   1740
gcatttgaag gcgcgtctgg tgtgaatgaa attcttctca ccagtaaccg tttggaaaat   1800
gttcagcata agatgttcaa aggactggag agcctcaaaa cattgatgct gagaagtaat   1860
cgaataagct gtgttgggaa cgacagtttc ataggactcg gctctgtgcg tctgctctct   1920
ttatatgaca atcaaattac cacagtggca ccaggagcat ttgattctct ccattcatta   1980
tccactctaa acctcttggc caatcctttc aactgtaact gtcacctggc atggctggga   2040
gaatggctca gaaggaaaag aattgtaaca ggaaatcctc gatgccaaaa accctacttc   2100
ctgaaggaaa tcccaatcca ggatgtagcc attcaggact tcacctgtga tgatggaaat   2160
gatgacaata gttgctctcc actctcccgt tgtccttctg aatgtacctg cttggataca   2220
gtggtacgat gtagcaacaa gggcttgaag gttttgccta aaggtattcc aaaagatgtc   2280
acagagctgt atctggatgg gaaccagttt acgctggtcc cgaaggaact ctctaactac   2340
aaacatttaa cacttataga cttaagtaac aaccgaataa gcaccctttc caatcaaagc   2400
ttcagcaaca tgacccagct tctcacctta atcctcagtt acaaccgtct gagatgtatc   2460
cctccacgaa cctttgatgg attgaagtct cttcggttac tgtctttaca tggaaatgac   2520
atttctgttg tgcctgaagg tgccttcaat gacttgtcag ccttgtcaca cttagcgatt   2580
ggagccaacc ctctttactg tgattgtaac atgcagtggt tatccgactg ggtgaagtcg   2640
gaatataagg aacctggaat tgcacgctgt gccggccctg gagaaatggc agataaatta   2700
ttactcacta ctccctccaa aaaatttaca tgtcaaggtc ccgtggatat cactattcaa   2760
gccaagtgta atccctgctt atcaaatcca tgtaaaaatg atggcacctg taacaatgac   2820
cccgttgatt tttatcgatg tacctgccca tatggattca agggtcagga ctgtgatgtc   2880
cccattcatg cttgtatcag taatccatgt aaacatggag gaacttgtca cttaaaggaa   2940
ggagagaatg ctggattctg gtgcacttgt gctgatgggt ttgaaggaga aaactgtgaa   3000
```

-continued

```
gtcaatattg atgattgtga agataatgat tgtgaaaata attctacatg cgttgatgga   3060
attaacaact acacatgtct ttgcccaccg gaatacacag ctgctaatct gaatgaggtg   3120
gaaaaaggtg aactgtgtga ggaaaagctg gacttctgtg cacaagactt gaatccctgc   3180
cagcatgact ccaagtgcat cctgactcca aagggattca agtgtgactg cactccagga   3240
tacattggtg agcactgtga cattgacttt gatgactgcc aagataacaa gtgtaaaaac   3300
ggtgctcact gcacagatgc cgtgaacgga tacacgtgcg tctgtcctga aggctacagt   3360
ggcttgttct gtgagttttc tccacccatg gtcctccctc gcaccagccc ctgtgataat   3420
tttgattgcc agaatggagc ccagtgtatc atcaggataa atgaaccaat atgccagtgt   3480
ttgcctggct acctgggaga gaagtgtgag aaattggtca gtgtgaattt tgtaaacaaa   3540
gagtcctatc ttcagattcc ttcagccaag gttcggcctc agacaaacat cacacttcag   3600
attgccacag atgaagacag cggcatcctc ttgtataaag gtgacaaaga ccacattgcc   3660
gtggaactct atagagggcg agttcgagcc agctatgaca ccggctctca tccggcttct   3720
gccatttaca gtgtggagac aatcaatgat ggaaacttcc acattgtgga gctactgacc   3780
ctggattcca gtctttccct ctctgtggat ggaggaagcc ctaaagtcat caccaatttg   3840
tcaaaacaat ctactctgaa tttcgactct ccactctatg taggaggcat gcctgggaaa   3900
aataacgtgg catccctgcg ccaggcccct gggcaaaatg gcaccagctt ccatggctgt   3960
atccggaacc tttacattaa cagtgagctg caggacttcc ggaaaatgcc tatgcaaacc   4020
ggaattctgc ctggctgtga accatgccac aagaaagtat gtgcccatgg catgtgccag   4080
cccagcagcc aatcaggctt cacctgtgaa tgtgaggaag ggtggatggg gcccctctgt   4140
gaccagagaa ccaatgatcc ctgcctcgga aacaaatgtg tgcatgggac ctgcctgccc   4200
atcaatgcct tctcctatag ttgcaagtgc ctggagggcc atggcggtgt cctctgtgat   4260
gaagaagaag atctctttaa cccctgccag atgatcaagt gcaagcatgg gaagtgcagg   4320
ctttctggag tgggccagcc ctattgtgaa tgcaacagtg gattcaccgg ggacagctgt   4380
gatagagaaa tttcttgtcg aggggaacgg ataagggact attaccagaa gcagcagggt   4440
tacgctgcct gtcaaacaac taagaaagta tctcgcttgg aatgcagagg cgggtgcgct   4500
ggaggccagt gctgtggacc tctgagaagc aagaggcgga aatactcttt cgaatgcaca   4560
gatggctcct catttgtgga cgaggttgag aaagtggtga agtgcggctg cgcgagatgt   4620
gcctcctaa                                                           4629
```

<210> SEQ ID NO 8
<211> LENGTH: 1542
<212> TYPE: PRT
<213> ORGANISM: Mus musculus

<400> SEQUENCE: 8

```
Met Ser Gly Ile Gly Trp Gln Thr Leu Ser Leu Ser Leu Gly Leu Val
1               5                   10                  15

Leu Ser Ile Leu Asn Lys Val Ala Pro Gln Ala Cys Pro Ala Gln Cys
            20                  25                  30

Ser Cys Ser Gly Ser Thr Val Asp Cys His Gly Leu Ala Leu Arg Ser
        35                  40                  45

Val Pro Arg Asn Ile Pro Arg Asn Thr Glu Arg Leu Asp Leu Asn Gly
    50                  55                  60

Asn Asn Ile Thr Arg Ile Thr Lys Ile Asp Phe Ala Gly Leu Arg His
65                  70                  75                  80
```

```
Leu Arg Val Leu Gln Leu Met Glu Asn Arg Ile Ser Thr Ile Glu Arg
                85                  90                  95

Gly Ala Phe Gln Asp Leu Lys Glu Leu Glu Arg Leu Arg Leu Asn Arg
            100                 105                 110

Asn Asn Leu Gln Leu Phe Pro Glu Leu Leu Phe Leu Gly Thr Ala Lys
        115                 120                 125

Leu Tyr Arg Leu Asp Leu Ser Glu Asn Gln Ile Gln Ala Ile Pro Arg
    130                 135                 140

Lys Ala Phe Arg Gly Ala Val Asp Ile Lys Asn Leu Gln Leu Asp Tyr
145                 150                 155                 160

Asn Gln Ile Ser Cys Ile Glu Asp Gly Ala Phe Arg Ala Leu Arg Asp
                165                 170                 175

Leu Glu Val Leu Thr Leu Asn Asn Asn Asn Ile Thr Arg Leu Ser Val
            180                 185                 190

Ala Ser Phe Asn His Met Pro Lys Leu Arg Thr Phe Arg Leu His Ser
        195                 200                 205

Asn Asn Leu Tyr Cys Asp Cys His Leu Ala Trp Leu Ser Asp Trp Leu
    210                 215                 220

Arg Gln Arg Pro Arg Val Gly Leu Tyr Thr Gln Cys Met Gly Pro Ser
225                 230                 235                 240

His Leu Arg Gly His Asn Val Ala Glu Val Gln Lys Arg Glu Phe Val
                245                 250                 255

Cys Ser Asp Glu Glu Glu Gly His Gln Ser Phe Met Ala Pro Ser Cys
            260                 265                 270

Ser Val Leu His Cys Pro Ala Ala Cys Thr Cys Ser Asn Asn Ile Val
        275                 280                 285

Asp Cys Arg Gly Lys Gly Leu Thr Glu Ile Pro Thr Asn Leu Pro Glu
    290                 295                 300

Thr Ile Thr Glu Ile Arg Leu Glu Gln Asn Ser Ile Arg Val Ile Pro
305                 310                 315                 320

Pro Gly Ala Phe Ser Pro Tyr Lys Lys Leu Arg Arg Leu Asp Leu Ser
                325                 330                 335

Asn Asn Gln Ile Ser Glu Leu Ala Pro Asp Ala Phe Gln Gly Leu Arg
            340                 345                 350

Ser Leu Asn Ser Leu Val Leu Tyr Gly Asn Lys Ile Thr Glu Leu Pro
        355                 360                 365

Lys Ser Leu Phe Glu Gly Leu Phe Ser Leu Gln Leu Leu Leu Leu Asn
    370                 375                 380

Ala Asn Lys Ile Asn Cys Leu Arg Val Asp Ala Phe Gln Asp Leu His
385                 390                 395                 400

Asn Leu Asn Leu Leu Ser Leu Tyr Asp Asn Lys Leu Gln Thr Val Ala
                405                 410                 415

Lys Gly Thr Phe Ser Ala Leu Arg Ala Ile Gln Thr Met His Leu Ala
            420                 425                 430

Gln Asn Pro Phe Ile Cys Asp Cys His Leu Lys Trp Leu Ala Asp Tyr
        435                 440                 445

Leu His Thr Asn Pro Ile Glu Thr Ser Gly Ala Arg Cys Thr Ser Pro
    450                 455                 460

Arg Arg Leu Ala Asn Lys Arg Ile Gly Gln Ile Lys Ser Lys Lys Phe
465                 470                 475                 480

Arg Cys Ser Ala Lys Glu Gln Tyr Phe Ile Pro Gly Thr Glu Asp Tyr
                485                 490                 495
```

-continued

```
Arg Ser Lys Leu Ser Gly Asp Cys Phe Ala Asp Leu Ala Cys Pro Glu
            500                 505                 510

Lys Cys Arg Cys Glu Gly Thr Thr Val Asp Cys Ser Asn Gln Arg Leu
        515                 520                 525

Asn Lys Ile Pro Asp His Ile Pro Gln Tyr Thr Ala Glu Leu Arg Leu
    530                 535                 540

Asn Asn Asn Glu Phe Thr Val Leu Glu Ala Thr Gly Ile Phe Lys Lys
545                 550                 555                 560

Leu Pro Gln Leu Arg Lys Ile Asn Phe Ser Asn Asn Lys Ile Thr Asp
                565                 570                 575

Ile Glu Glu Gly Ala Phe Glu Gly Ala Ser Gly Val Asn Glu Ile Leu
            580                 585                 590

Leu Thr Ser Asn Arg Leu Glu Asn Val Gln His Lys Met Phe Lys Gly
        595                 600                 605

Leu Glu Ser Leu Lys Thr Leu Met Leu Arg Ser Asn Arg Ile Ser Cys
    610                 615                 620

Val Gly Asn Asp Ser Phe Ile Gly Leu Gly Ser Val Arg Leu Leu Ser
625                 630                 635                 640

Leu Tyr Asp Asn Gln Ile Thr Thr Val Ala Pro Gly Ala Phe Asp Ser
                645                 650                 655

Leu His Ser Leu Ser Thr Leu Asn Leu Leu Ala Asn Pro Phe Asn Cys
            660                 665                 670

Asn Cys His Leu Ala Trp Leu Gly Glu Trp Leu Arg Arg Lys Arg Ile
        675                 680                 685

Val Thr Gly Asn Pro Arg Cys Gln Lys Pro Tyr Phe Leu Lys Glu Ile
    690                 695                 700

Pro Ile Gln Asp Val Ala Ile Gln Asp Phe Thr Cys Asp Asp Gly Asn
705                 710                 715                 720

Asp Asp Asn Ser Cys Ser Pro Leu Ser Arg Cys Pro Ser Glu Cys Thr
                725                 730                 735

Cys Leu Asp Thr Val Val Arg Cys Ser Asn Lys Gly Leu Lys Val Leu
            740                 745                 750

Pro Lys Gly Ile Pro Lys Asp Val Thr Glu Leu Tyr Leu Asp Gly Asn
        755                 760                 765

Gln Phe Thr Leu Val Pro Lys Glu Leu Ser Asn Tyr Lys His Leu Thr
    770                 775                 780

Leu Ile Asp Leu Ser Asn Asn Arg Ile Ser Thr Leu Ser Asn Gln Ser
785                 790                 795                 800

Phe Ser Asn Met Thr Gln Leu Leu Thr Leu Ile Leu Ser Tyr Asn Arg
                805                 810                 815

Leu Arg Cys Ile Pro Pro Arg Thr Phe Asp Gly Leu Lys Ser Leu Arg
            820                 825                 830

Leu Leu Ser Leu His Gly Asn Asp Ile Ser Val Val Pro Glu Gly Ala
        835                 840                 845

Phe Asn Asp Leu Ser Ala Leu Ser His Leu Ala Ile Gly Ala Asn Pro
    850                 855                 860

Leu Tyr Cys Asp Cys Asn Met Gln Trp Leu Ser Asp Trp Val Lys Ser
865                 870                 875                 880

Glu Tyr Lys Glu Pro Gly Ile Ala Arg Cys Ala Gly Pro Gly Glu Met
                885                 890                 895

Ala Asp Lys Leu Leu Leu Thr Thr Pro Ser Lys Lys Phe Thr Cys Gln
            900                 905                 910

Gly Pro Val Asp Ile Thr Ile Gln Ala Lys Cys Asn Pro Cys Leu Ser
```

-continued

```
        915                 920                 925

Asn Pro Cys Lys Asn Asp Gly Thr Cys Asn Asn Asp Pro Val Asp Phe
    930                 935                 940

Tyr Arg Cys Thr Cys Pro Tyr Gly Phe Lys Gly Gln Asp Cys Asp Val
945                 950                 955                 960

Pro Ile His Ala Cys Ile Ser Asn Pro Cys Lys His Gly Gly Thr Cys
                965                 970                 975

His Leu Lys Glu Gly Glu Asn Ala Gly Phe Trp Cys Thr Cys Ala Asp
            980                 985                 990

Gly Phe Glu Gly Glu Asn Cys Glu  Val Asn Ile Asp Asp  Cys Glu Asp
        995                 1000                1005

Asn Asp  Cys Glu Asn Asn Ser  Thr Cys Val Asp Gly  Ile Asn Asn
    1010                 1015                 1020

Tyr Thr  Cys Leu Cys Pro Pro  Glu Tyr Thr Ala Ala  Asn Leu Asn
    1025                 1030                 1035

Glu Val  Glu Lys Gly Glu Leu  Cys Glu Glu Lys Leu  Asp Phe Cys
    1040                 1045                 1050

Ala Gln  Asp Leu Asn Pro Cys  Gln His Asp Ser Lys  Cys Ile Leu
    1055                 1060                 1065

Thr Pro  Lys Gly Phe Lys Cys  Asp Cys Thr Pro Gly  Tyr Ile Gly
    1070                 1075                 1080

Glu His  Cys Asp Ile Asp Phe  Asp Asp Cys Gln Asp  Asn Lys Cys
    1085                 1090                 1095

Lys Asn  Gly Ala His Cys Thr  Asp Ala Val Asn Gly  Tyr Thr Cys
    1100                 1105                 1110

Val Cys  Pro Glu Gly Tyr Ser  Gly Leu Phe Cys Glu  Phe Ser Pro
    1115                 1120                 1125

Pro Met  Val Leu Pro Arg Thr  Ser Pro Cys Asp Asn  Phe Asp Cys
    1130                 1135                 1140

Gln Asn  Gly Ala Gln Cys Ile  Ile Arg Ile Asn Glu  Pro Ile Cys
    1145                 1150                 1155

Gln Cys  Leu Pro Gly Tyr Leu  Gly Glu Lys Cys Glu  Lys Leu Val
    1160                 1165                 1170

Ser Val  Asn Phe Val Asn Lys  Glu Ser Tyr Leu Gln  Ile Pro Ser
    1175                 1180                 1185

Ala Lys  Val Arg Pro Gln Thr  Asn Ile Thr Leu Gln  Ile Ala Thr
    1190                 1195                 1200

Asp Glu  Asp Ser Gly Ile Leu  Leu Tyr Lys Gly Asp  Lys Asp His
    1205                 1210                 1215

Ile Ala  Val Glu Leu Tyr Arg  Gly Arg Val Arg Ala  Ser Tyr Asp
    1220                 1225                 1230

Thr Gly  Ser His Pro Ala Ser  Ala Ile Tyr Ser Val  Glu Thr Ile
    1235                 1240                 1245

Asn Asp  Gly Asn Phe His Ile  Val Glu Leu Leu Thr  Leu Asp Ser
    1250                 1255                 1260

Ser Leu  Ser Leu Ser Val Asp  Gly Gly Ser Pro Lys  Val Ile Thr
    1265                 1270                 1275

Asn Leu  Ser Lys Gln Ser Thr  Leu Asn Phe Asp Ser  Pro Leu Tyr
    1280                 1285                 1290

Val Gly  Gly Met Pro Gly Lys  Asn Asn Val Ala Ser  Leu Arg Gln
    1295                 1300                 1305

Ala Pro  Gly Gln Asn Gly Thr  Ser Phe His Gly Cys  Ile Arg Asn
    1310                 1315                 1320
```

-continued

Leu Tyr Ile Asn Ser Glu Leu Gln Asp Phe Arg Lys Met Pro Met
1325 1330 1335

Gln Thr Gly Ile Leu Pro Gly Cys Glu Pro Cys His Lys Lys Val
1340 1345 1350

Cys Ala His Gly Met Cys Gln Pro Ser Ser Gln Ser Gly Phe Thr
1355 1360 1365

Cys Glu Cys Glu Glu Gly Trp Met Gly Pro Leu Cys Asp Gln Arg
1370 1375 1380

Thr Asn Asp Pro Cys Leu Gly Asn Lys Cys Val His Gly Thr Cys
1385 1390 1395

Leu Pro Ile Asn Ala Phe Ser Tyr Ser Cys Lys Cys Leu Glu Gly
1400 1405 1410

His Gly Gly Val Leu Cys Asp Glu Glu Glu Asp Leu Phe Asn Pro
1415 1420 1425

Cys Gln Met Ile Lys Cys Lys His Gly Lys Cys Arg Leu Ser Gly
1430 1435 1440

Val Gly Gln Pro Tyr Cys Glu Cys Asn Ser Gly Phe Thr Gly Asp
1445 1450 1455

Ser Cys Asp Arg Glu Ile Ser Cys Arg Gly Glu Arg Ile Arg Asp
1460 1465 1470

Tyr Tyr Gln Lys Gln Gln Gly Tyr Ala Ala Cys Gln Thr Thr Lys
1475 1480 1485

Lys Val Ser Arg Leu Glu Cys Arg Gly Gly Cys Ala Gly Gly Gln
1490 1495 1500

Cys Cys Gly Pro Leu Arg Ser Lys Arg Arg Lys Tyr Ser Phe Glu
1505 1510 1515

Cys Thr Asp Gly Ser Ser Phe Val Asp Glu Val Glu Lys Val Val
1520 1525 1530

Lys Cys Gly Cys Ala Arg Cys Ala Ser
1535 1540

<210> SEQ ID NO 9
<211> LENGTH: 4578
<212> TYPE: DNA
<213> ORGANISM: Mus musculus

<400> SEQUENCE: 9
atgagtggca ttggctggca gacactgtcc ctatcgctgg ggttagtgtt gtcgatcttg 60
aacaaggtgg cgccgcaggc gtgcccggcc cagtgctcct gttcaggcag cacggtggac 120
tgtcatgggc tggcactgcg cagtgtgccc aggaatatcc cccgcaacac cgagagactg 180
gatttgaatg gaaataacat cacgaggatc acgaagatag attttgctgg tctcaggcac 240
ctcagagttc ttcagctcat ggagaacaga atcagcacca tcgagagggg agcattccag 300
gatcttaagg agctggaaag actgcgttta aacagaaata accttcagtt gtttcctgag 360
ctgctgtttc tcgggactgc gaagctctac cggcttgatc tcagtgaaaa tcaaattcaa 420
gcaattccaa ggaaggcttt ccgtggggca gttgacatta aaaacctgca actggattac 480
aaccagatca gctgcattga agatggggcg ttcagagctc tacgagatct ggaagtgctc 540
actctgaaca ataacaatat tactagactt tcagtggcaa gtttcaacca tatgcctaaa 600
cttaggacat ttcgactcca ctcgaacaac ttgtactgcg actgccacct agcctggctc 660
tcagactggc ttcgccaaag gccacgggtg ggcttgtaca ctcagtgtat gggcccatcc 720
cacctgaggg gccacaatgt agcagaggtt caaaaacgag agtttgtctg cagtgatgag 780
gaagaaggtc accagtcatt catggctccc tcctgcagtg tgctgcactg ccccgctgct 840
tgtacctgta gcaacaacat tgtagactgc cgagggaaag gtctcactga gatccccaca 900
aatctgcctg agaccatcac agaaatacgt ttggaacaga actccatcag ggtcatccct 960
ccaggagcct tctcaccata caaaaagctt agacgactag acctgagcaa caaccagatc 1020
tctgaacttg caccagatgc cttccaagga ctgcgctctc tgaattcact tgtcctgtat 1080
ggaaataaaa tcacagaact cccaaaaagt ttattcgaag gactattttc cttgcagcta 1140
ctattattga atgccaacaa gataaactgc cttcgggtag atgcttttca ggacctgcac 1200
aacttgaacc ttctctcctt atatgacaat aagcttcaga cggttgccaa gggcaccttc 1260
tcagccctca gagccatcca aactatgcat ttggcccaga atcctttcat ttgtgactgc 1320
catctcaagt ggctagcgga ttatctccac accaacccaa ttgagaccag cggtgcccgt 1380
tgcaccagcc cccgccgcct ggcaaacaaa agaattggac agatcaaaag caagaaattc 1440
cgttgttcag gtacagaaga ttatcgatca aaattaagtg gagactgctt tgcagacttg 1500
gcttgtcctg agaagtgtcg ctgtgaaggg accacagtag actgctccaa tcaaagactc 1560
aacaaaatcc ctgaccatat tccccagtac acagcagagc tgcgtctcaa taataatgaa 1620
ttcacagtgt tagaagccac gggaatattt aagaaacttc ctcagttacg taaaatcaac 1680
tttagcaaca ataagatcac ggatatcgag gagggtgcat ttgaaggcgc gtctggtgtg 1740
aatgaaattc ttctcaccag taaccgtttg gaaaatgttc agcataagat gttcaaagga 1800
ctggagagcc tcaaaacatt gatgctgaga agtaatcgaa taagctgtgt tgggaacgac 1860
agtttcatag gactcggctc tgtgcgtctg ctctctttat atgacaatca aattaccaca 1920
gtggcaccag gagcatttga ttctctccat tcattatcca ctctaaacct cttggccaat 1980
cctttcaact gtaactgtca cctggcatgg ctgggagaat ggctcagaag gaaaagaatt 2040
gtaacaggaa atcctcgatg ccaaaaaccc tacttcctga aggaaatccc aatccaggat 2100
gtagccattc aggacttcac ctgtgatgat ggaaatgatg acaatagttg ctctccactc 2160
tcccgttgtc cttctgaatg tacctgcttg gatacagtgg tacgatgtag caacaagggc 2220
ttgaaggttt tgcctaaagg tattccaaaa gatgtcacag agctgtatct ggatgggaac 2280
cagtttacgc tggtcccgaa ggaactctct aactacaaac atttaacact tatagactta 2340
agtaacaacc gaataagcac cctttccaat caaagcttca gcaacatgac ccagcttctc 2400
accttaatcc tcagttacaa ccgtctgaga tgtatccctc cacgaacctt tgatggattg 2460
aagtctcttc ggttactgtc tttacatgga aatgacattt ctgttgtgcc tgaaggtgcc 2520
ttcaatgact tgtcagcctt gtcacactta gcgattggag ccaaccctct ttactgtgat 2580
tgtaacatgc agtggttatc cgactgggtg aagtcggaat ataaggaacc tggaattgca 2640
cgctgtgccg gccctggaga aatggcagat aaattattac tcactactcc ctccaaaaaa 2700
tttacatgtc aaggtcccgt ggatatcact attcaagcca agtgtaatcc ctgcttatca 2760
aatccatgta aaaatgatgg cacctgtaac aatgaccccg ttgattttta tcgatgtacc 2820
tgcccatatg gattcaaggg tcaggactgt gatgtcccca ttcatgcttg tatcagtaat 2880
ccatgtaaac atggaggaac ttgtcactta aaggaaggag agaatgctgg attctggtgc 2940
acttgtgctg atgggtttga aggagaaaac tgtgaagtca atattgatga ttgtgaagat 3000
aatgattgtg aaaataattc tacatgcgtt gatggaatta acaactacac atgtctttgc 3060
ccaccggaat acacaggtga actgtgtgag gaaaagctgg acttctgtgc acaagacttg 3120

```
aatccctgcc agcatgactc caagtgcatc ctgactccaa agggattcaa gtgtgactgc   3180

actccaggat acattggtga gcactgtgac attgactttg atgactgcca agataacaag   3240

tgtaaaaacg gtgctcactg cacagatgcc gtgaacggat acacgtgcgt ctgtcctgaa   3300

ggctacagtg gcttgttctg tgagttttct ccacccatgg tcctccctcg caccagcccc   3360

tgtgataatt ttgattgcca gaatggagcc cagtgtatca tcaggataaa tgaaccaata   3420

tgccagtgtt tgcctggcta cctgggagag aagtgtgaga aattggtcag tgtgaatttt   3480

gtaaacaaag agtcctatct tcagattcct tcagccaagg ttcggcctca gacaaacatc   3540

acacttcaga ttgccacaga tgaagacagc ggcatcctct tgtataaagg tgacaaagac   3600

cacattgccg tggaactcta tagagggcga gttcgagcca gctatgacac cggctctcat   3660

ccggcttctg ccatttacag tgtggagaca atcaatgatg gaaacttcca cattgtggag   3720

ctactgaccc tggattccag tctttccctc tctgtggatg gaggaagccc taaagtcatc   3780

accaatttgt caaaacaatc tactctgaat ttcgactctc cactctatgt aggaggcatg   3840

cctgggaaaa ataacgtggc atccctgcgc caggcccctg ggcaaaatgg caccagcttc   3900

catggctgta tccggaacct ttacattaac agtgagctgc aggacttccg gaaaatgcct   3960

atgcaaaccg gaattctgcc tggctgtgaa ccatgccaca agaaagtatg tgcccatggc   4020

atgtgccagc ccagcagcca atcaggcttc acctgtgaat gtgaggaagg gtggatgggg   4080

cccctctgtg accagagaac caatgatccc tgcctcggaa acaaatgtgt gcatgggacc   4140

tgcctgccca tcaatgcctt ctcctatagt tgcaagtgcc tggagggcca tggcggtgtc   4200

ctctgtgatg aagaagaaga tctctttaac ccctgccaga tgatcaagtg caagcatggg   4260

aagtgcaggc tttctggagt gggccagccc tattgtgaat gcaacagtgg attcaccggg   4320

gacagctgtg atagagaaat ttcttgtcga ggggaacgga taagggacta ttaccagaag   4380

cagcagggtt acgctgcctg tcaaacaact aagaaagtat ctcgcttgga atgcagaggc   4440

gggtgcgctg gaggccagtg ctgtggacct ctgagaagca agaggcggaa atactctttc   4500

gaatgcacag atggctcctc atttgtggac gaggttgaga aagtggtgaa gtgcggctgc   4560

gcgagatgtg cctcctaa                                                  4578
```

<210> SEQ ID NO 10
<211> LENGTH: 1525
<212> TYPE: PRT
<213> ORGANISM: Mus musculus

<400> SEQUENCE: 10

```
Met Ser Gly Ile Gly Trp Gln Thr Leu Ser Leu Ser Leu Gly Leu Val
1               5                   10                  15

Leu Ser Ile Leu Asn Lys Val Ala Pro Gln Ala Cys Pro Ala Gln Cys
            20                  25                  30

Ser Cys Ser Gly Ser Thr Val Asp Cys His Gly Leu Ala Leu Arg Ser
        35                  40                  45

Val Pro Arg Asn Ile Pro Arg Asn Thr Glu Arg Leu Asp Leu Asn Gly
    50                  55                  60

Asn Asn Ile Thr Arg Ile Thr Lys Ile Asp Phe Ala Gly Leu Arg His
65                  70                  75                  80

Leu Arg Val Leu Gln Leu Met Glu Asn Arg Ile Ser Thr Ile Glu Arg
                85                  90                  95

Gly Ala Phe Gln Asp Leu Lys Glu Leu Glu Arg Leu Arg Leu Asn Arg
            100                 105                 110
```

-continued

```
Asn Asn Leu Gln Leu Phe Pro Glu Leu Leu Phe Leu Gly Thr Ala Lys
        115                 120                 125

Leu Tyr Arg Leu Asp Leu Ser Glu Asn Gln Ile Gln Ala Ile Pro Arg
    130                 135                 140

Lys Ala Phe Arg Gly Ala Val Asp Ile Lys Asn Leu Gln Leu Asp Tyr
145                 150                 155                 160

Asn Gln Ile Ser Cys Ile Glu Asp Gly Ala Phe Arg Ala Leu Arg Asp
                165                 170                 175

Leu Glu Val Leu Thr Leu Asn Asn Asn Asn Ile Thr Arg Leu Ser Val
            180                 185                 190

Ala Ser Phe Asn His Met Pro Lys Leu Arg Thr Phe Arg Leu His Ser
        195                 200                 205

Asn Asn Leu Tyr Cys Asp Cys His Leu Ala Trp Leu Ser Asp Trp Leu
    210                 215                 220

Arg Gln Arg Pro Arg Val Gly Leu Tyr Thr Gln Cys Met Gly Pro Ser
225                 230                 235                 240

His Leu Arg Gly His Asn Val Ala Glu Val Gln Lys Arg Glu Phe Val
                245                 250                 255

Cys Ser Asp Glu Glu Glu Gly His Gln Ser Phe Met Ala Pro Ser Cys
            260                 265                 270

Ser Val Leu His Cys Pro Ala Ala Cys Thr Cys Ser Asn Asn Ile Val
        275                 280                 285

Asp Cys Arg Gly Lys Gly Leu Thr Glu Ile Pro Thr Asn Leu Pro Glu
    290                 295                 300

Thr Ile Thr Glu Ile Arg Leu Glu Gln Asn Ser Ile Arg Val Ile Pro
305                 310                 315                 320

Pro Gly Ala Phe Ser Pro Tyr Lys Lys Leu Arg Arg Leu Asp Leu Ser
                325                 330                 335

Asn Asn Gln Ile Ser Glu Leu Ala Pro Asp Ala Phe Gln Gly Leu Arg
            340                 345                 350

Ser Leu Asn Ser Leu Val Leu Tyr Gly Asn Lys Ile Thr Glu Leu Pro
        355                 360                 365

Lys Ser Leu Phe Glu Gly Leu Phe Ser Leu Gln Leu Leu Leu Leu Asn
    370                 375                 380

Ala Asn Lys Ile Asn Cys Leu Arg Val Asp Ala Phe Gln Asp Leu His
385                 390                 395                 400

Asn Leu Asn Leu Leu Ser Leu Tyr Asp Asn Lys Leu Gln Thr Val Ala
                405                 410                 415

Lys Gly Thr Phe Ser Ala Leu Arg Ala Ile Gln Thr Met His Leu Ala
            420                 425                 430

Gln Asn Pro Phe Ile Cys Asp Cys His Leu Lys Trp Leu Ala Asp Tyr
        435                 440                 445

Leu His Thr Asn Pro Ile Glu Thr Ser Gly Ala Arg Cys Thr Ser Pro
    450                 455                 460

Arg Arg Leu Ala Asn Lys Arg Ile Gly Gln Ile Lys Ser Lys Lys Phe
465                 470                 475                 480

Arg Cys Ser Gly Thr Glu Asp Tyr Arg Ser Lys Leu Ser Gly Asp Cys
                485                 490                 495

Phe Ala Asp Leu Ala Cys Pro Glu Lys Cys Arg Cys Glu Gly Thr Thr
            500                 505                 510

Val Asp Cys Ser Asn Gln Arg Leu Asn Lys Ile Pro Asp His Ile Pro
        515                 520                 525

Gln Tyr Thr Ala Glu Leu Arg Leu Asn Asn Asn Glu Phe Thr Val Leu
```

```
    530                 535                 540

Glu Ala Thr Gly Ile Phe Lys Lys Leu Pro Gln Leu Arg Lys Ile Asn
545                 550                 555                 560

Phe Ser Asn Asn Lys Ile Thr Asp Ile Glu Glu Gly Ala Phe Glu Gly
                565                 570                 575

Ala Ser Gly Val Asn Glu Ile Leu Leu Thr Ser Asn Arg Leu Glu Asn
            580                 585                 590

Val Gln His Lys Met Phe Lys Gly Leu Glu Ser Leu Lys Thr Leu Met
        595                 600                 605

Leu Arg Ser Asn Arg Ile Ser Cys Val Gly Asn Asp Ser Phe Ile Gly
    610                 615                 620

Leu Gly Ser Val Arg Leu Leu Ser Leu Tyr Asp Asn Gln Ile Thr Thr
625                 630                 635                 640

Val Ala Pro Gly Ala Phe Asp Ser Leu His Ser Leu Ser Thr Leu Asn
                645                 650                 655

Leu Leu Ala Asn Pro Phe Asn Cys Asn Cys His Leu Ala Trp Leu Gly
            660                 665                 670

Glu Trp Leu Arg Arg Lys Arg Ile Val Thr Gly Asn Pro Arg Cys Gln
        675                 680                 685

Lys Pro Tyr Phe Leu Lys Glu Ile Pro Ile Gln Asp Val Ala Ile Gln
    690                 695                 700

Asp Phe Thr Cys Asp Asp Gly Asn Asp Asp Asn Ser Cys Ser Pro Leu
705                 710                 715                 720

Ser Arg Cys Pro Ser Glu Cys Thr Cys Leu Asp Thr Val Val Arg Cys
                725                 730                 735

Ser Asn Lys Gly Leu Lys Val Leu Pro Lys Gly Ile Pro Lys Asp Val
            740                 745                 750

Thr Glu Leu Tyr Leu Asp Gly Asn Gln Phe Thr Leu Val Pro Lys Glu
        755                 760                 765

Leu Ser Asn Tyr Lys His Leu Thr Leu Ile Asp Leu Ser Asn Asn Arg
    770                 775                 780

Ile Ser Thr Leu Ser Asn Gln Ser Phe Ser Asn Met Thr Gln Leu Leu
785                 790                 795                 800

Thr Leu Ile Leu Ser Tyr Asn Arg Leu Arg Cys Ile Pro Pro Arg Thr
                805                 810                 815

Phe Asp Gly Leu Lys Ser Leu Arg Leu Leu Ser Leu His Gly Asn Asp
            820                 825                 830

Ile Ser Val Val Pro Glu Gly Ala Phe Asn Asp Leu Ser Ala Leu Ser
        835                 840                 845

His Leu Ala Ile Gly Ala Asn Pro Leu Tyr Cys Asp Cys Asn Met Gln
    850                 855                 860

Trp Leu Ser Asp Trp Val Lys Ser Glu Tyr Lys Glu Pro Gly Ile Ala
865                 870                 875                 880

Arg Cys Ala Gly Pro Gly Glu Met Ala Asp Lys Leu Leu Leu Thr Thr
                885                 890                 895

Pro Ser Lys Lys Phe Thr Cys Gln Gly Pro Val Asp Ile Thr Ile Gln
            900                 905                 910

Ala Lys Cys Asn Pro Cys Leu Ser Asn Pro Cys Lys Asn Asp Gly Thr
        915                 920                 925

Cys Asn Asn Asp Pro Val Asp Phe Tyr Arg Cys Thr Cys Pro Tyr Gly
    930                 935                 940

Phe Lys Gly Gln Asp Cys Asp Val Pro Ile His Ala Cys Ile Ser Asn
945                 950                 955                 960
```

```
Pro Cys Lys His Gly Gly Thr Cys His Leu Lys Glu Gly Glu Asn Ala
                965                 970                 975

Gly Phe Trp Cys Thr Cys Ala Asp Gly Phe Glu Gly Glu Asn Cys Glu
            980                 985                 990

Val Asn Ile Asp Asp Cys Glu Asp  Asn Asp Cys Glu Asn  Asn Ser Thr
        995                 1000                1005

Cys Val  Asp Gly Ile Asn Asn  Tyr Thr Cys Leu Cys  Pro Pro Glu
    1010                 1015                1020

Tyr Thr  Gly Glu Leu Cys Glu  Glu Lys Leu Asp Phe  Cys Ala Gln
    1025                 1030                1035

Asp Leu  Asn Pro Cys Gln His  Asp Ser Lys Cys Ile  Leu Thr Pro
    1040                 1045                1050

Lys Gly  Phe Lys Cys Asp Cys  Thr Pro Gly Tyr Ile  Gly Glu His
    1055                 1060                1065

Cys Asp  Ile Asp Phe Asp Asp  Cys Gln Asp Asn Lys  Cys Lys Asn
    1070                 1075                1080

Gly Ala  His Cys Thr Asp Ala  Val Asn Gly Tyr Thr  Cys Val Cys
    1085                 1090                1095

Pro Glu  Gly Tyr Ser Gly Leu  Phe Cys Glu Phe Ser  Pro Pro Met
    1100                 1105                1110

Val Leu  Pro Arg Thr Ser Pro  Cys Asp Asn Phe Asp  Cys Gln Asn
    1115                 1120                1125

Gly Ala  Gln Cys Ile Ile Arg  Ile Asn Glu Pro Ile  Cys Gln Cys
    1130                 1135                1140

Leu Pro  Gly Tyr Leu Gly Glu  Lys Cys Glu Lys Leu  Val Ser Val
    1145                 1150                1155

Asn Phe  Val Asn Lys Glu Ser  Tyr Leu Gln Ile Pro  Ser Ala Lys
    1160                 1165                1170

Val Arg  Pro Gln Thr Asn Ile  Thr Leu Gln Ile Ala  Thr Asp Glu
    1175                 1180                1185

Asp Ser  Gly Ile Leu Leu Tyr  Lys Gly Asp Lys Asp  His Ile Ala
    1190                 1195                1200

Val Glu  Leu Tyr Arg Gly Arg  Val Arg Ala Ser Tyr  Asp Thr Gly
    1205                 1210                1215

Ser His  Pro Ala Ser Ala Ile  Tyr Ser Val Glu Thr  Ile Asn Asp
    1220                 1225                1230

Gly Asn  Phe His Ile Val Glu  Leu Leu Thr Leu Asp  Ser Ser Leu
    1235                 1240                1245

Ser Leu  Ser Val Asp Gly Gly  Ser Pro Lys Val Ile  Thr Asn Leu
    1250                 1255                1260

Ser Lys  Gln Ser Thr Leu Asn  Phe Asp Ser Pro Leu  Tyr Val Gly
    1265                 1270                1275

Gly Met  Pro Gly Lys Asn Asn  Val Ala Ser Leu Arg  Gln Ala Pro
    1280                 1285                1290

Gly Gln  Asn Gly Thr Ser Phe  His Gly Cys Ile Arg  Asn Leu Tyr
    1295                 1300                1305

Ile Asn  Ser Glu Leu Gln Asp  Phe Arg Lys Met Pro  Met Gln Thr
    1310                 1315                1320

Gly Ile  Leu Pro Gly Cys Glu  Pro Cys His Lys Lys  Val Cys Ala
    1325                 1330                1335

His Gly  Met Cys Gln Pro Ser  Ser Gln Ser Gly Phe  Thr Cys Glu
    1340                 1345                1350
```

-continued

```
Cys Glu  Glu Gly Trp Met Gly  Pro Leu Cys Asp Gln  Arg Thr Asn
    1355                 1360                 1365

Asp Pro  Cys Leu Gly Asn Lys  Cys Val His Gly Thr  Cys Leu Pro
    1370                 1375                 1380

Ile Asn  Ala Phe Ser Tyr Ser  Cys Lys Cys Leu Glu  Gly His Gly
    1385                 1390                 1395

Gly Val  Leu Cys Asp Glu Glu  Glu Asp Leu Phe Asn  Pro Cys Gln
    1400                 1405                 1410

Met Ile  Lys Cys Lys His Gly  Lys Cys Arg Leu Ser  Gly Val Gly
    1415                 1420                 1425

Gln Pro  Tyr Cys Glu Cys Asn  Ser Gly Phe Thr Gly  Asp Ser Cys
    1430                 1435                 1440

Asp Arg  Glu Ile Ser Cys Arg  Gly Glu Arg Ile Arg  Asp Tyr Tyr
    1445                 1450                 1455

Gln Lys  Gln Gln Gly Tyr Ala  Ala Cys Gln Thr Thr  Lys Lys Val
    1460                 1465                 1470

Ser Arg  Leu Glu Cys Arg Gly  Gly Cys Ala Gly Gly  Gln Cys Cys
    1475                 1480                 1485

Gly Pro  Leu Arg Ser Lys Arg  Arg Lys Tyr Ser Phe  Glu Cys Thr
    1490                 1495                 1500

Asp Gly  Ser Ser Phe Val Asp  Glu Val Glu Lys Val  Val Lys Cys
    1505                 1510                 1515

Gly Cys  Ala Arg Cys Ala Ser
    1520                 1525
```

<210> SEQ ID NO 11
<211> LENGTH: 4566
<212> TYPE: DNA
<213> ORGANISM: Mus musculus

<400> SEQUENCE: 11

```
atgagtggca ttggctggca gacactgtcc ctatcgctgg ggttagtgtt gtcgatcttg     60

aacaaggtgg cgccgcaggc gtgcccggcc cagtgctcct gttcaggcag cacggtggac    120

tgtcatgggc tggcactgcg cagtgtgccc aggaatatcc cccgcaacac cgagagactg    180

gatttgaatg gaaataacat cacgaggatc acgaagatag attttgctgg tctcaggcac    240

ctcagagttc ttcagctcat ggagaacaga atcagcacca tcgagagggg agcattccag    300

gatcttaagg agctggaaag actgcgttta aacagaaata accttcagtt gtttcctgag    360

ctgctgtttc tcgggactgc gaagctctac cggcttgatc tcagtgaaaa tcaaattcaa    420

gcaattccaa ggaaggcttt ccgtggggca gttgacatta aaaacctgca actggattac    480

aaccagatca gctgcattga agatggggcg ttcagagctc tacgagatct ggaagtgctc    540

actctgaaca ataacaatat tactagactt tcagtggcaa gtttcaacca tatgcctaaa    600

cttaggacat ttcgactcca ctcgaacaac ttgtactgcg actgccacct agcctggctc    660

tcagactggc ttcgccaaag gccacgggtg ggcttgtaca ctcagtgtat gggcccatcc    720

cacctgaggg gccacaatgt agcagaggtt caaaaacgag agtttgtctg cagtggtcac    780

cagtcattca tggctccctc ctgcagtgtg ctgcactgcc ccgctgcttg tacctgtagc    840

aacaacattg tagactgccg agggaaaggt ctcactgaga tccccacaaa tctgcctgag    900

accatcacag aaatacgttt ggaacagaac tccatcaggg tcatccctcc aggagccttc    960

tcaccataca aaaagcttag acgactagac ctgagcaaca accagatctc tgaacttgca   1020

ccagatgcct tccaaggact gcgctctctg aattcacttg tcctgtatgg aaataaaatc   1080
```

-continued

```
acagaactcc caaaaagttt attcgaagga ctattttcct tgcagctact attattgaat   1140
gccaacaaga taaactgcct tcgggtagat gcttttcagg acctgcacaa cttgaacctt   1200
ctctccttat atgacaataa gcttcagacg gttgccaagg gcaccttctc agccctcaga   1260
gccatccaaa ctatgcattt ggcccagaat cctttcattt gtgactgcca tctcaagtgg   1320
ctagcggatt atctccacac caacccaatt gagaccagcg gtgcccgttg caccagcccc   1380
cgccgcctgg caaacaaaag aattggacag atcaaaagca agaaattccg ttgttcaggt   1440
acagaagatt atcgatcaaa attaagtgga gactgctttg cagacttggc ttgtcctgag   1500
aagtgtcgct gtgaagggac cacagtagac tgctccaatc aaagactcaa caaaatccct   1560
gaccatattc cccagtacac agcagagctg cgtctcaata ataatgaatt cacagtgtta   1620
gaagccacgg gaatatttaa gaaacttcct cagttacgta aaatcaactt tagcaacaat   1680
aagatcacgg atatcgagga gggtgcattt gaaggcgcgt ctggtgtgaa tgaaattctt   1740
ctcaccagta accgtttgga aaatgttcag cataagatgt tcaaaggact ggagagcctc   1800
aaaacattga tgctgagaag taatcgaata agctgtgttg ggaacgacag tttcatagga   1860
ctcggctctg tgcgtctgct ctctttatat gacaatcaaa ttaccacagt ggcaccagga   1920
gcatttgatt ctctccattc attatccact ctaaacctct tggccaatcc tttcaactgt   1980
aactgtcacc tggcatggct gggagaatgg ctcagaagga aaagaattgt aacaggaaat   2040
cctcgatgcc aaaaacccta cttcctgaag gaaatcccaa tccaggatgt agccattcag   2100
gacttcacct gtgatgatgg aaatgatgac aatagttgct ctccactctc ccgttgtcct   2160
tctgaatgta cctgcttgga tacagtggta cgatgtagca acaagggctt gaaggttttg   2220
cctaaaggta ttccaaaaga tgtcacagag ctgtatctgg atgggaacca gtttacgctg   2280
gtcccgaagg aactctctaa ctacaaacat ttaacactta tagacttaag taacaaccga   2340
ataagcaccc tttccaatca aagcttcagc aacatgaccc agcttctcac cttaatcctc   2400
agttacaacc gtctgagatg tatccctcca cgaacctttg atggattgaa gtctcttcgg   2460
ttactgtctt tacatggaaa tgacatttct gttgtgcctg aaggtgcctt caatgacttg   2520
tcagccttgt cacacttagc gattggagcc aaccctcttt actgtgattg taacatgcag   2580
tggttatccg actgggtgaa gtcggaatat aaggaacctg gaattgcacg ctgtgccggc   2640
cctggagaaa tggcagataa attattactc actactccct ccaaaaaatt tacatgtcaa   2700
ggtcccgtgg atatcactat tcaagccaag tgtaatccct gcttatcaaa tccatgtaaa   2760
aatgatggca cctgtaacaa tgaccccgtt gatttttatc gatgtacctg cccatatgga   2820
ttcaagggtc aggactgtga tgtccccatt catgcttgta tcagtaatcc atgtaaacat   2880
ggaggaactt gtcacttaaa ggaaggagag aatgctggat tctggtgcac ttgtgctgat   2940
gggtttgaag gagaaaactg tgaagtcaat attgatgatt gtgaagataa tgattgtgaa   3000
aataattcta catgcgttga tggaattaac aactacacat gtctttgccc accggaatac   3060
acaggtgaac tgtgtgagga aaagctggac ttctgtgcac aagacttgaa tccctgccag   3120
catgactcca agtgcatcct gactccaaag ggattcaagt gtgactgcac tccaggatac   3180
attggtgagc actgtgacat tgactttgat gactgccaag ataacaagtg taaaaacggt   3240
gctcactgca cagatgccgt gaacggatac acgtgcgtct gtcctgaagg ctacagtggc   3300
ttgttctgtg agttttctcc acccatggtc ctccctcgca ccagcccctg tgataatttt   3360
gattgccaga atggagccca gtgtatcatc aggataaatg aaccaatatg ccagtgtttg   3420
```

```
cctggctacc tgggagagaa gtgtgagaaa ttggtcagtg tgaattttgt aaacaaagag   3480

tcctatcttc agattccttc agccaaggtt cggcctcaga caaacatcac acttcagatt   3540

gccacagatg aagacagcgg catcctcttg tataaaggtg acaaagacca cattgccgtg   3600

gaactctata gagggcgagt tcgagccagc tatgacaccg gctctcatcc ggcttctgcc   3660

atttacagtg tggagacaat caatgatgga aacttccaca ttgtggagct actgaccctg   3720

gattccagtc tttccctctc tgtggatgga ggaagcccta aagtcatcac caatttgtca   3780

aaacaatcta ctctgaattt cgactctcca ctctatgtag gaggcatgcc tgggaaaaat   3840

aacgtggcat ccctgcgcca ggcccctggg caaaatggca ccagcttcca tggctgtatc   3900

cggaaccttt acattaacag tgagctgcag gacttccgga aaatgcctat gcaaaccgga   3960

attctgcctg gctgtgaacc atgccacaag aaagtatgtg cccatggcat gtgccagccc   4020

agcagccaat caggcttcac ctgtgaatgt gaggaagggt ggatggggcc cctctgtgac   4080

cagagaacca atgatccctg cctcggaaac aaatgtgtgc atgggacctg cctgcccatc   4140

aatgccttct cctatagttg caagtgcctg gagggccatg gcggtgtcct ctgtgatgaa   4200

gaagaagatc tctttaaccc ctgccagatg atcaagtgca agcatgggaa gtgcaggctt   4260

tctggagtgg gccagcccta ttgtgaatgc aacagtggat tcaccgggga cagctgtgat   4320

agagaaattt cttgtcgagg ggaacggata agggactatt accagaagca gcagggttac   4380

gctgcctgtc aaacaactaa gaaagtatct cgcttggaat gcagaggcgg gtgcgctgga   4440

ggccagtgct gtggacctct gagaagcaag aggcggaaat actctttcga atgcacagat   4500

ggctcctcat ttgtggacga ggttgagaaa gtggtgaagt gcggctgcgc gagatgtgcc   4560

tcctaa                                                              4566
```

<210> SEQ ID NO 12
<211> LENGTH: 1521
<212> TYPE: PRT
<213> ORGANISM: Mus musculus

<400> SEQUENCE: 12

```
Met Ser Gly Ile Gly Trp Gln Thr Leu Ser Leu Ser Leu Gly Leu Val
1               5                   10                  15

Leu Ser Ile Leu Asn Lys Val Ala Pro Gln Ala Cys Pro Ala Gln Cys
            20                  25                  30

Ser Cys Ser Gly Ser Thr Val Asp Cys His Gly Leu Ala Leu Arg Ser
        35                  40                  45

Val Pro Arg Asn Ile Pro Arg Asn Thr Glu Arg Leu Asp Leu Asn Gly
    50                  55                  60

Asn Asn Ile Thr Arg Ile Thr Lys Ile Asp Phe Ala Gly Leu Arg His
65                  70                  75                  80

Leu Arg Val Leu Gln Leu Met Glu Asn Arg Ile Ser Thr Ile Glu Arg
                85                  90                  95

Gly Ala Phe Gln Asp Leu Lys Glu Leu Glu Arg Leu Arg Leu Asn Arg
            100                 105                 110

Asn Asn Leu Gln Leu Phe Pro Glu Leu Leu Phe Leu Gly Thr Ala Lys
        115                 120                 125

Leu Tyr Arg Leu Asp Leu Ser Glu Asn Gln Ile Gln Ala Ile Pro Arg
    130                 135                 140

Lys Ala Phe Arg Gly Ala Val Asp Ile Lys Asn Leu Gln Leu Asp Tyr
145                 150                 155                 160

Asn Gln Ile Ser Cys Ile Glu Asp Gly Ala Phe Arg Ala Leu Arg Asp
```

-continued

```
                165                 170                 175

Leu Glu Val Leu Thr Leu Asn Asn Asn Asn Ile Thr Arg Leu Ser Val
            180                 185                 190

Ala Ser Phe Asn His Met Pro Lys Leu Arg Thr Phe Arg Leu His Ser
        195                 200                 205

Asn Asn Leu Tyr Cys Asp Cys His Leu Ala Trp Leu Ser Asp Trp Leu
    210                 215                 220

Arg Gln Arg Pro Arg Val Gly Leu Tyr Thr Gln Cys Met Gly Pro Ser
225                 230                 235                 240

His Leu Arg Gly His Asn Val Ala Glu Val Gln Lys Arg Glu Phe Val
                245                 250                 255

Cys Ser Gly His Gln Ser Phe Met Ala Pro Ser Cys Ser Val Leu His
            260                 265                 270

Cys Pro Ala Ala Cys Thr Cys Ser Asn Asn Ile Val Asp Cys Arg Gly
        275                 280                 285

Lys Gly Leu Thr Glu Ile Pro Thr Asn Leu Pro Glu Thr Ile Thr Glu
    290                 295                 300

Ile Arg Leu Glu Gln Asn Ser Ile Arg Val Ile Pro Pro Gly Ala Phe
305                 310                 315                 320

Ser Pro Tyr Lys Lys Leu Arg Arg Leu Asp Leu Ser Asn Asn Gln Ile
                325                 330                 335

Ser Glu Leu Ala Pro Asp Ala Phe Gln Gly Leu Arg Ser Leu Asn Ser
            340                 345                 350

Leu Val Leu Tyr Gly Asn Lys Ile Thr Glu Leu Pro Lys Ser Leu Phe
        355                 360                 365

Glu Gly Leu Phe Ser Leu Gln Leu Leu Leu Leu Asn Ala Asn Lys Ile
    370                 375                 380

Asn Cys Leu Arg Val Asp Ala Phe Gln Asp Leu His Asn Leu Asn Leu
385                 390                 395                 400

Leu Ser Leu Tyr Asp Asn Lys Leu Gln Thr Val Ala Lys Gly Thr Phe
                405                 410                 415

Ser Ala Leu Arg Ala Ile Gln Thr Met His Leu Ala Gln Asn Pro Phe
            420                 425                 430

Ile Cys Asp Cys His Leu Lys Trp Leu Ala Asp Tyr Leu His Thr Asn
        435                 440                 445

Pro Ile Glu Thr Ser Gly Ala Arg Cys Thr Ser Pro Arg Arg Leu Ala
    450                 455                 460

Asn Lys Arg Ile Gly Gln Ile Lys Ser Lys Lys Phe Arg Cys Ser Gly
465                 470                 475                 480

Thr Glu Asp Tyr Arg Ser Lys Leu Ser Gly Asp Cys Phe Ala Asp Leu
                485                 490                 495

Ala Cys Pro Glu Lys Cys Arg Cys Glu Gly Thr Thr Val Asp Cys Ser
            500                 505                 510

Asn Gln Arg Leu Asn Lys Ile Pro Asp His Ile Pro Gln Tyr Thr Ala
        515                 520                 525

Glu Leu Arg Leu Asn Asn Asn Glu Phe Thr Val Leu Glu Ala Thr Gly
    530                 535                 540

Ile Phe Lys Lys Leu Pro Gln Leu Arg Lys Ile Asn Phe Ser Asn Asn
545                 550                 555                 560

Lys Ile Thr Asp Ile Glu Glu Gly Ala Phe Glu Gly Ala Ser Gly Val
                565                 570                 575

Asn Glu Ile Leu Leu Thr Ser Asn Arg Leu Glu Asn Val Gln His Lys
            580                 585                 590
```

```
Met Phe Lys Gly Leu Glu Ser Leu Lys Thr Leu Met Leu Arg Ser Asn
        595                 600                 605

Arg Ile Ser Cys Val Gly Asn Asp Ser Phe Ile Gly Leu Gly Ser Val
    610                 615                 620

Arg Leu Leu Ser Leu Tyr Asp Asn Gln Ile Thr Thr Val Ala Pro Gly
625                 630                 635                 640

Ala Phe Asp Ser Leu His Ser Leu Ser Thr Leu Asn Leu Leu Ala Asn
                645                 650                 655

Pro Phe Asn Cys Asn Cys His Leu Ala Trp Leu Gly Glu Trp Leu Arg
            660                 665                 670

Arg Lys Arg Ile Val Thr Gly Asn Pro Arg Cys Gln Lys Pro Tyr Phe
        675                 680                 685

Leu Lys Glu Ile Pro Ile Gln Asp Val Ala Ile Gln Asp Phe Thr Cys
    690                 695                 700

Asp Asp Gly Asn Asp Asp Asn Ser Cys Ser Pro Leu Ser Arg Cys Pro
705                 710                 715                 720

Ser Glu Cys Thr Cys Leu Asp Thr Val Val Arg Cys Ser Asn Lys Gly
                725                 730                 735

Leu Lys Val Leu Pro Lys Gly Ile Pro Lys Asp Val Thr Glu Leu Tyr
            740                 745                 750

Leu Asp Gly Asn Gln Phe Thr Leu Val Pro Lys Glu Leu Ser Asn Tyr
        755                 760                 765

Lys His Leu Thr Leu Ile Asp Leu Ser Asn Asn Arg Ile Ser Thr Leu
    770                 775                 780

Ser Asn Gln Ser Phe Ser Asn Met Thr Gln Leu Leu Thr Leu Ile Leu
785                 790                 795                 800

Ser Tyr Asn Arg Leu Arg Cys Ile Pro Pro Arg Thr Phe Asp Gly Leu
                805                 810                 815

Lys Ser Leu Arg Leu Leu Ser Leu His Gly Asn Asp Ile Ser Val Val
            820                 825                 830

Pro Glu Gly Ala Phe Asn Asp Leu Ser Ala Leu Ser His Leu Ala Ile
        835                 840                 845

Gly Ala Asn Pro Leu Tyr Cys Asp Cys Asn Met Gln Trp Leu Ser Asp
    850                 855                 860

Trp Val Lys Ser Glu Tyr Lys Glu Pro Gly Ile Ala Arg Cys Ala Gly
865                 870                 875                 880

Pro Gly Glu Met Ala Asp Lys Leu Leu Leu Thr Thr Pro Ser Lys Lys
                885                 890                 895

Phe Thr Cys Gln Gly Pro Val Asp Ile Thr Ile Gln Ala Lys Cys Asn
            900                 905                 910

Pro Cys Leu Ser Asn Pro Cys Lys Asn Asp Gly Thr Cys Asn Asn Asp
        915                 920                 925

Pro Val Asp Phe Tyr Arg Cys Thr Cys Pro Tyr Gly Phe Lys Gly Gln
    930                 935                 940

Asp Cys Asp Val Pro Ile His Ala Cys Ile Ser Asn Pro Cys Lys His
945                 950                 955                 960

Gly Gly Thr Cys His Leu Lys Glu Gly Glu Asn Ala Gly Phe Trp Cys
                965                 970                 975

Thr Cys Ala Asp Gly Phe Glu Gly Glu Asn Cys Glu Val Asn Ile Asp
            980                 985                 990

Asp Cys Glu Asp Asn Asp Cys Glu  Asn Asn Ser Thr Cys  Val Asp Gly
        995                 1000                1005
```

-continued

```
Ile Asn  Asn Tyr Thr Cys Leu  Cys Pro Pro Glu Tyr  Thr Gly Glu
    1010                 1015                 1020

Leu Cys  Glu Glu Lys Leu Asp  Phe Cys Ala Gln Asp  Leu Asn Pro
    1025                 1030                 1035

Cys Gln  His Asp Ser Lys Cys  Ile Leu Thr Pro Lys  Gly Phe Lys
    1040                 1045                 1050

Cys Asp  Cys Thr Pro Gly Tyr  Ile Gly Glu His Cys  Asp Ile Asp
    1055                 1060                 1065

Phe Asp  Asp Cys Gln Asp Asn  Lys Cys Lys Asn Gly  Ala His Cys
    1070                 1075                 1080

Thr Asp  Ala Val Asn Gly Tyr  Thr Cys Val Cys Pro  Glu Gly Tyr
    1085                 1090                 1095

Ser Gly  Leu Phe Cys Glu Phe  Ser Pro Pro Met Val  Leu Pro Arg
    1100                 1105                 1110

Thr Ser  Pro Cys Asp Asn Phe  Asp Cys Gln Asn Gly  Ala Gln Cys
    1115                 1120                 1125

Ile Ile  Arg Ile Asn Glu Pro  Ile Cys Gln Cys Leu  Pro Gly Tyr
    1130                 1135                 1140

Leu Gly  Glu Lys Cys Glu Lys  Leu Val Ser Val Asn  Phe Val Asn
    1145                 1150                 1155

Lys Glu  Ser Tyr Leu Gln Ile  Pro Ser Ala Lys Val  Arg Pro Gln
    1160                 1165                 1170

Thr Asn  Ile Thr Leu Gln Ile  Ala Thr Asp Glu Asp  Ser Gly Ile
    1175                 1180                 1185

Leu Leu  Tyr Lys Gly Asp Lys  Asp His Ile Ala Val  Glu Leu Tyr
    1190                 1195                 1200

Arg Gly  Arg Val Arg Ala Ser  Tyr Asp Thr Gly Ser  His Pro Ala
    1205                 1210                 1215

Ser Ala  Ile Tyr Ser Val Glu  Thr Ile Asn Asp Gly  Asn Phe His
    1220                 1225                 1230

Ile Val  Glu Leu Leu Thr Leu  Asp Ser Ser Leu Ser  Leu Ser Val
    1235                 1240                 1245

Asp Gly  Gly Ser Pro Lys Val  Ile Thr Asn Leu Ser  Lys Gln Ser
    1250                 1255                 1260

Thr Leu  Asn Phe Asp Ser Pro  Leu Tyr Val Gly Gly  Met Pro Gly
    1265                 1270                 1275

Lys Asn  Asn Val Ala Ser Leu  Arg Gln Ala Pro Gly  Gln Asn Gly
    1280                 1285                 1290

Thr Ser  Phe His Gly Cys Ile  Arg Asn Leu Tyr Ile  Asn Ser Glu
    1295                 1300                 1305

Leu Gln  Asp Phe Arg Lys Met  Pro Met Gln Thr Gly  Ile Leu Pro
    1310                 1315                 1320

Gly Cys  Glu Pro Cys His Lys  Lys Val Cys Ala His  Gly Met Cys
    1325                 1330                 1335

Gln Pro  Ser Ser Gln Ser Gly  Phe Thr Cys Glu Cys  Glu Glu Gly
    1340                 1345                 1350

Trp Met  Gly Pro Leu Cys Asp  Gln Arg Thr Asn Asp  Pro Cys Leu
    1355                 1360                 1365

Gly Asn  Lys Cys Val His Gly  Thr Cys Leu Pro Ile  Asn Ala Phe
    1370                 1375                 1380

Ser Tyr  Ser Cys Lys Cys Leu  Glu Gly His Gly Gly  Val Leu Cys
    1385                 1390                 1395

Asp Glu  Glu Glu Asp Leu Phe  Asn Pro Cys Gln Met  Ile Lys Cys
```

-continued

```
    1400                1405                1410

Lys His  Gly Lys Cys Arg Leu  Ser Gly Val Gly Gln  Pro Tyr Cys
    1415                1420                1425

Glu Cys  Asn Ser Gly Phe Thr  Gly Asp Ser Cys Asp  Arg Glu Ile
    1430                1435                1440

Ser Cys  Arg Gly Glu Arg Ile  Arg Asp Tyr Tyr Gln  Lys Gln Gln
    1445                1450                1455

Gly Tyr  Ala Ala Cys Gln Thr  Thr Lys Lys Val Ser  Arg Leu Glu
    1460                1465                1470

Cys Arg  Gly Gly Cys Ala Gly  Gly Gln Cys Cys Gly  Pro Leu Arg
    1475                1480                1485

Ser Lys  Arg Arg Lys Tyr Ser  Phe Glu Cys Thr Asp  Gly Ser Ser
    1490                1495                1500

Phe Val  Asp Glu Val Glu Lys  Val Val Lys Cys Gly  Cys Ala Arg
    1505                1510                1515

Cys Ala  Ser
    1520
```

<210> SEQ ID NO 13
<211> LENGTH: 4519
<212> TYPE: DNA
<213> ORGANISM: Rattus norvegicus

<400> SEQUENCE: 13

```
atgagtggca ttggctggca gacactgtcc ctatctctgg cgttagtgtt gtcgatcttg     60

aaccaggtgg cgcctcaggc gtgcccggcc cagtgctcct gttcaggcag cacagtggac    120

tgtcatgggc tggcactgcg cagtgtgccc aggaatatcc cccgcaacac ggagagactg    180

gatttgaatg gaaataacat cacaaggatc acgaagacag attttgcggg tctcagacac    240

ctcagagttc ttcagctcat ggagaacaag atcagcacca tcgagagggg agcattccag    300

gatcttaagg agctagaaag actgcgttta aacagaaata accttcagtt gtttcctgag    360

ctgctgtttc ttgggactgc gaagctctac cggcttgatc tcagtgaaaa tcagattcaa    420

gcaattccaa ggaaggcttt ccgtggtgca gttgacatta aaaatctgca gttggattac    480

aaccagatca gctgcattga agatggggca ttccgagctc tgcgagatct ggaagtgctc    540

actctgaaca ataacaatat tactagactt tcagtggcaa gtttcaacca tatgcctaaa    600

cttaggacat ttcgactcca ctccaacaac ctatactgcg actgccacct ggcctggctc    660

tcggactggc ttcgccaaag gccacgggtg ggcttgtaca ctcagtgtat gggcccatcc    720

cacctgaggg gccataatgt agcagaggtt caaaaacgag agtttgtctg cagtgatgag    780

gaagaaggtc accagtcatt catggctccc tcctgcagtg tgctgcactg cccgattgct    840

tgtacctgta gcaacaacat tgtagactgc cgagggaaag gtctcactga gatccccaca    900

aatctgcctg agaccatcac agaaatacgt ttggaacaga actccataag ggtcatccct    960

ccaggagcat tctcaccata caaaaagctt cgacgactag acctgagtaa taaccagatc   1020

tcggaacttg ctccagatgc cttccaagga ctgcgttctc tgaattccct tgtcctgtat   1080

ggaaataaaa tcacagaact cccaaaaagt ttatttgaag gactgttttc cttacagcta   1140

ctattattga atgccaacaa gataaactgc cttcgggtag atgcttttca ggacctgcac   1200

aacttgaacc ttctctcctt atacgacaat aagcttcaga ctgttgccaa gggcaccttc   1260

tcagctctca gagccatcca aactatgcat ttggcccaga atcctttcat ttgtgactgc   1320

catctcaagt ggctagcgga ttatctccac accaacccaa ttgagaccag cggtgcccgt   1380
```

-continued

```
tgcaccagtc cccgccgcct ggctaacaaa agaattggac agatcaaaag caagaaattc   1440
cgttgttcag gtacagaaga ttatcgatca aaattaagtg gagactgctt tgcagacttg   1500
gcttgtcctg aaaaatgtcg ctgtgaaggg accacagtag actgctccaa tcaaaaactc   1560
aacaaaatcc cagaccatat tccccagtac acagcagagc tgcgtctcaa taataatgaa   1620
ttcacagtgt tagaagccac gggaatattt aagaaacttc ctcaattgcg taaaatcaac   1680
cttagcaaca ataagatcac tgatatcgag gagggggcat tcgaaggtgc gtctggtgtg   1740
aatgagattc tgcttaccag taaccgtttg gaaaatgttc agcataagat gttcaaagga   1800
ttggagagcc tcaaaacatt gatgctgaga agtaatcgaa taagctgtgt gggaaacgac   1860
agtttcacag gactcggttc tgtgcgtctg ctctctttat atgacaatca aattaccaca   1920
gttgcaccag gagcatttgg tactctccat tcattatcta cactaaacct cttggccaat   1980
cctttcaact gtaactgtca cctggcatgg cttggagaat ggctcagaag gaaaagaatt   2040
gtaacaggaa atcctcgatg ccaaaaaccc tacttcttga aggaaatacc aatccaggat   2100
gtagccattc aggacttcac ctgtgatgac ggaaacgatg ataatagctg ctctccactc   2160
tcccgttgtc cttcggaatg tacttgcttg gatacagtag tacgatgtag caacaagggc   2220
ttgaaggtct tacctaaagg cattccaaga gatgtcacag aactgtatct ggatgggaac   2280
cagtttacac tggtcccgaa ggaactctcc aactacaaac atttaacact tatagactta   2340
agtaacaaca gaataagcac cctttccaac caaagcttca gcaacatgac ccaacttctc   2400
accttaattc tcagttacaa ccgtctgaga tgtatccctc cacggacctt tgatggattg   2460
aaatctcttc gtttactgtc tctacatgga aatgacattt ctgtcgtgcc tgaaggtgcc   2520
tttggtgacc tttcagcctt gtcacactta gcaattggag ccaaccctct ttactgtgat   2580
tgtaacatgc agtggttatc cgactgggtg aagtcggaat ataaggaacc tggaattgcc   2640
cgctgtgccg gtcccggaga aatggcagat aaattgttac tcacaactcc ctccaaaaaa   2700
tttacatgtc aaggtcctgt ggatgttact attcaagcca agtgtaaccc ctgcttgtca   2760
aatccatgta aaaatgatgg cacctgtaac aatgacccgg tggattttta tcgatgcacc   2820
tgcccatatg gtttcaaggg ccaggactgt gatgtcccca ttcatgcctg tatcagtaat   2880
ccatgtaaac atggaggaac ttgccactta aaagaaggag agaatgatgg attctggtgt   2940
acttgtgctg atgggtttga aggagaaagc tgtgacatca atattgatga ttgcgaagat   3000
aatgattgtg aaaataattc tacatgcgtt gatggaatta acaactacac gtgtctttgc   3060
ccaccggaat acacaggcga actgtgtgag gaaaaactgg acttctgtgc acaagacctg   3120
aatccctgcc agcatgactc caagtgcatc ctgacgccaa agggattcaa gtgtgactgc   3180
actccgggat acattggtga gcactgtgac atcgactttg atgactgcca agataacaag   3240
tgcaaaaacg gtgctcattg cacagatgca gtgaacggat acacatgtgt ctgtcctgaa   3300
ggctacagtg gcttgttctg tgagttttct ccacccatgg tcctccctcg caccagcccc   3360
tgtgataatt ttgattgtca gaatggagcc cagtgtatca tcagggtgaa tgaaccaata   3420
tgccagtgtt tgcctggcta cttgggagag aagtgtgaga aattggtcag tgtgaatttt   3480
gtaaacaaag agtcctatct tcagattcct tcagccaagg ttcgacctca gacaaacatc   3540
acacttcaga ttgccacaga tgaagacagc ggcatcctct tgtacaaggg tgacaaggac   3600
cacattgctg tggaactcta tcgagggcga gttcgagcca gctatgacac cggctctcac   3660
ccggcttctg ccatttacag tgtggagaca atcaatgatg gaaacttcca cattgtagag   3720
```

```
ctactgaccc tggattcgag tctttccctc tctgtggatg gaggaagccc taaaatcatc   3780

accaatttgt caaaacaatc tactctgaat ttcgactctc cactttacgt aggaggtatg   3840

cctgggaaaa ataacgtggc ttcgctgcgc caggcccctg ggcagaacgg caccagcttc   3900

catggctgta tccggaacct ttacattaac agtgaactgc aggacttccg gaaagtgcct   3960

atgcaaaccg gaattctgcc tggctgtgaa ccatgccaca agaaagtgtg tgcccatggc   4020

acatgccagc ccagcagcca atcaggcttc acctgtgaat gtgaggaagg gtggatgggg   4080

cccctctgtg accagagaac caatgatccc tgtctcggaa acaaatgtgt acatgggacc   4140

tgcttgccca tcaacgcctt ctcctacagc tgcaagtgcc tggagggcca cggcggggtc   4200

ctctgtgatg aagaagaaga tctgtttaac ccctgccagg tgatcaagtg caagcacggg   4260

aagtgcaggc tctctgggct cgggcagccc tattgtgaat gcagcagtgg attcaccggg   4320

gacagctgtg acagagaaat ttcttgtcga ggggaacgga taagggatta ttaccaaaag   4380

cagcagggtt acgctgcctg tcaaacgact aagaaagtat ctcgcttgga gtgcagaggc   4440

gggtgtgctg gggggcagtg ctgtggacct ctgagaagca agaggcggaa atactctttc   4500

gaatgcacag atggatctt                                                 4519
```

<210> SEQ ID NO 14
<211> LENGTH: 1525
<212> TYPE: PRT
<213> ORGANISM: Rattus norvegicus

<400> SEQUENCE: 14

```
Met Ser Gly Ile Gly Trp Gln Thr Leu Ser Leu Ser Leu Ala Leu Val
1               5                   10                  15

Leu Ser Ile Leu Asn Gln Val Ala Pro Gln Ala Cys Pro Ala Gln Cys
            20                  25                  30

Ser Cys Ser Gly Ser Thr Val Asp Cys His Gly Leu Ala Leu Arg Ser
        35                  40                  45

Val Pro Arg Asn Ile Pro Arg Asn Thr Glu Arg Leu Asp Leu Asn Gly
    50                  55                  60

Asn Asn Ile Thr Arg Ile Thr Lys Thr Asp Phe Ala Gly Leu Arg His
65                  70                  75                  80

Leu Arg Val Leu Gln Leu Met Glu Asn Lys Ile Ser Thr Ile Glu Arg
                85                  90                  95

Gly Ala Phe Gln Asp Leu Lys Glu Leu Glu Arg Leu Arg Leu Asn Arg
            100                 105                 110

Asn Asn Leu Gln Leu Phe Pro Glu Leu Leu Phe Leu Gly Thr Ala Lys
        115                 120                 125

Leu Tyr Arg Leu Asp Leu Ser Glu Asn Gln Ile Gln Ala Ile Pro Arg
    130                 135                 140

Lys Ala Phe Arg Gly Ala Val Asp Ile Lys Asn Leu Gln Leu Asp Tyr
145                 150                 155                 160

Asn Gln Ile Ser Cys Ile Glu Asp Gly Ala Phe Arg Ala Leu Arg Asp
                165                 170                 175

Leu Glu Val Leu Thr Leu Asn Asn Asn Asn Ile Thr Arg Leu Ser Val
            180                 185                 190

Ala Ser Phe Asn His Met Pro Lys Leu Arg Thr Phe Arg Leu His Ser
        195                 200                 205

Asn Asn Leu Tyr Cys Asp Cys His Leu Ala Trp Leu Ser Asp Trp Leu
    210                 215                 220

Arg Gln Arg Pro Arg Val Gly Leu Tyr Thr Gln Cys Met Gly Pro Ser
```

```
225                 230                 235                 240

His Leu Arg Gly His Asn Val Ala Glu Val Gln Lys Arg Glu Phe Val
                245                 250                 255

Cys Ser Asp Glu Glu Glu Gly His Gln Ser Phe Met Ala Pro Ser Cys
            260                 265                 270

Ser Val Leu His Cys Pro Ile Ala Cys Thr Cys Ser Asn Asn Ile Val
        275                 280                 285

Asp Cys Arg Gly Lys Gly Leu Thr Glu Ile Pro Thr Asn Leu Pro Glu
    290                 295                 300

Thr Ile Thr Glu Ile Arg Leu Glu Gln Asn Ser Ile Arg Val Ile Pro
305                 310                 315                 320

Pro Gly Ala Phe Ser Pro Tyr Lys Lys Leu Arg Arg Leu Asp Leu Ser
                325                 330                 335

Asn Asn Gln Ile Ser Glu Leu Ala Pro Asp Ala Phe Gln Gly Leu Arg
            340                 345                 350

Ser Leu Asn Ser Leu Val Leu Tyr Gly Asn Lys Ile Thr Glu Leu Pro
        355                 360                 365

Lys Ser Leu Phe Glu Gly Leu Phe Ser Leu Gln Leu Leu Leu Leu Asn
    370                 375                 380

Ala Asn Lys Ile Asn Cys Leu Arg Val Asp Ala Phe Gln Asp Leu His
385                 390                 395                 400

Asn Leu Asn Leu Leu Ser Leu Tyr Asp Asn Lys Leu Gln Thr Val Ala
                405                 410                 415

Lys Gly Thr Phe Ser Ala Leu Arg Ala Ile Gln Thr Met His Leu Ala
            420                 425                 430

Gln Asn Pro Phe Ile Cys Asp Cys His Leu Lys Trp Leu Ala Asp Tyr
        435                 440                 445

Leu His Thr Asn Pro Ile Glu Thr Ser Gly Ala Arg Cys Thr Ser Pro
    450                 455                 460

Arg Arg Leu Ala Asn Lys Arg Ile Gly Gln Ile Lys Ser Lys Lys Phe
465                 470                 475                 480

Arg Cys Ser Gly Thr Glu Asp Tyr Arg Ser Lys Leu Ser Gly Asp Cys
                485                 490                 495

Phe Ala Asp Leu Ala Cys Pro Glu Lys Cys Arg Cys Glu Gly Thr Thr
            500                 505                 510

Val Asp Cys Ser Asn Gln Lys Leu Asn Lys Ile Pro Asp His Ile Pro
        515                 520                 525

Gln Tyr Thr Ala Glu Leu Arg Leu Asn Asn Asn Glu Phe Thr Val Leu
    530                 535                 540

Glu Ala Thr Gly Ile Phe Lys Lys Leu Pro Gln Leu Arg Lys Ile Asn
545                 550                 555                 560

Leu Ser Asn Asn Lys Ile Thr Asp Ile Glu Glu Gly Ala Phe Glu Gly
                565                 570                 575

Ala Ser Gly Val Asn Glu Ile Leu Leu Thr Ser Asn Arg Leu Glu Asn
            580                 585                 590

Val Gln His Lys Met Phe Lys Gly Leu Glu Ser Leu Lys Thr Leu Met
        595                 600                 605

Leu Arg Ser Asn Arg Ile Ser Cys Val Gly Asn Asp Ser Phe Thr Gly
    610                 615                 620

Leu Gly Ser Val Arg Leu Leu Ser Leu Tyr Asp Asn Gln Ile Thr Thr
625                 630                 635                 640

Val Ala Pro Gly Ala Phe Gly Thr Leu His Ser Leu Ser Thr Leu Asn
                645                 650                 655
```

```
Leu Leu Ala Asn Pro Phe Asn Cys Asn Cys His Leu Ala Trp Leu Gly
            660                 665                 670

Glu Trp Leu Arg Arg Lys Arg Ile Val Thr Gly Asn Pro Arg Cys Gln
        675                 680                 685

Lys Pro Tyr Phe Leu Lys Glu Ile Pro Ile Gln Asp Val Ala Ile Gln
    690                 695                 700

Asp Phe Thr Cys Asp Asp Gly Asn Asp Asp Asn Ser Cys Ser Pro Leu
705                 710                 715                 720

Ser Arg Cys Pro Ser Glu Cys Thr Cys Leu Asp Thr Val Val Arg Cys
                725                 730                 735

Ser Asn Lys Gly Leu Lys Val Leu Pro Lys Gly Ile Pro Arg Asp Val
            740                 745                 750

Thr Glu Leu Tyr Leu Asp Gly Asn Gln Phe Thr Leu Val Pro Lys Glu
        755                 760                 765

Leu Ser Asn Tyr Lys His Leu Thr Leu Ile Asp Leu Ser Asn Asn Arg
    770                 775                 780

Ile Ser Thr Leu Ser Asn Gln Ser Phe Ser Asn Met Thr Gln Leu Leu
785                 790                 795                 800

Thr Leu Ile Leu Ser Tyr Asn Arg Leu Arg Cys Ile Pro Pro Arg Thr
                805                 810                 815

Phe Asp Gly Leu Lys Ser Leu Arg Leu Leu Ser Leu His Gly Asn Asp
            820                 825                 830

Ile Ser Val Val Pro Glu Gly Ala Phe Gly Asp Leu Ser Ala Leu Ser
        835                 840                 845

His Leu Ala Ile Gly Ala Asn Pro Leu Tyr Cys Asp Cys Asn Met Gln
    850                 855                 860

Trp Leu Ser Asp Trp Val Lys Ser Glu Tyr Lys Glu Pro Gly Ile Ala
865                 870                 875                 880

Arg Cys Ala Gly Pro Gly Glu Met Ala Asp Lys Leu Leu Leu Thr Thr
                885                 890                 895

Pro Ser Lys Lys Phe Thr Cys Gln Gly Pro Val Asp Val Thr Ile Gln
            900                 905                 910

Ala Lys Cys Asn Pro Cys Leu Ser Asn Pro Cys Lys Asn Asp Gly Thr
        915                 920                 925

Cys Asn Asn Asp Pro Val Asp Phe Tyr Arg Cys Thr Cys Pro Tyr Gly
    930                 935                 940

Phe Lys Gly Gln Asp Cys Asp Val Pro Ile His Ala Cys Ile Ser Asn
945                 950                 955                 960

Pro Cys Lys His Gly Gly Thr Cys His Leu Lys Glu Gly Glu Asn Asp
                965                 970                 975

Gly Phe Trp Cys Thr Cys Ala Asp Gly Phe Glu Gly Glu Ser Cys Asp
            980                 985                 990

Ile Asn Ile Asp Asp Cys Glu Asp  Asn Asp Cys Glu Asn  Asn Ser Thr
        995                 1000                1005

Cys Val  Asp Gly Ile Asn Asn  Tyr Thr Cys Leu Cys  Pro Pro Glu
    1010                1015                1020

Tyr Thr  Gly Glu Leu Cys Glu  Glu Lys Leu Asp Phe  Cys Ala Gln
    1025                1030                1035

Asp Leu  Asn Pro Cys Gln His  Asp Ser Lys Cys Ile  Leu Thr Pro
    1040                1045                1050

Lys Gly  Phe Lys Cys Asp Cys  Thr Pro Gly Tyr Ile  Gly Glu His
    1055                1060                1065
```

```
Cys Asp Ile Asp Phe Asp Asp Cys Gln Asp Asn Lys Cys Lys Asn
    1070                1075                1080

Gly Ala His Cys Thr Asp Ala Val Asn Gly Tyr Thr Cys Val Cys
    1085                1090                1095

Pro Glu Gly Tyr Ser Gly Leu Phe Cys Glu Phe Ser Pro Pro Met
    1100                1105                1110

Val Leu Pro Arg Thr Ser Pro Cys Asp Asn Phe Asp Cys Gln Asn
    1115                1120                1125

Gly Ala Gln Cys Ile Ile Arg Val Asn Glu Pro Ile Cys Gln Cys
    1130                1135                1140

Leu Pro Gly Tyr Leu Gly Glu Lys Cys Glu Lys Leu Val Ser Val
    1145                1150                1155

Asn Phe Val Asn Lys Glu Ser Tyr Leu Gln Ile Pro Ser Ala Lys
    1160                1165                1170

Val Arg Pro Gln Thr Asn Ile Thr Leu Gln Ile Ala Thr Asp Glu
    1175                1180                1185

Asp Ser Gly Ile Leu Leu Tyr Lys Gly Asp Lys Asp His Ile Ala
    1190                1195                1200

Val Glu Leu Tyr Arg Gly Arg Val Arg Ala Ser Tyr Asp Thr Gly
    1205                1210                1215

Ser His Pro Ala Ser Ala Ile Tyr Ser Val Glu Thr Ile Asn Asp
    1220                1225                1230

Gly Asn Phe His Ile Val Glu Leu Leu Thr Leu Asp Ser Ser Leu
    1235                1240                1245

Ser Leu Ser Val Asp Gly Gly Ser Pro Lys Ile Ile Thr Asn Leu
    1250                1255                1260

Ser Lys Gln Ser Thr Leu Asn Phe Asp Ser Pro Leu Tyr Val Gly
    1265                1270                1275

Gly Met Pro Gly Lys Asn Asn Val Ala Ser Leu Arg Gln Ala Pro
    1280                1285                1290

Gly Gln Asn Gly Thr Ser Phe His Gly Cys Ile Arg Asn Leu Tyr
    1295                1300                1305

Ile Asn Ser Glu Leu Gln Asp Phe Arg Lys Val Pro Met Gln Thr
    1310                1315                1320

Gly Ile Leu Pro Gly Cys Glu Pro Cys His Lys Lys Val Cys Ala
    1325                1330                1335

His Gly Thr Cys Gln Pro Ser Ser Gln Ser Gly Phe Thr Cys Glu
    1340                1345                1350

Cys Glu Glu Gly Trp Met Gly Pro Leu Cys Asp Gln Arg Thr Asn
    1355                1360                1365

Asp Pro Cys Leu Gly Asn Lys Cys Val His Gly Thr Cys Leu Pro
    1370                1375                1380

Ile Asn Ala Phe Ser Tyr Ser Cys Lys Cys Leu Glu Gly His Gly
    1385                1390                1395

Gly Val Leu Cys Asp Glu Glu Glu Asp Leu Phe Asn Pro Cys Gln
    1400                1405                1410

Val Ile Lys Cys Lys His Gly Lys Cys Arg Leu Ser Gly Leu Gly
    1415                1420                1425

Gln Pro Tyr Cys Glu Cys Ser Ser Gly Phe Thr Gly Asp Ser Cys
    1430                1435                1440

Asp Arg Glu Ile Ser Cys Arg Gly Glu Arg Ile Arg Asp Tyr Tyr
    1445                1450                1455

Gln Lys Gln Gln Gly Tyr Ala Ala Cys Gln Thr Thr Lys Lys Val
```

```
    1460                1465                1470

Ser Arg  Leu Glu Cys Arg Gly  Gly Cys Ala Gly Gly  Gln Cys Cys
    1475                1480                1485

Gly Pro  Leu Arg Ser Lys Arg  Arg Lys Tyr Ser Phe  Glu Cys Thr
    1490                1495                1500

Asp Gly  Ser Ser Phe Val Asp  Glu Val Glu Lys Val  Val Lys Cys
    1505                1510                1515

Gly Cys  Thr Arg Cys Ala Ser
    1520                1525


<210> SEQ ID NO 15
<211> LENGTH: 4641
<212> TYPE: DNA
<213> ORGANISM: Canis familiaris

<400> SEQUENCE: 15

atgcgcgggg ccggccggcg ggcgctgccc gtgtcgctgg ggctcgtgct gctgatcctg     60

ggcgaggcgg cgccgcaggc gtgcccggcg cagtgctcct gctcgggcag caccgtggac    120

tgtcacgggc tggcgctgcg cagcgtgccc aggagcatcc cccgcaacac cgagaggctg    180

gatttgaatg gcaataacat cacacggatt accaagacag atttcgctgg tcttcgacac    240

ctaagagttc ttcagcttat ggagaataag attagcacca ttgaaagagg agcattccag    300

gatcttaagg aactggagag actgcgttta aacagaaatc accttcagct gtttcctgag    360

ttgctgtttc ttgggacttc gaagctgtac aggcttgatc tcagtgaaaa ccaaattcag    420

gcaattccaa ggaaggcttt ccgtggggca gttgacatta aaaatttgca actggattac    480

aaccagatca gctgtattga agatggggca tttagagctc tgcgggacct ggaagtgctc    540

actctcaaca ataacaacat tactagactt tctgtggcaa gtttcaacca tatgcctaaa    600

cttaggactt ttcggctgca ttcaaacaat ctgtattgcg actgccacct ggcctggctt    660

tctgactggc tgcgccaaag gccccgggtt ggtctctaca ctcagtgtat gggcccatcc    720

cacctgaggg gtcataacgt agccgaggtt caaaaacgcg aatttgtctg cagtggtaag    780

ggagaaagaa cctttctgtt gtcctattat cttatgctac tttgccacca gtccttcatg    840

gctccttctt gcagcgtcct gcattgtcca gccgcttgta cctgtagcaa caatatcgta    900

gactgtcgtg ggaaaggtct cactgagatc cccacgaacc tgccagagac catcacagaa    960

atacgtttgg aacagaactc aatcaaggtc atccctcctg gagctttctc accatataaa   1020

aagcttagaa gaattgacct gagcaataat cagatctctg aactagcacc ggacgctttc   1080

caaggactac gctctctgaa ttcacttgtc ctctatggaa ataaaatcac ggaactccca   1140

aaaagtttat ttgaaggact gttttcctta cagctgctat tattgaatgc caacaagata   1200

aactgccttc gggtagatgc ttttcaggat ctgcacaacc tgaatcttct ctccctgtac   1260

gacaacaagc tgcagaccat cgccaagggg accttctcac ctctccgggc cattcagacc   1320

atgcacctgg cccagaaccc ctttatttgt gactgccatc tcaagtggct ggcggactat   1380

ctccacacca accccatcga gaccagtggt gcccggtgca ccagcccccg gcgcctggca   1440

aacaaaagaa tcggacagat caaaagcaag aaattccgtt gttcagctaa agaacagtat   1500

ttcattccag gtacagaaga ttatcgatca aaattaagcg gggactgctt tgcagatctg   1560

gcttgccctg aaaagtgccg ctgtgaagga accacagtag attgctccaa tcaaaaactc   1620

accaaaatcc cagaccacat cccccagtac actgcagagc tgcgtctcaa taataatgaa   1680

ttcacagtgc tggaagctac aggaatcttc aagaaacttc cgcagttacg taaaataaac   1740
```

```
ttcagcaaca acaagatcac agacattgaa gaaggagcat ttgaaggagc agctggtgta   1800
aacgaaatcc ttctcacgag taaccgtttg gaaaatgttc agcataagat gttcaaggga   1860
ttggaaagcc tgaaaacgtt gatgttgcga agcaatcgca taagctgcgt tggcaacgat   1920
agcttcatag gcctgagctc tgtgcggttg ctttcgctgt acgataatca gatcgccacc   1980
atcgcgccgg gggcgttcga caccctgcac tcgttgtcca ccctaaacct gttggccaac   2040
ccttttaact gcaactgcta cctggcttgg ctgggcgagt ggctcaggaa gaaaagaatt   2100
gtaaccggaa atcctcgctg tcaaaaacca tacttcctca aagaaatccc catccaggac   2160
gtcgccattc aagacttcac gtgtgacgac ggaaatgacg acagtagctg ttctccactc   2220
tcgcgctgtc ccacggaatg cacgtgcttg gatacagttg tccgatgtag caacaagggc   2280
ctgaaggtct tgcccaaagg tattcccaga gacgtcactg aactgtatct ggatgggaac   2340
cactttacct tggttcccaa ggagctctat aactacaaac atctaacgct tatagacctg   2400
agcaacaacc gcataagcac tctttctaat cagagcttca gcaacatgac ccagctcctc   2460
accctaattc tcagttacaa ccgtttgaga tgtattcctc ctcgaacctt cgatggactc   2520
aagtctctcc gattactttc attacatgga aatgacattt ctgttgtgcc tgaaggtgct   2580
ttcagtgatc tctctgcatt atcacaccta gcaatcggag ccaaccccct ttactgtgat   2640
tgcaacatgc agtggttatc ggactgggta aagtcggaat acaaagaacc cgggattgct   2700
cgctgtgccg gccccggaga aatggcagat aaattattac tcacgactcc ctccaaaaaa   2760
tttacatgtc aaggtcctgt ggatatcaat attctagcta aatgtaatcc ctgcttatca   2820
aacccatgta agaatgatgg cacctgtaac aatgatccag tcgactttta tcgctgtacc   2880
tgtccgtatg gtttcaaggg gcaggactgt gatgtcccaa tccacgcatg catcagtaac   2940
ccgtgtacac atggaggaac ttgccactta aaggagggag aaaaagatgg attctggtgt   3000
atttgtgccg atggatttga aggagaaaat tgtgaagtca atgttgatga ctgtgaagat   3060
aatgactgtg aaaataactc tacgtgtgtc gatggaatta ataactacac atgcctttgt   3120
ccgcctgagt acacaggcga gttgtgtgag gagaagctgg acttctgcgc tcaggacctg   3180
aacccctgcc agcacgactc caagtgcatc ctgatgccca aaggattcaa atgcgactgc   3240
acgccggggt acgtgggcga gcactgcgac atcgacttcg acgactgcca ggatcacaag   3300
tgtaaaaacg gagcgcactg cacggacgcg gtgaacggct acacgtgcac ctgccccgaa   3360
ggctacagcg gcttgttctg tgaattctcc ccgcccatgg tcctcccacg caccagcccc   3420
tgtgacaact tcgactgtca gaacggggcg cagtgcatcg tcagggcggg cgagccaatc   3480
tgccagtgtc tgcccggcta ccagggggac aagtgtgaga agttggtcag cgtgaacttc   3540
gtgaacaaag agtcgtatct tcaaattcct tcagccaagg tccggcccca aacgaacatc   3600
accctgcaga ttgccaccga cgaagacagc gggatcctcc tgtacaaggg cgacaaggac   3660
cacattgccg tggagctgta tcggggacgg gtgcgcgcca gctacgacac cggctcgcac   3720
cccgcttctg ccatttacag cgtggagacg atcaatgatg gaaactttca cattgtggaa   3780
ctacttgccc tggatcagag cctgtccctc tccgtggatg gagggagccc caaaatcatc   3840
accaacttgt caaagcagtc cactctgaat tttgactctc cactctatgt aggaggcatg   3900
cccgggagga acaacgtggc cgcggccctg cgccaggccc cggggcacaa cggcaccagc   3960
ttccacggct gcatccggaa cctgtatatc aacagcgagc tccaggactt ccgccaggtg   4020
cccatgcaga ccggcatcct gcccggctgc gagccgtgcc acaggaaggt gtgtgcccac   4080
```

```
ggcgcgtgcc agcccagcag ccagtcgggc ttcacctgcg agtgcgagga gggctggacg   4140

gggcccctgt gtgaccagag gaccaacgac ccctgtctcg ggaacaaatg tgtgcacggc   4200

acctgcttgc ccatcaacgc cttctcctac agctgtaagt gtctggaggg ccacgggggc   4260

gtcctctgcg acgaagagga ggacctgttc aacccctgcc aggccatcag gtgcaagcac   4320

gggaaatgca ggctctcggg cctgggccag ccctactgcg aatgcagcag cgggtacacg   4380

ggggatagct gcgaccgaga agtgtcctgt cggggcgagc gcgtccggga ctactaccca   4440

aagcagcagg gctacgcggc ctgccagacc accaagaagg tgtcgcggct ggagtgcagg   4500

ggcggctgcg cggccgggca gtgctgcggg ccgctgcgga gcaagcggcg gaaatactcc   4560

ttcgagtgca cggacggctc gtcgttcgtg gacgaggtgg agaaggtggt caagtgcggc   4620

tgcagcaggt gcgccgcctg a                                             4641
```

<210> SEQ ID NO 16
<211> LENGTH: 1546
<212> TYPE: PRT
<213> ORGANISM: Canis familiaris

<400> SEQUENCE: 16

```
Met Arg Gly Ala Gly Arg Arg Ala Leu Pro Val Ser Leu Gly Leu Val
1               5                   10                  15

Leu Leu Ile Leu Gly Glu Ala Ala Pro Gln Ala Cys Pro Ala Gln Cys
            20                  25                  30

Ser Cys Ser Gly Ser Thr Val Asp Cys His Gly Leu Ala Leu Arg Ser
        35                  40                  45

Val Pro Arg Ser Ile Pro Arg Asn Thr Glu Arg Leu Asp Leu Asn Gly
    50                  55                  60

Asn Asn Ile Thr Arg Ile Thr Lys Thr Asp Phe Ala Gly Leu Arg His
65                  70                  75                  80

Leu Arg Val Leu Gln Leu Met Glu Asn Lys Ile Ser Thr Ile Glu Arg
                85                  90                  95

Gly Ala Phe Gln Asp Leu Lys Glu Leu Glu Arg Leu Arg Leu Asn Arg
            100                 105                 110

Asn His Leu Gln Leu Phe Pro Glu Leu Leu Phe Leu Gly Thr Ser Lys
        115                 120                 125

Leu Tyr Arg Leu Asp Leu Ser Glu Asn Gln Ile Gln Ala Ile Pro Arg
    130                 135                 140

Lys Ala Phe Arg Gly Ala Val Asp Ile Lys Asn Leu Gln Leu Asp Tyr
145                 150                 155                 160

Asn Gln Ile Ser Cys Ile Glu Asp Gly Ala Phe Arg Ala Leu Arg Asp
                165                 170                 175

Leu Glu Val Leu Thr Leu Asn Asn Asn Asn Ile Thr Arg Leu Ser Val
            180                 185                 190

Ala Ser Phe Asn His Met Pro Lys Leu Arg Thr Phe Arg Leu His Ser
        195                 200                 205

Asn Asn Leu Tyr Cys Asp Cys His Leu Ala Trp Leu Ser Asp Trp Leu
    210                 215                 220

Arg Gln Arg Pro Arg Val Gly Leu Tyr Thr Gln Cys Met Gly Pro Ser
225                 230                 235                 240

His Leu Arg Gly His Asn Val Ala Glu Val Gln Lys Arg Glu Phe Val
                245                 250                 255

Cys Ser Gly Lys Gly Glu Arg Thr Phe Leu Leu Ser Tyr Tyr Leu Met
            260                 265                 270
```

```
Leu Leu Cys His Gln Ser Phe Met Ala Pro Ser Cys Ser Val Leu His
        275                 280                 285

Cys Pro Ala Ala Cys Thr Cys Ser Asn Asn Ile Val Asp Cys Arg Gly
    290                 295                 300

Lys Gly Leu Thr Glu Ile Pro Thr Asn Leu Pro Glu Thr Ile Thr Glu
305                 310                 315                 320

Ile Arg Leu Glu Gln Asn Ser Ile Lys Val Ile Pro Pro Gly Ala Phe
                325                 330                 335

Ser Pro Tyr Lys Lys Leu Arg Arg Ile Asp Leu Ser Asn Asn Gln Ile
            340                 345                 350

Ser Glu Leu Ala Pro Asp Ala Phe Gln Gly Leu Arg Ser Leu Asn Ser
        355                 360                 365

Leu Val Leu Tyr Gly Asn Lys Ile Thr Glu Leu Pro Lys Ser Leu Phe
    370                 375                 380

Glu Gly Leu Phe Ser Leu Gln Leu Leu Leu Leu Asn Ala Asn Lys Ile
385                 390                 395                 400

Asn Cys Leu Arg Val Asp Ala Phe Gln Asp Leu His Asn Leu Asn Leu
                405                 410                 415

Leu Ser Leu Tyr Asp Asn Lys Leu Gln Thr Ile Ala Lys Gly Thr Phe
            420                 425                 430

Ser Pro Leu Arg Ala Ile Gln Thr Met His Leu Ala Gln Asn Pro Phe
        435                 440                 445

Ile Cys Asp Cys His Leu Lys Trp Leu Ala Asp Tyr Leu His Thr Asn
    450                 455                 460

Pro Ile Glu Thr Ser Gly Ala Arg Cys Thr Ser Pro Arg Arg Leu Ala
465                 470                 475                 480

Asn Lys Arg Ile Gly Gln Ile Lys Ser Lys Lys Phe Arg Cys Ser Ala
                485                 490                 495

Lys Glu Gln Tyr Phe Ile Pro Gly Thr Glu Asp Tyr Arg Ser Lys Leu
            500                 505                 510

Ser Gly Asp Cys Phe Ala Asp Leu Ala Cys Pro Glu Lys Cys Arg Cys
        515                 520                 525

Glu Gly Thr Thr Val Asp Cys Ser Asn Gln Lys Leu Thr Lys Ile Pro
    530                 535                 540

Asp His Ile Pro Gln Tyr Thr Ala Glu Leu Arg Leu Asn Asn Asn Glu
545                 550                 555                 560

Phe Thr Val Leu Glu Ala Thr Gly Ile Phe Lys Lys Leu Pro Gln Leu
                565                 570                 575

Arg Lys Ile Asn Phe Ser Asn Asn Lys Ile Thr Asp Ile Glu Glu Gly
            580                 585                 590

Ala Phe Glu Gly Ala Ala Gly Val Asn Glu Ile Leu Leu Thr Ser Asn
        595                 600                 605

Arg Leu Glu Asn Val Gln His Lys Met Phe Lys Gly Leu Glu Ser Leu
    610                 615                 620

Lys Thr Leu Met Leu Arg Ser Asn Arg Ile Ser Cys Val Gly Asn Asp
625                 630                 635                 640

Ser Phe Ile Gly Leu Ser Ser Val Arg Leu Leu Ser Leu Tyr Asp Asn
                645                 650                 655

Gln Ile Ala Thr Ile Ala Pro Gly Ala Phe Asp Thr Leu His Ser Leu
            660                 665                 670

Ser Thr Leu Asn Leu Leu Ala Asn Pro Phe Asn Cys Asn Cys Tyr Leu
        675                 680                 685

Ala Trp Leu Gly Glu Trp Leu Arg Lys Lys Arg Ile Val Thr Gly Asn
```

```
    690                 695                 700

Pro Arg Cys Gln Lys Pro Tyr Phe Leu Lys Glu Ile Pro Ile Gln Asp
705                 710                 715                 720

Val Ala Ile Gln Asp Phe Thr Cys Asp Asp Gly Asn Asp Asp Ser Ser
                725                 730                 735

Cys Ser Pro Leu Ser Arg Cys Pro Thr Glu Cys Thr Cys Leu Asp Thr
            740                 745                 750

Val Val Arg Cys Ser Asn Lys Gly Leu Lys Val Leu Pro Lys Gly Ile
        755                 760                 765

Pro Arg Asp Val Thr Glu Leu Tyr Leu Asp Gly Asn His Phe Thr Leu
    770                 775                 780

Val Pro Lys Glu Leu Tyr Asn Tyr Lys His Leu Thr Leu Ile Asp Leu
785                 790                 795                 800

Ser Asn Asn Arg Ile Ser Thr Leu Ser Asn Gln Ser Phe Ser Asn Met
                805                 810                 815

Thr Gln Leu Leu Thr Leu Ile Leu Ser Tyr Asn Arg Leu Arg Cys Ile
            820                 825                 830

Pro Pro Arg Thr Phe Asp Gly Leu Lys Ser Leu Arg Leu Leu Ser Leu
        835                 840                 845

His Gly Asn Asp Ile Ser Val Val Pro Glu Gly Ala Phe Ser Asp Leu
    850                 855                 860

Ser Ala Leu Ser His Leu Ala Ile Gly Ala Asn Pro Leu Tyr Cys Asp
865                 870                 875                 880

Cys Asn Met Gln Trp Leu Ser Asp Trp Val Lys Ser Glu Tyr Lys Glu
                885                 890                 895

Pro Gly Ile Ala Arg Cys Ala Gly Pro Gly Glu Met Ala Asp Lys Leu
            900                 905                 910

Leu Leu Thr Thr Pro Ser Lys Lys Phe Thr Cys Gln Gly Pro Val Asp
        915                 920                 925

Ile Asn Ile Leu Ala Lys Cys Asn Pro Cys Leu Ser Asn Pro Cys Lys
    930                 935                 940

Asn Asp Gly Thr Cys Asn Asn Asp Pro Val Asp Phe Tyr Arg Cys Thr
945                 950                 955                 960

Cys Pro Tyr Gly Phe Lys Gly Gln Asp Cys Asp Val Pro Ile His Ala
                965                 970                 975

Cys Ile Ser Asn Pro Cys Thr His Gly Gly Thr Cys His Leu Lys Glu
            980                 985                 990

Gly Glu Lys Asp Gly Phe Trp Cys  Ile Cys Ala Asp Gly  Phe Glu Gly
        995                 1000                1005

Glu Asn  Cys Glu Val Asn Val  Asp Asp Cys Glu Asp  Asn Asp Cys
    1010                1015                1020

Glu Asn  Asn Ser Thr Cys Val  Asp Gly Ile Asn Asn  Tyr Thr Cys
    1025                1030                1035

Leu Cys  Pro Pro Glu Tyr Thr  Gly Glu Leu Cys Glu  Glu Lys Leu
    1040                1045                1050

Asp Phe  Cys Ala Gln Asp Leu  Asn Pro Cys Gln His  Asp Ser Lys
    1055                1060                1065

Cys Ile  Leu Met Pro Lys Gly  Phe Lys Cys Asp Cys  Thr Pro Gly
    1070                1075                1080

Tyr Val  Gly Glu His Cys Asp  Ile Asp Phe Asp Asp  Cys Gln Asp
    1085                1090                1095

His Lys  Cys Lys Asn Gly Ala  His Cys Thr Asp Ala  Val Asn Gly
    1100                1105                1110
```

```
Tyr Thr  Cys Thr Cys Pro Glu  Gly Tyr Ser Gly Leu  Phe Cys Glu
    1115                 1120                 1125

Phe Ser  Pro Pro Met Val Leu  Pro Arg Thr Ser Pro  Cys Asp Asn
    1130                 1135                 1140

Phe Asp  Cys Gln Asn Gly Ala  Gln Cys Ile Val Arg  Ala Gly Glu
    1145                 1150                 1155

Pro Ile  Cys Gln Cys Leu Pro  Gly Tyr Gln Gly Asp  Lys Cys Glu
    1160                 1165                 1170

Lys Leu  Val Ser Val Asn Phe  Val Asn Lys Glu Ser  Tyr Leu Gln
    1175                 1180                 1185

Ile Pro  Ser Ala Lys Val Arg  Pro Gln Thr Asn Ile  Thr Leu Gln
    1190                 1195                 1200

Ile Ala  Thr Asp Glu Asp Ser  Gly Ile Leu Leu Tyr  Lys Gly Asp
    1205                 1210                 1215

Lys Asp  His Ile Ala Val Glu  Leu Tyr Arg Gly Arg  Val Arg Ala
    1220                 1225                 1230

Ser Tyr  Asp Thr Gly Ser His  Pro Ala Ser Ala Ile  Tyr Ser Val
    1235                 1240                 1245

Glu Thr  Ile Asn Asp Gly Asn  Phe His Ile Val Glu  Leu Leu Ala
    1250                 1255                 1260

Leu Asp  Gln Ser Leu Ser Leu  Ser Val Asp Gly Gly  Ser Pro Lys
    1265                 1270                 1275

Ile Ile  Thr Asn Leu Ser Lys  Gln Ser Thr Leu Asn  Phe Asp Ser
    1280                 1285                 1290

Pro Leu  Tyr Val Gly Gly Met  Pro Gly Arg Asn Asn  Val Ala Ala
    1295                 1300                 1305

Ala Leu  Arg Gln Ala Pro Gly  His Asn Gly Thr Ser  Phe His Gly
    1310                 1315                 1320

Cys Ile  Arg Asn Leu Tyr Ile  Asn Ser Glu Leu Gln  Asp Phe Arg
    1325                 1330                 1335

Gln Val  Pro Met Gln Thr Gly  Ile Leu Pro Gly Cys  Glu Pro Cys
    1340                 1345                 1350

His Arg  Lys Val Cys Ala His  Gly Ala Cys Gln Pro  Ser Ser Gln
    1355                 1360                 1365

Ser Gly  Phe Thr Cys Glu Cys  Glu Glu Gly Trp Thr  Gly Pro Leu
    1370                 1375                 1380

Cys Asp  Gln Arg Thr Asn Asp  Pro Cys Leu Gly Asn  Lys Cys Val
    1385                 1390                 1395

His Gly  Thr Cys Leu Pro Ile  Asn Ala Phe Ser Tyr  Ser Cys Lys
    1400                 1405                 1410

Cys Leu  Glu Gly His Gly Gly  Val Leu Cys Asp Glu  Glu Glu Asp
    1415                 1420                 1425

Leu Phe  Asn Pro Cys Gln Ala  Ile Arg Cys Lys His  Gly Lys Cys
    1430                 1435                 1440

Arg Leu  Ser Gly Leu Gly Gln  Pro Tyr Cys Glu Cys  Ser Ser Gly
    1445                 1450                 1455

Tyr Thr  Gly Asp Ser Cys Asp  Arg Glu Val Ser Cys  Arg Gly Glu
    1460                 1465                 1470

Arg Val  Arg Asp Tyr Tyr Pro  Lys Gln Gln Gly Tyr  Ala Ala Cys
    1475                 1480                 1485

Gln Thr  Thr Lys Lys Val Ser  Arg Leu Glu Cys Arg  Gly Gly Cys
    1490                 1495                 1500
```

-continued

```
Ala Ala  Gly Gln Cys Cys Gly  Pro Leu Arg Ser Lys  Arg Arg Lys
    1505                 1510                 1515

Tyr Ser  Phe Glu Cys Thr Asp  Gly Ser Ser Phe Val  Asp Glu Val
    1520                 1525                 1530

Glu Lys  Val Val Lys Cys Gly  Cys Ser Arg Cys Ala  Ala
    1535                 1540                 1545


<210> SEQ ID NO 17
<211> LENGTH: 4605
<212> TYPE: DNA
<213> ORGANISM: Bos taurus

<400> SEQUENCE: 17

atgcacggcg tcggctggca gacgctgtcc ctgtctctgg ggttagtgct ggcgatcctg     60

aacgaggtgg cgccgcaagc gtgtccggcg cagtgctcct gctccgggag cacagtggac    120

tgtcacgggc tggcgttgcg cagtgtgccc aggaatatcc cccgcaacac cgagagattg    180

gatttgaatg gaaataacat cacaaggatt accaagacag attttgctgg tcttcgacac    240

ctaagagttc ttcagcttat ggagaataag attaccacca ttgaaagagg agcattccag    300

gatcttaaag aactggagag actgcgttta aacagaaatc accttcagct gtttcctgag    360

ttgctgtttc ttgggacttc gaagctatac aggcttgacc tcagtgaaaa ccagattcag    420

gcaattccaa ggaaagcttt tcgtggggca gttgatatta aaaatctgca actggattac    480

aaccacatca gctgtattga agatggggca ttcagggctc tccgggacct ggaagtgctc    540

actctcaaca ataacaacat tactagactt tctgtggcaa gtttcaacca tatgcctaaa    600

cttaggactt ttcgactcca ttcgaacaac ctatattgtg actgccacct ggcctggctc    660

tcggactggc tgcgccaaag gcctcgggtg ggcctctaca ctcagtgtat ggggccatct    720

cacctgaggg gccacaatgt agctgaggtt caaaaacgag aatttgtctg cagcgatgag    780

gaagaaggtc accagtcatt tatggctcct tcttgcagtg ttttgcactg cccagctgct    840

tgtacctgta gcaacaacat cgtagattgc cgtgggaaag gtctcactga gatccccacg    900

aatctgccag agaccatcac agaaatacgt ttggaacaga actcaatcaa ggtcatccct    960

cctggagctt tctcaccata taaaaagctt agaagaatcg acctgagcaa taatcagatc   1020

tctgagctag caccagatgc tttccaagga ctacgctctc tgaattcact tgtcctctat   1080

ggaaataaaa tcacagaact cccaaaaagt ttatttgaag gactgttttc cttacagtta   1140

ctattactga atgccaacaa gataaactgc ctccgggtag atgcttttca ggatctgcac   1200

aacctgaacc ttctctcctt atatgacaac aagcttcaga ccatcgccaa ggggaccttt   1260

tcacctctcc gggccattca aaccatgcat ttggcccaga acccctttat ttgtgactgc   1320

catctcaagt ggctggcgga ttatctccat accaacccaa tcgagaccag tggtgcccgc   1380

tgcaccagtc cccggcgact ggcaaacaaa agaatcggac agatcaaaag caagaaattc   1440

cgttgttcag ctaaagaaca gtatttcatt ccaggtacag aagattatcg atcaaaatta   1500

agtggggact gctttgccga tttggcttgc cctgaaaagt gccgctgcga agggaccaca   1560

gtagactgct ccaatcaaaa actcaccaaa atcccagatc acattcccca gtacactgca   1620

gagctgcgcc tcaacaataa tgaatttaca gtgttggaag ctaccgggat cttcaagaaa   1680

cttcctcagt tacgtaaaat aaactttagc aacaataaga tcacagacat tgaagaggga   1740

gcgtttgaag gagcatctgg tgtgaatgaa atacttctca cgagtaatcg tttggaaaat   1800

gttcagcata agatgttcaa gggcttggaa agcctcaaga ctttgatgtt gagaagtaat   1860
```

-continued

```
cgcataagct gtgtagggaa tgacagtttc ataggactca gctctgtgcg tttgctttct   1920

ttatatgata atcagattac taccattgca ccaggagctt ttgatactct ccattcttta   1980

tctactctaa acctcttggc caatcctttc aactgtaact gctacctggc ttggttggga   2040

gaatggctta ggaagaaaag aattgtaaca ggaaatcctc gatgtcagaa accctatttc   2100

ctcaaagaaa tccccatcca ggatgtggcc attcaagact tcacttgtga tgatggaaat   2160

gatgacaata gctgttcccc actctctcgc tgtcctgccg agtgtacctg cttggacaca   2220

gtggttcgat gtagcaacaa agccttgaag gtcttgccca aaggaattcc aagagatgtc   2280

actgaattgt atctggatgg gaaccagttt accttggttc ctaaggaact ctctaactac   2340

aaacatttaa cacttataga cttaagtaac aacagaataa gcaccctctc taatcagagc   2400

ttcagcaaca tgacccagct cctcacttta attcttagtt acaaccgttt gagatgtatt   2460

cctcctcgaa ccttcgatgg actgaagtct cttcggttac tttctttaca tggaaacgac   2520

atttctgttg tgcctgaagg tgctttcaat gatcttgctg cattatcaca cctagcaatt   2580

ggagccaacc ctctttactg tgattgtaac atgcagtggt tatccgactg ggtaaagtcg   2640

gaatacaaag agccgggaat tgctcgctgt gctggtcctg gagaaatggc agataaacta   2700

cttctcacaa ctccctccaa aaaatttaca tgtcaaggtc ctgtggatgt caatattcta   2760

gctaaatgta atccctgctt atcaaatcca tgtaaaaatg atggcacctg taacaatgac   2820

ccagttgact tttatcgctg cacctgtcca tatggtttca aggggcagga ttgtgatgtt   2880

ccaattcatg cgtgcatcag caacccatgt aaacatggag gaacttgcca cttaaaagaa   2940

ggagaaaaag atggattctg gtgtatttgt gctgatggat ttgaaggaga aaattgtgaa   3000

atcaatgttg atgactgtga agataatgac tgtgaaaata actctacatg tgtcgatgga   3060

attaataact acacatgcct ttgcccacct gagtacacag gagagttgtg tgaggagaaa   3120

ctggacttct gtgcccagga cttgaacccc tgccagcatg actccaagtg catcctgacg   3180

ccaaagggat acaaatgtga ctgcactcca ggatacatag gcgaacattg tgacattgac   3240

ttcgatgact gccaagataa caagtgtaag aacggagccc actgcaccga tgcagtgaac   3300

ggttacacat gcacctgtcc tgaaggctac agtggcttgt tttgtgaatt ttctccacct   3360

atggttctcc ctcgtaccag cccctgtgat aattttgatt gtcagaatgg agctcaatgc   3420

atcatcagga tcaatgagcc aatatgccag tgtttgcctg gctaccaggg agaaaagtgt   3480

gaaaaactgg tcagtgtgaa ttttgtaaac aaagagtctt atcttcagat cccttccgcc   3540

aaggtccggc ctcaaacaaa catcactctt cagatcgcca cagatgaaga cagtggaatc   3600

ctcctgtata agggtgataa agaccatatt gctgtagaac tctaccgagg acgtgttcgt   3660

gccagctatg acaccggctc ccacccggct tctgccattt acagtgtgga gacaatcaat   3720

gacggaaatt ttcacattgt ggaactactt gccctggatc aaagtctctc cctctcagtg   3780

gatggaggga gccccaaaat cattaccaac ttgtcaaaac agtccactct gaattttgac   3840

tccccactct atgttggagg catgcccggg aagaacaacg tggccgcagc tctgcgccag   3900

gcccctgggc agaatggcac cagcttccac ggttgcatcc ggaaccttta catcaacagc   3960

gaacttcagg acttccggaa ggtgcccatg cagaccggca tcctgcctgg ctgtgaacca   4020

tgccacaaga aggtgtgtgc ccacggcaca tgccagccca gcagccaggc cggcttcacc   4080

tgcgagtgcg aggaaggatg gacagggccc ctctgtgatc agaggaccaa tgacccctgt   4140

cttggaaata aatgcgtcca cggcacctgc ctgcccatca atgcgttctc ctacagctgc   4200

aaatgcctag agggccatgg gggcgtcctc tgtgatgaag aggaggatct gtttaaccca   4260
```

```
tgccaggcga tcaagtgcaa gcatgggaaa tgcaggctct caggactggg gcagccctac   4320

tgtgaatgca gcagtggata caccggggac agctgtgatc gagaaatctc ttgtcgaggg   4380

gaacggataa gagattatta ccaaaagcag cagggctacg ccgcttgcca gacgaccaag   4440

aaggtgtctc ggttggaatg cagagggggc tgtgcaggcg ggcagtgctg cggacctctg   4500

aggagcaaga gaaggaaata ctctttcgaa tgcactgatg ggtcctcgtt tgtggacgag   4560

gtggagaagg tggtaaagtg tggctgtacc cgctgcgctt cctaa                    4605


<210> SEQ ID NO 18
<211> LENGTH: 1534
<212> TYPE: PRT
<213> ORGANISM: Bos taurus

<400> SEQUENCE: 18

Met His Gly Val Gly Trp Gln Thr Leu Ser Leu Ser Leu Gly Leu Val
1               5                   10                  15

Leu Ala Ile Leu Asn Glu Val Ala Pro Gln Ala Cys Pro Ala Gln Cys
            20                  25                  30

Ser Cys Ser Gly Ser Thr Val Asp Cys His Gly Leu Ala Leu Arg Ser
        35                  40                  45

Val Pro Arg Asn Ile Pro Arg Asn Thr Glu Arg Leu Asp Leu Asn Gly
    50                  55                  60

Asn Asn Ile Thr Arg Ile Thr Lys Thr Asp Phe Ala Gly Leu Arg His
65                  70                  75                  80

Leu Arg Val Leu Gln Leu Met Glu Asn Lys Ile Thr Thr Ile Glu Arg
                85                  90                  95

Gly Ala Phe Gln Asp Leu Lys Glu Leu Glu Arg Leu Arg Leu Asn Arg
            100                 105                 110

Asn His Leu Gln Leu Phe Pro Glu Leu Leu Phe Leu Gly Thr Ser Lys
        115                 120                 125

Leu Tyr Arg Leu Asp Leu Ser Glu Asn Gln Ile Gln Ala Ile Pro Arg
    130                 135                 140

Lys Ala Phe Arg Gly Ala Val Asp Ile Lys Asn Leu Gln Leu Asp Tyr
145                 150                 155                 160

Asn His Ile Ser Cys Ile Glu Asp Gly Ala Phe Arg Ala Leu Arg Asp
                165                 170                 175

Leu Glu Val Leu Thr Leu Asn Asn Asn Asn Ile Thr Arg Leu Ser Val
            180                 185                 190

Ala Ser Phe Asn His Met Pro Lys Leu Arg Thr Phe Arg Leu His Ser
        195                 200                 205

Asn Asn Leu Tyr Cys Asp Cys His Leu Ala Trp Leu Ser Asp Trp Leu
    210                 215                 220

Arg Gln Arg Pro Arg Val Gly Leu Tyr Thr Gln Cys Met Gly Pro Ser
225                 230                 235                 240

His Leu Arg Gly His Asn Val Ala Glu Val Gln Lys Arg Glu Phe Val
                245                 250                 255

Cys Ser Asp Glu Glu Glu Gly His Gln Ser Phe Met Ala Pro Ser Cys
            260                 265                 270

Ser Val Leu His Cys Pro Ala Ala Cys Thr Cys Ser Asn Asn Ile Val
        275                 280                 285

Asp Cys Arg Gly Lys Gly Leu Thr Glu Ile Pro Thr Asn Leu Pro Glu
    290                 295                 300

Thr Ile Thr Glu Ile Arg Leu Glu Gln Asn Ser Ile Lys Val Ile Pro
```

-continued

```
305                 310                 315                 320

Pro Gly Ala Phe Ser Pro Tyr Lys Lys Leu Arg Arg Ile Asp Leu Ser
                325                 330                 335

Asn Asn Gln Ile Ser Glu Leu Ala Pro Asp Ala Phe Gln Gly Leu Arg
            340                 345                 350

Ser Leu Asn Ser Leu Val Leu Tyr Gly Asn Lys Ile Thr Glu Leu Pro
        355                 360                 365

Lys Ser Leu Phe Glu Gly Leu Phe Ser Leu Gln Leu Leu Leu Leu Asn
    370                 375                 380

Ala Asn Lys Ile Asn Cys Leu Arg Val Asp Ala Phe Gln Asp Leu His
385                 390                 395                 400

Asn Leu Asn Leu Leu Ser Leu Tyr Asp Asn Lys Leu Gln Thr Ile Ala
                405                 410                 415

Lys Gly Thr Phe Ser Pro Leu Arg Ala Ile Gln Thr Met His Leu Ala
            420                 425                 430

Gln Asn Pro Phe Ile Cys Asp Cys His Leu Lys Trp Leu Ala Asp Tyr
        435                 440                 445

Leu His Thr Asn Pro Ile Glu Thr Ser Gly Ala Arg Cys Thr Ser Pro
    450                 455                 460

Arg Arg Leu Ala Asn Lys Arg Ile Gly Gln Ile Lys Ser Lys Lys Phe
465                 470                 475                 480

Arg Cys Ser Ala Lys Glu Gln Tyr Phe Ile Pro Gly Thr Glu Asp Tyr
                485                 490                 495

Arg Ser Lys Leu Ser Gly Asp Cys Phe Ala Asp Leu Ala Cys Pro Glu
            500                 505                 510

Lys Cys Arg Cys Glu Gly Thr Thr Val Asp Cys Ser Asn Gln Lys Leu
        515                 520                 525

Thr Lys Ile Pro Asp His Ile Pro Gln Tyr Thr Ala Glu Leu Arg Leu
    530                 535                 540

Asn Asn Asn Glu Phe Thr Val Leu Glu Ala Thr Gly Ile Phe Lys Lys
545                 550                 555                 560

Leu Pro Gln Leu Arg Lys Ile Asn Phe Ser Asn Asn Lys Ile Thr Asp
                565                 570                 575

Ile Glu Glu Gly Ala Phe Glu Gly Ala Ser Gly Val Asn Glu Ile Leu
            580                 585                 590

Leu Thr Ser Asn Arg Leu Glu Asn Val Gln His Lys Met Phe Lys Gly
        595                 600                 605

Leu Glu Ser Leu Lys Thr Leu Met Leu Arg Ser Asn Arg Ile Ser Cys
    610                 615                 620

Val Gly Asn Asp Ser Phe Ile Gly Leu Ser Ser Val Arg Leu Leu Ser
625                 630                 635                 640

Leu Tyr Asp Asn Gln Ile Thr Thr Ile Ala Pro Gly Ala Phe Asp Thr
                645                 650                 655

Leu His Ser Leu Ser Thr Leu Asn Leu Leu Ala Asn Pro Phe Asn Cys
            660                 665                 670

Asn Cys Tyr Leu Ala Trp Leu Gly Glu Trp Leu Arg Lys Lys Arg Ile
        675                 680                 685

Val Thr Gly Asn Pro Arg Cys Gln Lys Pro Tyr Phe Leu Lys Glu Ile
    690                 695                 700

Pro Ile Gln Asp Val Ala Ile Gln Asp Phe Thr Cys Asp Asp Gly Asn
705                 710                 715                 720

Asp Asp Asn Ser Cys Ser Pro Leu Ser Arg Cys Pro Ala Glu Cys Thr
                725                 730                 735
```

```
Cys Leu Asp Thr Val Val Arg Cys Ser Asn Lys Ala Leu Lys Val Leu
            740                 745                 750

Pro Lys Gly Ile Pro Arg Asp Val Thr Glu Leu Tyr Leu Asp Gly Asn
        755                 760                 765

Gln Phe Thr Leu Val Pro Lys Glu Leu Ser Asn Tyr Lys His Leu Thr
    770                 775                 780

Leu Ile Asp Leu Ser Asn Asn Arg Ile Ser Thr Leu Ser Asn Gln Ser
785                 790                 795                 800

Phe Ser Asn Met Thr Gln Leu Leu Thr Leu Ile Leu Ser Tyr Asn Arg
                805                 810                 815

Leu Arg Cys Ile Pro Pro Arg Thr Phe Asp Gly Leu Lys Ser Leu Arg
            820                 825                 830

Leu Leu Ser Leu His Gly Asn Asp Ile Ser Val Val Pro Glu Gly Ala
        835                 840                 845

Phe Asn Asp Leu Ala Ala Leu Ser His Leu Ala Ile Gly Ala Asn Pro
    850                 855                 860

Leu Tyr Cys Asp Cys Asn Met Gln Trp Leu Ser Asp Trp Val Lys Ser
865                 870                 875                 880

Glu Tyr Lys Glu Pro Gly Ile Ala Arg Cys Ala Gly Pro Gly Glu Met
                885                 890                 895

Ala Asp Lys Leu Leu Leu Thr Thr Pro Ser Lys Lys Phe Thr Cys Gln
            900                 905                 910

Gly Pro Val Asp Val Asn Ile Leu Ala Lys Cys Asn Pro Cys Leu Ser
        915                 920                 925

Asn Pro Cys Lys Asn Asp Gly Thr Cys Asn Asn Asp Pro Val Asp Phe
    930                 935                 940

Tyr Arg Cys Thr Cys Pro Tyr Gly Phe Lys Gly Gln Asp Cys Asp Val
945                 950                 955                 960

Pro Ile His Ala Cys Ile Ser Asn Pro Cys Lys His Gly Gly Thr Cys
                965                 970                 975

His Leu Lys Glu Gly Glu Lys Asp Gly Phe Trp Cys Ile Cys Ala Asp
            980                 985                 990

Gly Phe Glu Gly Glu Asn Cys Glu  Ile Asn Val Asp Asp  Cys Glu Asp
        995                 1000                1005

Asn Asp  Cys Glu Asn Asn Ser  Thr Cys Val Asp Gly  Ile Asn Asn
    1010                 1015                 1020

Tyr Thr  Cys Leu Cys Pro Pro  Glu Tyr Thr Gly Glu  Leu Cys Glu
    1025                 1030                 1035

Glu Lys  Leu Asp Phe Cys Ala  Gln Asp Leu Asn Pro  Cys Gln His
    1040                 1045                 1050

Asp Ser  Lys Cys Ile Leu Thr  Pro Lys Gly Tyr Lys  Cys Asp Cys
    1055                 1060                 1065

Thr Pro  Gly Tyr Ile Gly Glu  His Cys Asp Ile Asp  Phe Asp Asp
    1070                 1075                 1080

Cys Gln  Asp Asn Lys Cys Lys  Asn Gly Ala His Cys  Thr Asp Ala
    1085                 1090                 1095

Val Asn  Gly Tyr Thr Cys Thr  Cys Pro Glu Gly Tyr  Ser Gly Leu
    1100                 1105                 1110

Phe Cys  Glu Phe Ser Pro Pro  Met Val Leu Pro Arg  Thr Ser Pro
    1115                 1120                 1125

Cys Asp  Asn Phe Asp Cys Gln  Asn Gly Ala Gln Cys  Ile Ile Arg
    1130                 1135                 1140
```

```
Ile Asn  Glu Pro Ile Cys Gln  Cys Leu Pro Gly Tyr  Gln Gly Glu
    1145                 1150                 1155

Lys Cys  Glu Lys Leu Val Ser  Val Asn Phe Val Asn  Lys Glu Ser
    1160                 1165                 1170

Tyr Leu  Gln Ile Pro Ser Ala  Lys Val Arg Pro Gln  Thr Asn Ile
    1175                 1180                 1185

Thr Leu  Gln Ile Ala Thr Asp  Glu Asp Ser Gly Ile  Leu Leu Tyr
    1190                 1195                 1200

Lys Gly  Asp Lys Asp His Ile  Ala Val Glu Leu Tyr  Arg Gly Arg
    1205                 1210                 1215

Val Arg  Ala Ser Tyr Asp Thr  Gly Ser His Pro Ala  Ser Ala Ile
    1220                 1225                 1230

Tyr Ser  Val Glu Thr Ile Asn  Asp Gly Asn Phe His  Ile Val Glu
    1235                 1240                 1245

Leu Leu  Ala Leu Asp Gln Ser  Leu Ser Leu Ser Val  Asp Gly Gly
    1250                 1255                 1260

Ser Pro  Lys Ile Ile Thr Asn  Leu Ser Lys Gln Ser  Thr Leu Asn
    1265                 1270                 1275

Phe Asp  Ser Pro Leu Tyr Val  Gly Gly Met Pro Gly  Lys Asn Asn
    1280                 1285                 1290

Val Ala  Ala Ala Leu Arg Gln  Ala Pro Gly Gln Asn  Gly Thr Ser
    1295                 1300                 1305

Phe His  Gly Cys Ile Arg Asn  Leu Tyr Ile Asn Ser  Glu Leu Gln
    1310                 1315                 1320

Asp Phe  Arg Lys Val Pro Met  Gln Thr Gly Ile Leu  Pro Gly Cys
    1325                 1330                 1335

Glu Pro  Cys His Lys Lys Val  Cys Ala His Gly Thr  Cys Gln Pro
    1340                 1345                 1350

Ser Ser  Gln Ala Gly Phe Thr  Cys Glu Cys Glu Glu  Gly Trp Thr
    1355                 1360                 1365

Gly Pro  Leu Cys Asp Gln Arg  Thr Asn Asp Pro Cys  Leu Gly Asn
    1370                 1375                 1380

Lys Cys  Val His Gly Thr Cys  Leu Pro Ile Asn Ala  Phe Ser Tyr
    1385                 1390                 1395

Ser Cys  Lys Cys Leu Glu Gly  His Gly Gly Val Leu  Cys Asp Glu
    1400                 1405                 1410

Glu Glu  Asp Leu Phe Asn Pro  Cys Gln Ala Ile Lys  Cys Lys His
    1415                 1420                 1425

Gly Lys  Cys Arg Leu Ser Gly  Leu Gly Gln Pro Tyr  Cys Glu Cys
    1430                 1435                 1440

Ser Ser  Gly Tyr Thr Gly Asp  Ser Cys Asp Arg Glu  Ile Ser Cys
    1445                 1450                 1455

Arg Gly  Glu Arg Ile Arg Asp  Tyr Tyr Gln Lys Gln  Gln Gly Tyr
    1460                 1465                 1470

Ala Ala  Cys Gln Thr Thr Lys  Lys Val Ser Arg Leu  Glu Cys Arg
    1475                 1480                 1485

Gly Gly  Cys Ala Gly Gly Gln  Cys Cys Gly Pro Leu  Arg Ser Lys
    1490                 1495                 1500

Arg Arg  Lys Tyr Ser Phe Glu  Cys Thr Asp Gly Ser  Ser Phe Val
    1505                 1510                 1515

Asp Glu  Val Glu Lys Val Val  Lys Cys Gly Cys Thr  Arg Cys Ala
    1520                 1525                 1530

Ser
```

<210> SEQ ID NO 19
<211> LENGTH: 4587
<212> TYPE: DNA
<213> ORGANISM: Gallus gallus

<400> SEQUENCE: 19
atgatgtgcg cctgggggag gctccccctg gccctggggc tgctgctggt gctggcgggc 60
gaggcggcgc cgcagccgtg cccggcgcag tgctcctgct caggaagcac ggtggactgt 120
cacgggctgg cgctgcgcgg cgtcccgagg aacatccccc gcaacactga gcggctggac 180
cttaatggaa ataacatcac cagaatcacc aagaccgact ttgctggtct aaggcacctt 240
cgagttcttc agctcatgga gaacaagatt agcactattg agagaggagc attccaggat 300
ttaaaagaac tggagaggct gcgcctaaac agaaataacc tccagttgct ttctgaactg 360
ctctttctgg ggacgccgaa gttatacagg cttgatctta gtgaaaatca gattcaagcc 420
atacccagga aggcatttcg tggagcagta gacataaaaa atctgcaact ggattacaac 480
cagatcagct gtattgaaga tggggcattt agggctctac gcgacctgga agtgctcact 540
ctcaacaaca ataacattac tcgactgtcc gtcgcaagtt tcaatcatat gcccaaactc 600
agaacttttc gcctgcactc caacaacctc tactgtgact gccacctggc ctggctgtcg 660
gactggctgc ggcagcggcc acgtgtaggc ctctacactc agtgcatggg cccagcacac 720
ctgcggggcc ataacgtggc tgaggtccag aagcgggagt tcgtctgcag tggtcaccaa 780
tcatttatgg ctccatcctg cagtgtcttg cattgtcctg ctgcatgcac ctgtagtaac 840
aacattgtgg actgtcgtgg gaaaggcctt actgaaattc caacaaatct tccagaaacc 900
attactgaaa tacggttaga acaaaattca atcaaagtca tacctcctgg agctttctca 960
ccctataaaa agcttcgaag aattgacctg agcaataacc agatctctga agcagctcca 1020
gatgctttcc agggcttacg ttctctcaat tcacttgtcc tctatggcaa taaaattaca 1080
gaacttccaa aaggcctatt tgaaggactg ttttctctgc aattgctatt attaaatgcc 1140
aacaagatca attgcctgcg tgttgatgct tttcaagatc tgcacaactt gaatctccta 1200
tctttatatg acaacaagct tcagaccatt gcaaaaggca ccttttcacc tctacgtgca 1260
attcagacct tgcatttggc tcagaaccca tttatctgtg actgccatct gaagtggctg 1320
gcggattatc ttcatacaaa ccccattgag accagtggtg cccgctgcac cagcccccgc 1380
cgtctggcaa acaaaaggat cggccagatc aaaagcaaga aattccgctg ctcagctaaa 1440
gagcagtatt tcattccagg cactgaagat tacagatcca aattaagtgg tgactgcttt 1500
gcagatttgg cttgccctga gaaatgtcgc tgtgaaggga ccacagtgga ctgctccaat 1560
cagaaactca acaaaattcc tgatcacatc ccacagtaca cagcagagtt gcgactcaat 1620
aacaatgaat tttcagtcct ggaagctact gggatcttta agaagcttcc tcaactgcga 1680
aaaataaacc tgagcaataa caagattaca gatattgaag aaggtgcatt tgatggagcc 1740
tctggtgtca atgaactatt gctcactagc aatcgtttgg aaactgttag agacaaaatg 1800
ttcaaaggac tggaaagtct taaaacactg atgctgagga gtaaccgtgt gagctgtgtg 1860
gggaacgaca gtttcacagg cctgagctct gtccgtctgc tctcactata tgacaaccag 1920
atcaccaccg tggcacccgg ctccttcgat accctgcatt cactctctac attaaacctc 1980
ttggccaatc ctttcaactg caactgccat cttgcatggc ttggagattg gctaaggaag 2040
aaacgcattg tgacgggaaa ccctcgctgt cagaaacctt atttcctcaa agagattcct 2100

-continued

```
atccaggatg tggcaattca ggattttaca tgtgatgatg gaaatgatga caatagctgc   2160
tctccgctgt cccgctgtcc tgcagaatgt acttgtctag acacagttgt tcgctgcagc   2220
aacaaaggcc taaaagcttt gcctaaaggc atcccaaaag atgtaactga actatatttg   2280
gatggaaacc agtttactct tgttcctaaa gagctctcca actacaaaca tttaacactt   2340
atagatttaa gtaacaacag aatcagcact ctttctaatc agagcttcag caacatgact   2400
cagctgctca ccttaattct tagttacaac cgcctgaggt gtatccctgc acggactttt   2460
gatgggttga aatcacttag gttgctgtct ttacatggca atgatatttc tgtggttcct   2520
gaaggagcct ttaatgatct ttcagcgtta tcacacctgg ctattggagc aaatcctctt   2580
tattgtgatt gtaacatgca atggctgtct gactgggtaa aatcagaata caaagaacct   2640
ggtattgcac gatgtgctgg ccctggagaa atggcagata aacttctact tacaactcca   2700
tctaaaaaat ttacttgcca agggcccgtg gatgtcaata ttcttgctaa gtgtaacccc   2760
tgcttatcaa atccatgtaa aaatgatgga acctgcaata atgatccagt tgacttctat   2820
agatgtactt gcccatatgg tttcaagggt caagactgtg atattcccat tcatgcctgc   2880
attagtaacc cttgcaacca tggtggaact tgtcatttga aagaaggaga aaaagatggt   2940
ttctggtgca cttgtgcaga tggatttgaa ggagaaaatt gtgaaataaa tgttgatgac   3000
tgtgaagaca atgactgtga aaataactct acttgtgtgg atggaattaa taattatact   3060
tgcctttgtc cacctgaata tacaggtgag ctctgtgagg agaaactaga tttctgtgct   3120
caaaacctga acccttgcca gcacgactca aagtgtatct tgactcccaa aggttacaag   3180
tgtgattgca cacctggata tgtaggtgaa cactgcgata ttgacttcga tgactgccag   3240
gacaataaat gtaaaaacgg agcacagtgt acggatgcag ttaacgggta tacttgtatt   3300
tgcccagagg gatacagtgg cttgttttgt gagttttcgc caccaatggt tttacctcgc   3360
accagccctt gtgataatta tgaatgccaa aatggagccc agtgtattgt aaaggagagt   3420
gaaccaatct gccagtgttt atcaggctac cagggtgaga aatgtgaaaa gctgatcagt   3480
ataaactttg tcaacaaaga atcctatcta caaatccctt cagctaagat acactcccaa   3540
accaatatca ctcttcagat tgccacagac gaagacagtg ggatcctgct ctacaaaggc   3600
gataaggatc atatagcagt agagctgtac cgtggtagag tgagggtcag ttatgacaca   3660
ggatcttatc cagcctctgc tatttacagt gtggaaacta ttaatgatgg caatttccac   3720
attgtggagc tgcttgccat ggatcagatt ctgtctttgt ctattgatgg aggaagcccc   3780
aagataatta ccaatttgtc caagcagtcc actttgaatt ttgattctcc actgtatgtc   3840
ggaggcatgc ctgtgaaaaa taacattgca gctctacgtc agtctccagg acagaatggc   3900
acaagcttcc atggctgcat ccgtaatctg tatatcaaca gcgaactcca ggacttcaga   3960
aatgtgccac tgcaagtggg aattctgcca ggttgcgagc cttgtcacaa gaaagtttgt   4020
gtgcatggaa catgccatgc taccagccag tcaagcttta cctgtgagtg tgaaggagga   4080
tggactggac ccctctgtga tcaacaaact aatgacccgt gtctcggaaa taaatgtgtg   4140
catggtacct gcttgccgat caatgcattt tcatacagtt gtaaatgcct gcagggacat   4200
gggggagtcc tctgtgatga agaggaaatg ctgtttaacc cctgccaatc catcaggtgt   4260
aaacatggca aatgcaggct ttcaggactt gggaaaccat attgcgaatg cagcagcgga   4320
tacacggggg acagctgtga taaagaaatc tcttgtcgag gggaacgaat ccgagattac   4380
taccaaaagc agcaagggta tgctgcgtgc cagacgacca agaaggtatc gagactagaa   4440
tgtaaaggag gatgttcaac cgggcagtgc tgtggaccac taaggagcaa gagacggaaa   4500
```

tactcttttg aatgcactga tgggtcgtca tttgtggacg agattgaaaa agtggtgaag 4560
tgtggctgta caaattgtcc ctcctaa 4587

<210> SEQ ID NO 20
<211> LENGTH: 1528
<212> TYPE: PRT
<213> ORGANISM: Gallus gallus

<400> SEQUENCE: 20

Met Met Cys Ala Trp Gly Arg Leu Pro Leu Ala Leu Gly Leu Leu Leu
1 5 10 15

Val Leu Ala Gly Glu Ala Ala Pro Gln Pro Cys Pro Ala Gln Cys Ser
20 25 30

Cys Ser Gly Ser Thr Val Asp Cys His Gly Leu Ala Leu Arg Gly Val
35 40 45

Pro Arg Asn Ile Pro Arg Asn Thr Glu Arg Leu Asp Leu Asn Gly Asn
50 55 60

Asn Ile Thr Arg Ile Thr Lys Thr Asp Phe Ala Gly Leu Arg His Leu
65 70 75 80

Arg Val Leu Gln Leu Met Glu Asn Lys Ile Ser Thr Ile Glu Arg Gly
85 90 95

Ala Phe Gln Asp Leu Lys Glu Leu Glu Arg Leu Arg Leu Asn Arg Asn
100 105 110

Asn Leu Gln Leu Leu Ser Glu Leu Leu Phe Leu Gly Thr Pro Lys Leu
115 120 125

Tyr Arg Leu Asp Leu Ser Glu Asn Gln Ile Gln Ala Ile Pro Arg Lys
130 135 140

Ala Phe Arg Gly Ala Val Asp Ile Lys Asn Leu Gln Leu Asp Tyr Asn
145 150 155 160

Gln Ile Ser Cys Ile Glu Asp Gly Ala Phe Arg Ala Leu Arg Asp Leu
165 170 175

Glu Val Leu Thr Leu Asn Asn Asn Asn Ile Thr Arg Leu Ser Val Ala
180 185 190

Ser Phe Asn His Met Pro Lys Leu Arg Thr Phe Arg Leu His Ser Asn
195 200 205

Asn Leu Tyr Cys Asp Cys His Leu Ala Trp Leu Ser Asp Trp Leu Arg
210 215 220

Gln Arg Pro Arg Val Gly Leu Tyr Thr Gln Cys Met Gly Pro Ala His
225 230 235 240

Leu Arg Gly His Asn Val Ala Glu Val Gln Lys Arg Glu Phe Val Cys
245 250 255

Ser Gly His Gln Ser Phe Met Ala Pro Ser Cys Ser Val Leu His Cys
260 265 270

Pro Ala Ala Cys Thr Cys Ser Asn Asn Ile Val Asp Cys Arg Gly Lys
275 280 285

Gly Leu Thr Glu Ile Pro Thr Asn Leu Pro Glu Thr Ile Thr Glu Ile
290 295 300

Arg Leu Glu Gln Asn Ser Ile Lys Val Ile Pro Pro Gly Ala Phe Ser
305 310 315 320

Pro Tyr Lys Lys Leu Arg Arg Ile Asp Leu Ser Asn Asn Gln Ile Ser
325 330 335

Glu Ala Ala Pro Asp Ala Phe Gln Gly Leu Arg Ser Leu Asn Ser Leu
340 345 350

```
Val Leu Tyr Gly Asn Lys Ile Thr Glu Leu Pro Lys Gly Leu Phe Glu
        355                 360                 365

Gly Leu Phe Ser Leu Gln Leu Leu Leu Leu Asn Ala Asn Lys Ile Asn
    370                 375                 380

Cys Leu Arg Val Asp Ala Phe Gln Asp Leu His Asn Leu Asn Leu Leu
385                 390                 395                 400

Ser Leu Tyr Asp Asn Lys Leu Gln Thr Ile Ala Lys Gly Thr Phe Ser
                405                 410                 415

Pro Leu Arg Ala Ile Gln Thr Leu His Leu Ala Gln Asn Pro Phe Ile
            420                 425                 430

Cys Asp Cys His Leu Lys Trp Leu Ala Asp Tyr Leu His Thr Asn Pro
        435                 440                 445

Ile Glu Thr Ser Gly Ala Arg Cys Thr Ser Pro Arg Arg Leu Ala Asn
    450                 455                 460

Lys Arg Ile Gly Gln Ile Lys Ser Lys Lys Phe Arg Cys Ser Ala Lys
465                 470                 475                 480

Glu Gln Tyr Phe Ile Pro Gly Thr Glu Asp Tyr Arg Ser Lys Leu Ser
                485                 490                 495

Gly Asp Cys Phe Ala Asp Leu Ala Cys Pro Glu Lys Cys Arg Cys Glu
            500                 505                 510

Gly Thr Thr Val Asp Cys Ser Asn Gln Lys Leu Asn Lys Ile Pro Asp
        515                 520                 525

His Ile Pro Gln Tyr Thr Ala Glu Leu Arg Leu Asn Asn Asn Glu Phe
    530                 535                 540

Ser Val Leu Glu Ala Thr Gly Ile Phe Lys Lys Leu Pro Gln Leu Arg
545                 550                 555                 560

Lys Ile Asn Leu Ser Asn Asn Lys Ile Thr Asp Ile Glu Glu Gly Ala
                565                 570                 575

Phe Asp Gly Ala Ser Gly Val Asn Glu Leu Leu Leu Thr Ser Asn Arg
            580                 585                 590

Leu Glu Thr Val Arg Asp Lys Met Phe Lys Gly Leu Glu Ser Leu Lys
        595                 600                 605

Thr Leu Met Leu Arg Ser Asn Arg Val Ser Cys Val Gly Asn Asp Ser
    610                 615                 620

Phe Thr Gly Leu Ser Ser Val Arg Leu Leu Ser Leu Tyr Asp Asn Gln
625                 630                 635                 640

Ile Thr Thr Val Ala Pro Gly Ser Phe Asp Thr Leu His Ser Leu Ser
                645                 650                 655

Thr Leu Asn Leu Leu Ala Asn Pro Phe Asn Cys Asn Cys His Leu Ala
            660                 665                 670

Trp Leu Gly Asp Trp Leu Arg Lys Lys Arg Ile Val Thr Gly Asn Pro
        675                 680                 685

Arg Cys Gln Lys Pro Tyr Phe Leu Lys Glu Ile Pro Ile Gln Asp Val
    690                 695                 700

Ala Ile Gln Asp Phe Thr Cys Asp Asp Gly Asn Asp Asp Asn Ser Cys
705                 710                 715                 720

Ser Pro Leu Ser Arg Cys Pro Ala Glu Cys Thr Cys Leu Asp Thr Val
                725                 730                 735

Val Arg Cys Ser Asn Lys Gly Leu Lys Ala Leu Pro Lys Gly Ile Pro
            740                 745                 750

Lys Asp Val Thr Glu Leu Tyr Leu Asp Gly Asn Gln Phe Thr Leu Val
        755                 760                 765

Pro Lys Glu Leu Ser Asn Tyr Lys His Leu Thr Leu Ile Asp Leu Ser
```

```
    770                 775                 780

Asn Asn Arg Ile Ser Thr Leu Ser Asn Gln Ser Phe Ser Asn Met Thr
785                 790                 795                 800

Gln Leu Leu Thr Leu Ile Leu Ser Tyr Asn Arg Leu Arg Cys Ile Pro
                805                 810                 815

Ala Arg Thr Phe Asp Gly Leu Lys Ser Leu Arg Leu Leu Ser Leu His
            820                 825                 830

Gly Asn Asp Ile Ser Val Val Pro Glu Gly Ala Phe Asn Asp Leu Ser
        835                 840                 845

Ala Leu Ser His Leu Ala Ile Gly Ala Asn Pro Leu Tyr Cys Asp Cys
    850                 855                 860

Asn Met Gln Trp Leu Ser Asp Trp Val Lys Ser Glu Tyr Lys Glu Pro
865                 870                 875                 880

Gly Ile Ala Arg Cys Ala Gly Pro Gly Glu Met Ala Asp Lys Leu Leu
                885                 890                 895

Leu Thr Thr Pro Ser Lys Lys Phe Thr Cys Gln Gly Pro Val Asp Val
            900                 905                 910

Asn Ile Leu Ala Lys Cys Asn Pro Cys Leu Ser Asn Pro Cys Lys Asn
        915                 920                 925

Asp Gly Thr Cys Asn Asn Asp Pro Val Asp Phe Tyr Arg Cys Thr Cys
    930                 935                 940

Pro Tyr Gly Phe Lys Gly Gln Asp Cys Asp Ile Pro Ile His Ala Cys
945                 950                 955                 960

Ile Ser Asn Pro Cys Asn His Gly Gly Thr Cys His Leu Lys Glu Gly
                965                 970                 975

Glu Lys Asp Gly Phe Trp Cys Thr Cys Ala Asp Gly Phe Glu Gly Glu
            980                 985                 990

Asn Cys Glu Ile Asn Val Asp Asp  Cys Glu Asp Asn Asp  Cys Glu Asn
        995                 1000                1005

Asn Ser  Thr Cys Val Asp Gly  Ile Asn Asn Tyr Thr  Cys Leu Cys
    1010                 1015                 1020

Pro Pro  Glu Tyr Thr Gly Glu  Leu Cys Glu Glu Lys  Leu Asp Phe
    1025                 1030                 1035

Cys Ala  Gln Asn Leu Asn Pro  Cys Gln His Asp Ser  Lys Cys Ile
    1040                 1045                 1050

Leu Thr  Pro Lys Gly Tyr Lys  Cys Asp Cys Thr Pro  Gly Tyr Val
    1055                 1060                 1065

Gly Glu  His Cys Asp Ile Asp  Phe Asp Asp Cys Gln  Asp Asn Lys
    1070                 1075                 1080

Cys Lys  Asn Gly Ala Gln Cys  Thr Asp Ala Val Asn  Gly Tyr Thr
    1085                 1090                 1095

Cys Ile  Cys Pro Glu Gly Tyr  Ser Gly Leu Phe Cys  Glu Phe Ser
    1100                 1105                 1110

Pro Pro  Met Val Leu Pro Arg  Thr Ser Pro Cys Asp  Asn Tyr Glu
    1115                 1120                 1125

Cys Gln  Asn Gly Ala Gln Cys  Ile Val Lys Glu Ser  Glu Pro Ile
    1130                 1135                 1140

Cys Gln  Cys Leu Ser Gly Tyr  Gln Gly Glu Lys Cys  Glu Lys Leu
    1145                 1150                 1155

Ile Ser  Ile Asn Phe Val Asn  Lys Glu Ser Tyr Leu  Gln Ile Pro
    1160                 1165                 1170

Ser Ala  Lys Ile His Ser Gln  Thr Asn Ile Thr Leu  Gln Ile Ala
    1175                 1180                 1185
```

-continued

Thr Asp Glu Asp Ser Gly Ile Leu Leu Tyr Lys Gly Asp Lys Asp
1190 1195 1200

His Ile Ala Val Glu Leu Tyr Arg Gly Arg Val Arg Val Ser Tyr
1205 1210 1215

Asp Thr Gly Ser Tyr Pro Ala Ser Ala Ile Tyr Ser Val Glu Thr
1220 1225 1230

Ile Asn Asp Gly Asn Phe His Ile Val Glu Leu Leu Ala Met Asp
1235 1240 1245

Gln Ile Leu Ser Leu Ser Ile Asp Gly Gly Ser Pro Lys Ile Ile
1250 1255 1260

Thr Asn Leu Ser Lys Gln Ser Thr Leu Asn Phe Asp Ser Pro Leu
1265 1270 1275

Tyr Val Gly Gly Met Pro Val Lys Asn Asn Ile Ala Ala Leu Arg
1280 1285 1290

Gln Ser Pro Gly Gln Asn Gly Thr Ser Phe His Gly Cys Ile Arg
1295 1300 1305

Asn Leu Tyr Ile Asn Ser Glu Leu Gln Asp Phe Arg Asn Val Pro
1310 1315 1320

Leu Gln Val Gly Ile Leu Pro Gly Cys Glu Pro Cys His Lys Lys
1325 1330 1335

Val Cys Val His Gly Thr Cys His Ala Thr Ser Gln Ser Ser Phe
1340 1345 1350

Thr Cys Glu Cys Glu Gly Gly Trp Thr Gly Pro Leu Cys Asp Gln
1355 1360 1365

Gln Thr Asn Asp Pro Cys Leu Gly Asn Lys Cys Val His Gly Thr
1370 1375 1380

Cys Leu Pro Ile Asn Ala Phe Ser Tyr Ser Cys Lys Cys Leu Gln
1385 1390 1395

Gly His Gly Gly Val Leu Cys Asp Glu Glu Glu Met Leu Phe Asn
1400 1405 1410

Pro Cys Gln Ser Ile Arg Cys Lys His Gly Lys Cys Arg Leu Ser
1415 1420 1425

Gly Leu Gly Lys Pro Tyr Cys Glu Cys Ser Ser Gly Tyr Thr Gly
1430 1435 1440

Asp Ser Cys Asp Lys Glu Ile Ser Cys Arg Gly Glu Arg Ile Arg
1445 1450 1455

Asp Tyr Tyr Gln Lys Gln Gln Gly Tyr Ala Ala Cys Gln Thr Thr
1460 1465 1470

Lys Lys Val Ser Arg Leu Glu Cys Lys Gly Gly Cys Ser Thr Gly
1475 1480 1485

Gln Cys Cys Gly Pro Leu Arg Ser Lys Arg Arg Lys Tyr Ser Phe
1490 1495 1500

Glu Cys Thr Asp Gly Ser Ser Phe Val Asp Glu Ile Glu Lys Val
1505 1510 1515

Val Lys Cys Gly Cys Thr Asn Cys Pro Ser
1520 1525

<210> SEQ ID NO 21
<211> LENGTH: 1088
<212> TYPE: PRT
<213> ORGANISM: Homo sapiens

<400> SEQUENCE: 21

Gln Ala Cys Pro Ala Gln Cys Ser Cys Ser Gly Ser Thr Val Asp Cys

-continued

```
1               5                   10                  15

His Gly Leu Ala Leu Arg Ser Val Pro Arg Asn Ile Pro Arg Asn Thr
            20                  25                  30

Glu Arg Leu Asp Leu Asn Gly Asn Asn Ile Thr Arg Ile Thr Lys Ile
        35                  40                  45

Asp Phe Ala Gly Leu Arg His Leu Arg Val Leu Gln Leu Met Glu Asn
    50                  55                  60

Arg Ile Ser Thr Ile Glu Arg Gly Ala Phe Gln Asp Leu Lys Glu Leu
65                  70                  75                  80

Glu Arg Leu Arg Leu Asn Arg Asn Asn Leu Gln Leu Phe Pro Glu Leu
                85                  90                  95

Leu Phe Leu Gly Thr Ala Lys Leu Tyr Arg Leu Asp Leu Ser Glu Asn
            100                 105                 110

Gln Ile Gln Ala Ile Pro Arg Lys Ala Phe Arg Gly Ala Val Asp Ile
        115                 120                 125

Lys Asn Leu Gln Leu Asp Tyr Asn Gln Ile Ser Cys Ile Glu Asp Gly
    130                 135                 140

Ala Phe Arg Ala Leu Arg Asp Leu Glu Val Leu Thr Leu Asn Asn Asn
145                 150                 155                 160

Asn Ile Thr Arg Leu Ser Val Ala Ser Phe Asn His Met Pro Lys Leu
                165                 170                 175

Arg Thr Phe Arg Leu His Ser Asn Asn Leu Tyr Cys Asp Cys His Leu
            180                 185                 190

Ala Trp Leu Ser Asp Trp Leu Arg Gln Arg Pro Arg Val Gly Leu Tyr
        195                 200                 205

Thr Gln Cys Met Gly Pro Ser His Leu Arg Gly His Asn Val Ala Glu
    210                 215                 220

Val Gln Lys Arg Glu Phe Val Cys Ser Gly His Gln Ser Phe Met Ala
225                 230                 235                 240

Pro Ser Cys Ser Val Leu His Cys Pro Ala Ala Cys Thr Cys Ser Asn
                245                 250                 255

Asn Ile Val Asp Cys Arg Gly Lys Gly Leu Thr Glu Ile Pro Thr Asn
            260                 265                 270

Leu Pro Glu Thr Ile Thr Glu Ile Arg Leu Glu Gln Asn Ser Ile Arg
        275                 280                 285

Val Ile Pro Pro Gly Ala Phe Ser Pro Tyr Lys Lys Leu Arg Arg Leu
    290                 295                 300

Asp Leu Ser Asn Asn Gln Ile Ser Glu Leu Ala Pro Asp Ala Phe Gln
305                 310                 315                 320

Gly Leu Arg Ser Leu Asn Ser Leu Val Leu Tyr Gly Asn Lys Ile Thr
                325                 330                 335

Glu Leu Pro Lys Ser Leu Phe Glu Gly Leu Phe Ser Leu Gln Leu Leu
            340                 345                 350

Leu Leu Asn Ala Asn Lys Ile Asn Cys Leu Arg Val Asp Ala Phe Gln
        355                 360                 365

Asp Leu His Asn Leu Asn Leu Leu Ser Leu Tyr Asp Asn Lys Leu Gln
    370                 375                 380

Thr Val Ala Lys Gly Thr Phe Ser Ala Leu Arg Ala Ile Gln Thr Met
385                 390                 395                 400

His Leu Ala Gln Asn Pro Phe Ile Cys Asp Cys His Leu Lys Trp Leu
                405                 410                 415

Ala Asp Tyr Leu His Thr Asn Pro Ile Glu Thr Ser Gly Ala Arg Cys
            420                 425                 430
```

-continued

```
Thr Ser Pro Arg Arg Leu Ala Asn Lys Arg Ile Gly Gln Ile Lys Ser
        435                 440                 445

Lys Lys Phe Arg Cys Ser Gly Thr Glu Asp Tyr Arg Ser Lys Leu Ser
    450                 455                 460

Gly Asp Cys Phe Ala Asp Leu Ala Cys Pro Glu Lys Cys Arg Cys Glu
465                 470                 475                 480

Gly Thr Thr Val Asp Cys Ser Asn Gln Arg Leu Asn Lys Ile Pro Asp
                485                 490                 495

His Ile Pro Gln Tyr Thr Ala Glu Leu Arg Leu Asn Asn Asn Glu Phe
            500                 505                 510

Thr Val Leu Glu Ala Thr Gly Ile Phe Lys Lys Leu Pro Gln Leu Arg
        515                 520                 525

Lys Ile Asn Phe Ser Asn Asn Lys Ile Thr Asp Ile Glu Glu Gly Ala
    530                 535                 540

Phe Glu Gly Ala Ser Gly Val Asn Glu Ile Leu Leu Thr Ser Asn Arg
545                 550                 555                 560

Leu Glu Asn Val Gln His Lys Met Phe Lys Gly Leu Glu Ser Leu Lys
                565                 570                 575

Thr Leu Met Leu Arg Ser Asn Arg Ile Ser Cys Val Gly Asn Asp Ser
            580                 585                 590

Phe Ile Gly Leu Gly Ser Val Arg Leu Leu Ser Leu Tyr Asp Asn Gln
        595                 600                 605

Ile Thr Thr Val Ala Pro Gly Ala Phe Asp Ser Leu His Ser Leu Ser
    610                 615                 620

Thr Leu Asn Leu Leu Ala Asn Pro Phe Asn Cys Asn Cys His Leu Ala
625                 630                 635                 640

Trp Leu Gly Glu Trp Leu Arg Arg Lys Arg Ile Val Thr Gly Asn Pro
                645                 650                 655

Arg Cys Gln Lys Pro Tyr Phe Leu Lys Glu Ile Pro Ile Gln Asp Val
            660                 665                 670

Ala Ile Gln Asp Phe Thr Cys Asp Asp Gly Asn Asp Asp Asn Ser Cys
        675                 680                 685

Ser Pro Leu Ser Arg Cys Pro Ser Glu Cys Thr Cys Leu Asp Thr Val
    690                 695                 700

Val Arg Cys Ser Asn Lys Gly Leu Lys Val Leu Pro Lys Gly Ile Pro
705                 710                 715                 720

Lys Asp Val Thr Glu Leu Tyr Leu Asp Gly Asn Gln Phe Thr Leu Val
                725                 730                 735

Pro Lys Glu Leu Ser Asn Tyr Lys His Leu Thr Leu Ile Asp Leu Ser
            740                 745                 750

Asn Asn Arg Ile Ser Thr Leu Ser Asn Gln Ser Phe Ser Asn Met Thr
        755                 760                 765

Gln Leu Leu Thr Leu Ile Leu Ser Tyr Asn Arg Leu Arg Cys Ile Pro
    770                 775                 780

Pro Arg Thr Phe Asp Gly Leu Lys Ser Leu Arg Leu Leu Ser Leu His
785                 790                 795                 800

Gly Asn Asp Ile Ser Val Val Pro Glu Gly Ala Phe Asn Asp Leu Ser
                805                 810                 815

Ala Leu Ser His Leu Ala Ile Gly Ala Asn Pro Leu Tyr Cys Asp Cys
            820                 825                 830

Asn Met Gln Trp Leu Ser Asp Trp Val Lys Ser Glu Tyr Lys Glu Pro
        835                 840                 845
```

-continued

```
Gly Ile Ala Arg Cys Ala Gly Pro Gly Glu Met Ala Asp Lys Leu Leu
    850                 855                 860

Leu Thr Thr Pro Ser Lys Lys Phe Thr Cys Gln Gly Pro Val Asp Ile
865                 870                 875                 880

Thr Ile Gln Ala Lys Cys Asn Pro Cys Leu Ser Asn Pro Cys Lys Asn
                885                 890                 895

Asp Gly Thr Cys Asn Asn Asp Pro Val Asp Phe Tyr Arg Cys Thr Cys
            900                 905                 910

Pro Tyr Gly Phe Lys Gly Gln Asp Cys Asp Val Pro Ile His Ala Cys
        915                 920                 925

Ile Ser Asn Pro Cys Lys His Gly Gly Thr Cys His Leu Lys Glu Gly
    930                 935                 940

Glu Asn Ala Gly Phe Trp Cys Thr Cys Ala Asp Gly Phe Glu Gly Glu
945                 950                 955                 960

Asn Cys Glu Val Asn Ile Asp Asp Cys Glu Asp Asn Asp Cys Glu Asn
                965                 970                 975

Asn Ser Thr Cys Val Asp Gly Ile Asn Asn Tyr Thr Cys Leu Cys Pro
            980                 985                 990

Pro Glu Tyr Thr Gly Glu Leu Cys  Glu Glu Lys Leu Asp  Phe Cys Ala
        995                 1000                1005

Gln Asp  Leu Asn Pro Cys Gln  His Asp Ser Lys Cys  Ile Leu Thr
    1010                1015                1020

Pro Lys  Gly Phe Lys Cys Asp  Cys Thr Pro Gly Tyr  Ile Gly Glu
    1025                1030                1035

His Cys  Asp Ile Asp Phe Asp  Asp Cys Gln Asp Asn  Lys Cys Lys
    1040                1045                1050

Asn Gly  Ala His Cys Thr Asp  Ala Val Asn Gly Tyr  Thr Cys Val
    1055                1060                1065

Cys Pro  Glu Gly Tyr Ser Gly  Leu Phe Cys Glu Phe  Ser Pro Pro
    1070                1075                1080

Met Val  Leu Pro Arg
    1085
```

<210> SEQ ID NO 22
<211> LENGTH: 408
<212> TYPE: PRT
<213> ORGANISM: Homo sapiens

<400> SEQUENCE: 22

```
Thr Ser Pro Cys Asp Asn Phe Asp Cys Gln Asn Gly Ala Gln Cys Ile
1               5                   10                  15

Ile Arg Ile Asn Glu Pro Ile Cys Gln Cys Leu Pro Gly Tyr Leu Gly
            20                  25                  30

Glu Lys Cys Glu Lys Leu Val Ser Val Asn Phe Val Asn Lys Glu Ser
        35                  40                  45

Tyr Leu Gln Ile Pro Ser Ala Lys Val Arg Pro Gln Thr Asn Ile Thr
    50                  55                  60

Leu Gln Ile Ala Thr Asp Glu Asp Ser Gly Ile Leu Leu Tyr Lys Gly
65                  70                  75                  80

Asp Lys Asp His Ile Ala Val Glu Leu Tyr Arg Gly Arg Val Arg Ala
                85                  90                  95

Ser Tyr Asp Thr Gly Ser His Pro Ala Ser Ala Ile Tyr Ser Val Glu
            100                 105                 110

Thr Ile Asn Asp Gly Asn Phe His Ile Val Glu Leu Leu Thr Leu Asp
        115                 120                 125
```

Ser Ser Leu Ser Leu Ser Val Asp Gly Gly Ser Pro Lys Val Ile Thr
130 135 140

Asn Leu Ser Lys Gln Ser Thr Leu Asn Phe Asp Ser Pro Leu Tyr Val
145 150 155 160

Gly Gly Met Pro Gly Lys Asn Asn Val Ala Ser Leu Arg Gln Ala Pro
165 170 175

Gly Gln Asn Gly Thr Ser Phe His Gly Cys Ile Arg Asn Leu Tyr Ile
180 185 190

Asn Ser Glu Leu Gln Asp Phe Arg Lys Met Pro Met Gln Thr Gly Ile
195 200 205

Leu Pro Gly Cys Glu Pro Cys His Lys Lys Val Cys Ala His Gly Met
210 215 220

Cys Gln Pro Ser Ser Gln Ser Gly Phe Thr Cys Glu Cys Glu Glu Gly
225 230 235 240

Trp Met Gly Pro Leu Cys Asp Gln Arg Thr Asn Asp Pro Cys Leu Gly
245 250 255

Asn Lys Cys Val His Gly Thr Cys Leu Pro Ile Asn Ala Phe Ser Tyr
260 265 270

Ser Cys Lys Cys Leu Glu Gly His Gly Gly Val Leu Cys Asp Glu Glu
275 280 285

Glu Asp Leu Phe Asn Pro Cys Gln Met Ile Lys Cys Lys His Gly Lys
290 295 300

Cys Arg Leu Ser Gly Val Gly Gln Pro Tyr Cys Glu Cys Asn Ser Gly
305 310 315 320

Phe Thr Gly Asp Ser Cys Asp Arg Glu Ile Ser Cys Arg Gly Glu Arg
325 330 335

Ile Arg Asp Tyr Tyr Gln Lys Gln Gln Gly Tyr Ala Ala Cys Gln Thr
340 345 350

Thr Lys Lys Val Ser Arg Leu Glu Cys Arg Gly Gly Cys Ala Gly Gly
355 360 365

Gln Cys Cys Gly Pro Leu Arg Ser Lys Arg Arg Lys Tyr Ser Phe Glu
370 375 380

Cys Thr Asp Gly Ser Ser Phe Val Asp Glu Val Glu Lys Val Val Lys
385 390 395 400

Cys Gly Cys Ala Arg Cys Ala Ser
405

<210> SEQ ID NO 23
<211> LENGTH: 9
<212> TYPE: PRT
<213> ORGANISM: Artificial Sequence
<220> FEATURE:
<223> OTHER INFORMATION: /note="Description of Artificial Sequence:
(Gly)4Ala(Gly)4 linker"

<400> SEQUENCE: 23

Gly Gly Gly Gly Ala Gly Gly Gly Gly
1 5

<210> SEQ ID NO 24
<211> LENGTH: 21
<212> TYPE: DNA
<213> ORGANISM: Artificial Sequence
<220> FEATURE:
<223> OTHER INFORMATION: /note="Description of Artificial Sequence:
Synthetic primer"

<400> SEQUENCE: 24
tgttcctctt aatcctgccc a 21

<210> SEQ ID NO 25
<211> LENGTH: 21
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 25
ccaacctgca caagttccct t 21

<210> SEQ ID NO 26
<211> LENGTH: 20
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 26
gatctggtgg aacgaggcaa 20

<210> SEQ ID NO 27
<211> LENGTH: 20
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 27
cttcgggttc tggaggcttg 20

<210> SEQ ID NO 28
<211> LENGTH: 22
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 28
gcccaactgt gacttccatt aa 22

<210> SEQ ID NO 29
<211> LENGTH: 21
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 29
gtagcactcc cctcgagtga t 21

<210> SEQ ID NO 30
<211> LENGTH: 23
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 30
aaggtgaaga gcatcataac cct 23

<210> SEQ ID NO 31
<211> LENGTH: 23
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 31
tcacgccttt cataacacat tcc 23

<210> SEQ ID NO 32
<211> LENGTH: 22
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 32
cagcacattt atcccggtgt ac 22

<210> SEQ ID NO 33
<211> LENGTH: 20
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 33
aaatgccgcc atccacatag 20

<210> SEQ ID NO 34
<211> LENGTH: 20
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 34
cacaatgcag gaaaggatca 20

<210> SEQ ID NO 35
<211> LENGTH: 20
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 35
ggtcatcagc aggcacatag 20

<210> SEQ ID NO 36
<211> LENGTH: 22
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 36
acttttggtg ttgttctggg aa 22

<210> SEQ ID NO 37
<211> LENGTH: 20
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 37
gcatgaacag gatctcaggc 20

<210> SEQ ID NO 38
<211> LENGTH: 22
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 38
tctggtagtg tcctgctcac ag 22

<210> SEQ ID NO 39
<211> LENGTH: 20
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 39
tcgtaacggc caaaacaaat 20

<210> SEQ ID NO 40
<211> LENGTH: 20
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 40
acgctggtgc tctatgcaag 20

<210> SEQ ID NO 41
<211> LENGTH: 21
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 41
tcagttgctg cccattcatc a 21

<210> SEQ ID NO 42
<211> LENGTH: 21
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 42
aaggctgggt gaagaccctt a 21

<210> SEQ ID NO 43
<211> LENGTH: 21
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 43
tgaatggccg tttctggaag t 21

<210> SEQ ID NO 44
<211> LENGTH: 21
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 44
tgctcttctg tatcgcccag t 21

<210> SEQ ID NO 45
<211> LENGTH: 21
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 45
gccgtgttaa ggaatctgct g 21

<210> SEQ ID NO 46
<211> LENGTH: 20
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 46
gccgactaaa tcaagcaaca 20

<210> SEQ ID NO 47
<211> LENGTH: 20
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 47
caatgggcat aaagctatgg 20

<210> SEQ ID NO 48
<211> LENGTH: 19
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 48
gcacatggga gtgttgtga 19

<210> SEQ ID NO 49
<211> LENGTH: 20
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 49
ccttctcctt ctccttcagc 20

<210> SEQ ID NO 50
<211> LENGTH: 20
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 50
gggtcacacg agacagatga 20

<210> SEQ ID NO 51
<211> LENGTH: 21
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 51
ggaaccagat catagccaac a 21

<210> SEQ ID NO 52
<211> LENGTH: 20
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 52
gaaccatgaa gtcaacgact 20

<210> SEQ ID NO 53
<211> LENGTH: 20
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 53
gcgaagttca cagtggttcc 20

<210> SEQ ID NO 54
<211> LENGTH: 20
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 54
catttattat cgcggcccta 20

<210> SEQ ID NO 55

<211> LENGTH: 20
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 55
tgttgggttg tttgatcctg 20

<210> SEQ ID NO 56
<211> LENGTH: 19
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 56
ggagatggca caggaggaa 19

<210> SEQ ID NO 57
<211> LENGTH: 19
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 57
gcccgtagtg cttcagctt 19

<210> SEQ ID NO 58
<211> LENGTH: 23
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 58
cagtgtggtg cacgtctcca atc 23

<210> SEQ ID NO 59
<211> LENGTH: 21
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 59
tgaaccaaag ttgaccacca g 21

<210> SEQ ID NO 60
<211> LENGTH: 20
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 60
cctgtaaccc cagaactcca 20

<210> SEQ ID NO 61
<211> LENGTH: 20

-continued

<212> TYPE: DNA
<213> ORGANISM: Artificial Sequence
<220> FEATURE:
<223> OTHER INFORMATION: /note="Description of Artificial Sequence:
Synthetic primer"

<400> SEQUENCE: 61
cagatgagca aaggtgcaaa 20

<210> SEQ ID NO 62
<211> LENGTH: 21
<212> TYPE: DNA
<213> ORGANISM: Artificial Sequence
<220> FEATURE:
<223> OTHER INFORMATION: /note="Description of Artificial Sequence:
Synthetic primer"

<400> SEQUENCE: 62
tccgcgttct catgtaggtc t 21

<210> SEQ ID NO 63
<211> LENGTH: 21
<212> TYPE: DNA
<213> ORGANISM: Artificial Sequence
<220> FEATURE:
<223> OTHER INFORMATION: /note="Description of Artificial Sequence:
Synthetic primer"

<400> SEQUENCE: 63
ggacctgatg caaccctatg a 21

<210> SEQ ID NO 64
<211> LENGTH: 19
<212> TYPE: DNA
<213> ORGANISM: Artificial Sequence
<220> FEATURE:
<223> OTHER INFORMATION: /note="Description of Artificial Sequence:
Synthetic primer"

<400> SEQUENCE: 64
gcagggcagt gggaagcta 19

<210> SEQ ID NO 65
<211> LENGTH: 21
<212> TYPE: DNA
<213> ORGANISM: Artificial Sequence
<220> FEATURE:
<223> OTHER INFORMATION: /note="Description of Artificial Sequence:
Synthetic primer"

<400> SEQUENCE: 65
cctcttgaag aaggctttgc a 21

<210> SEQ ID NO 66
<211> LENGTH: 22
<212> TYPE: DNA
<213> ORGANISM: Artificial Sequence
<220> FEATURE:
<223> OTHER INFORMATION: /note="Description of Artificial Sequence:
Synthetic primer"

<400> SEQUENCE: 66
ccacttctcc tgagtttaca gc 22

<210> SEQ ID NO 67
<211> LENGTH: 23
<212> TYPE: DNA

<213> ORGANISM: Artificial Sequence
<220> FEATURE:
<223> OTHER INFORMATION: /note="Description of Artificial Sequence:
      Synthetic primer"

<400> SEQUENCE: 67
gcattttaac cgaacatctg tcc 23

<210> SEQ ID NO 68
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 68
aggtggtgat agccggtatg t 21

<210> SEQ ID NO 69
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 69
tgggtaatcc atagagccca g 21

<210> SEQ ID NO 70
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 70
gacctggtct tgtgctctcc 20

<210> SEQ ID NO 71
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 71
gggatgactg gtgttggagg 20

<210> SEQ ID NO 72
<211> LENGTH: 19
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 72
gggctgccag gttctagtc 19

<210> SEQ ID NO 73
<211> LENGTH: 18
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 73
cctccgaggt ccttctca 18

<210> SEQ ID NO 74
<211> LENGTH: 16
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 74
agagtctaaa gcgcct 16

<210> SEQ ID NO 75
<211> LENGTH: 16
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 75
ccgagaccaa cgtgaa 16

<210> SEQ ID NO 76
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 76
gctggaggag tgtttttttg c 21

<210> SEQ ID NO 77
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 77
agttgaacca agcaggtcac a 21

<210> SEQ ID NO 78
<211> LENGTH: 19
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 78
gagacccctg tgtcggttc 19

<210> SEQ ID NO 79
<211> LENGTH: 22
<212> TYPE: DNA
<213> ORGANISM: Artificial Sequence
<220> FEATURE:

<223> OTHER INFORMATION: /note="Description of Artificial Sequence:
Synthetic primer"

<400> SEQUENCE: 79
ctgcgtgtgt gaaatgtcat tg 22

<210> SEQ ID NO 80
<211> LENGTH: 20
<212> TYPE: DNA
<213> ORGANISM: Artificial Sequence
<220> FEATURE:
<223> OTHER INFORMATION: /note="Description of Artificial Sequence:
Synthetic primer"

<400> SEQUENCE: 80
aggagtgtcg acttcgcaaa 20

<210> SEQ ID NO 81
<211> LENGTH: 21
<212> TYPE: DNA
<213> ORGANISM: Artificial Sequence
<220> FEATURE:
<223> OTHER INFORMATION: /note="Description of Artificial Sequence:
Synthetic primer"

<400> SEQUENCE: 81
ctcttcttgc cgcttcagtt t 21

<210> SEQ ID NO 82
<211> LENGTH: 19
<212> TYPE: DNA
<213> ORGANISM: Artificial Sequence
<220> FEATURE:
<223> OTHER INFORMATION: /note="Description of Artificial Sequence:
Synthetic primer"

<400> SEQUENCE: 82
ctcccaccca cgcttacac 19

<210> SEQ ID NO 83
<211> LENGTH: 21
<212> TYPE: DNA
<213> ORGANISM: Artificial Sequence
<220> FEATURE:
<223> OTHER INFORMATION: /note="Description of Artificial Sequence:
Synthetic primer"

<400> SEQUENCE: 83
gccctaacct ctctccactc a 21

<210> SEQ ID NO 84
<211> LENGTH: 19
<212> TYPE: DNA
<213> ORGANISM: Artificial Sequence
<220> FEATURE:
<223> OTHER INFORMATION: /note="Description of Artificial Sequence:
Synthetic primer"

<400> SEQUENCE: 84
gggctgtgct gtctgttga 19

<210> SEQ ID NO 85
<211> LENGTH: 21
<212> TYPE: DNA
<213> ORGANISM: Artificial Sequence
<220> FEATURE:
<223> OTHER INFORMATION: /note="Description of Artificial Sequence:

Synthetic primer"

<400> SEQUENCE: 85
tgattccctt caggtaaggc a 21

<210> SEQ ID NO 86
<211> LENGTH: 21
<212> TYPE: DNA
<213> ORGANISM: Artificial Sequence
<220> FEATURE:
<223> OTHER INFORMATION: /note="Description of Artificial Sequence:
Synthetic primer"

<400> SEQUENCE: 86
ttacagcttt gggtccagac a 21

<210> SEQ ID NO 87
<211> LENGTH: 21
<212> TYPE: DNA
<213> ORGANISM: Artificial Sequence
<220> FEATURE:
<223> OTHER INFORMATION: /note="Description of Artificial Sequence:
Synthetic primer"

<400> SEQUENCE: 87
ggagttctcc ctttacagca c 21

<210> SEQ ID NO 88
<211> LENGTH: 20
<212> TYPE: DNA
<213> ORGANISM: Artificial Sequence
<220> FEATURE:
<223> OTHER INFORMATION: /note="Description of Artificial Sequence:
Synthetic primer"

<400> SEQUENCE: 88
gaactgccaa ccacagtcac 20

<210> SEQ ID NO 89
<211> LENGTH: 20
<212> TYPE: DNA
<213> ORGANISM: Artificial Sequence
<220> FEATURE:
<223> OTHER INFORMATION: /note="Description of Artificial Sequence:
Synthetic primer"

<400> SEQUENCE: 89
tttgttccac ctctccatca 20

<210> SEQ ID NO 90
<211> LENGTH: 22
<212> TYPE: DNA
<213> ORGANISM: Artificial Sequence
<220> FEATURE:
<223> OTHER INFORMATION: /note="Description of Artificial Sequence:
Synthetic primer"

<400> SEQUENCE: 90
gtgtgtactg ggaaggcatt ga 22

<210> SEQ ID NO 91
<211> LENGTH: 20
<212> TYPE: DNA
<213> ORGANISM: Artificial Sequence
<220> FEATURE:
<223> OTHER INFORMATION: /note="Description of Artificial Sequence:
Synthetic primer"

<400> SEQUENCE: 91
gccacgaggt tatggtgaca 20

<210> SEQ ID NO 92
<211> LENGTH: 21
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 92
caggatcgaa agcaagacag t 21

<210> SEQ ID NO 93
<211> LENGTH: 21
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 93
aagtcctctt ccgacatcca g 21

<210> SEQ ID NO 94
<211> LENGTH: 26
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 94
tgatgtgaat gacttggata cagaca 26

<210> SEQ ID NO 95
<211> LENGTH: 26
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 95
gctcattgtt gtactggttg gatatg 26

<210> SEQ ID NO 96
<211> LENGTH: 19
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 96
cagcacggtg aagccattc 19

<210> SEQ ID NO 97
<211> LENGTH: 17
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 97
gcgtgcatcc gcttgtg 17

<210> SEQ ID NO 98
<211> LENGTH: 20
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 98
gtgagtgtgc ccaggtatgc 20

<210> SEQ ID NO 99
<211> LENGTH: 19
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 99
cgacaggttg caccacttc 19

<210> SEQ ID NO 100
<211> LENGTH: 20
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 100
ccagaaggca cagcagtctt 20

<210> SEQ ID NO 101
<211> LENGTH: 19
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 101
ccgacatcag gaagcgacc 19

<210> SEQ ID NO 102
<211> LENGTH: 20
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 102
ctgctccccg gatatgaacc 20

<210> SEQ ID NO 103
<211> LENGTH: 20
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 103
tagcatgcac tcacacctgg 20

<210> SEQ ID NO 104
<211> LENGTH: 21
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 104
gattctggtg cacttgtgct g 21

<210> SEQ ID NO 105
<211> LENGTH: 20
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 105
tgtgtattcc ggtgggcaaa 20

<210> SEQ ID NO 106
<211> LENGTH: 20
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 106
gctgtgaacc atgccacaag 20

<210> SEQ ID NO 107
<211> LENGTH: 21
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 107
cacacatttg tttccgaggc a 21

<210> SEQ ID NO 108
<211> LENGTH: 21
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 108
gcaacaccga gagactggat t 21

<210> SEQ ID NO 109
<211> LENGTH: 20
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 109
agatcctgga atgctcccct 20

<210> SEQ ID NO 110
<211> LENGTH: 20
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 110
ccacgctgat cctgagctac 20

<210> SEQ ID NO 111
<211> LENGTH: 20
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 111
gcactcggag ggatcttagc 20

<210> SEQ ID NO 112
<211> LENGTH: 20
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 112
ccacctgcaa gaccatcgac 20

<210> SEQ ID NO 113
<211> LENGTH: 21
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 113
ctggcgagcc ttagtttgga c 21

<210> SEQ ID NO 114
<211> LENGTH: 19
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 114
caggcggtgc ctatgtctc 19

<210> SEQ ID NO 115
<211> LENGTH: 22
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 115
cgatcacccc gaagttcagt ag 22

<210> SEQ ID NO 116
<211> LENGTH: 22
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 116
gtctcagagc aggataccaa gc 22

<210> SEQ ID NO 117
<211> LENGTH: 21
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 117
ctctcctcga ataccacagc c 21

<210> SEQ ID NO 118
<211> LENGTH: 19
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 118
cactgctttg ggagccttc 19

<210> SEQ ID NO 119
<211> LENGTH: 21
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 119
ggggcagcga ttcatttttc t 21

<210> SEQ ID NO 120
<211> LENGTH: 20
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 120
aagctgtgcg atgtccatgt 20

<210> SEQ ID NO 121
<211> LENGTH: 21
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 121
aagccacaaa ccctttgaaa a 21

<210> SEQ ID NO 122
<211> LENGTH: 20
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 122
aggcttcctg aggaccttta 20

<210> SEQ ID NO 123
<211> LENGTH: 21
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 123
tccttaggca agatctgatg c 21

<210> SEQ ID NO 124
<211> LENGTH: 25
<212> TYPE: PRT
<213> ORGANISM: Mus musculus

<400> SEQUENCE: 124

Met Ser Gly Ile Gly Trp Gln Thr Leu Ser Leu Ser Leu Gly Leu Val
1 5 10 15

Leu Ser Ile Leu Asn Lys Val Ala Pro
20 25

<210> SEQ ID NO 125
<211> LENGTH: 1521
<212> TYPE: PRT
<213> ORGANISM: Mus musculus

<400> SEQUENCE: 125

Met Ser Gly Ile Gly Trp Gln Thr Leu Ser Leu Ser Leu Gly Leu Val
1 5 10 15

Leu Ser Ile Leu Asn Lys Val Ala Pro Gln Ala Cys Pro Ala Gln Cys
20 25 30

Ser Cys Ser Gly Ser Thr Val Asp Cys His Gly Leu Ala Leu Arg Ser
35 40 45

Val Pro Arg Asn Ile Pro Arg Asn Thr Glu Arg Leu Asp Leu Asn Gly
50 55 60

Asn Asn Ile Thr Arg Ile Thr Lys Ile Asp Phe Ala Gly Leu Arg His
65 70 75 80

Leu Arg Val Leu Gln Leu Met Glu Asn Arg Ile Ser Thr Ile Glu Arg
85 90 95

Gly Ala Phe Gln Asp Leu Lys Glu Leu Glu Arg Leu Arg Leu Asn Arg
100 105 110

Asn Asn Leu Gln Leu Phe Pro Glu Leu Leu Phe Leu Gly Thr Ala Lys
115 120 125

Leu Tyr Arg Leu Asp Leu Ser Glu Asn Gln Ile Gln Ala Ile Pro Arg
130 135 140

Lys Ala Phe Arg Gly Ala Val Asp Ile Lys Asn Leu Gln Leu Asp Tyr
145 150 155 160

Asn Gln Ile Ser Cys Ile Glu Asp Gly Ala Phe Arg Ala Leu Arg Asp

```
                165                 170                 175

Leu Glu Val Leu Thr Leu Asn Asn Asn Asn Ile Thr Arg Leu Ser Val
            180                 185                 190

Ala Ser Phe Asn His Met Pro Lys Leu Arg Thr Phe Arg Leu His Ser
        195                 200                 205

Asn Asn Leu Tyr Cys Asp Cys His Leu Ala Trp Leu Ser Asp Trp Leu
    210                 215                 220

Arg Gln Arg Pro Arg Val Gly Leu Tyr Thr Gln Cys Met Gly Pro Ser
225                 230                 235                 240

His Leu Arg Gly His Asn Val Ala Glu Val Gln Lys Arg Glu Phe Val
                245                 250                 255

Cys Ser Gly His Gln Ser Phe Met Ala Pro Ser Cys Ser Val Leu His
            260                 265                 270

Cys Pro Ala Ala Cys Thr Cys Ser Asn Asn Ile Val Asp Cys Arg Gly
        275                 280                 285

Lys Gly Leu Thr Glu Ile Pro Thr Asn Leu Pro Glu Thr Ile Thr Glu
    290                 295                 300

Ile Arg Leu Glu Gln Asn Ser Ile Arg Val Ile Pro Pro Gly Ala Phe
305                 310                 315                 320

Ser Pro Tyr Lys Lys Leu Arg Arg Leu Asp Leu Ser Asn Asn Gln Ile
                325                 330                 335

Ser Glu Leu Ala Pro Asp Ala Phe Gln Gly Leu Arg Ser Leu Asn Ser
            340                 345                 350

Leu Val Leu Tyr Gly Asn Lys Ile Thr Glu Leu Pro Lys Ser Leu Phe
        355                 360                 365

Glu Gly Leu Phe Ser Leu Gln Leu Leu Leu Leu Asn Ala Asn Lys Ile
    370                 375                 380

Asn Cys Leu Arg Val Asp Ala Phe Gln Asp Leu His Asn Leu Asn Leu
385                 390                 395                 400

Leu Ser Leu Tyr Asp Asn Lys Leu Gln Thr Val Ala Lys Gly Thr Phe
                405                 410                 415

Ser Ala Leu Arg Ala Ile Gln Thr Met His Leu Ala Gln Asn Pro Phe
            420                 425                 430

Ile Cys Asp Cys His Leu Lys Trp Leu Ala Asp Tyr Leu His Thr Asn
        435                 440                 445

Pro Ile Glu Thr Ser Gly Ala Arg Cys Thr Ser Pro Arg Arg Leu Ala
    450                 455                 460

Asn Lys Arg Ile Gly Gln Ile Lys Ser Lys Lys Phe Arg Cys Ser Gly
465                 470                 475                 480

Thr Glu Asp Tyr Arg Ser Lys Leu Ser Gly Asp Cys Phe Ala Asp Leu
                485                 490                 495

Ala Cys Pro Glu Lys Cys Arg Cys Glu Gly Thr Thr Val Asp Cys Ser
            500                 505                 510

Asn Gln Arg Leu Asn Lys Ile Pro Asp His Ile Pro Gln Tyr Thr Ala
        515                 520                 525

Glu Leu Arg Leu Asn Asn Asn Glu Phe Thr Val Leu Glu Ala Thr Gly
    530                 535                 540

Ile Phe Lys Lys Leu Pro Gln Leu Arg Lys Ile Asn Phe Ser Asn Asn
545                 550                 555                 560

Lys Ile Thr Asp Ile Glu Glu Gly Ala Phe Glu Gly Ala Ser Gly Val
                565                 570                 575

Asn Glu Ile Leu Leu Thr Ser Asn Arg Leu Glu Asn Val Gln His Lys
            580                 585                 590
```

```
Met Phe Lys Gly Leu Glu Ser Leu Lys Thr Leu Met Leu Arg Ser Asn
        595                 600                 605

Arg Ile Ser Cys Val Gly Asn Asp Ser Phe Ile Gly Leu Gly Ser Val
    610                 615                 620

Arg Leu Leu Ser Leu Tyr Asp Asn Gln Ile Thr Thr Val Ala Pro Gly
625                 630                 635                 640

Ala Phe Asp Ser Leu His Ser Leu Ser Thr Leu Asn Leu Leu Ala Asn
                645                 650                 655

Pro Phe Asn Cys Asn Cys His Leu Ala Trp Leu Gly Glu Trp Leu Arg
            660                 665                 670

Arg Lys Arg Ile Val Thr Gly Asn Pro Arg Cys Gln Lys Pro Tyr Phe
        675                 680                 685

Leu Lys Glu Ile Pro Ile Gln Asp Val Ala Ile Gln Asp Phe Thr Cys
    690                 695                 700

Asp Asp Gly Asn Asp Asp Asn Ser Cys Ser Pro Leu Ser Arg Cys Pro
705                 710                 715                 720

Ser Glu Cys Thr Cys Leu Asp Thr Val Val Arg Cys Ser Asn Lys Gly
                725                 730                 735

Leu Lys Val Leu Pro Lys Gly Ile Pro Lys Asp Val Thr Glu Leu Tyr
            740                 745                 750

Leu Asp Gly Asn Gln Phe Thr Leu Val Pro Lys Glu Leu Ser Asn Tyr
        755                 760                 765

Lys His Leu Thr Leu Ile Asp Leu Ser Asn Asn Arg Ile Ser Thr Leu
    770                 775                 780

Ser Asn Gln Ser Phe Ser Asn Met Thr Gln Leu Leu Thr Leu Ile Leu
785                 790                 795                 800

Ser Tyr Asn Arg Leu Arg Cys Ile Pro Pro Arg Thr Phe Asp Gly Leu
                805                 810                 815

Lys Ser Leu Arg Leu Leu Ser Leu His Gly Asn Asp Ile Ser Val Val
            820                 825                 830

Pro Glu Gly Ala Phe Asn Asp Leu Ser Ala Leu Ser His Leu Ala Ile
        835                 840                 845

Gly Ala Asn Pro Leu Tyr Cys Asp Cys Asn Met Gln Trp Leu Ser Asp
    850                 855                 860

Trp Val Lys Ser Glu Tyr Lys Glu Pro Gly Ile Ala Arg Cys Ala Gly
865                 870                 875                 880

Pro Gly Glu Met Ala Asp Lys Leu Leu Leu Thr Thr Pro Ser Lys Lys
                885                 890                 895

Phe Thr Cys Gln Gly Pro Val Asp Ile Thr Ile Gln Ala Lys Cys Asn
            900                 905                 910

Pro Cys Leu Ser Asn Pro Cys Lys Asn Asp Gly Thr Cys Asn Asn Asp
        915                 920                 925

Pro Val Asp Phe Tyr Arg Cys Thr Cys Pro Tyr Gly Phe Lys Gly Gln
    930                 935                 940

Asp Cys Asp Val Pro Ile His Ala Cys Ile Ser Asn Pro Cys Lys His
945                 950                 955                 960

Gly Gly Thr Cys His Leu Lys Glu Gly Glu Asn Ala Gly Phe Trp Cys
                965                 970                 975

Thr Cys Ala Asp Gly Phe Glu Gly Glu Asn Cys Glu Val Asn Ile Asp
            980                 985                 990

Asp Cys Glu Asp Asn Asp Cys Glu  Asn Asn Ser Thr Cys  Val Asp Gly
        995                 1000                 1005
```

```
Ile Asn  Asn Tyr Thr Cys Leu  Cys Pro Pro Glu Tyr  Thr Gly Glu
    1010                 1015                 1020

Leu Cys  Glu Glu Lys Leu Asp  Phe Cys Ala Gln Asp  Leu Asn Pro
    1025                 1030                 1035

Cys Gln  His Asp Ser Lys Cys  Ile Leu Thr Pro Lys  Gly Phe Lys
    1040                 1045                 1050

Cys Asp  Cys Thr Pro Gly Tyr  Ile Gly Glu His Cys  Asp Ile Asp
    1055                 1060                 1065

Phe Asp  Asp Cys Gln Asp Asn  Lys Cys Lys Asn Gly  Ala His Cys
    1070                 1075                 1080

Thr Asp  Ala Val Asn Gly Tyr  Thr Cys Val Cys Pro  Glu Gly Tyr
    1085                 1090                 1095

Ser Gly  Leu Phe Cys Glu Phe  Ser Pro Pro Met Val  Leu Pro Arg
    1100                 1105                 1110

Thr Ser  Pro Cys Asp Asn Phe  Asp Cys Gln Asn Gly  Ala Gln Cys
    1115                 1120                 1125

Ile Ile  Arg Ile Asn Glu Pro  Ile Cys Gln Cys Leu  Pro Gly Tyr
    1130                 1135                 1140

Leu Gly  Glu Lys Cys Glu Lys  Leu Val Ser Val Asn  Phe Val Asn
    1145                 1150                 1155

Lys Glu  Ser Tyr Leu Gln Ile  Pro Ser Ala Lys Val  Arg Pro Gln
    1160                 1165                 1170

Thr Asn  Ile Thr Leu Gln Ile  Ala Thr Asp Glu Asp  Ser Gly Ile
    1175                 1180                 1185

Leu Leu  Tyr Lys Gly Asp Lys  Asp His Ile Ala Val  Glu Leu Tyr
    1190                 1195                 1200

Arg Gly  Arg Val Arg Ala Ser  Tyr Asp Thr Gly Ser  His Pro Ala
    1205                 1210                 1215

Ser Ala  Ile Tyr Ser Val Glu  Thr Ile Asn Asp Gly  Asn Phe His
    1220                 1225                 1230

Ile Val  Glu Leu Leu Thr Leu  Asp Ser Ser Leu Ser  Leu Ser Val
    1235                 1240                 1245

Asp Gly  Gly Ser Pro Lys Val  Ile Thr Asn Leu Ser  Lys Gln Ser
    1250                 1255                 1260

Thr Leu  Asn Phe Asp Ser Pro  Leu Tyr Val Gly Gly  Met Pro Gly
    1265                 1270                 1275

Lys Asn  Asn Val Ala Ser Leu  Arg Gln Ala Pro Gly  Gln Asn Gly
    1280                 1285                 1290

Thr Ser  Phe His Gly Cys Ile  Arg Asn Leu Tyr Ile  Asn Ser Glu
    1295                 1300                 1305

Leu Gln  Asp Phe Arg Lys Met  Pro Met Gln Thr Gly  Ile Leu Pro
    1310                 1315                 1320

Gly Cys  Glu Pro Cys His Lys  Lys Val Cys Ala His  Gly Met Cys
    1325                 1330                 1335

Gln Pro  Ser Ser Gln Ser Gly  Phe Thr Cys Glu Cys  Glu Glu Gly
    1340                 1345                 1350

Trp Met  Gly Pro Leu Cys Asp  Gln Arg Thr Asn Asp  Pro Cys Leu
    1355                 1360                 1365

Gly Asn  Lys Cys Val His Gly  Thr Cys Leu Pro Ile  Asn Ala Phe
    1370                 1375                 1380

Ser Tyr  Ser Cys Lys Cys Leu  Glu Gly His Gly Gly  Val Leu Cys
    1385                 1390                 1395

Asp Glu  Glu Glu Asp Leu Phe  Asn Pro Cys Gln Met  Ile Lys Cys
```

```
    1400                1405                1410

Lys His  Gly Lys Cys Arg Leu  Ser Gly Val Gly Gln  Pro Tyr Cys
    1415                1420                1425

Glu Cys  Asn Ser Gly Phe Thr  Gly Asp Ser Cys Asp  Arg Glu Ile
    1430                1435                1440

Ser Cys  Arg Gly Glu Arg Ile  Arg Asp Tyr Tyr Gln  Lys Gln Gln
    1445                1450                1455

Gly Tyr  Ala Ala Cys Gln Thr  Thr Lys Lys Val Ser  Arg Leu Glu
    1460                1465                1470

Cys Arg  Gly Gly Cys Ala Gly  Gly Gln Cys Cys Gly  Pro Leu Arg
    1475                1480                1485

Ser Lys  Arg Arg Lys Tyr Ser  Phe Glu Cys Thr Asp  Gly Ser Ser
    1490                1495                1500

Phe Val  Asp Glu Val Glu Lys  Val Val Lys Cys Gly  Cys Ala Arg
    1505                1510                1515

Cys Ala  Ser
    1520


<210> SEQ ID NO 126
<211> LENGTH: 1523
<212> TYPE: PRT
<213> ORGANISM: Mus musculus

<400> SEQUENCE: 126

Met Ala Leu Gly Arg Thr Gly Ala Gly Ala Ala Val Arg Ala Arg Leu
1               5                   10                  15

Ala Leu Gly Leu Ala Leu Ala Ser Ile Leu Ser Gly Pro Pro Ala Ala
            20                  25                  30

Ala Cys Pro Thr Lys Cys Thr Cys Ser Ala Ala Ser Val Asp Cys His
        35                  40                  45

Gly Leu Gly Leu Arg Ala Val Pro Arg Gly Ile Pro Arg Asn Ala Glu
    50                  55                  60

Arg Leu Asp Leu Asp Arg Asn Asn Ile Thr Arg Ile Thr Lys Met Asp
65                  70                  75                  80

Phe Ala Gly Leu Lys Asn Leu Arg Val Leu His Leu Glu Asp Asn Gln
                85                  90                  95

Val Ser Ile Ile Glu Arg Gly Ala Phe Gln Asp Leu Lys Gln Leu Glu
            100                 105                 110

Arg Leu Arg Leu Asn Lys Asn Lys Leu Gln Val Leu Pro Glu Leu Leu
        115                 120                 125

Phe Gln Ser Thr Pro Lys Leu Thr Arg Leu Asp Leu Ser Glu Asn Gln
    130                 135                 140

Ile Gln Gly Ile Pro Arg Lys Ala Phe Arg Gly Val Thr Gly Val Lys
145                 150                 155                 160

Asn Leu Gln Leu Asp Asn Asn His Ile Ser Cys Ile Glu Asp Gly Ala
                165                 170                 175

Phe Arg Ala Leu Arg Asp Leu Glu Ile Leu Thr Leu Asn Asn Asn Asn
            180                 185                 190

Ile Ser Arg Ile Leu Val Thr Ser Phe Asn His Met Pro Lys Ile Arg
        195                 200                 205

Thr Leu Arg Leu His Ser Asn His Leu Tyr Cys Asp Cys His Leu Ala
    210                 215                 220

Trp Leu Ser Asp Trp Leu Arg Gln Arg Arg Thr Ile Gly Gln Phe Thr
225                 230                 235                 240
```

-continued

```
Leu Cys Met Ala Pro Val His Leu Arg Gly Phe Ser Val Ala Asp Val
                245                 250                 255

Gln Lys Lys Glu Tyr Val Cys Pro Gly Pro His Ser Glu Ala Pro Ala
            260                 265                 270

Cys Asn Ala Asn Ser Leu Ser Cys Pro Ser Ala Cys Ser Cys Ser Asn
        275                 280                 285

Asn Ile Val Asp Cys Arg Gly Lys Gly Leu Thr Glu Ile Pro Ala Asn
    290                 295                 300

Leu Pro Glu Gly Ile Val Glu Ile Arg Leu Glu Gln Asn Ser Ile Lys
305                 310                 315                 320

Ser Ile Pro Ala Gly Ala Phe Thr Gln Tyr Lys Lys Leu Lys Arg Ile
                325                 330                 335

Asp Ile Ser Lys Asn Gln Ile Ser Asp Ile Ala Pro Asp Ala Phe Gln
            340                 345                 350

Gly Leu Lys Ser Leu Thr Ser Leu Val Leu Tyr Gly Asn Lys Ile Thr
        355                 360                 365

Glu Ile Pro Lys Gly Leu Phe Asp Gly Leu Val Ser Leu Gln Leu Leu
    370                 375                 380

Leu Leu Asn Ala Asn Lys Ile Asn Cys Leu Arg Val Asn Thr Phe Gln
385                 390                 395                 400

Asp Leu Gln Asn Leu Asn Leu Leu Ser Leu Tyr Asp Asn Lys Leu Gln
                405                 410                 415

Thr Ile Ser Lys Gly Leu Phe Val Pro Leu Gln Ser Ile Gln Thr Leu
            420                 425                 430

His Leu Ala Gln Asn Pro Phe Val Cys Asp Cys His Leu Lys Trp Leu
        435                 440                 445

Ala Asp Tyr Leu Gln Asp Asn Pro Ile Glu Thr Ser Gly Ala Arg Cys
    450                 455                 460

Ser Ser Pro Arg Arg Leu Ala Asn Lys Arg Ile Ser Gln Ile Lys Ser
465                 470                 475                 480

Lys Lys Phe Arg Cys Ser Gly Ser Glu Asp Tyr Arg Asn Arg Phe Ser
                485                 490                 495

Ser Glu Cys Phe Met Asp Leu Val Cys Pro Glu Lys Cys Arg Cys Glu
            500                 505                 510

Gly Thr Ile Val Asp Cys Ser Asn Gln Lys Leu Ala Arg Ile Pro Ser
        515                 520                 525

His Leu Pro Glu Tyr Thr Thr Asp Leu Arg Leu Asn Asp Asn Asp Ile
    530                 535                 540

Ser Val Leu Glu Ala Thr Gly Ile Phe Lys Lys Leu Pro Asn Leu Arg
545                 550                 555                 560

Lys Ile Asn Leu Ser Asn Asn Arg Ile Lys Glu Val Arg Glu Gly Ala
                565                 570                 575

Phe Asp Gly Ala Ala Gly Val Gln Glu Leu Met Leu Thr Gly Asn Gln
            580                 585                 590

Leu Glu Thr Met His Gly Arg Met Phe Arg Gly Leu Ser Ser Leu Lys
        595                 600                 605

Thr Leu Met Leu Arg Ser Asn Leu Ile Ser Cys Val Ser Asn Asp Thr
    610                 615                 620

Phe Ala Gly Leu Ser Ser Val Arg Leu Leu Ser Leu Tyr Asp Asn Arg
625                 630                 635                 640

Ile Thr Thr Ile Thr Pro Gly Ala Phe Thr Thr Leu Val Ser Leu Ser
                645                 650                 655

Thr Ile Asn Leu Leu Ser Asn Pro Phe Asn Cys Asn Cys His Met Ala
```

```
            660                 665                 670

Trp Leu Gly Arg Trp Leu Arg Lys Arg Arg Ile Val Ser Gly Asn Pro
        675                 680                 685

Arg Cys Gln Lys Pro Phe Phe Leu Lys Glu Ile Pro Ile Gln Asp Val
    690                 695                 700

Ala Ile Gln Asp Phe Thr Cys Asp Gly Asn Glu Glu Ser Ser Cys Gln
705                 710                 715                 720

Leu Ser Pro Arg Cys Pro Glu Gln Cys Thr Cys Val Glu Thr Val Val
                725                 730                 735

Arg Cys Ser Asn Arg Gly Leu His Ala Leu Pro Lys Gly Met Pro Lys
            740                 745                 750

Asp Val Thr Glu Leu Tyr Leu Glu Gly Asn His Leu Thr Ala Val Pro
        755                 760                 765

Lys Glu Leu Ser Ala Phe Arg Gln Leu Thr Leu Ile Asp Leu Ser Asn
    770                 775                 780

Asn Ser Ile Ser Met Leu Thr Asn His Thr Phe Ser Asn Met Ser His
785                 790                 795                 800

Leu Ser Thr Leu Ile Leu Ser Tyr Asn Arg Leu Arg Cys Ile Pro Val
                805                 810                 815

His Ala Phe Asn Gly Leu Arg Ser Leu Arg Val Leu Thr Leu His Gly
            820                 825                 830

Asn Asp Ile Ser Ser Val Pro Glu Gly Ser Phe Asn Asp Leu Thr Ser
        835                 840                 845

Leu Ser His Leu Ala Leu Gly Thr Asn Pro Leu His Cys Asp Cys Ser
    850                 855                 860

Leu Arg Trp Leu Ser Glu Trp Val Lys Ala Gly Tyr Lys Glu Pro Gly
865                 870                 875                 880

Ile Ala Arg Cys Ser Ser Pro Glu Ser Met Ala Asp Arg Leu Leu Leu
                885                 890                 895

Thr Thr Pro Thr His Arg Phe Gln Cys Lys Gly Pro Val Asp Ile Asn
            900                 905                 910

Ile Val Ala Lys Cys Asn Ala Cys Leu Ser Ser Pro Cys Lys Asn Asn
        915                 920                 925

Gly Thr Cys Ser Gln Asp Pro Val Glu Gln Tyr Arg Cys Thr Cys Pro
    930                 935                 940

Tyr Ser Tyr Lys Gly Lys Asp Cys Thr Val Pro Ile Asn Thr Cys Val
945                 950                 955                 960

Gln Asn Pro Cys Glu His Gly Gly Thr Cys His Leu Ser Glu Asn Leu
                965                 970                 975

Arg Asp Gly Phe Ser Cys Ser Cys Pro Leu Gly Phe Glu Gly Gln Arg
            980                 985                 990

Cys Glu Ile Asn Pro Asp Asp Cys  Glu Asp Asn Asp Cys  Glu Asn Ser
        995                 1000                1005

Ala Thr  Cys Val Asp Gly Ile  Asn Asn Tyr Ala Cys  Leu Cys Pro
    1010                1015                1020

Pro Asn  Tyr Thr Gly Glu Leu  Cys Asp Glu Val Ile  Asp Tyr Cys
    1025                1030                1035

Val Pro  Glu Met Asn Leu Cys  Gln His Glu Ala Lys  Cys Ile Ser
    1040                1045                1050

Leu Asp  Lys Gly Phe Arg Cys  Glu Cys Val Pro Gly  Tyr Ser Gly
    1055                1060                1065

Lys Leu  Cys Glu Thr Asn Asn  Asp Asp Cys Val Ala  His Lys Cys
    1070                1075                1080
```

```
Arg His Gly Ala Gln Cys Val Asp Glu Val Asn Gly Tyr Thr Cys
    1085                1090                1095

Ile Cys Pro Gln Gly Phe Ser Gly Leu Phe Cys Glu His Pro Pro
    1100                1105                1110

Pro Met Val Leu Leu Gln Thr Ser Pro Cys Asp Gln Tyr Glu Cys
    1115                1120                1125

Gln Asn Gly Ala Gln Cys Ile Val Val Gln Gln Glu Pro Thr Cys
    1130                1135                1140

Arg Cys Pro Pro Gly Phe Ala Gly Pro Arg Cys Glu Lys Leu Ile
    1145                1150                1155

Thr Val Asn Phe Val Gly Lys Asp Ser Tyr Val Glu Leu Ala Ser
    1160                1165                1170

Ala Lys Val Arg Pro Gln Ala Asn Ile Ser Leu Gln Val Ala Thr
    1175                1180                1185

Asp Lys Asp Asn Gly Ile Leu Leu Tyr Lys Gly Asp Asn Asp Pro
    1190                1195                1200

Leu Ala Leu Glu Leu Tyr Gln Gly His Val Arg Leu Val Tyr Asp
    1205                1210                1215

Ser Leu Ser Ser Pro Pro Thr Thr Val Tyr Ser Val Glu Thr Val
    1220                1225                1230

Asn Asp Gly Gln Phe His Ser Val Glu Leu Val Met Leu Asn Gln
    1235                1240                1245

Thr Leu Asn Leu Val Val Asp Lys Gly Ala Pro Lys Ser Leu Gly
    1250                1255                1260

Lys Leu Gln Lys Gln Pro Ala Val Gly Ser Asn Ser Pro Leu Tyr
    1265                1270                1275

Leu Gly Gly Ile Pro Thr Ser Thr Gly Leu Ser Ala Leu Arg Gln
    1280                1285                1290

Gly Ala Asp Arg Pro Leu Gly Gly Phe His Gly Cys Ile His Glu
    1295                1300                1305

Val Arg Ile Asn Asn Glu Leu Gln Asp Phe Lys Ala Leu Pro Pro
    1310                1315                1320

Gln Ser Leu Gly Val Ser Pro Gly Cys Lys Ser Cys Thr Val Cys
    1325                1330                1335

Arg His Gly Leu Cys Arg Ser Val Glu Lys Asp Ser Val Val Cys
    1340                1345                1350

Glu Cys His Pro Gly Trp Thr Gly Pro Leu Cys Asp Gln Glu Ala
    1355                1360                1365

Arg Asp Pro Cys Leu Gly His Ser Cys Arg His Gly Thr Cys Met
    1370                1375                1380

Ala Thr Gly Asp Ser Tyr Val Cys Lys Cys Ala Glu Gly Tyr Gly
    1385                1390                1395

Gly Ala Leu Cys Asp Gln Lys Asn Asp Ser Ala Ser Ala Cys Ser
    1400                1405                1410

Ala Phe Lys Cys His His Gly Gln Cys His Ile Ser Asp Arg Gly
    1415                1420                1425

Glu Pro Tyr Cys Leu Cys Gln Pro Gly Phe Ser Gly His His Cys
    1430                1435                1440

Glu Gln Glu Asn Pro Cys Met Gly Glu Ile Val Arg Glu Ala Ile
    1445                1450                1455

Arg Arg Gln Lys Asp Tyr Ala Ser Cys Ala Thr Ala Ser Lys Val
    1460                1465                1470
```

```
Pro Ile  Met Glu Cys Arg Gly  Gly Cys Gly Ser Gln  Cys Cys Gln
    1475                 1480                 1485

Pro Ile  Arg Ser Lys Arg Arg  Lys Tyr Val Phe Gln  Cys Thr Asp
    1490                 1495                 1500

Gly Ser  Ser Phe Val Glu Glu  Val Glu Arg His Leu  Glu Cys Gly
    1505                 1510                 1515

Cys Arg  Ala Cys Ser
    1520

<210> SEQ ID NO 127
<211> LENGTH: 4
<212> TYPE: PRT
<213> ORGANISM: Artificial Sequence
<220> FEATURE:
<223> OTHER INFORMATION: /note="Description of Artificial Sequence:
      RRX(S/T) motif"
<220> FEATURE:
<221> NAME/KEY: misc_feature
<222> LOCATION: (3)..(3)
<223> OTHER INFORMATION: Xaa = any amino acid
<220> FEATURE:
<221> NAME/KEY: misc_feature
<222> LOCATION: (4)..(4)
<223> OTHER INFORMATION: Xaa = S or T

<400> SEQUENCE: 127

Arg Arg Xaa Xaa
1
```

METHODS FOR IDENTIFICATION, ASSESSMENT, PREVENTION, AND TREATMENT OF METABOLIC DISORDERS USING SLIT2

CROSS-REFERENCE TO RELATED APPLICATIONS

This application is a divisional of U.S. application Ser. No. 15/741,326, filed 2 Jan. 2018, which is the U.S. national phase of International Patent Application Serial No. PCT/US2016/042543, filed 15 Jul. 2016, which claims the benefit of priority from U.S. Provisional Application Ser. No. 62/193,359, filed 16 Jul. 2015, the entire contents of each of said applications are hereby incorporated herein in their entirety by this reference.

STATEMENT OF RIGHTS

This invention was made with government support under Grant DK031405 awarded by the National Institutes of Health. The U.S. government has certain rights in the invention.

SEQUENCE LISTING

The present specification makes reference to a Sequence Listing (submitted electronically as a .txt file named "DFS16002SequenceListing" on Feb. 28, 2022). The .txt file was generated on Feb. 18, 2020 and is 257,921 bytes in size. The entire contents of the Sequence Listing are herein incorporated by reference.

BACKGROUND OF THE INVENTION

Metabolic disorders comprise a collection of health disorders or risks that increase the risk of morbidity and loss of qualify of life. For example, diabetes, obesity, including central obesity (disproportionate fat tissue in and around the abdomen), atherogenic dyslipidemia (including a family of blood fat disorders, e.g., high triglycerides, low HDL cholesterol, and high LDL cholesterol that can foster plaque buildups in the vascular system, including artery walls), high blood pressure (130/85 mmHg or higher), insulin resistance or glucose intolerance (the inability to properly use insulin or blood sugar), a chronic prothrombotic state (e.g., characterized by high fibrinogen or plasminogen activator inhibitor-1 levels in the blood), and a chronic proinflammatory state (e.g., characterized by higher than normal levels of high-sensitivity C-reactive protein in the blood), are all metabolic disorders collectively afflicting greater than 50 million people in the United States.

Brown fat has attracted significant interest as an antidiabetic tissue owing to its ability to dissipate energy as heat (Cannon and Nedergaard (2004) *Physiol. Rev.* 84:277-359; Lowell and Spiegelman (2000) Nature 404:652-660). Activation of brown fat thermogenesis involves the induction of a program of genes, including uncoupling protein 1 (UCP1), which uncouples respiration and increases heat production in fat cells (Kozak and Harper (2000) *Annu. Rev. Nutr.* 20:339-363). Other non-UCP1 pathways may also contribute to non-shivering thermogenesis (Kazak et al. (2015) *Cell* 163:643-655). It is now recognized that at least two types of thermogenic fat cells exist—classical interscapular brown fat, as well as inducible brown-like adipocytes in white fat (also known as beige fat), which tends to be dispersed among white fat depots (Wu et al. (2012) *Cell* 150:366-376; Shinoda et al. (2015) *Nat. Med.* 4:389-394). BAT has high basal levels of UCP1, whereas beige fat has low basal levels that are highly inducible upon stimulation with cold or other agents (Wu et al. (2012) *Cell* 150:366-376). Despite their common ability to exhibit adaptive thermogenesis, brown and beige cells do not derive from the same lineage precursors (Lepper and Fan (2010) *Genesis* 48:424-436; Long et al. (2014) *Cell Metabolism* 19:810-820; Seale et al. (2008) *Nature* 454:961-967) and express different molecular signatures (Long et al. (2014) *Cell Metabolism* 19:810-820; Sharp et al. (2012) *PLoS One* 7:e49452; Wu et al. (2012) *Cell* 150:366-376; Harms and Seale (2013) *Nat. Med.* 19:1252-1263). Mouse models resistant to weight gain through enhanced brown and beige fat content or activity have demonstrated that activation of thermogenesis in fat can be a powerful strategy to improve metabolic health and prevent weight gain (Cederberg and Enerback (2003) *Curr. Mol. Med.* 3:107-125; Fisher et al. (2012) *Genes Dev.* 26:271-281; Vegiopoulos et al. (2010) *Science* 328:1158-1161; Ye et al. (2012) *Cell* 151:96-110). Ablation of UCP1+ cells in transgenic mice have an increased propensity toward obesity and diabetes (Lowell et al. (1993) *Nature* 366:740-742), whereas UCP1 knockout mice develop obesity under thermoneutrality conditions when fed a high fat diet (Feldmann et al. (2009) *Cell Metabolism* 9:203-209).

A physiological stimulus for inducing active thermogenic fat in mice and humans is a cold environment, which causes the release of neurotransmitters, such as catecholamines, from nerve terminals or M2 macrophages (Morrison et al. (2012) *Front. Endocrinol.* 3:5; Nguyen et al. (2011) *Nature* 480:103-108). Brown fat has relatively recently been found to exist and be functional in adult humans based on studies observing increased symmetrical glucose uptake in supraclavicular regions upon exposure to cold environment (Cypess et al. (2009) *N. Engl. J. Med.* 360:1509-1517; Virtanen et al. (2009) *N. Engl. J. Med.* 360:1518-1525; Yoneshiro et al. (2011) *Obesity* 19:13-16). Brown fat has also been shown to be activated by the 03-agonist, mirabegron, illustrating that the canonical cAMP pathway for adipose thermogenesis is likely to be function in humans and raising the possibility of additional, yet unknown pathways of activation (Cypess et al. (2014) *Cell Metab.* 21:33-38). The functional characteristics of human BAT has yet to be determined, but several papers have shown that supraclavicular human brown fat is most similar to the beige fat of rodents (Wu et al. (2012) *Cell* 150:366-376; Sharp et al. (2012) *PLoS ONE* 7:e49452; Shinoda et al. (2015) *Nat. Med.* 4:389-394). Thus, it is believed that brown and beige fat likely have complementary and overlapping functions in the maintenance of whole body energy homeostasis.

The transcriptional regulator PRDM16 is critical to the development of both brown and beige fat (Seale et al. (2007) *Cell Metabolism* 6:38-54; Seale et al. (2008) *Nature* 454:961-967; Kajimura et al. (2009) *Nature* 460:1154-1158; Seale et al. (2011) J. *Clin. Invest.* 121:96-105). Mice with fat-specific ablation of PRDM16 demonstrate significantly lower basal thermogenic gene expression in the subcutaneous fat: these animals are also resistant to browning of the white fat when stimulated with a cold environment or 03-agonism (Cohen et al. (2014) *Cell* 156:304-316). Conversely, aP2-PRDM16 transgenic mice show enhanced "browning" of their subcutaneous adipose depots, leading to augmented energy expenditure, reduced weight gain on high fat diet, and improved glucose and insulin homeostasis (Seale et al. (2011) *J. Clin. Invest.* 121:96-105). As the classical brown fat in this model was found to be relatively unaffected, adiponectin (aP)-driven deletion of PRDM16 mice provide the opportunity to specifically study beige fat function. These mice develop a moderate obese phenotype compared to littermate controls, which is accompanied by an expansion of the subcutaneous depots with increased infiltration of inflammatory immune cells.

Despite decades of scientific research, such factors have not been identified and few effective therapies have emerged to treat metabolic disorders. The various metabolic benefits of activating brown or beige fat have raised interest in the discovery of hormones and secreted proteins that can act on fat tissue locally or systemically to induce browning. Beige fat development occurs in distinct pockets of cells, consistent with the possibility of a paracrine regulatory factor at work. White adipose tissues secrete many proteins factors (adipokines) that influence local and systemic metabolism, including adipsin, adiponectin, leptin and TNFα (Rosen and Spiegelman (2014) *Cell.* 156:20-44; Blüher and Mantzoros (2015) *Metabolism.* 64:131.45). However, there is a great need to identify molecular regulators of metabolic disorders, especially those unknown secretory proteins from brown and/or beige fat. Such molecular regulators would also be useful in the generation of diagnostic, prognostic, and therapeutic agents to effectively control metabolic disorders in subjects.

SUMMARY OF THE INVENTION

The present invention is based in part on the discovery that Slit2 and biologically active fragments thereof are polypeptides secreted by beige fat cells that have the ability to modulate many metabolic processes, including modulating adipose thermogenesis, energy expenditure, and glucose homeostasis. Expression of Slit2 and its biologically active fragments is regulated by thermogenic stimuli (e.g., Prdm16 and cold exposure), their expression is downregulated in the white adipose tissue of obese animals, and they induce activation of PKA signaling, which is required for its pro-thermogenic activity. Slit2 and its biologically active fragments protect against diet-induced insulin resistance when circulating levels of Slit2 are increased in the blood, as it induces a thermogenic gene expression program in the subcutaneous white fat. Slit2 and its biologically active fragments act in a cell-autonomous manner to induce a cAMP cellular signaling program, induce thermogenic gene expression, and increase whole body energy expenditure. Based on this role in peripheral tissue for Slit and its biologically active fragments to modulate adipose tissue homeostasis and glucose metabolism, they have the therapeutic ability to treat metabolic disorders, especially obesity-induced metabolic disorders.

In one aspect, a use of an agent that modulates expression and/or activity of Slit2 or a biologically active fragment thereof in a subject for the preparation of a medicament for modulating a metabolic response in the subject is provided.

The compositions and methods of the present invention are characterized by many embodiments and each such embodiment can be applied to any combination of embodiments described herein. For example, in one embodiment, the expression and/or activity of Slit2 or the biologically active fragment thereof is upregulated. In another embodiment, expression and/or activity of Slit2 or the biologically active fragment thereof is upregulated using an agent selected from the group consisting of a nucleic acid molecule encoding a Slit2 polypeptide or fragment thereof, and a Slit2 polypeptide or fragment thereof. In still another embodiment, the medicament further comprises an additional agent that increases the metabolic response. In yet another embodiment, expression and/or activity of Slit2 or the biologically active fragment thereof is downregulated. In still another embodiment, expression and/or activity of Slit2 or the biologically active fragment thereof is downregulated using an agent selected from the group consisting of an anti-Slit2 antisense nucleic acid molecule, an anti-Slit2 RNA interference molecule, a blocking anti-Slit2 antibody, a non-activating form of Slit2 polypeptide or fragment thereof, and a small molecule that binds to Slit2. In yet another embodiment, the medicament further comprises an additional agent that decreases the metabolic response. In another embodiment, the metabolic response is selected from the group consisting of: a) modified expression of a marker selected from the group consisting of: cidea, adiponectin, adipsin, otopetrin, type II deiodinase, cig30, ppar gamma 2, pgc1α, ucp1, elovl3, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, dio2, fatty acid synthase (fas), leptin, resistin, and nuclear respiratory factor-1 (nrf1); b) modified thermogenesis in adipose cells; c) modified differentiation of adipose cells; d) modified insulin sensitivity of adipose cells; e) modified basal respiration or uncoupled respiration; f) modified whole body oxygen consumption; g) modified obesity or appetite; h) modified insulin secretion of pancreatic beta cells; i) modified glucose tolerance; j) modified phosphorylation of EGFR, ERK, AMPK, protein kinase A (PKA) substrates having an RRX(S/T) (SEQ ID NO: 127) motif, wherein the X is any amino acid and the (S/T) residue is a serine or threonine, HSL; and k) modified expression of UCP1 protein. In still another embodiment, the metabolic response is upregulated. In yet another embodiment, the metabolic response is downregulated.

In another aspect, a method for modulating a metabolic response comprising contacting a cell with an agent that modulates expression and/or activity of Slit2 or a biologically active fragment thereof to thereby modulate the metabolic response is provided.

As described above, the compositions and methods of the present invention are characterized by many embodiments and each such embodiment can be applied to any combination of embodiments described herein. For example, in one embodiment, expression and/or activity of Slit2 or the biologically active fragment thereof is upregulated. In another embodiment, expression and/or activity of Slit2 or the biologically active fragment thereof is upregulated using an agent selected from the group consisting of a nucleic acid molecule encoding a Slit2 polypeptide or fragment thereof, and a Slit2 polypeptide or fragment thereof. In still another embodiment, the method further comprises contacting the cell with an additional agent that increases the metabolic response. In yet another embodiment, expression and/or activity of Slit2 or the biologically active fragment thereof is downregulated. In another embodiment, expression and/or activity of Slit2 or the biologically active fragment thereof is downregulated using an agent selected from the group consisting of an anti-Slit2 antisense nucleic acid molecule, an anti-Slit2 RNA interference molecule, a blocking anti-Slit2 antibody, a non-activating form of Slit2 polypeptide or fragment thereof, and a small molecule that binds to Slit2. In still another embodiment, the method further comprises contacting the cell with an additional agent that decreases the metabolic response. In yet another embodiment, the step of contacting occurs in vivo. In another embodiment, the step of contacting occurs in vitro. In still another embodiment, the cell is selected from the group consisting of fibroblasts, adipoblasts, preadipocytes, adipocytes, white adipocytes, brown adipocytes, and beige adipocytes. In yet another embodiment, the metabolic response is selected from the group consisting of: a) modified expression of a marker selected from the group consisting of: cidea, adiponectin, adipsin, otopetrin, type II deiodinase, cig30, ppar gamma 2, pgc1α, ucp1, elovl3, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, dio2, fatty acid synthase (fas), leptin, resistin, and nuclear respiratory factor-1 (nrf1); b) modified thermogenesis in adipose cells; c) modified differentiation of adipose cells; d) modified insulin sensitivity of adipose cells; e) modified basal respiration or uncoupled respiration; f) modified whole body oxygen consumption; g) modified obesity or appetite; h) modified insulin secretion of pancreatic beta cells; i) modified glucose tolerance; j) modified phosphorylation of EGFR, ERK, AMPK, protein kinase A (PKA) substrates having an RRX(S/T) (SEQ ID NO: 127) motif, wherein the X is any amino acid and the (S/T) residue is a serine or threonine, HSL; and k) modified expression of UCP1 protein. In another embodiment, the metabolic response is upregulated. In still another embodiment, the metabolic response is downregulated.

In still another aspect, a method of preventing or treating a metabolic disorder in a subject comprising administering to the subject an agent that promotes expression and/or activity of Slit2 or a biologically active fragment thereof in the subject, thereby preventing or treating the metabolic disorder in the subject is provided. In one embodiment, the agent is selected from the group consisting of a nucleic acid molecule encoding a Slit2 polypeptide or fragment thereof, and a Slit2 polypeptide or fragment thereof. In another embodiment, the agent is administered by intravenous or subcutaneous injection. In still another embodiment, the agent is administered in a pharmaceutically acceptable formulation. In yet another embodiment, the metabolic disorder is selected from the group consisting of insulin resistance, hyperinsulinemia, hypoinsulinemia, type II diabetes, hypertension, hyperhepatosteatosis, hyperuricemia, fatty liver, non-alcoholic fatty liver disease, polycystic ovarian syndrome, acanthosis nigricans, hyperphagia, endocrine abnormalities, triglyceride storage disease, Bardet-Biedl syndrome, Lawrence-Moon syndrome, and Prader-Labhart-Willi syndrome. In another embodiment, the subject is a non-human animal or a human.

In yet another aspect, a method for preventing or treating a metabolic disorder in a subject comprising administering to the subject an agent that inhibits Slit2 expression and/or activity in the subject, thereby preventing or treating the metabolic disorder in the subject is provided. In one embodiment, the agent is selected from the group consisting of an anti-Slit2 antisense nucleic acid molecule, an anti-Slit2 RNA interference molecule, a blocking anti-Slit2 antibody, a non-activating form of Slit2 polypeptide or fragment thereof, and a small molecule that binds to Slit2. In another embodiment, the agent is administered by intravenous or subcutaneous injection. In still another embodiment, the agent is administered in a pharmaceutically acceptable formulation. In yet another embodiment, the metabolic disorder is selected from the group consisting of obesity-associated cancer, anorexia, and cachexia. In another embodiment, the subject is a non-human animal or a human.

In another aspect, a cell-based assay for screening for agents that modulate a metabolic response in a cell by modulating the expression and/or activity of Slit2 or a biologically active fragment comprising contacting the cell expressing Slit2 or the biologically active fragment thereof with a test agent the modulates the expression and/or activity of Slit2 and determining the ability of the test agent to modulate a metabolic response in the cell is provided.

In still another aspect, a method for assessing the efficacy of an agent that modulates Slit2 expression and/or activity for modulating a metabolic response in a subject, comprising a) detecting in a subject sample at a first point in time, the expression and/or activity of Slit2; b) repeating step a) during at least one subsequent point in time after administration of the agent; and c) comparing the expression and/or activity detected in steps a) and b), wherein a significantly lower expression and/or activity of a marker listed in Table 1 or 2 in the first subject sample relative to at least one subsequent subject sample, indicates that the agent increases the metabolic response in the subject and/or wherein a significantly higher expression and/or activity of a marker listed in Table 1 or 2 in the first subject sample relative to at least one subsequent subject sample, indicates that the test agent decreases the metabolic response in the subject is provided.

As described above, the compositions, assays, and methods of the present invention are characterized by many embodiments and each such embodiment can be applied to any combination of embodiments described herein. For example, in one embodiment, expression and/or activity of Slit2 or the biologically active fragment thereof is upregulated. In another embodiment, expression and/or activity of Slit2 or the biologically active fragment thereof is downregulated. In still another embodiment, the agent is selected from the group consisting of a nucleic acid molecule encoding a Slit2 polypeptide or fragment thereof, a Slit2 polypeptide or fragment thereof, a small molecule that binds to Slit2, an anti-Slit2 antisense nucleic acid molecule, an anti-Slit2 RNA interference molecule, an anti-Slit2 siRNA molecule, a blocking anti-Slit2 antibody, and a non-activating form of Slit2 polypeptide or fragment thereof. In yet another embodiment, the subject has undergone treatment for the metabolic disorder, has completed treatment for the metabolic disorder, and/or is in remission from the metabolic disorder between the first point in time and the subsequent point in time. In another embodiment, the first and/or at least one subsequent sample is selected from the group consisting of ex vivo and in vivo samples. In still another embodiment, the first and/or at least one subsequent sample is obtained from an animal model of a metabolic disorder. In yet another embodiment, the first and/or at least one subsequent sample is selected from the group consisting of tissue, whole blood, serum, plasma, buccal scrape, saliva, cerebrospinal fluid, urine, stool, and bone marrow. In another embodiment, the first and/or at least one subsequent sample is a portion of a single sample or pooled samples obtained from the subject. In still another embodiment, a significantly higher expression and/or activity comprises upregulating the expression and/or activity by at least 25% relative to the second sample. In yet another embodiment, a significantly lower expression and/or activity comprises downregulating the expression and/or activity by at least 25% relative to the second sample. In another embodiment, the amount of the marker is compared. In still another embodiment, the amount of the marker is determined by determining the level of protein expression of the marker. In yet another embodiment, the presence of the protein is detected using a reagent which specifically binds with the protein. In another embodiment, the reagent is selected from the group consisting of an antibody, an antibody derivative, and an antibody fragment. In still another embodiment, the level of expression of the marker in the sample is assessed by detecting the presence in the sample of a transcribed polynucleotide or portion thereof. In yet another embodiment, the transcribed polynucleotide is an mRNA or a cDNA. In another embodiment, the step of detecting further comprises amplifying the transcribed polynucleotide. In still another embodiment, the level of expression of the marker in the sample is assessed by detecting the presence in the sample of a transcribed polynucleotide which anneals with the marker or anneals with a portion of a polynucleotide under stringent hybridization conditions. In yet another embodiment, the metabolic response is selected from the group consisting of: a) modified expression of a marker selected from the group consisting of: cidea, adiponectin, adipsin, otopetrin, type II deiodinase, cig30, ppar gamma 2, pgc1α, ucp1, elovl3, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, dio2, fatty acid synthase (fas), leptin, resistin, and nuclear respiratory factor-1 (nrf1); b) modified thermogenesis in adipose cells; c) modified differentiation of adipose cells; d) modified insulin sensitivity of adipose cells; e) modified basal respiration or uncoupled respiration; f) modified whole body oxygen consumption; g) modified obesity or appetite; h) modified insulin secretion of pancreatic beta cells; i) modified glucose tolerance; j) modified phosphorylation of EGFR, ERK, AMPK, protein kinase A (PKA) substrates having an RRX(S/T) (SEQ ID NO: 127) motif, wherein the X is any amino acid and the (S/T) residue is a serine or threonine, HSL; and k) modified expression of UCP1 protein. In another embodiment, the metabolic response is upregulated. In still another embodiment, the metabolic response is downregulated. In yet another embodiment, Slit2 is selected from the group of Slit2 sequences shown in Table 1.

Figure 1A:
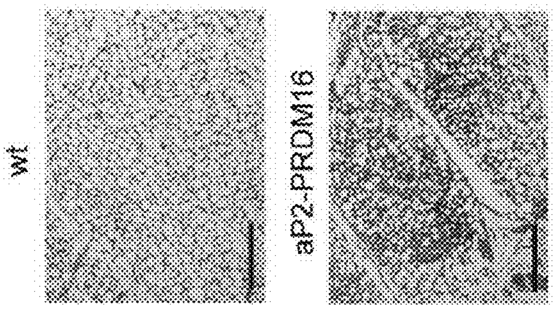
FIG. 1 includes 7 panels, identified as panels A, B, C, D, E, F, and G which show that Slit2 is a PRDM16-regulated secreted protein in adipose cells. Panel A representative images from UCP1 immunohistochemistry on sections of inguinal subcutaneous adipose tissue from aP2-PRDM16 and wild type mice. Images are shown at 10× magnification. Scale bar, 100 μm. Panel B shows normalized thermogenic gene expression in primary inguinal cells from aP2-PRDM16 and wild type mice at day 7 of differentiation. Panel C shows a heat map of relative protein levels in conditioned medium from wild type or ap2-PRDM16 primary inguinal cells (n=2 per group) as determined by TMT labeling and mass spectrometry. Shown is a short list of detected secreted proteins. The fold change for each individual sample is shade-coded according to the key. Panel D shows the normalized mRNA expression of Slit1, Slit2 and Slit3 in BAT and iWAT from 6 week-old mice chronically housed at 30° C. thermoneutrality (TN) or exposed to a 4° C. cold challenge for the indicated time points (n=3 per group). Gene expression of Ap2, Ucp1, Adipsin, F4/80, Slit2 and Slit3 in iWAT (Panel E) and Slit2 and Slit3 in eWAT (Panel F) from C57/b6 mice fed a chow diet or a high fat diet for 16 weeks is shown. Panel G shows primary inguinal cells treated with forskolin for 4 h before gene expression analysis of Adiponectin, Ucp1, Slit2 and Slit3. Data are presented as mean±SEM. * $p<0.05$,  $p<0.01$, * $p<0.001$.

Boxed immunoreactive bands were analyzed using mass spectrometry. Panel B shows matched peptides to Slit2-FL or Slit2-C (bold text) using C-terminal FLAG-tagged Slit2 overexpression in primary inguinal cells. Panel C shows a cloning scheme for Slit2 full-length protein, Slit2-N, and Slit2-C protein domains. Panel D shows the results of Western blotting of overexpressed LacZ, Slit2-N, and Slit2-C in primary inguinal cells detected with a V5 antibody. Panel E shows Western blotting results for V5-expression in liver tissue after 6 days post-injection with LacZ, Slit2-N, or Slit2-C adenovirus. Panel F shows Western blotting results of mouse plasma after 6 days post-injection with LacZ, Slit2-N or Slit2-C adenovirus.

FIG. 6 includes 8 panels, identified as panels A, B, C, D, E, F, G, and H, which show that Slit2-C is sufficient to recapitulate the thermogenic activity of full-length Slit2. Panels A and B show normalized thermogenic mRNA expression in primary inguinal cells (Panel A) or primary brown fat cells (Panel B) overexpressing Ad-Slit2-N, Ad-Slit2-C, or Ad-lacZ control. Panels C and D show thermogenic mRNA expression in iWAT (Panel C) and BAT (Panel D) in mice overexpressing LacZ or Slit2-C. Panel E shows representative images from UCP1 immunohistochemistry on sections of inguinal subcutaneous adipose tissue (upper panel) and BAT (lower panel) from mice injected with Slit2-C or LacZ control at day 7. Images are shown at 10× magnification. Scale bar, 100 μm. Panel F shows 02 consumption in inguinal white fat tissue (left panel) and brown fat tissue (right panel) from 6 week-old mice fed a chow diet. Animal number, n=10 per group. Data are presented as mean±SEM. * $p<0.05$,  $p<0.01$, * $p<0.001$. Panel G shows UCP1 immunohistochemistry of iWAT (upper panel) and BAT (lower panel) from mice injected with Slit2-C or LacZ at day 7. Scale bar, 100 μm. Panel H shows 02 consumption in iWAT (left panel) and BAT (right panel) from mice injected with Slit2-C or LacZ at day 7. n=10 per group. Data are presented as mean±SEM. * $p<0.05$,  $p<0.01$, * $p<0.001$.

FIG. 7 includes 4 panels, identified as panels A, B, C, and D, which further show that Slit2-C is sufficient to recapitulate the thermogenic activity of full-length Slit2. Panel A shows normalized mRNA expression of fatty acid synthase (fas) and hormone-sensitive lipase (hsl) in inguinal fat 7 days post-injection with LacZ or Slit2-C adenovirus in DIO mice. Panel B shows normalized mRNA expression of fatty acid synthase (fas), adipose triglyceride lipase (atgl), and hormone-sensitive lipase (hsl) in BAT 7 days post-injection with LacZ or Slit2-C adenovirus in DIO mice. Panel C shows normalized mRNA expression of white fat selective genes, resistin and leptin, in BAT 7 days post-injection with LacZ or Slit2-C adenovirus. Panel D shows Western blot of UCP1 protein (left) and quantification of UCP1 protein intensities relative tubulin (right) in BAT 7 days post-injection with LacZ or Slit2-C adenovirus in DIO mice.

FIG. 8 includes 9 panels, identified as panels A, B, C, D, E, F, G, H, and I, which show that increased circulating Slit2-C augments whole body energy expenditure and improves glucose homeostasis in obese mice. Panels A-E shows the results of whole body energy expenditure measured in DIO mice 6 days after injection with LacZ or Slit2-C adenovirus. Oxygen ($O_2$) consumption (Panel A), respiratory exchange ratio (Panel B), locomotor activity (Panel C), food intake (Panel D), and body weight (Panel E) were measured at day 7. Panel F shows tissue weights of brown fat (BAT), inguinal fat (Ing), and epididymal fat (Epi) at day 7 post-njection with LacZ or Slit2-C adenovirus. Panel G shows the results of intraperitoneal glucose tolerance tests in 16 weeks diet-induced obese mice injected with Slit2-C or LacZ performed at day 7 (n=9-10). Data are presented as mean±SEM. * $p<0.05$,  $p<0.01$, * $p<0.001$. Panel H shows averaged oxygen consumption at days 5-7 in mice with no significant different in body weight between the groups. Panel I shows tissue weights of BAT, iWAT and eWAT at day 7 post-injection with LacZ or Slit2-C adenovirus.

FIG. 9 includes 9 panels, identified as panels A, B, C, D, E, F, G, H, and I, which show that increased circulating full-length Slit2 (Slit2-FL) augments whole body energy expenditure and improves glucose homeostasis in obese mice. Panels A-E show the results of whole body energy expenditure measured in lean mice under 6 days after injection with with LacZ or Slit2-FL adenovirus. Oxygen ($O_2$) consumption (Panel A), respiratory exchange ratio (Panel B), food intake (Panel C), locomotor activity (Panel D), and body weight (Panel D) were measured at day 7. Panel F shows the results of intraperitoneal glucose tolerance tests in 16 weeks diet-induced obese mice injected with Slit2-FL or LacZ performed at day 7 (n=9-10). Panels G-I show plasma levels of total cholesterol (Panel G), triglycerides (Panel H), and non-fasting insulin (Panel I) in mice 7 days post-injection with LacZ or Slit2-C adenovirus.

FIG. 10 includes 14 panels, identified as panels A, B, C, D, E, F, G, H, I, J, K, L, M, and N, which show that Slit2-C induces a thermogenesis program through the protein kinase A (PKA) signaling pathway in adipocytes. Panels A and B show the results of primary inguinal cells treated with Slit2-C or LacZ control at day 2 of differentiation ($10^8$ pfu/well), starved overnight at day 6, and analyzed at day 7 by Western blotting for phosphorylated (phospho-) and total protein amounts of epidermal growth factor receptor (EGFR), ERK1/2, and AMPK (Panel A), as well as PKA substrates, HSL, UCP1, α-tubulin protein (Panel B). As a positive control, similar samples were treated with 100 nM NE for 30 minutes. Panels C and D show the results of primary inguinal cells treated with Slit2-C or LacZ control at day 2 of differentiation ($10^8$ pfu/well) and then treated with PKA inhibitor, H89 (30 μM), for 2 h before either Western blot analysis for PKA signaling (Panel C) or gene expression analysis for aP2, Ucp1, and Dio2 (Panel D). Panel E shows primary cells treated as in Panel A and blotted for phospho-and total ATGL and phosphorylated PKC substrates. Panel F shows quantification of UCP1 protein levels relative α-tubulin in Panel B, n=3. Panel G shows Western blot analysis for PKA substrate phosphorylation upon acute treatment (30 min) with conditioned medium from cells expressing LacZ, Slit2-FL or Slit2-C. Panels H and I show thermogenic gene expression in primary inguinal cells overexpressing Slit2-C or LacZ at day and treated with O-receptor antagonist propranolol (100 nM) for 24 h (Panel H) or adenylyl cyclase inhibitor SQ-22536 (10 μM) for 24 h (Panel I). Panel J shows silverstain of immunopurified Slit2-C FLAG protein compared with an albumin standard. Panel K shows Western blot of immunopurified Slit2-C FLAG protein using antibodies for FLAG or Slit2. Panel L shows cell surface binding of FLAG peptide or Slit2-C protein to primary inguinal adipocytes. Panel M shows treatment of primary inguinal cells with 20 nM NE or 20 nM Slit2-C protein for 0, 5, 15, 30, 60 and 90 min. Panel N shows normalized gene expression in primary inguinal cells after treatment with Slit2-C protein for 2 h. Comparisons are presented as Slit2-C vs. LacZ (*), LacZ vs. Slit2-C with drug treatment (#) or LacZ vs. drug treatment ($). Data are presented as mean±SEM. * $p<0.05$,  $p<0.01$, * $p<0.001$.

FIG. 11 includes 7 panels, identified as panels A, B, C, D, E, F, and G, which show that the EGFR and ERK pathways are activated by, but not required for, Slit2-C activity. Panel A shows the results of a phosphokinase array used to detect phosphorylated forms of proteins in LacZ or Slit2-C treated primary inguinal cells at day 7 of differentiation. Panel B show Western blot results of phosphorylated EGFR in response to increasing concentrations of EGFR tyrosine kinase inhibitors, erlotinib and lapatinib. Panel C shows normalized mRNA expression in primary inguinal cells treated with LacZ or Slit2-C adenovirus in the presence or absence of the EGFR inhibitors, erlotinib and lapatinib. Panel D shows normalized mRNA expression in primary inguinal cells treated with LacZ or Slit2-C adenovirus in the presence or absence of the ERK inhibitor, PD0325901. Panel E shows cell surface binding of either FLAG peptide, PM20D1 protein (100 nM) or Slit2-C protein (100 nM) to primary inguinal adipocytes. Panel F shows Western blot of phosphorylated PKA substrates after 60 min incubation with increasing concentrations of Slit2-C FLAG purified protein. Panel G shows quantification of phosphorylated PKA substrates in FIG. 6, Panel L after incubation with Slit2-C FLAG purified protein relative time point 0.

FIG. 12 includes 6 panels, identified as panels A, B, C, D, E, and F, which show that Slit2 promotes a thermogenesis program in cells and in mice. Panels A and B show normalized thermogenic mRNA expression (Panel A) and (Panel B) oxygen consumption measured by Seahorse in primary brown fat cells from Slit2$^{flox/flox}$ mice transduced with adenovirus expressing LacZ (Slit2$^{flox/flox}$) or CRE (Slit2$^{KO}$). Panel C shows total body weight in Slit2$^{flox/flox}$ mice infected with AAV8-GFP (Slit2$^{flox/flox}$-AAV8-GFP) or CRE virus (Slit2$^{flox/flox}$-AAV8-CRE) (n=8). Panels D-F show normalized mRNA expression of vascular and neuronal markers in BAT (Panel D), iWAT (Panel E) and quadriceps muscle (Panel F) 7 days postinjection with LacZ or Slit2-FL adenovirus.

Figure 13A:
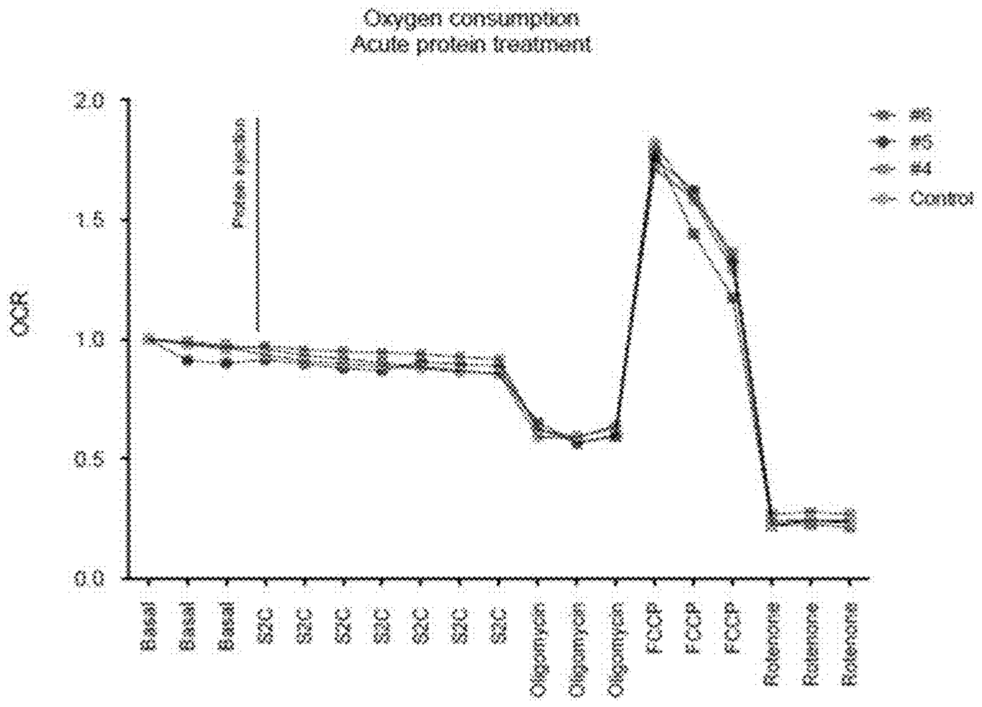
Figure 13B:
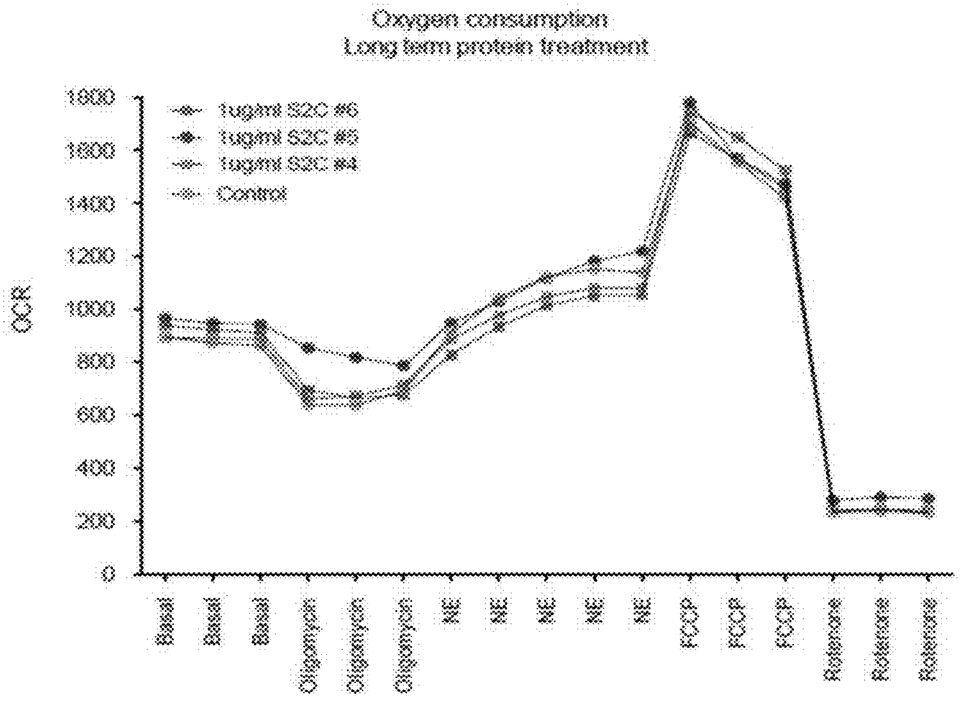
Figure 13C:
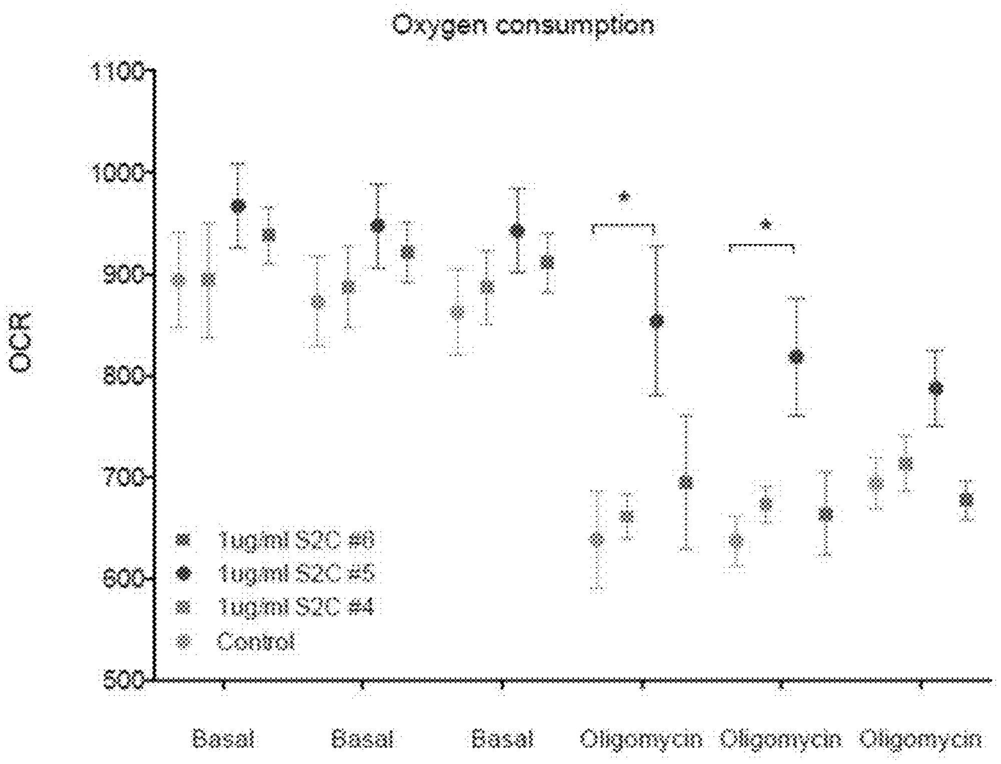

FIG. 13 includes 3 panels, identified as panels A, B, and C showing cellular oxygen consumption measured by Seahorse in primary inguinal fat cells after (Panel A) acute treatment (4 minutes) (Panel A) or long term treatment (2 h) (Panels B and C). Panel C shows statistical analysis of basal and oligomycin induced respiration shown in Panel B.

Note that for every figure containing a histogram, the bars from left to right for each discreet measurement correspond to the figure boxes from top to bottom in the figure legend as indicated.

DETAILED DESCRIPTION OF THE INVENTION

The present invention is based in part on the discovery that Slit2 and biologically active fragments thereof are secreted polypeptides that have the ability to modulate adipose thermogenesis and related metabolic activity (e.g., modulate one or more biological activities of a) brown fat and/or beige fat gene expression, such as expression of a marker selected from the group consisting of: cidea, adiponectin, adipsin, otopetrin, type II deiodinase, cig30, ppar gamma 2, pgc1α, ucp1, elovl3, cAMP, Prdml6, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, dio2, fatty acid synthase (fas), leptin, resistin, and nuclear respiratory factor-1 (nrf1); b) thermogenesis in adipose cells; c) differentiation of adipose cells; d) insulin sensitivity of adipose cells; e) basal respiration or uncoupled respiration; f) whole body oxygen consumption; g) obesity or appetite; h) insulin secretion of pancreatic beta cells; i) glucose tolerance; j) modified phosphorylation of EGFR, ERK, AMPK, protein kinase A (PKA) substrates having an RRX(S/T) (SEQ ID NO: 127) motif, wherein the X is any amino acid and the (S/T) residue is a serine or threonine, HSL; and k) modified expression of UCP1 protein.

It is demonstrated herein that Slit2 and its biologically active cleavage products are secreted by beige fat cells and can act systemically on cells in culture and in vivo to stimulate a broad program of brown fat-like development. Slit2 and its biologically active cleavage products is induced by natural stimuli, such as cold and Prdm16 gene expression, and they can cause an increase in energy expenditure in mice with no change in movement or food intake. This results in improvement in metabolic disorders (e.g., obesity and glucose homeostasis).

In order that the present invention may be more readily understood, certain terms are first defined. Additional definitions are set forth throughout the detailed description.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing. The names of the natural amino acids are abbreviated herein in accordance with the recommendations of IUPAC-IUB.

The term "antisense" nucleic acid refers to oligonucleotides which specifically hybridize (e.g., bind) under cellular conditions with a gene sequence, such as at the cellular mRNA and/or genomic DNA level, so as to inhibit expression of that gene, e.g., by inhibiting transcription and/or translation. The binding may be by conventional base pair complementarity, or, for example, in the case of binding to DNA duplexes, through specific interactions in the major groove of the double helix.

The terms "beige fat" or "brite (brown in white) fat" or "iBAT (induced brown adipose tissue)" or "recruitable BAT (brown adipose tissue)" or "wBAT (white adipose BAT)" refer to clusters of UCP1-expressing adipocytes having thermogenic capacity that develop in white adipose tissue (WAT). Beige fat can develop in subcutaneous WAT, such as in inguinal WAT, or in intra-abdominal WAT such as in epididymal WAT. Similar to adipocytes in brown adipose tissue (BAT), beige cells are characterized by a) multilocular lipid droplet morphology, b), high mitochondrial content, and/or c) expression of a core set of brown fat-specific genes, such as Ucp1, Cidea, Pgc1a, and other listed in Table 2. BAT and beige fat both are able to undergo thermogenesis, but these are distinct cell types since beige cells do not derive from Myf5 precursor cells like BAT cells, beige fat express thermogenic genes only in response to activators like beta-adrenergic receptor or PPARgamma agonists unlike constitutive expression in BAT cells (Harms and Seale (2013) *Nat. Med.* 19:1252-1263).

The term "binding" or "interacting" refers to an association, which may be a stable association, between two molecules, e.g., between a polypeptide of the invention and a binding partner, due to, for example, electrostatic, hydrophobic, ionic and/or hydrogen-bond interactions under physiological conditions. Exemplary interactions include protein-protein, protein-nucleic acid, protein-small molecule, and small molecule-nucleic acid interactions.

The term "biological sample" when used in reference to a diagnostic assay is intended to include tissues, cells and biological fluids isolated from a subject, as well as tissues, cells and fluids present within a subject.

The term "isolated polypeptide" refers to a polypeptide, in certain embodiments prepared from recombinant DNA or RNA, or of synthetic origin, or some combination thereof, which (1) is not associated with proteins that it is normally found within nature, (2) is isolated from the cell in which it normally occurs, (3) is isolated free of other proteins from the same cellular source, (4) is expressed by a cell from a different species, or (5) does not occur in nature.

The terms "label" or "labeled" refer to incorporation or attachment, optionally covalently or non-covalently, of a detectable marker into a molecule, such as a polypeptide. Various methods of labeling polypeptides are known in the art and may be used. Examples of labels for polypeptides include, but are not limited to, the following: radioisotopes, fluorescent labels, heavy atoms, enzymatic labels or reporter genes, chemiluminescent groups, biotinyl groups, predetermined polypeptide epitopes recognized by a secondary reporter (e.g., leucine zipper pair sequences, binding sites for secondary antibodies, metal binding domains, epitope tags). Examples and use of such labels are described in more detail below. In some embodiments, labels are attached by spacer arms of various lengths to reduce potential steric hindrance.

The terms "metabolic disorder" and "obesity related disorders" are used interchangeably herein and include a disorder, disease or condition which is caused or characterized by an abnormal or unwanted metabolism (i.e., the chemical changes in living cells by which energy is provided for vital processes and activities) in a subject. Metabolic disorders include diseases, disorders, or conditions associated with aberrant or unwanted (higher or lower) thermogenesis or aberrant or unwanted levels (high or low) adipose cell (e.g., brown or white adipose cell) content or function. Metabolic disorders can be characterized by a misregulation (e.g., downregulation or upregulation) of PGC-1 activity. Metabolic disorders can detrimentally affect cellular functions such as cellular proliferation, growth, differentiation, or migration, cellular regulation of homeostasis, inter- or intracellular communication; tissue function, such as liver function, muscle function, or adipocyte function; systemic responses in an organism, such as hormonal responses (e.g., insulin response). Examples of metabolic disorders include obesity, insulin resistance, type II diabetes, hypertension, hyperuricemia, fatty liver, non-alcoholic fatty liver disease, polycystic ovarian syndrome, acanthosis nigricans, hyperphagia, endocrine abnormalities, triglyceride storage disease, Bardet-Biedl syndrome, Lawrence-Moon syndrome, Prader-Labhart-Willi syndrome, anorexia, and cachexia.

As used herein, "obesity" refers to a body mass index (BMI) of 30 $kg/m^2$ or more (National Institute of Health, Clinical Guidelines on the Identification, Evaluation, and Treatment of Overweight and Obesity in Adults (1998)). However, the present invention is also intended to include a disease, disorder, or condition that is characterized by a body mass index (BMI) of 25 $kg/m^2$ or more, 26 $kg/m^2$ or more, 27 $kg/m^2$ or more, 28 $kg/m^2$ or more, 29 $kg/m^2$ or more, 29.5 $kg/m^2$ or more, or 29.9 $kg/m^2$ or more, all of which are typically referred to as overweight (National Institute of Health, Clinical Guidelines on the Identification, Evaluation, and Treatment of Overweight and Obesity in Adults (1998)). The obesity described herein may be due to any cause, whether genetic or environmental. Examples of disorders that may result in obesity or be the cause of obesity include overeating and bulimia, polycystic ovarian disease, craniopharyngioma, the Prader-Willi Syndrome, Frohlich's syndrome, Type II diabetics, GH-deficient subjects, normal variant short stature, Turner's syndrome, and other pathological conditions showing reduced metabolic activity or a decrease in resting energy expenditure as a percentage of total fat-free mass, e.g., children with acute lymphoblastic leukemia.

As used herein, the term "Slit2" refers to the Slit2 family member of the slit family of secreted proteins and is intended to include fragments, variants (e.g., allelic variants) and derivatives thereof unless otherwise specified. Slit proteins are secreted extracellular matrix proteins bound to the cell surface by the extracellular matrix (e.g., heparan sulfates) (Liang et al. (1999) *J. Biol. Chem.* 274:17885-17892; Ronca et al. (2001) *J. Biol. Chem.* 276:29141-29147). Slit proteins have four leucine-rich repeat (LRR) domains connected by disulfide bonds, followed by six epidermal growth factor (EGF) repeats, a beta-sandwich domain similar to that of laminin G called a LamG domain, one to three additional EGF repeats, and a C-terminal cysteine knot (Holmes et al. (1998) *Mech. Dev.* 79:57-72; Itoh et al. (1998) *Brain Res. Mol. Brain Res.* 62:175-186; Brose et al. (1999) *Cell* 96:795-806; Rothberg and Artavanis-Tsakonas (1992) *J. Mol. Biol.* 227:367-370; Hohenester et al. (1999) *Mol. Cell* 4:783-792; Nguyen-Ba-Carvet and Chedotal (2002) *Neuron* 22:463-473). Slit2 is proteolytically cleaved within the EGF domain region (Brose et al. (1999) *Cell* 96:795-806; Patel et al. (2001) *Development* 128:5031-5037; Condac et al. (2012) *Glycobiol.* 22:1183-1192. Following proteolytic cleavage of Slit2, the canonical 140 kDa N-terminal fragment remains associated with the cell surface, whereas the 50-60 kDa C-terminal fragment can be detected in conditioned cell media (Brose et al. (1999) *Cell* 96:795-806; Wang et al. (1999) *Cell* 96:771-784. Slit2 protein is known to interact with the transmembrane receptor Roundabout, also known as Robo, and is known to be involved in neuronal guidance, kidney development, blood cell migration, and osteoblast differentiation. However, Slit2 has not heretofore been implicated in the regulation of cellular metabolism. Mature slit proteins lack a signal sequence and Slit2 sequences of the present invention can comprise a signal sequence, as well as lack a signal sequence. The Slit2 signal sequence is generally the most N-terminal 20, 21, 22, 23, 24, 25, 26, 27, 28, 29, or 30 amino acids. In one embodiment, the Slit2 signal sequence is MSGIGWQTLSLSLGLVLSILNKVAP (SEQ ID NO: 124).

At least three splice variants encoding distinct human Slit2 isoforms exist. Slit2 isoform 1 (NM_004787.2 and NP_004778.1), also referred to as Slit2A, is the longest human Slit2 protein and is encoded by the longest transcript. Slit2 isoform 2 (NM_001289135.1 and NP_001276064.1), also referred to as Slit2C, lacks an alternate in-frame exon in the 5' coding region relative to the Slit2 transcript variant 1 and therefore encodes a smaller isoform relative to the Slit2 isoform 1. Slit2 isoform 3 (NM_001289136.1 and NP_001276065.1), also referred to as Slit2B, also lacks an alternate in-frame exon in the 5' coding region relative to the Slit2 transcript variant 1 and therefore encodes a smaller isoform relative to the Slit2 isoform 1. The nucleic acid and polypeptide sequences for each transcript variant and isoform is provided herein as SEQ ID NOs:1-6, respectively. Nucleic acid and polypeptide sequences of Slit2 orthologs in organisms other than humans are well known and include, for example, *Mus musculus* Slit2 (NM_001291227.1, NP 001278156.1, NM_001291228.1, NP_001278157.1, NM_178804.4, and NP_848919.3); *Rattus norvegicus* Slit2

(NM_022632.2 and NP_072154.2); *Canis lupus familiaris* Slit2 (XM_005618749.1 and XP_005618806.1); *Bos taurus* Slit2 (NM_001191516.2 and NP_001178445.2); and *Gallus gallus* Slit2 (NM_001267075.1 and NP_001254004.1).

In some embodiments, fragments of Slit2 having one or more biological activities of the full-length Slit2 protein are described and employed. Such fragments can comprise or consist of at least one domain of a Slit2 protein without containing the full-length Slit2 protein sequence. In some embodiments, Slit2 fragments can comprise, or consist of, an N-terminal signal peptide sequence (SS) domain, a leucine-rich repeat (LRR) domain, an EGF domain, a LamG domain, and a C-terminal cysteine knot domain, without containing the full-length Slit2 protein sequence. As further indicated in the Examples, Slit2 orthologs are highly homologous and retain common structural domains well known in the art.

Biologically active fragments, such as Slit2-N and Slit2-C, are also described herein.

TABLE 1

| SEQ ID NO: 1 Human Slit2 Transcript Variant 1 cDNA Sequence | | | | | | |
|---|---|---|---|---|---|---|
| 1 | atgcgcggcg | ttggctggca | gatgctgtcc | ctgtcgctgg | ggttagtgct | ggcgatcctg |
| 61 | aacaaggtga | caccgcaagc | gtgcccggcg | cagtgctctt | gctcgggcag | cacagtggac |
| 121 | tgtcacgggc | tggcgctgcg | cagcgtgccc | aggaatatcc | cccgcaacac | cgagagactg |
| 181 | gatttaaatg | gaaataacat | cacaagaatt | acgaagacag | attttgctgg | tcttagacat |
| 241 | ctaagagttc | ttcagcttat | ggagaataag | attagcacca | ttgaaagagg | agcattccag |
| 301 | gatcttaaag | aactagagag | actgcattta | aacagaaatc | accttcagct | gtttcctgag |
| 361 | ttgctgtttc | ttaggactgc | gaagctatac | aggcttgatc | tcagtgaaaa | ccaaattcag |
| 421 | gcaatcccaa | ggaaagcttt | ccgtggggca | gttgacataa | aaaatttgca | actggattac |
| 481 | aaccagatca | gctgtattga | agatggggca | ttcagggctc | tccgggacct | ggaagtgctc |
| 541 | actctcaaca | ataacaacat | tactagactt | tctgtggcaa | gtttcaacca | tatgcctaaa |
| 601 | cttaggactt | ttcgactaca | ttcaaacaac | ctgtattgtg | actgccacct | ggcctggctc |
| 661 | tccgactggc | ttcgccaaag | gcctcgggtt | ggtctgtaca | ctcagtgtat | gggcccctcc |
| 721 | cacctgagag | gccataatgt | agccgaggtt | caaaaacgag | aatttgtctg | cagtggtcac |
| 781 | cagtcattta | tggctccttc | ttgtagtgtt | ttgcactgcc | ctgccgcctg | tacctgtagc |
| 841 | aacaatatcg | tagactgtcg | tgggaaaggt | ctcactgaga | tccccacaaa | tcttccagag |
| 901 | accatcacag | aaatacgttt | ggaacagaac | acaatcaaag | tcatccctcc | tggagctttc |
| 961 | tcaccatata | aaaagcttag | acgaattgac | ctgagcaata | atcagatctc | tgaacttgca |
| 1021 | ccagatgctt | tccaaggact | acgctctctg | aattcacttg | tcctctatgg | aaataaaatc |
| 1081 | acagaactcc | ccaaaagttt | atttgaagga | ctgttttcct | tacagctcct | attattgaat |
| 1141 | gccaacaaga | taaactgcct | tcgggtagat | gcttttcagg | atctccacaa | cttgaacctt |
| 1201 | ctctccctat | ataacaacaa | gcttcagacc | atcgccaagg | ggaccttttc | acctcttcgg |
| 1261 | gccattcaaa | ctatgcattt | ggcccagaac | ccctttattt | gtgactgcca | tctcaagtgg |
| 1321 | ctagcggatt | atctccatac | caacccgatt | gagaccagtg | gtgcccgttg | caccagcccc |
| 1381 | cgccgcctgg | caaacaaaag | aattggacag | atcaaaagca | agaaattccg | ttgttcagct |
| 1441 | aaagaacagt | atttcattcc | aggtacagaa | gattatcgat | caaaattaag | tggagactgc |
| 1501 | tttgcggatc | tggcttgccc | tgaaaagtgt | cgctgtgaag | gaaccacagt | agattgctct |
| 1561 | aatcaaaagc | tcaacaaaat | cccggagcac | attccccagt | acactgcaga | gttgcgtctc |
| 1621 | aataataatg | aatttaccgt | gttggaagcc | acaggaatct | ttaagaaact | tcctcaatta |
| 1681 | cgtaaaataa | actttagcaa | caataagatc | acagatattg | aggagggagc | atttgaagga |
| 1741 | gcatctggta | taaatgaaat | acttcttacg | agtaatcgtt | tggaaaatgt | gcagcataag |
| 1801 | atgttcaaga | gattggaaag | cctcaaaact | ttgatgttga | gaagcaatcg | aataacctat |
| 1861 | gtggggaatg | acagtttcat | aggactcagt | tctgtgcgtt | tgctttcttt | gtatgataat |
| 1921 | caaattacta | cagttgcacc | aggggcattt | gatactctcc | attctttatc | tactctaaac |
| 1981 | ctcttggcca | atccttttaa | ctgtaactgc | tacctggctt | ggttgggaga | gtggctgaga |
| 2041 | aagaagagaa | ttatcacagg | aaatcctaga | tgtcaaaaac | catacttcct | gaaagaaata |
| 2101 | cccatccagg | atgtggccat | tcaggacttc | acttgtgatg | acggaaatga | tgacaatagt |
| 2161 | tgctccccac | tttctcgctg | tcctactgaa | tgtacttgct | tggatacagt | cgtccgatgt |
| 2221 | agcaacaagg | gtttgaaggt | cttaccgaaa | ggtattccaa | gagatgtcac | agagttgtat |
| 2281 | ctggatggaa | accaatttac | actggttccc | aaggaactct | ccaactacaa | acatttaaca |
| 2341 | cttatagact | taagtaacaa | cagaataagc | acgctttcta | atcagagctt | cagcaacatg |
| 2401 | acccagctcc | tcaccttaat | tcttagttac | aaccgtctga | gatgtattcc | tcctcgcacc |
| 2461 | tttgatggat | taaagtctct | tcgattactt | tctctacatg | gaaatgacat | ttctgttgtg |
| 2521 | cctgaaggtg | ctttcaatga | tctttctgca | ttatcacatc | tagcaattgg | agccaaccct |
| 2581 | ctttactgtg | attgtaacat | gcagtggtta | tccgactggg | tgaagtcgga | atataaggag |
| 2641 | cctggaatta | ctcgttgtgc | tggtcctgga | gaaatggcag | ataaactttt | actcacaact |
| 2701 | ccctccaaaa | aatttacctg | tcaaggtcct | gtggatgtca | atattctagc | taagtgtaac |
| 2761 | ccctgcctat | caaatccgtg | taaaaatgat | ggcacatgta | atagtgatcc | agttgacttt |
| 2821 | taccgatgca | cctgtccata | tggtttcaag | ggcaggactt | gtgatgtccc | aattcatgcc |
| 2881 | tgcatcagta | acccatgtaa | acatggagga | acttgccact | taaaggaagg | agaagaagat |
| 2941 | agattctggt | gtatttgtgc | tgatgaattt | gaaagagaaa | attgtgaagt | caacgttgat |
| 3001 | gattgtgaag | ataatgactg | tgaaaataat | tctacatgtg | tcgatggcat | taataactac |
| 3061 | acatgccttt | gcccacctga | gtatacaggt | gagttgtgtg | aggagaagct | ggacttctgt |
| 3121 | gcccaggacc | tgaacccctg | ccagcacgat | tcaaagtgca | tcctaactcc | aaagggattc |
| 3181 | aaatgtgact | gcacaccagg | gtacgtaggt | gaacactgcg | acatcgattt | tgacgactgc |
| 3241 | caagacaaca | agtgtaaaaa | cggagcccac | tgcacagatg | cagtgaacgg | ctatacgtgc |
| 3301 | atatgccccg | aaggttacag | tggcttgttc | tgtgagtttt | ctccacccat | ggtcctccct |
| 3361 | cgtaccagcc | cctgtgataa | ttttgattgt | cagaatggag | ctcagtgtat | cgtcagaata |
| 3421 | aatgagccaa | tatgtcagtg | tttgcctggc | tatcagggag | aaaagtgtga | aaaattggtt |
| 3481 | agtgtgaatt | ttataaacaa | agagtcttat | cttcagattc | cttcagccaa | ggttcggcct |
| 3541 | cagacgaaca | taacacttca | gattgccaca | gataaagaca | gcggaatcct | cctgtataag |
| 3601 | ggtgacaaag | accatatcgc | ggtagaactc | tatcgggggc | gtgttcgtgc | cagctatgac |
| 3661 | accggctctc | atccagcttc | tgccatttac | agtgtggaga | caatcaatga | tggaaacttc |
| 3721 | cacattgtgg | aactacttgc | cttggatcag | agtctctctt | tgtccgtgga | tggtgggaac |
| 3781 | cccaaaatca | tcactaactt | gtcaaagcag | tccactctga | attttgactc | tccactctat |
| 3841 | gtaggaggca | tgccagggaa | gagtaacgtg | gcatctctgc | gccaggcccc | tgggcagaac |
| 3901 | ggaaccagct | tccacggctg | catccggaac | ctttacatca | acagtgagct | gcaggacttc |

TABLE 1-continued

```
3961 cagaaggtgc cgatgcaaac aggcattttg cctggctgtg agccatgcca caagaaggtg
4021 tgtgcccatg gcacatgcca gcccagcagc caggcaggct tcacctgcga gtgccaggaa
4081 ggatggatgg ggcccctctg tgaccaacgg accaatgacc cttgccttgg aaataaatac
4141 gtacatggca cctgcttgcc catcaatgcg ttctcctaca gctgtaagtg cttggagggc
4201 catggaggtg tcctctgtga tgaagaggag gatctgttta acccatgcca ggcgatcaag
4261 tgcaagcatg ggaagtgcag gctttcaggt ctggggcagc cctactgtga atgcagcagt
4321 ggatacacgg gggacagctg tgatcgagaa atctcttgtc gaggggaaag gataagagat
4381 tattaccaaa agcagcaagg ctatgctgct tgccaaacaa ccaagaaggt gtcccgatta
4441 gagtgcagag gtgggtgtgc aggagggcag tgctgtggac cgctgaggag caagcggcgg
4501 aaatactctt tcgaatgcac tgacggctcc tcctttgtgg acgaggttga gaaagtggtg
4561 aagtgcggct gtacgaggtg tgtgtcctaa

SEQ ID NO: 2 Human Slit Isoform 1 Amino Acid Sequence
   1 mrgvgwqmls lslglvlail nkvapqacpa qcscsgstvd chglalrsvp rniprnterl
  61 dlngnnitri tktdfaglrh lrvlqlmenk istiergafq dlkelerlrl nrnhlqlfpe
 121 llflgtakly rldlsenqiq aiprkafrga vdiknlqldy nqisciedga fralrdlevl
 181 tlnnnnitrl svasfnhmpk lrtfrlhsnn lycdchlawl sdwlrqrprv glytqcmgps
 241 hlrghnvaev qkrefvcsgh qsfmapscsv lhcpaactcs nnivdcrgkg lteiptnlpe
 301 titeirleqn tikvippgaf spykklrrid lsnnqisela pdafqglrsl nslvlygnki
 361 telpkslfeg lfslqlllln ankinclrvd afqdlhnlnl lslydnklqt iakgtfsplr
 421 aiqtmnlaqn pficdchlkw ladylhtnpi etsgarctsp rrlankrigq ikskkfrcsa
 481 keqyfipgte dyrsklsgdc fadlacpekc rcegttvdcs nqklnkipeh ipqytaelrl
 541 nnneftvlea tgifkklpql rkinfsnnki tdieegafeg asgvneillt snrlenvqhk
 601 mfkgleslkt lmlrsnritc vgndsfigls svrllslydn qittvapgaf dtlhslstln
 661 llanpfncnc ylawlgewlr kkrivtgnpr cqkpyflkei piqdvaiqdf tcddgnddns
 721 csplsrcpte ctcldtvvrc snkglkvlpk giprdvtely ldgnqftlvp kelsnykhlt
 781 lidlsnnris tlsnqsfsnm tqlltlilsy nrlrcipprt fdglkslrll slhgndisvv
 841 pegafndlsa lshlaiganp lycdcnmqwl sdwvkseyke pgiarcagpg emadkllltt
 901 pskkftcqgp vdvnilakcn pclsnpcknd gtcnsdpvdf yrctcpygfk gqdcdvpiha
 961 cisnpckhgg tchikegeed gfwcicadgf egercevnyd dcedndcenn stcvdginny
1021 tclcppeytg elceekldfc aqdlnpcqhd skciltpkgf kcdctpgyvg ehcdidfddc
1081 qdnkckngah ctdavngytc icpegysglf cefsppmvlp rtspcdnfdc qngaqcivri
1141 nepicqclpg yqgekceklv svnfinkesy lqipsakvrp qtnitlqiat dedsgillyk
1201 gdkdhiavel yrgrvrasyd tgshpasaiy svetindgnf hivellaidg slslsvdggn
1261 pkiitnlskg stanfdsply vggmpgksnv aslrqapgqn gtsfhgcirn lyinselqdf
1321 qkvpmqtgil pgcepchkkv cahgtcqpss qagftcecqe gwmgplcdgr tndpclgnkc
1381 vhgtclpina fsysckcleg hggvlcdeee dlfnpcqaik ckhgkcrlsg lgqpycecss
1441 gytgdscdre iscrgerird yyqkqqgyaa cqttkkvsrl ecrggcaggq ccgplrskrr
1501 kysfectdgs sfvdevekvv kcgctrcvs

SEQ ID NO: 3 Human Slit2 Transcript Variant 2 cDNA Sequence
   1 atgcgcggcg ttggctggca gatgctgtcd ctgtcgctgg ggttagtgct ggcgatcctg
  61 aacaaggtgg caccgcaggc gtgcccggcg cagtgctctt gctcgggcag cacagtggac
 121 tgtcacgggc tggcgctgcg cagcgtgccc aggaatatcc cccgcaacac cgagagactg
 181 aatttaaata gaaataacat cacaagaatt acgaagacag attttgctgg tcttagacat
 241 ctaagagttc ttcagcttat ggagaataag attagcacca ttgaaagagg agcattccag
 301 gatcttaaag aactagagag actgcgttta aacagaaatc accttcagct gtttcctgag
 361 ttgctgtttc ttgggactgc gaagctatac aggcttgatc tcagtgaaaa ccaaattcag
 421 gcaatcccaa ggaaagcttt ccgtggggca gttgacataa aaaatttgca actggattac
 481 aaccagatca gctgtattga agatggggca ttcagggctc tccgggacct ggaagtgctc
 541 actctcaaca ataacaacat tactagactt tctgtggcaa gtttcaacca tatgcctaaa
 601 cttaggactt ttcgactgca ttcaaacaac ctgtattgtg actgccacct ggcctggctc
 661 tccgactggc ttcgccaaag gcctcgggtt ggtctgtaca ctcagtgtat gggcccctcc
 721 cacctgagag gccataatgt agccgaggtt caaaaacgag aatttgtctg cagtgatgag
 781 gaagaagdtc accagtcatt tatggctcct tcttgtagtg ttttgcactg ccctgccgcc
 841 tgtacctgta gcaacaatat cgtagactgt cgtgggaaag gtctcactga gatccccaca
 901 aatcttccag agaccatcac agaaatacgt ttggaacaga acacaatcaa agtcatccct
 961 cctggagctt tctcaccata taaaaagctt agacgaattg acctgagcaa taatcagatc
1021 tctgaacttg caccagatgc tttccaagga ctacgctctc tgaattcact tgtcctctat
1081 ggaaataaaa tcacagaact ccccaaaagt ttatttgaag gactgttttc cttacagctc
1141 ctattattga atgccaacaa gataaactgc cttcgggtag atgcttttca ggatctccac
1201 aacttgaacc ttctctccct atatgacaac aagcttcaga ccatcgccaa ggggaccttt
1261 tcacctcttc gggccattca aactatgcat ttggcccaga acccctttat ttgtgactgc
1321 catctcaagt ggctagcaga ttatctccat accaacccga ttgagaccag tggtgcccat
1381 tgcaccagcc cccgccgcct ggcaaacaaa agaattggac agatcaaaag caagaaattc
1441 cgttgttcag gtacagaaga ttatcgatca aaattaagtg gagactgctt tgcggatctg
1501 gcttgccctg aaaagtgtcg ctgtgaagga accacagtag attgctctaa tcaaaagctc
1561 aacaaaatcc cggagcacat tccccagtac actgcagagt tgcgtctcaa taataatgaa
1621 tttaccgtgt tggaagccac aggaatcttt aagaaacttc ctcaattacg taaaataaac
1681 tttagcaaca ataagatcac agatattgag gagggagcat ttgaaggagc atctggtgta
1741 aatgaaatac ttcttacgag taatcgtttg gaaaatgtgc agcataagat gttcaaggga
1801 ttggaaagcc tcaaaacttt gatgttgaga agcaatcgaa taacctgtgt ggggaatgac
1861 agtttcatag gactcagttc tgtgcgtttg ctttctttgt atgataatca aattactaca
1921 gttgcaccag gggcatttga tactctccat tctttatcta ctctaaacct cttggccaat
1981 ccttttaact gtaactgcta cctggcttgg ttgggagagt ggctgagaaa gaagagaatt
2041 gtcacgggaa atcctagatg tcaaaaacca tacttcctga aagaaatacc catccaggat
2101 gtggccattc aggacttcac ttgtgatgac ggaaatgatg acaatagttg ctccccactt
2161 tctcgctgtc ctactgaatg tacttgcttg gatacagtcg tccgatgtag caacaagggt
2221 ttgaaggtct tgccgaaagg tattccaaga gatgtcacag agttgtatct ggatggaaac
2281 caatttacac tggttcccaa ggaactctcc aactacaaac atttaacact tatagactta
```

TABLE 1-continued 2341 agtaacaaca gaataagcac gctttctaat cagagcttca gcaacatgac ccagctcctc
2401 accttaattc ttagttacaa ccgtctgaga tgtattcctc ctcgcacctt tgatggatta
2461 aagtctcttc gattactttc tctacatgga aatgacattt ctgttgtgcc tgaaggtgct
2521 ttcaatgatc tttctgcatt atcacatcta gcaattggag ccaaccctct ttactgtgat
2581 tgtaacatgc agtggttatc cgactgggtg aagtcggaat ataaggagcc tggaattgct
2641 cgttgtgcta gtcctggaga aatggcagat aaacttttac tcacaactcc ctccaaaaaa
2701 tttacctgtc aaggtcctgt ggatgtcaat attctagcta agtgtaaccc ctgcctatca
2761 aatccgtgta aaaatgatgg cacatgtaat agtgatccag ttgactttta ccgatgcacc
2821 tgtccatatg gtttcaaggg gcaggactgt gatgtcccaa ttcatgcctg catcagtaac
2881 ccatgtaaac atggaggaac ttgccactta aaggaaggag aagaagatgg attctggtgt
2941 atttgtgcta atggatttga aggagaaaat tgtgaagtca acgttgatga ttgtgaagat
3001 aatgactgtg aaaataattc tacatgtgtc gatggcatta ataactacac atgcctttgc
3061 ccacctgagt atacaggtga gttgtgtgag gagaagctgg acttctgtgc ccaggacctg
3121 aacccctgcc agcacgattc aaagtgcatc ctaactccaa agggattcaa atgtgactgc
3181 acaccagggt acgtaggtga acactgcgac atcgattttg acgactgcca agacaacaag
3241 tgtaaaaacg gagcccactg cacagatgca gtgaacggct atacgtgcat atgccccgaa
3301 ggttacagtg gcttgttctg tgagttttct ccacccatgg tcctccctcg taccagcccc
3361 tgtgataatt ttgattgtca gaatggagct cagtgtatcg tcagaataaa tgagccaata
3421 tgtcagtgtt tgcctggcta tcagggagaa aagtgtgaaa aattggttag tgtgaatttt
3481 ataaacaaaa agtcttatct tcagattcct tcagccaagg ttcggcctca gacgaacata
3541 acacttcaga ttgccacaga tgaagacagc ggaatcctcc tatataaggg tgacaaagac
3601 catatcgcgg tagaactcta tcgggggcgt gttcgtgcca gctatgacac cggctctcat
3661 ccagcttctg ccatttacag tgtggagaca atcaatgatg gaaacttcca cattgtggaa
3721 ctacttgcct tggatcagag tctctctttg tccgtggatg gtgggaaccc caaaatcatc
3781 actaacttgt caaagcaatc cactctgaat tttaactctc cactctatgt aggaggcatg
3841 ccagggaaga gtaacgtggc atctctgcgc caggcccctg ggcagaacgg aaccagcttc
3901 cacggctgca tccggaacct ttacatcaac agtgagctgc aggacttcca gaaggtgccg
3961 atgcaaacag gcattttgcc tggctgtgag ccatgccaca agaaggtgtg tgcccatggc
4021 acatgccagc ccagcagcca ggcaggcttc acctgcgagt gccaggaagg atggatgggg
4081 cccctctgtg accaacgaac caatgaccct tgccttggaa ataaatgcgt acatggcacc
4141 tgcttgccca tcaatgcgtt ctcctacagc tgtaagtgct tggagggcca tggaggtgtc
4201 ctctgtgatg aagaggagga tctgtttaac ccatgccagg cgatcaagtg caagcatggg
4261 aagtgcaggc tttcaggtct ggggcagccc tactgtgaat gcagcagtgg atacacgggg
4321 gacagctgtg atcgagaaat ctcttgtcga ggggaaagga taagagatta ttaccaaaag
4381 cagcagggct atgctgcttg ccaaacaacc aagaaggtgt cccgattaga gtgcagagat
4441 gggtgtgcag gagggcagtg ctgtggaccg ctgaggagca agcggcggaa atactctttc
4501 gaatgcactg acggctcctc ctttgtggac gaggttgaga aagtggtgaa gtgcggctgt
4561 acgaggtgtg tgtcctaa SEQ ID NO: 4 Human Slit2 Isoform 2 Amino Acid Sequence
1 mrgvgwqmls lslglvlail nkvapqacpa qcscsgstvd chglalrsvp rniprnterl
61 dlngnnitri tktdfaglrh lrvlqlmenk istiergafq dlkelerlrl nrnhlqlfpe
121 llflgtakly rldlsenqiq aiprkafrga vdiknlqldy nqisciedga fralrdlevl
181 tlnnnnitrl svasfnhmpk lrtfrlhsnn lycdchlawl sdwlrqrprv glytqcmgps
241 hlrghnvaev qkrefvcsde eeghqsfmap scsvlhcpaa ctcsnnivdc rgkglteipt
301 nlpetiteir leqntikvip pgafspykkl rridlsnnqi selapdafqg lrslnslvly
361 gnkitelpks lfeglfslql lllnankinc lrvdafqdlh nlnllslydn klqtiakgtf
421 splraiqtmh laqnpficdc hlkwladylh tnpietsgar ctsprrlank rigqikskkf
481 rcsgtedyrs klsgdcfadl acpekcrceg ttvdcsnqkl nkipehipqy taelrlnnne
541 ftvleatgif kklpqlrkin fsnnkitdie egafegasgv neilltsnrl envqhkmfkg
601 leslktlmlr snritcvgnd sfiglssvrl lslydnqitt vapgafdtlh slstlnllan
661 pfncncylaw lgewarkkri vtgnprcqkp vflkeipiqd vaigdftcdd gnddnscspl
721 srcptectcl dtvvrcsnkg lkvlpkgipr dvtelyldgn qftlvpkels nykhltlidl
781 snnristlsn qsfsnmtqll tlilsynrlr cipprtfdgl kslrllslhg ndisvvpega
841 fndlsalshl aiganplycd cnmqwlsdwv ksevkepgia rcagpgemad klllttpskk
901 ftcqgpvdvn ilakcnpcls npckndgtcn sdpvdfyrct cpygfkgqdc dvpihacisn
961 pckhggtchl kegeedgfwc icadgfeqen cevnvddced ndcennstcv dginnytclc
1021 ppeytgelce ekldfcagdl npcqhdskci ltpkgfkcdc tpgyvgehcd idfddcqdnk
1081 ckngahctda vngytcicpe gysglfcefs ppmvlprtsp cdnfdcqnga qcivrinepi
1141 cqclpgyqge kceklvsvnf inkesylqip sakvrpqtni tlgiatdeds gillykgdkd
1201 hiavelyrgr vrasydtgsh pasaiysvet indgnfhive llaldqslsl svdggnpkii
1261 tnlskqstln fdsplyvggm pgksnvaslr qapgqngtsf hgcirnlyin selqdfqkvp
1321 mqtqilpgce pchkkvcahg tcgpssqagf tcecqegwmg plcdqrtndp clgnkcvhgt
1381 clpinafsys ckcleghggv lcdeeedlfn pcqaikckhg kcrlsglggp ycecssgytg
1441 dscdreiscr gerirdyyqk qqgvaacqtt kkvsrlecrg gcaggqccgp lrskrrkysf
1501 ectdgssfvd evekvvkcgc trcvs SEQ ID NO: 5 Human Slit2 Transcript Variant 3 cDNA Sequence
1 atgcgcggcg ttggctggca gatgctgtcc ctgtcgctgg ggttagtgct ggcgatcctg
61 aacaaggtgg caccgcaggc gtgcccggcg cagtgctctt gctcgggcag cacagtggac
121 tgtcacgggc tggcgctgcg cagcgtgccc aggaatatcc cccgcaacac cgagagactg
181 gatttaaatg gaaataacat cacaagaatt acgaagacag attttgctgg tcttagacat
241 ctaagagttc ttcagcttat ggagaataag attagcacca ttgaaagagg agcattccag
301 gatcttaaag aactagagag actgcgttta aacagaaatc accttcagct gtttcctgag
361 ttgctgtttc ttgggactgc gaagctatac aggcttgatc tcagtgaaaa ccaaattcag
421 gcaatcccaa ggaaagcttt ccgtggggca gttgacataa aaaatttgca actggattac
401 aaccagatca gctgtattga agatggggca ttcagggctc tccgggacct ggaagtgctc
541 actctcaaca ataacaacat tactagactt tctgtggcaa gtttcaacca tatgcctaaa
601 cttaggactt ttcgactgca ttcaaacaac ctgtattgtg actgccacct ggcctggctc
661 tccgactggc ttcgccaaag gcctcaggtt ggtctgtaca ctcagtgtat gggcccctcc TABLE 1-continued

```
 721 cacctgagag gccataatgt agccgaggtt caaaaacgag aatttgtctg cagtggtcac
 781 cagtcattta tggctccttc ttgtagtgtt ttgcactgcc ctgccgcctg tacctgtagc
 841 aacaatatcg tagactgtcg tgggaaaggt ctcactgaga tccccacaaa tcttccagag
 901 accatcacag aaatacgttt ggaacagaac acaatcaaag tcatccctcc tggagctttc
 961 tcaccatata aaaagcttag acgaattgac ctgagcaata atcagatctc tgaacttgca
1021 ccagatgctt tccaaggact acgctctctg aattcacttg tcctctatgg aaataaaatc
1081 acagaactcc ccaaaagttt atttgaagga ctgttttcct tacagctcct attattgaat
1141 gccaacaaga taaactgcct tcgggtagat gcttttcagg atctccacaa cttgaacctt
1201 ctctccctat atgacaacaa gcttcagacc atcgccaagg ggaccttttc acctcttcgg
1261 gccattcaaa ctatgcattt ggcccagaac ccctttattt gtgactgcca tctcaagtgg
1321 ctagcggatt atctccatac caacccgatt gagaccagtg gtgcccgttg caccagcccc
1381 cgccgcctgg caaacaaaag aattggacag atcaaaagca agaaattccg ttgttcaggt
1441 acagaagatt atcgatcaaa attaagtgga gactgctttg cggatctggc ttgccctgaa
1501 aagtgtcgct gtgaaggaac cacagtagat tgctctaatc aaaagctcaa caaaatcccg
1561 gagcacattc cccagtacac tgcagagttg cgtctcaata ataatgaatt taccgtgttg
1621 gaagccacag gaatctttaa gaaacttcct caattacgta aaataaactt tagcaacaat
1681 aagatcacag atattgagga gggagcattt gaaggagcat ctggtgtaaa tgaaatactt
1741 cttacgagta atcgtttgga aaatgtgcag cataagatgt tcaagggatt ggaaagcctc
1801 aaaactttga tgttgagaag caatcgaata acctgtgtgg ggaatgacag tttcatagga
1861 ctcagttctg tgcgtttgct ttctttgtat gataatcaaa ttactacagt tgcaccaggg
1921 gcatttgata ctctccattc tttatctact ctaaacctct tggccaatcc ttttaactgt
1981 aactgctacc tggcttggtt gggagagtgg ctgagaaaga agagaattgt cacgggaaat
2041 cctagatgtc aaaaaccata cttcctgaaa gaaataccca tccaggatgt ggccattcag
2101 aacttcactt gtgatgacgg aaatgatgac aatagttgct ccccactttc tcgctgtcct
2161 actgaatgta cttgcttgga tacagtcgtc cgatgtagca acaagggttt gaaggtcttg
2221 ccgaaaggta ttccaagaga tgtcacagag ttgtatctgg atggaaacca atttacactg
2281 gttcccaagg aactctccaa ctacaaacat ttaacactta tagacttaag taacaacaga
2341 ataagcacgc tttctaatca gagcttcagc aacatgaccc aactcctcac cttaattctt
2401 agttacaacc gtctgagatg tattcctcct cgcacctttg atggattaaa gtctcttcga
2461 ttactttctc tacatggaaa tgacatttct gttgtgcctg aaggtgcttt caatgatctt
2521 tctgcattat cacatctagc aattggagcc aaccctcttt actgtgattg taacatgcag
2581 tggttatccg actgggtgaa gtcggaatat aaggagcctg gaattgctcg ttgtgctggt
2641 cctggagaaa tggcagataa acttttactc acaactccct ccaaaaaatt tacctgtcaa
2701 ggtcctgtga atgtcaatat tctagctaag tgtaacccct gcctatcaaa tccgtgtaaa
2761 aatgatggca catgtaatag tgatccagtt gacttttacc gatgcacctg tccatatggt
2821 ttcaaggggc aggactgtga tgtcccaatt catgcctgca tcagtaaccc atgtaaacat
2881 ggaggaactt gccacttaaa ggaaggagaa gaagatggat tctggtgtat ttgtgctgat
2941 ggatttgaag gagaaaattg tgaagtcaac gttgatgatt gtgaagataa tgactgtgaa
3001 aataattcta catgtgtcga tggcattaat aactacacat gcctttgccc acctgagtat
3061 acaggtgagt tgtgtgagga gaagctggac ttctgtgccc aggacctgaa cccctgccag
3121 cacgattcaa agtgcatcct aactccaaag ggattcaaat gtgactgcac accagggtac
3181 gtaggtgaac actgcgacat cgattttgac gactgccaag acaacaagtg taaaaacgga
3241 gcccactgca cagatgcagt gaacggctat acgtgcatat gccccgaagg ttacagtggc
3301 ttgttctgtg agtttctcc acccatggtc ctccctcgta ccagcccctg tgataatttt
3361 gattgtcaga atggagctca gtgtatcgtc agaataaatg agccaatatg tcagtgtttg
3421 cctggctatc agggagaaaa gtgtgaaaaa ttggttagtg tgaattttat aaacaaagag
3481 tcttatcttc agattccttc agccaaggtt cggcctcaga cgaacataac acttcagatt
3541 gccacagatg aagacagcgg aatcctcctg tataagggtg acaaagacca tatcgcggta
3601 aaactctatc gggggcgtgt tcgtgccagc tataacaccg gctctcatcc agcttctgcc
3661 atttacagtg tggagacaat caatgatgga aacttccaca ttgtggaact acttgccttg
3721 gatcagagtc tctctttgtc cgtggatggt gggaacccca aaatcatcac taacttgtca
3701 aagcagtcca ctctgaattt tgactctcca ctctatgtag gaggcatgcc agggaagagt
3841 aacgtggcat ctctgcgcca ggcccctggg cagaacggaa ccagcttcca cggctgcatc
3901 cggaaccttt acatcaacag tgagctgcag gacttccaga aggtgccgat gcaaacaggc
3961 attttgcctg gctgtgdgcc atgccacaag aaggtgtgtg cccatggcac atgccagccc
4021 agcagccagg caggcttcac ctgcgagtgc caggaaggat ggatggggcc cctctgtgac
4081 caacggacca atgacccttg ccttggaaat aaatgcgtac atggcacctg cttgcccatc
4141 aatgcgttct cctacagctg taagtacttg gagagccatg gaggtgtcct ctgtgatgaa
4201 gaggaggatc tgtttaaccc atgccaggcg atcaagtgca agcatgggaa gtgcaggctt
4261 tcaggtctgg ggcagcccta ctgtgaatgc agcagtggat acacggggga cagctgtgat
4321 cgagaaatct cttgtcgagg ggaaaggata agagattatt accaaaagca gcagggctat
4381 gctgcttgcc aaacaaccaa gaaggtgtcc cgattagagt gcagaggtgg gtgtgcagga
4441 aggcagtgct gtggaccact gaggaacaag cggcggaaat actctttcga atgcactgac
4301 ggctcctcct ttgtggacga ggttgagaaa gtggtgaagt gcggctgtac gaggtgtgtg
4561 tcctaa
```

SEQ ID NO: 6 Human Slit2 Isoform 3 Amino Acid Sequence

```
  1 mrgvgwqmls lslglvlail nkvapqacpa qcscsgstvd chglalrsvp rniprnterl
 61 dlngnnitri tktdfaglrh lrvlqlmenk istiergafq dlkelerlrl nrnhlqlfpe
121 llflgtakly rldlsenqiq aiprkafrga vdiknlqldy nqisciedga fralrdlevl
181 tlnnnnitrl svasfnhmpk lrtfrlhsnn lycdchlawl sdwlrqrprv glytqcmgps
241 hlrghnvaev qkrefvcsgh qsfmapscsv lhcpaactcs nnivdcrgkg lteiptnlpe
301 titeirleqn tikvippgaf spykklrrid lsnnqisela pdafqqlrsl nslvlygnki
361 telpkslfeg lfslqlllln ankinclrvd afqdlhnlnl lslydnklgt iakgtfsplr
421 aiqtmhlaqn pficdchlkw ladylhtnpi etsgarctsp rrlankriqg ikskkfrcsg
481 tedyrsklsg dcfadlacpe kcrcegttvd csnqklnkip ehipqytael rlnnneftvl
541 eatgifkklp qlrkinfsnn kitdieegaf egasgvneil ltsnrlenvq hkmfkglesl
601 ktlmlrsnri tcvgndsfig lssvrllsly dnqittvapg afdtlhslst lnllanpfnc
661 ncylawlgew lrkkrivtgn prcqkpyflk eipigdvaiq dftcddgndd nscsplsrcp
721 tectcldtvv rcsnkglkvl pkgiprdvte lyldgnqftl vpkelsnvkh ltlidlsnnr
```

TABLE 1-continued

```
 781 istlsnqsfs nmtqlltlil synrlrcipp rtfdglkslr llslhgndis vvpegafndl
 841 salshlaiga nplycdcnmq wlsdwvksey kepgiarcag pgemadklll ttpskkftcq
 901 gpvdvnilak cnpclsnpck ndgtcnsdpv dfyrctcpyg fkgqdcdvpi hacisnpckh
 961 ggtchlkege edgfwcicad gfegencevn vddcedndce nnstcvdgin nytclcppey
1021 tgelceekld fcagdlnpcg hdskciltpk gfkcdctpgy vgehcdidfd dcqdnkckng
1081 ahctdavngy tcicpegysg lfcefsppmv lprtspcdnf dcqngaqciv rinepicqcl
1141 pgyqgekcek lvsvnfinke sylqipsakv rpqtnitlqi atdedsgill ykgdkdhiav
1201 elyrgrvras ydtgshpasa iysvetindg nfhivellal dqslslsvdg gnpkiitnls
1261 kqstlnfdsp lyvggmpgks nvaslrqapg qngtsfhgci rnlyinselq dfqkvpmqtg
1321 ilpgcepchk kvcahgtcqp ssqagftcec qegwmgplcd qrtndpclgn kcvhgtclpi
1381 nafsysckcl eghggvlcde eedlfnpcqa ikckhgkcrl sglgqpycec ssgytgdscd
1441 reiscrgeri rdyyqkqqgy aacqttkkvs rlecrggcag gqccgplrsk rrkysfectd
1501 gssfvdevek vvkcgctrcv s
```

SEQ ID NO: 7 Mouse Slit2 Transcript Variant 1 cDNA Sequence

```
   1 atgagtggca ttggctggca gacactgtcc ctatcgctgg ggttagtgtt gtcgatcttg
  61 aacaaggtgg cgccgcaggc gtgcccggcc cagtgctcct gttcaggcag cacggtggac
 121 tgtcatgggc tggcactacg cagtgtgccc aggaatatcc cccgcaacac cgagagactg
 181 gatttgaatg gaaataacat cacgaggatc acgaagatag attttgctgg tctcaggcac
 241 ctcagagttc ttcagctcat ggagaacaga atcagcacca tcgagagggg agcattccag
 301 gatcttaagg agctggaaag actgcgttta aacagaaata accttcagtt gtttcctgag
 361 ctgctgtttc tcgggactgc gaagctctac cggcttgatc tcagtgaaaa tcaaattcaa
 421 acaattccaa ggaaggcttt ccgtgaggca gttaacatta aaaacctgca actggattac
 481 aaccagatca gctgcattga agatggggcg ttcagagctc tacgagatct ggaagtgctc
 541 actctgaaca ataacaatat tactagactt tcagtggcaa gtttcaacca tatgcctaaa
 601 cttaggacat ttcgactcca ctcgaacaac ttgtactgcg actgccacct agcctggctc
 661 tcagactggc ttcgccaaag gccacgggtg ggcttgtaca ctcagtgtat gggcccatcc
 721 cacctgagga gccacaatgt agcagaggtt caaaaacgag actttgtctg cagtgatgag
 781 gaagaaggtc accagtcatt catggctccc tcctgcagtg tgctgcactg ccccgctgct
 841 tgtacctgta gcaacaacat tgtagactgc cgagggaaag gtctcactga gatccccaca
 901 aatctgcctg agaccatcac agaaatacgt ttggaacaga actccatcag ggtcatccct
 961 ccaggagcct tctcaccata caaaaagctt agacgactag acctgagcaa caaccagatc
1021 tctgaacttg caccagatgc cttccaagga ctgcgctctc tgaattcact tgtcctgtat
1081 ggaaataaaa tcacagaact cccaaaaagt ttattcgaag gactattttc cttgcagcta
1141 ctattattga atgccaacaa gataaactgc cttcgggtag atgcttttca ggacctgcac
1201 aacttgaacc ttctctcctt atatgacaat aagcttcaga cggttgccaa gggcaccttc
1261 tcagccctca gagccatcca aactatgcat ttggcccaga atcctttcat ttgtgactgc
1321 catctcaagt ggctagcgga ttatctccac accaacccaa ttgagaccag cggtgcccgt
1381 tgcaccagcc cccgccgcct ggcaaacaaa agaattggac agatcaaaag caagaaattc
1441 cgttgttcag ctaaagaaca gtatttcatt ccaggtacag aagattatcg atcaaaatta
1501 agtggagact gctttgcaga cttggcttgt cctgagaagt gtcgctgtga agggaccaca
1561 atagactgct ccaatcaaag actcaacaaa atccctgacc atattcccca gtacacagca
1621 gagctgcgtc tcaataataa tgaattcaca gtgttagaag ccacgggaat atttaagaaa
1681 cttcctcagt tacgtaaaat caactttagc aacaataaga tcacggatat cgaggagggt
1741 gcatttgaag gcgcgtctgg tgtgaatgaa attcttctca ccagtaaccg tttggaaaat
1801 gttcagcata agatgttcaa aggactggag agcctcaaaa cattgatgct gagaagtaat
1861 cgaataagct gtgttgggaa cgacagtttc ataggactcg gctctgtgcg tctgctctct
1921 ttatatgaca atcaaattac cacagtggca ccaggagcat ttgattctct ccattcatta
1981 tccactctaa acctcttggc caatcctttc aactgtaact gtcacctggc atggctggga
2041 gaatggctca gaaggaaaag aattgtaaca ggaaatcctc gatgccaaaa accctacttc
2101 ctgaaggaaa tcccaatcca ggatgtagcc attcaggact tcacctgtga tgatggaaat
2161 gatgacaata gttgctctcc actctcccgt tgtccttctg aatgtacctg cttggataca
2221 gtggtacgat gtagcaacaa gggcttgaag gttttgccta aaggtattcc aaaagatgtc
2201 acagagctgt atctggatgg gaaccagttt acgctggtcc cgaaggaact ctctaactac
2341 aaacatttaa cacttataga cttaagtaac aaccgaataa gcaccctttc caatcaaagc
2401 ttcagcaaca tgacccagct tctcacctta atcctcagtt acaaccgtct gagatgtatc
2461 cctccacgaa cctttgatgg attgaagtct cttcggttac tgtctttaca tggaaatgac
2521 atttctgttg tgcctgaagg tgccttcaat gacttgtcag ccttgtcaca cttagcgatt
2581 ggagccaacc ctctttactg tgattgtaac atgcagtggt tatccgactg ggtgaagtcg
2641 gaatataagg aacctggaat tgcacgctgt gccggccctg gagaaatggc agataaatta
2701 ttactcacta ctccctccaa aaaatttaca tgtcaaggtc ccgtggatat cactattcaa
2761 gccaagtgta atccctgctt atcaaatcca tgtaaaaatg atggcacctg taacaatgac
2821 cccgttgatt tttatcgatg tacctgccca tatggattca agggtcagga ctgtgatgtc
2881 cccattcatg cttgtatcag taatccatgt aaacatggag gaacttgtca cttaaaggaa
2941 ggagagaatg ctggattctg gtgcacttgt gctgatgggt ttgaaggaga aaactgtgaa
3001 gtcaatattg atgattgtga agataatgat tgtgaaaata attctacatg cgttgatgga
3061 attaacaact acacatgtct ttgaccaccg gaatacacag ctgctaatct gaatgaggtg
3121 gaaaaaggtg aactgtgtga ggaaaagctg gacttctgtg cacaagactt gaatccctgc
3181 cagcatgact ccaagtgcat cctgactcca aagggattca agtgtgactg cactccagga
3241 tacattggtg agcactgtga cattgacttt gatgactgcc aagataacaa gtgtaaaaac
3301 ggtgctcact gcacagatgc cgtgaacgga tacacgtgcg tctgtcctga aggctacagt
3361 ggcttgttct gtgagttttc tccacccatg gtcctccctc gcaccagccc ctgtgataat
3421 tttgattgcc agaatggagc ccagtgtatc atcaggataa atgaaccaat atgccagtgt
3481 ttgcctggct acctgggaga gaagtgtgag aaattggtca gtgtgaattt tgtaaacaaa
3541 gagtcctatc ttcagattcc ttcagccaag gttcggcctc agacaaacat cacacttcag
3601 attgccacag atgaagacag cggcatcctc ttgtataaag gtgacaaaga ccacattgcc
3661 gtggaactct atagaggacg agttcaagcc agctatgaca ccggctctca tccggcttct
3721 gccatttaca gtgtggagac aatcaatgat ggaaacttcc acattgtgga gctactgacc
3701 ctggattcca gtctttccct ctctgtggat ggaggaagcc ctaaagtcat caccaatttg
3041 tcaaaacaat ctactctgaa tttcgactct ccactctatg taggaggcat gcctgggaaa
```

TABLE 1-continued

```
3901 aataacgtgg catccctgcg ccaggcccct gggcaaaatg gcaccagctt ccatggctgt
3961 atccggaacc tttacattaa cagtgagctg caggacttcc ggaaaatgcc tatgcaaacc
4021 ggaattctgc ctggctgtga accatgccac aagaaagtat gtgcccatgg catgtgccag
4081 cccagcagcc aatcaggctt cacctgtgaa tgtgaggaag ggtggatggg gcccctctgt
4141 gaccagagaa ccaatgatcc ctgcctcgga aacaaatgtg tgcatgggac ctgcctgccc
4201 atcaatgcct tctcctatag ttgcaagtgc ctgaagggcc atggcggtgt cctctgtgat
4261 gaagaagaag atctctttaa cccctgccag atgatcaagt gcaagcatgg gaagtgcagg
4321 ctttctggag tgggccagcc ctattgtgaa tgcaacagtg gattcaccgg ggacagctgt
4381 gatagagaaa tttcttgtcg aggggaacgg ataagggact attaccagaa gcagcagggt
4441 tacgctgcct gtcaaacaac taagaaagta tctcgcttgg aatgcagagg cgggtgcgct
4501 ggaggccagt gctgtggacc tctgaaaagc aagaggcgga aatactcttt cgaatgcaca
4561 gatggctcct catttgtgga cgaggttgag aaagtggtga agtgcggctg cgcgagatgt
4621 gcctcctaa
```

SEQ ID NO: 8 Mouse Slit2 Isoform 1 Amino Acid Sequence

```
   1 msgigwqtls lsaglvlsil nkvapqacpa qcscsgstvd chglalrsvp rniprnterl
  61 dlngnnitri tkidfaglrh lrvlqlmenr istiergafq dlkelerlrl nrnnlqlfpe
 121 llflgtakly rldlsenqiq aiprkafrga vdiknlqldy nqisciedga fralrdlevl
 181 tlnnnnitrl svasfnhmpk lrtfrlhsnn lycdchlawl sdwlrqrprv glytqcmgps
 241 hlrghnvaev qkrefvcsde eeghqsfmap scsvlhcpaa ctcsnnivdc rgkglteipt
 301 nlpetiteir leqnsirvip pgafspykkl rrldlsnnqi selapdafqg lrslnslvly
 361 gnkitelpks lfeglfslql lllnankinc lrvdafqdlh nlnllslydn klqtvakgtf
 421 salraiqtmh laqnpficdc hlkwladylh tnpietsgar ctsprrlank rigqikskkf
 481 rcsakeqyfi pgtedyrskl sgdcfadlac pekcrcegtt vdcsnqrlnk ipdhipqyta
 541 elrlnnneft vleatgifkk lpqlrkinfs nnkitdieeg afegasgvne illtsnrlen
 601 vqhkmfkgle slktlmlrsn riscvgndsf iglgsvrlls lydnqittva pgafdslhsl
 661 stlnllanpf ncnchlawlg ewlrrkrivt gnprcqkpyf lkeipiqdva iqdftcddgn
 721 ddnscsplsr cpsectcldt vvrcsnkqlk vlpkgipkdv telyldgnqf tlvpkelsny
 781 khltlidlsn nristlsnqs fsnmtqlltl ilsynrlrci pprtfdglks lrllslhgnd
 841 isvvpegafn dlsalshlal ganplycdcn mqwlsdwvks eykepgiarc agpgemadkl
 901 llttpskkft cqgpvditiq akcnpclsnp ckndgtcnnd pvdfyrctcp ygfkgqdcdv
 961 pihacisnpc khggtchlke genagfwctc adgfegence vniddcednd cennstcvdg
1021 innytclcpp eytaanlnev ekgelceekl dfcagdlnpc qhdskciltp kgfkcdctpg
1081 yigehcdidf ddcqdnkckn gahctdavng ytcvcpegys glfcefsppm vlprtspcdh
1141 fdcqngaqci irinepicqc lpgylgekce klvsvnfvnk esylqipsak vrpqtnitlq
1201 iatdedsgil lykgdkdhia velvrgrvra svdtgshpas aiysvetind gnfhivellt
1261 ldsslslsvd ggspkvitnl skqstlnfds plyvggmpgk nnvaslrgap gqngtsfhgc
1321 irnlyinsel qdfrkmpmqt gilpgcepch kkvcahgmcq pssqsgftce ceegwmgplc
1381 dqrtndpclg nkcvhgtclp inafsysckc leghggvlcd eeedlfnpcq mikckhgkcr
1441 lsgvgqpyce cnsgftgdsc dreiscrger irdyyqkqqg yaacqttkkv srlecrggca
1501 ggqccgplrs krrkysfect dgssfvdeve kvvkcgcarc as
```

SEQ ID No: 9 Mouse Slit2 Transcript Variant 2 CDNA Sequence

```
   1 atgagtggca ttggctggca gacactgtcc ctatcgctgg ggttagtgtt gtcgatcttg
  61 aacaaggtgg cgccgcaggc gtgcccggcc cagtgctcct gttcaggcag cacggtggac
 121 tgtcatgggc tggcactacg cagtgtgccc aggaatatcc cccgcaacac cgagagactg
 181 gatttgaatg gaaataacat cacgaggatc acgaagatag attttgctgg tctcaggcac
 241 ctcagagttc ttcagctcat ggagaacaga atcagcacca tcgagagggg agcattccag
 301 gatcttaagg agctggaaag actgcgttta aacagaaata accttcagtt gtttcctgag
 361 ctgctgtttc tcgggactgc gaagctctac cggcttgatc tcagtgaaaa tcaaattcaa
 421 gcaattccaa ggaaggcttt ccgtgaggca gttcacatta aaaacctgca actggattac
 481 aaccagatca gctgcattga agatggggcg ttcagagctc tacgagatct ggaagtgctc
 541 actctgaaca ataacaatat tactagactt tcagtggcaa gtttcdacca tatgcctaaa
 601 cttaggacat ttcgactcca ctcgaacaac ttgtactgcg actgccacct agcctggctc
 661 tcagactggc ttcgccaaag gccacgggtg ggcttgtaca ctcagtgtat gggcccatcc
 721 cacctgaggc gccacaatgt agcagaggtt caaaaacgag actttgtctg cagtgatgag
 701 gaagaaggtc accagtcatt catggctccc tcctgcagtg tgctgcactg ccccgctgct
 841 tgtacctgta gcaacaacat tgtagactgc cgagggaaag gtctcactga gatccccaca
 901 aatctgcctg agaccatcac agaaatacgt ttggaacaga actccatcag ggtcatccct
 961 ccaggagcct tctcaccata caaaaagctt agacgactag acctgagcaa caaccagatc
1021 tctgaacttg caccagatgc cttccaagga ctgcgctctc tgaattcact tgtcctgtat
1081 ggaaataaaa tcacagaact cccaaaaagt ttattcgaag gactattttc cttgcagcta
1141 ctattattga atgccaacaa gataaactgc cttcgggtag atgcttttca ggacctgcac
1201 aacttgaacc ttctctcctt atatgacaat aagcttcaga cggttgccaa gggcaccttc
1261 tcagccctca gagccatcca aactatgcat ttggcccaga atcctttcat ttgtgactgc
1321 catctcaagt ggctagcgga ttatctccac accaacccaa ttgagaccag cggtgcccgt
1381 tgcaccagcc cccgccgcct ggcaaacaaa agaattggac agatcaaaag caagaaattc
1441 cgttgttcag gtacagaaga ttatcgatca aaattaagtg gagactgctt tgcagacttg
1501 gcttgtcctg agaagtgtcg ctgtgaaggg accacagtag actgctccaa tcaaagactc
1561 aacaaaatcc ctgaccatat tccccagtac acaacagagc tacgtctcaa taataatgaa
1621 ttcacagtgt tagaagccac gggaatattt aagaaacttc ctcagttacg taaaatcaac
1681 tttagcaaca ataagatcac ggatatcgag gagggtgcat ttgaaggcgc gtctggtgtg
1741 aatgaaattc ttctcaccag taaccgtttg gaaaatgttc agcataagat gttcaaagga
1801 ctggagagcc tcaaaacatt gatgctgaga agtaatcgaa taagctgtgt tgggaacgac
1861 agtttcatag gactcggctc tgtgcgtctg ctctctttat atgacaatca aattaccaca
1921 gtggcaccag gagcatttga ttctctccat tcattatcca ctctaaacct cttggccaat
1981 cctttcaact gtaactgtca cctggcatgg ctgggagaat ggctcagaag gaaaagaatt
2041 gtaacaggaa atcctcgatg ccaaaaaccc tacttcctga aggaaatccc aatccaggat
2101 gtagccattc aggacttcac ctgtgatgat ggaaatgatg acaatagttg ctctccactc
2161 tcccgttgtc cttctgaatg tacctacttg gatacagtgg tacgatgtag caacaaggac
```

TABLE 1-continued

```
2221 ttgaaggttt tgcctaaagg tattccaaaa gatgtcacag agctgtatct ggatgggaac
2201 cagtttacgc tggtcccgaa ggaactctct aactacaaac atttaacact tatagactta
2341 agtaacaacc gaataagcac cctttccaat caaagcttca gcaacatgac ccagcttctc
2401 accttaatcc tcagttacaa ccgtctgaga tgtatccctc cacgaacctt tgatggattg
2461 aagtctcttc ggttactatc tttacatgga aatgacattt ctgttgtgcc tgaaggtgcc
2521 ttcaatgact tgtcagcctt gtcacactta gcgattggag ccaaccctct ttactgtgat
2581 tgtaacatgc agtggttatc cgactgggtg aagtcggaat ataaggaacc tggaattgca
2641 cgctgtgccg gccctggaga aatggcagat aaattattac tcactactcc ctccaaaaaa
2701 tttacatgtc aaggtcccgt ggatatcact attcaagcca agtgtaatcc ctgcttatca
2761 aatccatgta aaaatgatgg cacctataac aataaccccg ttgattttta tcgatgtacc
2821 tgcccatatg gattcaaggg tcaggactgt gatgtcccca ttcatgcttg tatcagtaat
2881 ccatgtaaac atggaggaac ttgtcactta aaggaaggag agaatgctgg attctggtgc
2941 acttgtgctg atgggtttga aggagaaaac tgtgaagtca atattgatga ttgtgaagat
3001 aatgattgtg aaaataattc tacatgcgtt gatggaatta acaactacac atgtctttgc
3061 ccaccggaat acacaggtga actgtatgag gaaaagctgg acttctgtgc acaagacttg
3121 aatccctgcc agcatgactc caagtgcatc ctgactccaa agggattcaa gtgtgactgc
3181 actccaggat acattggtga gcactgtgac attgactttg atgactgcca agataacaag
3241 tgtaaaaacg gtgctcactg cacagatgcc gtgaacggat acadgtgcgt ctgtcctgaa
3301 ggctacagtg gcttgttctg tgagttttct ccacccatgg tcctccctcg caccagcccc
3361 tgtgataatt ttgattgcca gaatggagcc cagtgtatca tcaggataaa tgaaccaata
3421 tgccagtgtt tgcctggcta cctgggagag aagtgtgaga aattggtcag tgtgaatttt
3481 gtaaacaaag agtcctatct tcagattcct tcagccaagg ttcggcctca gacaaacatc
3541 acacttcaga ttgccacaga tgaagacagc ggcatectct tgtataaagg tgacaaagac
3601 cacattgcca tggaactcta tagagggcga gttcgagcca gctatgacac cggctctcat
3661 ccggcttcta ccatttacag tgtggagaca atcaatgatg gaaacttcca cattgtggag
3721 ctactgaccc tggattccag tctttccctc tctgtggatg gaggaagccc taaagtcatc
3781 accaatttgt caaaacaatc tactctgaat ttcgactctc cactctatgt aggadgcatg
3841 cctgggaaaa ataacgtggc atccctgcgc caggcccctg ggcaaaatgg caccagcttc
3901 catggctgta tccggaacct ttacattaac agtgagctgc aggacttccg gaaaatgcct
3961 atgcaaaccg gaattctgcc tggctgtgaa ccatgccaca agaaagtatg tgcccatggc
4021 atgtgccagc ccagcagcca atcaggcttc acctgtgaat gtgaggaagg gtggatgggg
4081 cccctctgtg accagagaac caatgatccc tgcctcggaa acaaatgtgt gcatgggacc
4141 tgcctgccca tcaatgcctt ctcctatagt tgcaagtgcc tggagggcca tggcggtgtc
4201 ctctgtgata aagaagaaga tctctttaac ccctgccaga taatcaagtg caagcatgag
4261 aagtgcaggc tttctggagt gggccagccc tattgtgaat gcaacagtgg attcaccggg
4321 gacagctgtg atagagaaat ttcttgtcga ggggaacgga taagggacta ttaccagaag
4381 cagcagggtt acgctgcctg tcaaacaact aagaaagtat ctcgcttgga atgcagaggc
4441 gggtgcgctg gaggccagtg ctgtggacct ctgagaagca agaggcggaa atactctttc
4501 gaatgcacag atggctcctc atttgtggac gaggttgaga aagtggtgaa gtgcggctgc
4561 gcgagatgtg cctcctaa
```

SEQ ID NO: 10 Mouse Slit2 Isoform 2 Amino Acid Sequence

```
   1 msgigwqtls lslglvlsil nkvapqacpa qcscsgstvd chglalrsvp rniprnterl
  61 dlnqnnitri tkldfaglrh lrvlqlmenr istiergafq dlkelerlrl nrnnlqlfpe
 121 llflgtakly ridlsenqiq aiprkafrga vdiknlqldy nqisciedqa fralrdlevl
 181 tlnnnnitrl svasfnhmpk lrtfrlhsnn lycdchlawl sdwlrqrpry glytqcmgps
 241 hlrghnvaev qkrefvcsde eeghgsfmap scsvlhcpaa ctcsnnivdc rgkglteipt
 301 nlpetiteir legnsirvip pgafspykkl rrldlsnnqi selapdafqg lrslnslvly
 361 gnkitelpks lfeglfslgl lllnankinc lrvdafqdlh nlnllslydn klqtvakgtf
 421 salraiqtmh lagnpficdc hlkwiadylh tnpietsgar ctsprrlank rigqikskkf
 481 rcsgtedyrs klsqdcfadl acpekcrceg ttvddsnqrl nkipdhipqy taelrlnnne
 541 ftvleatgif kklpqlrkin fsnnkitdie egafegasgv neilltsnrl envqhkmfkg
 601 leslktlmlr snriscvgnd sfiglgsvrl lslydnqitt vapgafdslh slstlnllan
 661 pfncnchlaw lgewlrrkri vtgnprcgkp yflkeipiqd vaiqdftcdd gnddnscspl
 721 srcpsectcl dtvvrcsnkg lkvlpkgipk dvtelyidgn qftlvpkels nykhitlidl
 781 snnristlsn qsfsnmtqll tlilsynrlr cipprtfdgl kslrlislhg ndisvvpega
 841 fndlsalshl aiganplvcd cnmgwlsdwv ksevkepgia rcagpgemad klllttpskk
 901 ftcqgpvdit i1akcnpcls npckndgtcn ndpvdfyrct cpygfkgqdc dvpihacisn
 961 pckhggtchl kegenagfwc tcadgfegen cevniddced ndcennstcv dginnytclc
1021 ppeytgelce ekldfcaqdl npcqhdskci ltpkgfkcdc tpgyigehcd idfddcqdnk
1081 ckngahctda vngytcvcpe gvsglfcefs ppmvlprtsp cdnfdcqnga qciirinepi
1141 cqclpgylge kceklvsynf vnkesylqip sakvrpqtni tlqiatdeds gillykgdkd
1201 hiavelyrgr vrasydtgsh pasaiysvet indgnfhive lltldsslsl svdggspkvi
1261 tnlskqstln fdsplyvggm pgknnvaslr qapgqngtsf hgcirnlyin selgdfrkmp
1321 mqtgilpgce pchkkvcahg mcgpssqsgf tceceegwmg plcdqrtndp clgnkcvhgt
1381 clpinafsys ckcleghggv lcdeeedlfn pcqmikckhg kcrlsgvgqp ycecnsgftg
1441 dscdreiscr gerirdyyqk qqgyaacqtt kkvsrlecrg gcagggccgp lrskrrkysf
1501 ectdgssfvd evekvvkcgc arcas
```

SEQ ID NO: 11 Mouse Slit2 Transcript Variant 3 cDNA Sequence

```
   1 atgagtggca ttggctggca gacactgtcc ctatcgctgg ggttagtgtt gtcgatcttg
  61 aacaaggtgg cgccgcaggc gtgcccggcc cagtgctcct gttcaggcag cacggtggac
 171 tgtcatgggc tggcactacg cagtgtgccc aggaatatcc cccgcaacac cgagagactg
 181 gatttgaatg gaaataacat cacgaggatc acgaagatag attttgctgg tctcaggcac
 241 ctcagagttc ttcagctcat ggagaacaga atcagcacca tcgagagggg agcattccag
 301 gatcttaagg agctggaaag actgcgttta aacagaaata accttcagtt gtttcctgag
 361 ctgctgtttc tcgggactgc gaagctctac cggcttgatc tcagtgaaaa tcaaattcaa
 421 acaattccaa ggaaggcttt ccgtgaggca gttaacatta aaaacctgca actggattac
 481 aaccagatca gctgcattga agatggggcg ttcagagctc tacgagatct ggaagtgctc
 541 actctgaaca ataacaatat tactagactt tcagtggcaa gtttcaacca tatgcctaaa
```

TABLE 1-continued

```
 601 cttaggacat ttcgactcca ctcgaacaac ttgtactgcg actgccacct agcctggctc
 661 tcagactggc ttcgccaaag gccacgggtg ggcttgtaca ctcagtgtat gggcccatcc
 721 cacctgaggg gccacaatgt agcagaggtt caaaaacgag agtttgtctg cagtggtcac
 781 cagtcattca tggctccctc ctgcagtgtg ctgcactgcc ccgctgcttg tacctgtagc
 841 aacaacattg tagactgccg agggaaaggt ctcactgaga tccccacaaa tctgcctgag
 901 accatcacag aaatacgttt ggaacagaac tccatcaggg tcatccctcc aggagccttc
 961 tcaccataca aaaagcttag acgactagac ctgagcaaca accagatctc tgaacttgca
1021 ccagatgcct tccaaggact gcgctctctg aattcacttg tcctgtatgg aaataaaatc
1081 acagaactcc caaaaagttt attcgaagga ctattttcct tgcagctact attattgaat
1141 gccaacaaga taaactgcct tcgggtagat gcttttcagg acctgcacaa cttgaacctt
1201 ctctccttat atgacaataa gcttcagacg gttgccaagg gcaccttctc agccctcaga
1261 gccatccaaa ctatgcattt ggcccagaat cctttcattt gtgactgcca tctcaagtgg
1321 ctagcggatt atctccacac caacccaatt gagaccagcg gtgcccgttg caccagcccc
1381 cgccgcctgg caaacaaaag aattggacag atcaaaagca agaaattccg ttgttcaggt
1441 acagaagatt atcgatcaaa attaagtgga gactgctttg cagacttggc ttgtcctgag
1501 aagtgtcgct gtgaagggac cacagtagac tgctccaatc aaagactcaa caaaatccct
1561 gaccatattc cccagtacac agcagagctg cgtctcaata ataatgaatt cacagtgtta
1621 gaagccacgg gaatatttaa gaaacttcct cagttacgta adatcaactt tagcaacaat
1681 aagatcacgg atatcgagga gggtgcattt gaaggcgcgt ctggtgtgaa tgaaattctt
1741 ctcaccagta accgtttgga aaatgttcag cataagatgt tcaaaggact ggagagcctc
1801 aaaacattga tgctgagaag taatcgaata agctgtgttg ggaacgacag tttcatagga
1861 ctcggctcta tgcgtctact ctctttatat gacaatcaaa ttaccacagt ggcaccagaa
1921 gcatttgatt ctctccattc attatccact ctaaacctct tggccaatcc tttcaactgt
1981 aactgtcacc tggcatggct gggagaatgg ctcagaagga aaagaattgt aacaggaaat
2041 cctcgatgcc aaaaacccta cttcctgaag gaaatcccaa tccaggatgt agccattcag
2101 gacttcacct gtgatgatgg aaatgatgac aatagttgct ctccactctc ccgttgtcct
2161 tctgaatgta cctgcttgga tacagtggta cgatgtagca acaagggctt gaaggttttg
2221 cctaaaggta ttccaaaaga tgtcacagag ctgtatctgg atgggaacca gtttacgctg
2281 gtcccgaagg aactctctaa ctacaaacat ttaacactta tagacttaag taacaaccga
2341 ataagcaccc tttccaatca aagcttcagc aacatgaccc agcttctcac cttaatcctc
2401 agttacaacc gtctgagatg tatccctcca cgaacctttg atggattgaa gtctcttcgg
2461 ttactgtctt tacatggaaa tgacatttct gttgtgcctg aaggtgcctt caatgacttg
2521 tcagccttgt cacacttagc gattggagcc aaccctcttt actgtgattg taacatgcag
2581 tggttatccg actgggtgaa gtcggaatat aaggaacctg gaattgcacg ctgtgccggc
2641 cctggagaaa tggcagataa attattactc actactccct ccaaaaaatt tacatgtcaa
2701 ggtcccgtgg atatcactat tcaagccaag tgtaatccct gcttatcaaa tccatgtaaa
2761 aatgatggca cctgtaacaa tgaccccgtt gatttttatc gatgtacctg cccatatgga
2821 ttcaagggtc aggactgtga tgtccccatt catacttgta tcagtaatcc atgtaaacat
2881 ggaggaactt gtcacttaaa ggaaggagag aatgctggat tctggtgcac ttgtgctgat
2941 gggtttgaag gagaaaactg tgaagtcaat attgatgatt gtgaagataa tgattgtgaa
3001 aataattcta catgcgttga tggaattaac aactacacat gtctttgccc adcggaatac
3061 acaggtgaac tgtgtgagga aaagctggac ttctgtgcac aagacttgaa tccctgccag
3121 catgactcca agtgcatcct gactccaaag ggattcaagt gtgactgcac tccaggatac
3181 attggtgagc actgtgacat tgactttgat gactgccaag ataacaagtg taaaaacggt
3241 gctcactgca cagatgccgt gaacggatac acgtgcgtct gtcctgaagg ctacagtggc
3301 ttgttctgtg agttttctcc acccatggtc ctccctcgca ccagcccctg tgataatttt
3361 gattgccaga atggagccca gtgtatcatc aggataaatg aaccaatatg ccagtgtttg
3421 cctggctacc tgggagagaa gtgtgagaaa ttggtcagtg tgaattttgt aaacaaagag
3481 tcctatctcc agattccttc agccaaggtt cggcctcaga caaacatcac acttcagatt
3541 gccacagatg aagacagcgg catectcttg tataaaggtg acaaagacca cattgdcgtg
3601 gaactctata gagggcgagt tcgagccagc tatgacaccg gctctcatcc ggcttctgcc
3661 atttacagtg tggagacaat caatgatgga aacttccaca ttgtggagct actgaccctg
3721 aattccagtc tttccctctc tgtggatgga ggaagcccta aagtcatcac caatttgtca
3781 aaacaatcta ctctgaattt cgactctcca ctctatgtag gaggcatgcc tgggaaaaat
3841 aacgtggcat ccctgcgcca ggcccctggg caaaatggca ccagcttcca tggctgtatc
3901 cggaaccttt acattaacag tgagctgcag gacttccgga aaatgcctat gcaaaccgga
3961 attctgcctg gctgtgaacc atgccacaag aaagtatgtg cccatggcat gtgccagccc
4021 agcagccaat caggcttcac ctgtgaatgt gaggaagggt ggatggggcc cctctgtgac
4081 cagagaacca atgatccctg cctcggaaac aaatgtgtgc atgggacctg cctgcccatc
4141 aatgccttct cctatagttg caagtgcctg gagggccatg gcggtgtcct ctgtgatgaa
4201 gaagaagatc tctttaaccc ctgccagatg atcaagtgca agcatgggaa gtgcaggctt
4261 tctggagtga gccagcccta ttgtgaatgc aacagtggat tcaccgggga cagctgtgat
4321 agagaaattt cttgtcgagg ggaacggata agggactatt accagaagca gcagggttac
4381 gctgcctgtc aaacaactaa gaaagtatct cgcttggaat gcagaggcgg gtgcgctgga
4441 ggccagtgct gtggacctct gagaagcaag aggcggaaat actctttcga atgcacagat
4501 ggctectcat ttgtggacga ggttgagaaa gtggtgaagt gcggctgcgc gagatgtgcc
4561 tcctaa
```

SEQ ID NO: 12 Mouse Slit2 Isoform 3 Amino Acid Sequence

```
  1 msgigwqtls lslglvlsil nkvapqacpa qcscsqstvd chglalrsvp rniprnterl
 61 dlngnnitri tkidfaglrh lrvlqlmenr istiergafg dlkelerlrl nrnnlqlfpe
121 llflgtakly rldlsenqiq aiprkafrga vdiknlqldy nqisciedga fralrdlevl
181 tlnnnnitrl svasfnhmpk lrtfrlhsnn lycdchlawl sdwlrgrpry glytqcmgps
241 hlrghnvaev qkrefvcsgh qsfmapscsv lhcpaactcs nnivdcrgkg lteiptnlpe
301 titeirlegn sirvippgaf spykklrrld lsnnqisela pdafqglrsl nslvlygnki
361 telpkslfeg lfslqlllln ankinclrvd afgdlhnlnl lslydnklgt vakgtfsalr
421 aiqtmhlaqn pficdchlkw ladylhtnpi etsgarctsp rrlankrigq ikskkfrcsg
481 tedyrsklsg dcfadlacpe kcrcegttvd csnqrlnkip dhipgvtael rlnnneftvl
541 eatgifkklp qlrkinfsnn kitdieegaf egasgvneil ltsnrlenvq hkmfkglesl
601 ktlmlrsnri scvgndsfig lgsvrllsly dnqittvapg afdslhslst lnllanpfnc
```

TABLE 1-continued 661 nchlawlgew lrrkrivtgn prcqkpyflk eipiqdvaiq dftcddgndd nscsplsrcp
721 sectcldtvv rcsnkglkvl pkgipkdvte lyldgnqftl vpkelsnykh ltlidlsnhr
781 istlsnqsfs nmtglitlil svnrlrcipp rtfdglkslr llslhgndis vvpegafndl
841 salshlaiga nplycdcnmg wlsdwvksey kepgiarcag pgemadklll ttpskkftcg
901 gpvditiqak cnpclsnpck ndgtcnndpv dfyrctcpyg fkggdcdvpi hacisnpckh
961 ggtchlkege nagfwctcad gfegencevn iddcedndce nnstcvdgin nytclcppey
1021 tgelceekld fcaqdlnpcq hdskciltpk gfkcdctpgy igehcdidfd dcqdnkckng
1081 ahctdavngy tcvcpegysg lfcefsppmv lprtspcdnf dcqngaqcii rinepicqcl
1141 pgvlgekcek lvsvnfvnke sylqipsakv rpqtnitlqi atdedsgill ykgdkdhiav
1201 elyrgrvras ydtgshpasa iysvetindg nfhivelltl dsslslsvdg gspkvitnls
1261 kqstlnfdsp lyvggmpgkn nvaslrqapg qngtsfhgci rnlyinselq dfrkmpmqtg
1321 ilpgcepchk kvcahgmcqp ssqsgftcec eegwmgplcd qrtndpclgn kcvhgtclpi
1381 nafsysckcl eqhggvlcde eedlfnpcqm ikckhgkcrl sgvgqpycec nsgftgdscd
1441 reiscrgeri rdyyqkqqgy aacqttkkvs rlecrggcag gqccgplrsk rrkysfectd
1501 gssfvdevek vvkcgcarca s SEQ ID NO: 13 Rat Slit2 cDNA Sequence 1 atgagtggca ttggctggca gacactgtcc ctatctctgg cgttagtgtt gtcgatcttg
61 aaccaggtgg cgcctcaggc gtgcccggcc cagtgctcct gttcaggcag cacagtggac
121 tgtcatgggc tggcactgcg cagtgtgccc aggaatatcc cccgcaacac ggagagactg
181 gatttgaata gaaataacat cacaaagatc acgaagacag attttgcggg tctcagacac
241 ctcagagttc ttcagctcat ggagaacaag atcagcacca tcgagagggg agcattccag
301 gatcttaagg agctagaaag actgcgttta aacagaaata accttcagtt gtttcctgag
361 ctgctgtttc ttgggactgc gaagctctac cggcttgatc tcagtgaaaa tcagattcaa
421 gcaattccaa ggaaggcttt ccgtggtgca gttgacatta aaaatctgca gttggattac
481 aaccagatca gctgcattga agatgaggca ttccgagctc tacgagatct ggaagtgctc
341 actctgaaca ataacaatat tactagactt tcagtggcaa gtttcaacca tatgcctaaa
601 cttaggacat ttcgactcca ctccaacaac ctatactgcg actgccacct ggcctggctc
661 tcggactggc ttcgccaaag gccacgggtg ggcttgtaca ctcagtgtat gggcccatcc
721 cacctgaggg gccataatgt agcagaggtt caaaaacgag agtttgtctg cagtgatgag
781 gaagaaggtc accagtcatt catggctccc tcctgcagtg tgctgcactg cccgattgct
841 tgtacctgta gcaacaacat tgtagactgc cgagggaaag gtctcactga gatccccaca
901 aatctgcctg agaccatcac agaaatacgt ttggaacaga actccataag ggtcatccct
961 ccaggagcat tctcaccata caaaaagctt cgacgactag acctgagtaa taaccagatc
1021 tcggaacttg ctccagatgc cttccaagga ctgcgttctc tgaattccct tgtcctgtat
1081 ggaaataaaa tcacagaact cccaaaaagt ttatttgaag gactgttttc cttacagcta
1141 ctattattga atgccaacaa gataaactgc cttcgggtag atgcttttca ggacctgcac
1201 aacttgaacc ttctctcctt atacgacaat aagcttcaga ctgttgccaa gggcaccttc
1261 tcagctctca gagccatcca aactatgcat ttggcccaga atcctttcat ttgtgactgc
1321 catctcaagt ggctagcgga ttatctccac accaacccaa ttgagaccag cggtgcccgt
1301 tgcaccagtc cccgccgcct ggctaacaaa agaattggac agatcaaaag caagaaattc
1441 cgttgttcag gtacagaaga ttatcgatca aaattaagtg gagactgctt tgcagacttg
1501 gcttgtcctg aaaaatgtcg ctgtgaaggg accacagtag actgctccaa tcaaaaactc
1561 aacaaaatcc cagaccatat tccccagtac acagcagagc tgcgtctcaa taataatgaa
1621 ttcacagtgt tagaagccac gggaatattt aagaadcttc ctcaattgcg taaaatcaac
1681 cttagcaaca ataagatcac tgatatcgag gagggggcat tcgaaggtgc gtctggtgtg
1741 aatgagattc tgcttaccag taaccgtttg gaaaatgttc agcataagat gttcaaagga
1801 ttggagagcc tcaaaacatt gatgctgaga agtaatcgaa taagctgtgt gggaaacgac
1861 agtttcacag gactcggttc tgtgcgtctg ctctctttat atgacaatca aattaccaca
1921 gttgcaccaa gagcatttgg tactctccat tcattatcta cactaaacct cttggccaat
1981 cctttcaact gtaactgtca cctggcatgg cttggagaat ggctcagaag gaaaagaatt
2041 gtaacaggaa atcctcgatg ccaaaaaccc tacttcttga aggaaatacc aatccaggat
2101 gtagccattc aggacttcac ctgtgatgac ggaaacgatg ataatagctg ctctccactc
2161 tcccgttgtc cttcggaatg tacttgcttg gatacagtag tacgatgtag caacaagggc
2221 ttgaaggtct tacctaaagg cattccaaga gatgtcacag aactgtatct ggatgggaac
2281 cagtttacac tggtcccgaa ggaactctcc aactacaaac atttaacact tatagactta
2341 agtaacaaca gaataagcac cctttccaac caaagcttca gcaacatgac ccaacttctc
2401 accttaattc tcagttacaa ccgtctgaga tgtatccctc cacggacctt tgatggattg
2461 aaatctcttc gtttactgtc tctacatgga aatgacattt ctgtcgtgcc tgaaggtgcc
2521 tttggtgacc tttcagcctt gtcacactta gcaattggag ccaaccctct ttactgtgat
2581 tgtaacatgc agtggttatc cgactgggtg aagtcggaat ataaggaacc tggaattgcc
2641 cgctgtgccg gtcccggaga aatggcagat aaattgttac tcacaactcc ctccaaaaaa
2701 tttacatgtc aaggtcctgt ggatgttact attcaagcca agtgtaaccc ctgcttgtca
2761 aatccatgta aaaatgatgg cacctgtaac aatgacccgg tggattttta tcgatgcacc
2821 tgcccatatg gtttcaaggg ccaggactgt gatgtcccca ttcatgcctg tatcagtaat
2881 ccatgtaaac atggaggaac ttgccactta aaaaaaggag aaaatgatgg attctggtat
2941 acttgtgctg atgggtttga aggagaaagc tgtgacatca atattgatga ttgcgaagat
3001 aatgattgtg aaaataattc tacatgcgtt gatggaatta acaactacac gtgtctttgc
3061 ccaccggaat acacaggcga actgtgtgag gaaaaactgg acttctgtgc acaagacctg
3121 aatccctgcc agcatgactc caagtgcatc ctgacgccaa agggattcaa gtgtgactgc
3181 actccgggat acattggtga gcactatgac atcaactttg atgactgcca agataacaag
3241 tgcaaaaacg gtgctcattg cacagatgca gtgaacggat acacatgtgt ctgtcctgaa
3301 ggctacagtg gcttgttctg tgagttttct ccacccatgg tcctccctcg caccagcccc
3361 tgtgataatt ttgattgtca gaatggagcc cagtgtatca tcagggtgaa tgaaccaata
3421 tgccagtgtt tgcctggcta cttgggagag aagtgtgaga aattggtcag tgtgaatttt
3481 gtaaacaaag agtcctatct tcagattcct tcagccaagg ttcgacctca gacaaacatc
3541 acacttcaga ttgccacaga tgaagacagc ggcatcctct tgtacaaggg tgacaaggac
3601 cacattgctg tggaactcta tcgagggcga gttcgagcca gctatgacac cggctctcac
3661 ccggcttctg ccatttacag tgtggagaca atcaatgatg gaaacttcca cattgtagag
3721 ctactgaccc tggattcaag tctttccctc tctatggatg gaggaagccc taaaatcatc TABLE 1-continued

```
3781 accaatttgt caaaacaatc tactctgaat ttcaactctc cactttacgt aggaggtatg
3841 cctgggaaaa ataacgtggc ttcgctgcgc caggcccctg ggcagaacgg caccagcttc
3901 catggctgta tccggaacct ttacattaac agtgaactgc aggacttccg gaaagtgcct
3961 atgcaaaccg gaattctgcc tggctgtgaa ccatgccaca agaaagtgtg tgcccatggc
4021 acatgccagc ccagcagcca atcaggcttc acctgtgaat gtgaggaagg gtggatgggg
4081 cccctctgtg accagagaac caatgatccc tgtctcggaa acaaatgtgt acatgggacc
4141 tgcttgccca tcaacgcctt ctcctacagc tgcaagtgcc tggagggcca cggcggggtc
4201 ctctgtgatg aagaagaaga tctgtttaac ccctgccagg tgatcaagtg caagcacggg
4261 aagtgcaggc tctctgggct cgggcagccc tattgtgaat gcagcagtgg attcaccggg
4321 gacagctgta acagagaaat ttcttatcga gggaaacgga taagggatta ttaccaaaag
4381 cagcagggtt acgctgcctg tcaaacgact aagaaagtat ctcgcttgga gtgcagaggc
4441 gggtgtgctg gggggcagtg ctgtggacct ctgagaagca agaggcggaa atactctttc
4501 gaatgcacag atggatctt
```

SEQ ID NO: 14 Rat Slit2 Amino Acid Sequence

```
   1 msgigwqtls lslalvlsil nqvapqacpa gcscsgstvd chglalrsvp rniprnterl
  61 dlngnnitri tktdfaglrh lrvlqlmenk istiergafq dlkelerlrl nrnnlqlfpe
 121 llflgtakly rldlsenqiq aiprkafrga vdiknlqldy nqisciedga frairdlevl
 181 tlnnnnitrl svasfnhmpk lrtfrlhsnn lycdchlawl sdwlrqrprv glytqcmgps
 241 hlrghnvaev qkrefvcsde eeghqsfmap scsvlhcpia ctcsnnivdc rgkglteipt
 301 nlpetiteir leqnsirvip pgafspykkl rrldlsnnqi selapdafqg lrslnslvly
 361 gnkitelpks lfeglfslql lllnankinc lrvdafqdlh nlnllslydn klqtvakgtf
 421 sairaiqtmh laqnpficdc hlkwladylh tnpietsgar ctsprrlank rigqikskkf
 481 rcsgtedyrs klsgdcfadl acpekcrceg ttvdcsnqkl nkipdhipqy taelrlnnne
 541 ftvleatgif kklpglrkin lsnnkitdie egafegasgv neilltsnrl envqhkmfkg
 601 leslktlmlr snriscvgnd sftglgsvrl lslvdnqitt vapgafgtlh sistlnllan
 661 pfncnchlaw lgewlrrkri vtgnprcqkp yflkeipiqd vaigdftcdd ghddnscspl
 721 srcpsectcl dtvvrcsnkg lkvlpkgipr dvtelyldgn qftlvpkels nykhatlidl
 781 snnristlsn gsfsnmtqll tlilsynrlr cipprtfdgl ksarllslhg ndisvvpega
 841 fgdlsalshl aiganplycd cnmqwlsdwv kseykepgia rcagpgemad klllttpskk
 901 ftcqgpvdvt iqakcnpcls npckndgtcn ndpvdfyrct cpygfkgqdc dvpihacisn
 961 pckhggtchl kegendgfwc tcadgfeges cdiniddced ndcennstcv dginnytclc
1021 ppeytgelce ekldfcaqdl npcqndskci ltpkgfkcdc tpgyigehcd idfddcqdnk
1081 cknganctda vngytcvcpe gysqlfcefs ppmvlprtsp cdnfdcqnga qciirvnepi
1141 cqclpgylge kceklvsvnf vnkesylqip sakvrpqtni tlgiatdeds gillykgdkd
1201 hiavelyrgr vrasydtgsh pasaiysvet indgnfhive lltldsslsl svdggspkii
1261 tnlskqstln fdsplyvggm pgknnvaslr qapgqngtsf hgcirnlyin selqdfrkvp
1321 mqtgilpgce pchkkvcahg tcgpssgsgf tceceegwmg plcdqrtndp clgnkcvhgt
1381 clpinafsys ckcleghggv lcdeeedlfn pcqvikckhg kcrlsglgqp ycecssgftg
1441 dscdreiscr gerirdyyqk qqgvaacqtt kkvsrlecrg gcaggqccgp lrskrrkysf
1501 ectdgssfvd evekvvkcgc trcas
```

SEQ ID NO: 15 Dog Slit2 cDNA Sequence

```
   1 atgcgcgggg ccggccggcg ggcgctgccc gtgtcgctgg ggctcgtgct gctgatcctg
  61 ggcgaggcgg cgccgcaggc gtgcccggcg cagtgctcct gctcgggcag caccgtggac
 121 tgtcacgggc tggcgctgcg cagcgtgccc aggagcatcc cccgcaacac cgagaggctg
 181 gatttgaatg gcsataacat cacacggatt accaagacag atttcgctgg tcttcgacac
 241 ctaagagttc ttcagcttat ggagaataag attagcacca ttgaaagagg agcattccag
 301 aatcttaaga aactggaaag actgcattta aacagaaatc accttcagct gtttcctgag
 361 ttgctgtttc ttgggacttc gaagctgtac aggcttgatc tcagtgaaaa ccaaattcag
 421 gcaattccaa ggaaggcttt ccgtggggca gttgacatta aaaatttgca actggattac
 481 aaccagatca gctgtattga agatggggca tttagagctc tgcgggacct ggaagtgctc
 541 actctcaaca ataacaacat tactagactt tctgtggcaa gtttcaacca tatgcctaaa
 601 cttaggactt ttcggctaca ttcaaacaat ctgtattgcg actgccacct ggcctggctt
 661 tctgactggc tgcgccaaag gccccgggtt ggtctctaca ctcagtgtat gggcccatcc
 721 cacctgaggg gtcataacgt agccgaggtt caaaaacgcg aatttgtctg cagtggtaag
 781 ggagaaagaa cctttctgtt gtcctattat cttatgctac tttgccacca gtccttcatg
 841 gctccttctt gcagcgtcct gcattgtcca gccgcttgta cctgtagcaa caatatcgta
 901 gactgtcgtg ggaaaggtct cactgagatc cccacgaacc tgccagagac catcacagaa
 961 atacgtttgg aacagaactc aatcaaggtc atccctcctg gagctttctc accatataaa
1021 aagcttagaa gaattgacct gagcaataat cagatctctg aactagcacc ggacgctttc
1081 caaggactac gctctctgaa ttcacttgtc ctctatggaa ataaaatcac ggaactccca
1141 aaaagtttat ttgaaggact gttttcctta cagctgctat tattgaatgc caacaagata
1201 aactgccttc gggtagatgc ttttcaggat ctgcacaacc tgaatcttct ctccctgtac
1261 gacaacaagc tgcagaccat cgccaagggg accttctcac ctctccgggc cattcagacc
1321 atgcacctgg cccagaaccc ctttatttgt gactgccatc tcaagtggct ggcggactat
1381 ctccacacca accccatcga gaccagtggt gcccggtgca ccagcccccg gcgcctggca
1441 aacaaaagaa tcggacagat caaaagcaag aaattccgtt gttcagctaa agaacagtat
1501 ttcattccag gtacagaaga ttatcgatca aaattaagcg gggactgctt tgcagatctg
1561 gcttgccctg aaaagtgccg ctgtgaagga accacagtag attgctccaa tcaaaaactc
1621 accaaaatcc cagaccacat cccctagtac actgcagagc tgcgtctcaa taataatgaa
1681 ttcacagtgc tggaagctac aggaatcttc aagaaacttc cgcagttacg taaaataaac
1741 ttcagcaaca acaagatcac agacattgaa gaaagagcat ttgaaggagc agctggtgta
1801 aacgaaatcc ttctcacgag taaccgtttg gaaaatgttc agcataagat gttcaaggga
1861 ttggaaagcc tgaaaacgtt gatgttgcga agcaatcgca taagctgcgt tggcaacgat
1921 agcttcatag gcctgagctc tgtgcggttg ctttcgctgt acgataatca gatcgccacc
1981 atcgcgccgg gggcgttcga caccctgcac tcgttgtcca ccctaaacct gttggccaac
2041 ccttttaact gcaactgcta cctggcttgg ctgagcgagt gactcaggaa gaaaagaatt
2101 gtaaccggaa atcctcgctg tcaaaaacca tacttcctca aagaaatccc catccaggac
2161 gtcgccattc aagacttcac gtgtgacgac ggaaatgacg acagtagctg ttctccactc
```

TABLE 1-continued 2221 tcgcgctgtc ccacggaatg cacgtgcttg gatacagttg tccgatgtag caacaagggc
2281 ctgaaggtct tgcccaaagg tattcccaga gacgtcactg aactgtatct ggatgggaac
2341 cactttacct tggttcccaa ggagctctat aactacaaac atctaacgct tatagacctg
2401 agcaacaacc gcataagcac tctttctaat cagagcttca gcaacatgac ccagctactc
2461 accctaattc tcagttacaa ccgtttgaga tgtattcctc ctcgaacctt cgatggactc
2521 aagtctctcc gattactttc attacatgga aatgacattt ctgttgtgcc tgaaggtgct
2581 ttcagtgatc tctctgcatt atcacaccta gcaatcggag ccaaccccct ttactgtgat
2641 tgcaacatgc agtggttatc ggactgggta aagtcggaat acaaagaacc cgggattgct
2701 cgctgtgccg gccccggaga aatggcagat aaattattac tcacgactcc ctccaaaaaa
2761 tttacatgtc aaggtcctgt ggatatcaat attctagcta aatgtaatcc ctgcttatca
2821 aacccatgta agaatgatgg cacctgtaac aatgatccag tcgactttta tcgctgtacc
2881 tgtccgtatg gtttcaaggg gcaggactgt gatgtcccaa tccacgcatg catcagtaac
2941 ccgtgtacac atggaggaac ttgccactta aaggagggag aaaaagatgg attctggtgt
3001 atttgtgccg atggatttga aggagaaaat tgtaaagtca atgttgatga ctgtgaagat
3061 aatgactgtg aaaataactc tacgtgtgtc gatggaatta ataactacac atgcctttgt
3121 ccgcctgagt acacaggcga gttgtgtgag gagaagctgg acttctgcgc tcaggacctg
3181 aacccctgcc agcacgactc caagtgcatc ctgatgccca aaggattcaa atgcgactgc
3241 acgccggggt acgtgggcga gcactgcgac atcgacttcg acgactgcca ggatcacaag
3301 tgtaaaaacg gagcgcactg cacggacgcg gtgaacggct acacgtgcac ctgccccgaa
3361 ggctacagcg gcttgttctg tgaattctcc ccgcccatgg tcctcccacg caccagcccc
3421 tgtgacaact tcgactgtca gaacggggcg cagtgcatcg tcagggcggg cgagccaatc
3481 tgccagtgtc tgcccggcta ccagggggac aagtgtgaga agttggtcag cgtgaacttc
3541 gtgaacaaag agtcgtatct tcaaattcct tcagccaagg tccggcccca aacgaacatc
3601 accctgcaga ttgccaccga cgaagacagc gggatcctcc tgtacaaggg cgacaaggac
3661 cacattgccg tggagctgta tcggggacgg gtgcgcgcca gctacgacac cggctcgcac
3721 cccgcttctg ccatttacag cgtggagacg atcaatgatg gaaactttca cattgtggaa
3781 ctacttgccc tggatcagag cctgtccctc tccgtggatg gagggagccc caaaatcatc
3841 accaacttgt caaagcagtc cactctgaat tttgactctc cactctatgt aggaggcatg
3901 cccgggagga acaacgtagc cgcggccctg cgccaggccc cagggcacaa cggcaccaac
3961 ttccacggct gcatccggaa cctgtatatc aacagcgagc tccaggactt ccgccaggtg
4021 cccatgcaga ccggcatcct gcccggctgc gagccgtgcc acaggaaggt gtgtgcccac
4001 ggcgcgtgcc agcccagcag ccagtcgggc ttcacctgcg agtgcgagga gggctggacg
4141 gggcccctgt gtgaccagag gaccaacgac ccctgtctcg ggaacaaatg tgtgcacggc
4201 acctgcttgc ccatcaacgc cttctcctac agctgtaagt gtctggaggg ccacgggggc
4261 gtcctctgcg acgaagagga ggacctgttc aacccctgcc aggccatcag gtgcaagcac
4321 gggaaatgca ggctctcggg cctgggccag ccctactgcg aatgcagcag cgggtacacg
4381 ggggatagct gcgaccgaga agtgtcctgt cggggcgagc gcgtccggga ctactaccca
4441 aagcagcaga gctacgcagc ctgccagacc accaagaagg tatcgcggct ggagtgcaag
4501 ggcggctgcg cggccgggca gtgctgcggg ccgctgcgga gcaagcggcg gaaatactcc
4561 ttcgagtgca cggacggctc gtcgttcgtg gacgaggtgg agaaggtggt caagtgcggc
4621 tgcagcaggt gcgccgcctg a SEQ ID NO: 16 Dog Slit2 Amino Acid Sequence
1 mrgagrralp vslglvllil geaapqacpa qcscsgstvd chglalrsvp rsiprnterl
61 dlngnnitri tktdfaglrh lrvlglmenk istiergafq dlkelerlrl nrnhlqlfpe
121 llflgtskly rldlsenqiq aiprkafrga vdiknlqldy nqisciedga fralrdlevl
181 tlnnhnitrl svasfnhmpk lrtfrlnsnn lycdchlawl sdwlrqrprv glytqcmgps
241 hlrghnvaev qkrefvcsgk gertfllsyy lmllchqsfm apscsvlhcp aactcsnniv
301 dcrgkgltei ptnlpetite irlegnsikv ippgafspyk kirridlsnn giselapdaf
361 gglrslnslv lygnkitelp kslfeglfsl qllllnanki nclrvdafgd lhnlnllsly
421 dnklqtiakg tfsplraiqt mhlaqnpfic dchlkwlady ihtnpietsg arctsprrla
481 nkrigqiksk kfrcsakeqy fipgtedyrs klsgdcfadl acpekcrceg ttvdcsnqkl
541 tkipdhipqy taelrlnnne ftvleatqif kklpglrkin fsnnkitdie egafegaagv
601 neilltsnrl envqhkmfkg ieslktlmlr snriscvgnd sfiglssvrl lslvdnqiat
661 iapgafdtlh slstlnllan pfncncylaw lgewlrkkri vtgnprcqkp yflkeipiqd
721 vaiqdftcdd gnddsscspl srcptectcl dtvvrcsnkg lkvlpkgipr dvtelyldgn
781 hftlvpkely nykhltlidi snnristlsn gsfsnmtqll tlilsynrlr cipprtfdgl
841 kslrllslhg ndisvvpega fsdlsalshl aiganplycd cnmgwlsdwv kseykepgia
901 rcagpgemad kllltpskk ftcqgpvdin ilakcnpcls npckndgtcn ndpvdfyrct
961 cpygfkgqdc dvpihacisn pcthggtchl kegekdgfwc icadgfegen cevnvddced
1021 ndcennstcv dginnytclc ppeytgelce ekldfcaqdl npcqhdskci lmpkgfkcdc
1081 tpgyvgehcd idfddcqdhk cknqahctda vngytctcpe gysglfcefs ppmvlprtsp
1141 cdnfdcqnga qcivragepi cqclpgyqgd kceklvsvnf vnkesylqip sakvrpqtni
1201 tlqiatdeds gillykgdkd hiavelyrgr vrasydtgsh pasaiysvet indgnfhive
1261 llaldqslsl svdggspkii tnlskqstln fdsplyvggm pgrnnvaaal rqapghngts
1321 fhgcirnlyi nselqdfrqv pmqtgilpgc epchrkvcah gacqpssqsg ftceceegwt
1381 gplcdqrtnd pclgnkcvhg tclpinafsy sckcleghgg vlcdeeedlf npcqairckh
1441 gkcrlsglgq pycecssgyt gdscdrevsc rgervrdyyp kqqgyaacqt tkkvsrlecr
1501 ggcaagqccg plrskrrkys fectdgssfv devekvvkcg csrcaa SEQ ID NO: 17 Cow Slit2 cDNA Sequence
1 atgcacggcg tcggctggca gacgctgtcc ctgtctctgg ggttagtgct ggcgatcctg
61 aacgaggtgg cgccgcaagc gtgtccggcg cagtgctcct gctccgggag cacagtggac
121 tgtcacgggc tggcgttgcg cagtgtgccc aggaatatcc cccgcaacac cgagagattg
181 gatttgaatg gaadtaacat cacaaggatt accaagacag attttgctgg tcttcgacac
241 ctaagagttc ttcagcttat ggagaataag attaccacca ttgaaagagg agcattccag
301 aatcttaaag aactggaaag actgcgttta aacagaaatc accttcagct gtttcctgag
361 ttgctgtttc ttgggacttc gaagctatac aggcttgacc tcagtgaaaa ccagattcag
421 gcaattccaa ggaaagcttt tcgtggggca gttgatatta aaaatctgca actggattac
481 aaccacatca gctgtattga agatggggca ttcagggctc tccgggacct ggaagtgctc TABLE 1-continued 541 actctcaaca ataacaacat tactagactt tctgtggcaa gtttcaacca tatgcctaaa
601 cttaggactt ttcgactcca ttcgaacaac ctatattgtg actgccacct ggcctggctc
661 tcggactggc tgcgccaaag gcctcgggtg ggcctctaca ctcagtgtat ggggccatct
721 cacctgaggg gccacaatgt agctgaggtt caaaaacgag aatttgtctg cagcgatgag
781 gaagaaggtc accagtcatt tatggctcct tcttgcagtg ttttgcactg cccagctgct
841 tgtacctgta gcaacaacat cgtagattgc cgtgggaaag gtctcactga gatccccacg
901 aatctgccag agaccatcac agaaatacgt ttggaacaga actcaatcaa ggtcatccct
961 cctggagctt tctcaccata taaaaagctt agaagaatcg acctgagcaa taatcagatc
1021 tctgagctag caccagatgc tttccaagga ctacgctctc tgaattcact tgtcctctat
1081 ggaaataaaa tcacagaact cccaaaaagt ttatttgaag gactgttttc cttacagtta
1141 ctattactga atgccaacaa gataaactgc ctccgggtag atgcttttca ggatctgcac
1201 aacctgaacc ttctctcctt atatgacaac aagcttcaga ccatcgccaa ggggaccttt
1261 tcacctctcc gggccattca aaccatgcat ttggcccaga acccctttat ttgtgactgc
1321 catctcaagt ggctggcgga ttatctccat accaacccaa tcgagaccag tggtgcccgc
1381 tgcaccagtc cccggcgact ggcaaacaaa agaatcggac agatcaaaag caagaaattc
1441 cgttgttcag ctaaagaaca gtatttcatt ccaggtacag aagattatcg atcaaaatta
1501 agtggggact gctttgccga tttggcttgc cctgaaaagt gccgctgcga agggaccaca
1561 gtagactgct ccaatcaaaa actcaccaaa atcccagatc acattcccca gtacactgca
1621 gagctgcgcc tcaacaataa tgaatttaca gtgttggaag ttaccgggat cttcaagaaa
1681 cttcctcagt tacgtaaaat aaactttagc aacaataaga tcacagacat tgaagaggga
1741 acgtttgaaa gagcatctgg tgtgaatgaa atacttctca ccagtaatcg tttggaaaat
1801 gttcagcata agatgttcaa gggcttggaa agcctcaaga ctttgatgtt gagaagtaat
1861 cgcataagct gtgtagggaa tgacagtttc ataggactca gctctgtgcg tttgctttct
1921 ttatatgata atcagattac taccattgca ccaggagctt ttgatactct ccattcttta
1981 tctactctaa acctcttggc caatcctttc aactgtaact gctacctggc ttggttggga
2041 gaatggctta ggaagaaaag aattgtaaca ggaaatcctc gatgtcagaa accctatttc
2101 ctcaaagaaa tccccatcca ggatgtggcc attcaagact tcacttgtga tgatggaaat
2161 gatgacaata gctgttcccc actctctcgc tgtcctgccg agtgtacctg cttggacaca
2221 gtggttcgat gtagcaacaa agccttgaag gtcttgccca aaggaattcc aagagatgtc
2281 actgaattgt atctggatgg gaaccagttt accttggttc ctaaggaact ctctaactac
2341 aaacatttaa cacttataga cttaagtaac aacagaataa gcaccctctc taatcagagc
2401 ttcagcaaca tgacccagct cctcacttta attcttagtt acaaccgttt gagatgtatt
2461 cctcctcgaa ccttcgatgg actgaagtct cttcggttac tttctttaca tggaaacgac
2521 atttctgttg tgcctgaagg tgctttcaat gatcttgctg cattatcaca cctagcaatt
2581 ggagccaacc ctctttactg tgattgtaac atgcagtggt tatccgactg ggtaaagtcg
2641 gaatacaaag agccgggaat tgctcgctgt gctggtcctg gagaaatggc agataaacta
2701 cttctcacaa ctccctccaa aaaatttaca tgtcaaggtc ctgtggatgt caatattcta
2761 gctaaatgta atccctgctt atcaaatcca tgtaaaaatg atggcacctg taacaatgac
2821 ccagttgact tttatcgctg cacctgtcca tatggtttca aggggcagga ttgtgatgtt
2881 ccaattcatg cgtgcatcag caacccatgt aaacatggag gaacttgcca cttaaaagaa
2941 ggagaaaaag atggattctg gtgtatttgt gctgatggat ttgaaggaga aaattgtgaa
3001 atcaatgttg atgactgtga agataatgac tgtaaaaata actctacatg tgtcgatgaa
3061 attaataact acacatgcct ttgcccacct gagtacacag gagagttgtg tgaggagaaa
3121 ctggacttct gtgcccagga cttgaacccc tgccagcatg actccaagtg catcctgacg
3181 ccaaagggat acaaatgtga ctgcactcca ggatacatag gcgaacattg tgacattgac
3241 ttcgatgact gccaagataa caagtgtaag aacggagccc actgcaccga tgcagtgaac
3301 agttacacat gcacctgtcc tgaagactac agtagcttgt tttgtgaatt ttctccacct
3361 atggttctcc ctcgtaccag cccctgtgat aattttgatt gtcagaatgg agctcaatgc
3421 atcatcagga tcaatgagcc aatatgccag tgtttgcctg gctaccaggg agaaaagtgt
3481 gaaaaactgg tcagtgtgaa ttttgtaaac aaagagtctt atcttcagat cccttccgcc
3541 aaggtccggc ctcaaacaaa catcactctt cagatcgcca cagatgaaga cagtggaatc
3601 ctcctgtata agggtgataa agaccatatt gctgtagaac tctaccgagg acgtgttcgt
3661 gccagctatg acaccggctc ccacccggct tctgccattt acagtgtgga gacaatcaat
3721 gacggaaatt ttcacattgt ggaactactt gccctggatc aaagtctctc cctctcagtg
3781 gatggaggga gccccaaaat cattaccaac ttgtcaaaac agtccactct gaattttgac
3841 tccccactct atgttggagg catgcccggg aagaacaacg tggccgcagc tctgcgccag
3901 acccctgggc agaatggcac cagcttccac ggttgcatcc gaaaccttta catcaacaac
3961 gaacttcagg acttccggaa ggtgcccatg cagaccggca tcctgcctgg ctgtgaacca
4021 tgccacaaga aggtgtgtgc ccacggcaca tgccagccca gcagccaggc cggcttcacc
4001 tgcgagtgcg aggaaggatg gacagggccc ctctgtgatc agaggaccaa tgacccctgt
4141 cttggaaata aatgcgtcca cggcacctgc ctgcccatca atgcgttctc ctacagctgc
4201 aaatgcctag agggccatgg gggcgtcctc tgtgatgaag aggaggatct gtttaaccca
4261 tgccaggcga tcaagtgcaa gcatgggaaa tgcaggctct caggactggg gcagccctac
4321 tgtgaatgca gcagtggata caccggggac agctgtgatc gagaaatctc ttgtcgaggg
4381 gaacggataa gagattatta ccaaaagcag cagggctacg ccgcttgcca gacgaccaag
4441 aaggtgtctc ggttggaatg cagagagggc tgtacaggcg gacagtgctg cggacctctg
4501 aggagcaaga gaaggaaata ctctttcgaa tgcactgatg ggtcctcgtt tgtggacgag
4561 gtggagaagg tggtaaagtg tggctgtacc cgctgcgctt cctaa SEQ ID NO: 18 Cow Slit2 Amino Acid Sequence 1 mhgvgwqtls lslglvlail nevapqacpa qcscsgstvd chglalrsvp rniprnterl
61 dlngnnitri tktdfaglrh lrvlqlmenk ittiergafq dikelerlrl nrnhlqlfpe
721 llflgtskly rldlsenqiq aiprkafrga vdiknlqldy nhisciedga fralrdlevl
181 tlnnnnitrl svasfnhmpk lrtfrlhsnn lycdchlawl sdwlrqrprv glytqcmgps
241 hlrghnvaev qkrefvcsde eeghqsfmap scsvlhcpaa ctcsnnivdc rgkglteipt
301 nlpetiteir legnsikvip pgafspykkl rridlsnnqi selapdafqg lrslnslvly
361 gnkitelpks lfeglfslql lllnankinc lrvdafqdlh nlnllslydn klqtiakgtf
421 splraiqtmh laqnpficdc hlkwladylh tnpietsgar ctsprrlank rigqikskkf
481 rcsakeqyfi pgtedyrskl sgdcfadlac pekcrcegtt vdcsnqkltk ipdhipqyta
541 elrlnnneft vleatgifkk lpqlrkinfs nnkitdieeg afegasgvne illtsnrlen TABLE 1-continued 601 vqhkmfkgle slktlmlrsn riscvgndsf iglssvrlls lydnqittia pgafdtlhsl
661 stanllanpf ncncylawlg ewlrkkrivt gnprcqkpvf lkeipiqdva iqdftcddgn
721 ddnscsplsr cpaectcldt vvrcsnkalk vlpkgiprdv telyldgnqf tlvpkelsny
781 khltlidlsn nristlsnqs fsnmtqlltl ilsynrlrci pprtfdglks lrllslhgnd
841 isvvpegafn dlaalshlai ganplycdcn mgwlsdwvks eykepgiarc agpgemadkl
901 llttpskkft cqgpvdvnil akcnpclsnp ckndgtcnnd pvdfyrctcp ygfkgqdcdv
961 pihacisnpc khggtchlke gekdgfwcic adgfegence invddcednd cennstcvdg
1021 innytclcpp eytgelceek ldfcaqdlnp cqhdskcilt pkgykcdctp gyigehcdid
1081 fddcqdnkck ngahctdavn gytctcpegy sglfcefspp mvlprtspcd nfdcqngaqc
1147 iirinepicq clpgyqgekc eklvsvnfvn kesylqipsa kvrpqtnitl qiatdedsgi
1201 llvkqdkdhi avelyrgrvr asydtgshpa saivsvetin dgnfhivell aldqslslsv
1261 dggspkiitn lskqstlnfd splyvggmpg knnvaaalrq apgqngtsfh gcirnlyins
1321 elqdfrkvpm qtgilpgcep chkkvcahgt cqpssqagft ceceegwtgp lcdqrtndpc
1381 lgnkcvhgtc lpinafsysc kcleghggvl cdeeedlfnp cqaikckhgk crlsqlgqpy
1441 cecssgytgd scdreiscrg erirdyyqkq qgyaacqttk kvsrlecrgg caggqccgpl
1501 rskrrkysfe ctdgssfvde vekvvkcgct rcas SEQ ID NO: 19 Chicken Slit2 cDNA Sequence 1 atgatgtgcg cctgggggag gctccccctg gccctggggc tgctgctggt gctggcgggc
61 gaggcggcgc cgcagccgtg cccggcgcag tgctcctgct caggaagcac ggtggactgt
121 cacgggctgg cgctgcgcgg cgtcccgagg aacatccccc gcaacactga gcggctggac
181 cttaatggaa ataacatcac cagaatcacc aagaccgact ttgctggtct aaggcacctt
241 cgagttcttc agctcatgga gdacaagatt agcactattg agagaggagc attccaggat
301 ttaaaagaac tggagaggct gcgcctaaac agaaataacc tccagttgct ttctgaactg
361 ctctttctga ggacgccaaa gttatacagg cttaatctta gtgaaaatca gattcaagcc
421 atacccagga aggcatttcg tggagcagta gacataaaaa atctgcaact ggattacaac
481 cagatcagct gtattgaaga tggggcattt agggctctac gcgacctgga agtgctcact
541 ctcaacaaca ataacattac tcgactgtcc gtcgcaagtt tcaatcatat gcccaaactc
601 agaacttttc gcctgcactc caacaacctc tactgtgact gccacctggc ctggctgtcg
661 gactggctgc ggcagcgacc acgtgtaggc ctctacactc aatgcatggg cccagcacac
721 ctgcggggcc ataacgtggc tgaggtccag aagegggagt tcgtctgcag tggtcaccaa
781 tcatttatgg ctccatcctg cagtgtcttg cattgtcctg ctgcatgcac ctgtagtaac
841 aacattgtgg actgtcgtgg gaaaggcctt actgaaattc caacaaatct tccagaaacc
901 attactgaaa tacggttaga acaaaattca atcaaagtca tacctcctgg agctttctca
961 ccctataaaa agcttcgaag aattgacctg agcaataacc agatctctga agcagctcca
1021 gatgctttcc agggcttacg ttctctcaat tcacttgtcc tctatggcaa taaaattaca
1081 gaacttccaa aaggcctatt tgaaggactg ttttctctgc aattgctatt attaaatgcc
1141 aacaagatca attgcctgcg tgttgatgct tttcaagatc tgcacaactt gaatctccta
1201 tctttatatg acaacaagct tcagaccatt gcaaaaggca ccttttcacc tctacgtgca
1261 attcagacct tgcatttggc tcagaaccca tttatctgtg actgccatct gaagtggctg
1321 gcggattatc ttcatacaaa ccccattgag accagtggtg cccgctgcac cagcccccgc
1381 cgtctggcaa acaaaaggat cggccagatc aaaagcaaga aattccgctg ctcagctaaa
1441 gagcagtatt tcattccagg cactgaagat tacagatcca aattaagtgg tgactgcttt
1501 gcagatttgg cttgccctga gaaatgtcgc tgtgaaggga ccacagtgga ctgctccaat
1561 cagaaactca acaaaattcc tgatcacatc ccacagtaca cagcagagtt gcgactcaat
1621 aacaatgaat tttcagtcct ggaagctact gggatcttta agaagcttcc tcaactgcga
1681 aaaataaacc tgagcaataa caagattaca gatattgaag aaggtgcatt tgatagagcc
1741 tctggtgtca atgaactatt gctcactagc aatcgtttgg aaactgttag agacaaaatg
1801 ttcaaaggac tggaaagtct taaaacactg atgctgagga gtaaccgtgt gagctgtgtg
1861 gggaacgaca gtttcacagg cctgagctct gtccgtctgc tctcactata tgacaaccag
1921 atcaccaccg tggcacccgg ctccttcgat accctgcatt cactctctac attaaacctc
1981 ttggccaatc ctttcaactg caactgccat cttgcatggc ttggagattg gctaaggaag
2041 aaacgcattg tgacgggaaa ccctcgctgt cagaaacctt atttcctcaa agagattcct
2101 atccaggata tggcaattca ggattttaca tgtaatgatg gaaatgatga caatagctac
2161 tctccgctgt cccgctgtcc tgcagaatgt acttgtctag acacagttgt tcgctgcagc
2221 aacaaaggcc taaaagcttt gcctaaaggc atcccaaaag atgtaactga actatatttg
2281 gatggaaacc agtttactct tgttcctaaa gagctctcca actacaaaca tttaacactt
2341 atagatttaa gtaacaacag aatcagcact ctttctaatc agagcttcag caacatgact
2401 cagctgctca ccttaattct tagttacaac cgcctgaggt gtatccctgc acggactttt
2461 gatgggttga aatcacttag gttgctgtct ttacatggca atgatatttc tgtggttcct
2521 gaaggagcct ttaatgatct ttcagcgtta tcacacctgg ctattggagc aaatcctctt
2581 tattgtgatt gtaacatgca atggctgtct gactgggtaa aatcagaata caaagaacct
2641 ggtattgcac gatgtgctgg ccctggagaa atggcagata aacttctact tacaactcca
2701 tctaaaaaat ttacttgcca agggcccgtg gatgtcaata ttcttgctaa gtgtaacccc
2761 tgcttatcaa atccatgtaa aaatgatgga acctgcaata atgatccagt tgacttctat
2821 agatgtactt gcccatatgg tttcaagggt caagactgtg atattcccat tcatgcctgc
2881 attagtaacc cttgcaacca tggtggaact tgtcatttga aagaaggaga aaaagatggt
2941 ttctggtgca cttgtgcaga tggatttgaa ggagaaaatt gtgaaataaa tgttgatgac
3001 tgtgaagaca atgactgtga aaataactct acttgtgtgg atggaattaa taattatact
3061 tgcctttgtc cacctgaata tacagatgag ctctgtgagg agaaactaga tttctgtgct
3121 caaaacctga acccttgcca gcacgactca aagtgtatct tgactcccaa aggttacaag
3181 tgtgattgca cacctggata tgtaggtgaa cactgcgata ttgacttcga tgactgccag
3241 gacaataaat gtaaaaacgg agcacagtgt acggatgcag ttaacgggta tacttgtatt
3301 tgcccagagg gatacagtgg cttgttttgt gagttttcgc caccaatggt tttacctcgc
3361 accagccctt gtgataatta tgaataccaa aatagagccc aatgtattgt aaaggagaat
3421 gaaccaatct gccagtgttt atcaggctac cagggtgaga aatgtgaaaa gctgatcagt
3481 ataaactttg tcaacaaaga atcctatcta caaatccctt cagctaagat acactcccaa
3541 accaatatca ctcttcagat tgccacagac gaagacagtg ggatcctgct ctacaaaggc
3601 gataaggatc atatagcagt agagctgtac cgtggtagag tgagggtcag ttatgacaca
3661 ggatcttatc cagcctctgc tatttacagt gtggaaacta ttaatgatgg caatttccac TABLE 1-continued

```
3721 attgtggagc tgcttgccat ggatcagatt ctgtctttgt ctattgatgg aggaagaccc
3781 aagataatta ccaatttgtc caagcagtcc actttgaatt ttgattctcc actgtatgtc
3841 ggaggcatgc ctgtgaaaaa taacattgca gctctacgtc agtctccagg acagaatggc
3901 acaagcttcc atggctgcat ccgtaatctg tatatcaaca gcgaactcca ggacttcaga
3961 aatgtgccac tgcaagtggg aattctgcca ggttgcgagc cttgtcacaa gaaagtttat
4021 gtgcatggaa catgccatgc taccagccag tcaagcttta cctgtgagtg tgaaggagga
4081 tggactggac ccctctgtga tcaacaaact aatgacccgt gtctcggaaa taaatgtgtg
4141 catggtacct gcttgccgat caatgcattt tcatacagtt gtaaatgcct gcagggacat
4201 gggggagtcc tctgtgatga agaggaaatg ctgtttaacc cctyccaatc catcaggtgt
4261 aaacatggca aatgcaggct ttcaggacSt gggaaaccat attgcgaatg cagcagcgga
4321 tacacggggg acagctgtga taaagaaatc tcttgtcgag gggaacgaat ccgagattac
4381 taccaaaagc agcaagggta tgctgcgtgc cagacgacca agaaggtatc gagactagaa
4441 tgtaaaggag gatgttcaac cgggcagtgc tgtggaccac taaggagcaa gagacggaaa
4501 tactctttta aatgcactga tgggtcgtca tttatggacg aaattgaaaa agtggtgaag
4561 tgtggctgta caaattgtcc ctcctaa
```

SEQ ID NO: 20 Chicken Slit2 Amino Acid Sequence

```
   1 mmcawgrlpl alglllvlag eaapgpcpaq cscsgstvdc hglalrgvpr niprnterld
  61 lngnnitrit ktdfaglrhl rvlglmenki stiergafgd lkelerlrln rnnlqllsel
 121 lflgtpklyr ldlsenqiqa iprkafrqav diknlqldyn qisciedgaf ralrdlevlt
 181 lnnnnitrls vasfnhmpkl rtfrlhsnnl ycdchlawls dwlrgrprvg lytqcmgpah
 241 lrghnvaevq krefvcsghq sfmapscsvl hcpaactcsn nivdcrgkgl teiptnlpet
 301 iteirleqns lkvippgafs pykklrrldl snnqiseaap dlfggarsln slvaygnkit
 361 elpkgafegl fslglllllna nkinclrvda fqdlhnlnll slydnklqti akgtfsplra
 421 iqtlhlagnp ficdchlkwl adylhtnpie tsgarctspr rlankrigqi kskkfrcsak
 481 eqyfipgted yrskisgdcf adlacpekcr cegttvdcsn qklnkipdhi pgytaelrln
 541 nnefsvleat gifkklpqlr kinasnnkit dieegafdga sgvnelllts nrletvrdkm
 601 fkgleslktl mlrsnrvscv gndsftglss vrllslydnq ittvapgsfd tlhslstlnl
 661 lanpfncnch lawlgdwlrk krivtgnprc qkpyfikeip igdvaiqdft cddgnddnsc
 721 splsrcpaec tcldtvvrcs nkglkalpkg ipkdvtelyl dgnqftlvpk elsnykhltl
 781 idlsnnrist lsnqsfsnmt qlltlilsyn rlrcipartf dglkslrlls lhgndisvvp
 841 egafndlsal shlaiganpl ycdcnmqwls dwvkseykep giarcagpge madkllltp
 901 skkftcqgpv dvnilakcnp clsnpckndg tcnndpvdfy rctcpygfkg qdcdipihac
 961 isnpcnhggt chlkegekdq fwctcadqfe genceinvdd cedndcenns tcvdginnyt
1021 clcppeytge lceekldfca qnlnpcqhds kciltpkgyk cdctpgyvge hcdidfddcq
1081 dnkckngaqc tdavngytci cpegysglfc efsppmvlpr tspcdnyecq ngaqcivkes
1141 epicqcisgy qgekceklis infvnkesyl gipsakihsg tnitlqiatd edsgillykg
1201 dkdhiavely rgrvrvsydt gsypasaiys vetindgnfh ivellamdqi lslsidggsp
1261 kiitnlskqs tlnfdsplyv ggmpvknnia alrqspgqng tsfhgcirnl yinselqdfr
1321 nvplqvgilp gcepchkkvc vhgtchatsq ssftcecegg wtgplcdqqt ndpclgnkcv
1381 hgtclpinaf syscckclqgh ggvlcdeeem lfnpcqsirc khgkcrlsgl gkpycecssg
1441 ytgdscdkei scrgerirdy yqkqqgyaac qttkkvsrle ckggcstgqc cgplrskrrk
1501 ysfectdgss fvdeiekvvk cgctncps
```

SEQ ID NO: 21 Human Slit2-N Fragment Amino Acid Sequence

```
QACPAQCSCSGSTVDCHGLALRSVPRNIPRNTERLDLNGNNITRITKIDFAGLRHLR
VLQLMENRISTIERGAFQDLKELERLRLNRNNLQLFPELLFLGTAKLYRLDLSENQI
QAIPRKAFRGAVDIKNLQLDYNQISCIEDGAFRALRDLEVLTLNNNNITRLSVASFN
HMPKLRTFRLHSNNLYCDCHLAWLSDWLRQRPRVGLYTQCMGPSHLRGHNVAEV
QKREFVCSGHQSFMAPSCSVLHCPAACTCSNNIVDCRGKGLTEIPTNLPETITEIRLE
QNSIRVIPPGAFSPYKKLRRLDLSNNQISELAPDAFQGLRSLNSLVLYGNKITELPKS
LFEGLFSLQLLLLNANKINCLRVDAFQDLHNLNLLSLYDNKLQTVAKGTFSALRAI
QTMHLAQNPFICDCHLKWLADYLHTNPIETSGARCTSPRRLANKRIGQIKSKKFRCS
GTEDYRSKLSGDCFADLACPEKCRCEGTTVDCSNQRLNKIPDHIPQYTAELRLNNN
EFTVLEATGIFKKLPQLRKINFSNNKITDIEEGAFEGASGVNEILLTSNRLENVQHKM
FKGLESLKTLMLRSNRISCVGNDSFIGLGSVRLLSLYDNQITTVAPGAFDSLHSLSTL
NLLANPFNCNCHLAWLGEWLRRKRIVTGNPRCQKPFLKEIPIQDVAIQDFTCDDG
NDDNSCSPLSRCPSECTCLDTVVRCSNKGLKVLPKGIPKDVTELYLDGNQFTLVPK
ELSNYKHLTLIDLSNNRISTLSNQSFSNMTQLLTLILSYNRLRCIPPRTFDGLKSLRLL
SLHGNDISVVPEGAFNDLSALSHLAIGAINPLYCDCNMQWLSDWVKSEYKEPGIAR
CAGPGEMADKLLLTTPSKKFTCQGPVDITIQAKCNPCLSNPCKNDGTCNNDPVDFY
RCTCPYGFKGQDCDVPIHACISNPCKHGGTCHLKEGENAGFWCTCADGFEGENCE
VNIDDCEDNDCENNSTCVDGINNYTCLCPPEYTGELCEEKLDFCAQDLNPCQHDSK
CILTPKGFKCDCTPGYIGEHCDIDFDDCQDNKCKNGAHCTDAVNGYTCVCPEGYS
GLFCEFSPPMVLPR
```

SEQ ID NO: 22 Human Slit2-C Fragment Amino Acid Sequence

```
TSPCDNFDCQNGAQCIIRINEPICQCLPGYLGEKCEKLVSVNFVNKESYLQTPSAKVR
PQTNITLQIATDEDSGILLYKGDKDHIAVELYRGRVRASYDTGSHPASAIYSVETIND
GNFHIVELLTLDSSLSLSVDGGSPKVITNLSKQSTLNFDSPLYVGGMPGKNNVASLR
QAPGQNGTSFHGCIRNLYINSELQDFRKMPMQTGILPGCEPCHKKVCAHGMCQPSS
QSGFTCECEEGWMGPLCDQRTNDPCLGNKCVHGTCLPINAFSYSCKCLEGHGGVL
CDEEEDLFNPCQMIKCKHGKCRLSGVGQPYCECNSGFTGDSCDREISCRGERIRDY
YQKQQGYAACQTTKKVSRLECRGGCAGGQCCGPLRSKRRKYSFECTDGSSFVDEV
EKVVKCGCARCAS
```

Included in Table 1 are variations of 1, 2, 3, 4, 5, 6, 7, 8, 9, 10, 11, 12, 13, 14, 15, 16, 17, 18, 19, 20, or more nucleotides or amino acids on the 5' (N-terminal) end, on the 3' (C-terminal) end, or on both the 5' (N-terminal) and 3' (C-terminal) ends, of the domain sequences as long as the sequence variations encode or maintain the recited function and/or homology Included in Table 1 are nucleic acid and amino acid molecules comprising, consisting essentially of, or consisting of:

1) a nucleic acid or amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with a sequence of SEQ ID NO:1-22, or a biologically active fragment thereof;
2) a nucleic acid or amino acid sequence having at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3500, 4000, 4500, 5000, 5500, 6000, 6500, 7000, 7500, 8000, 8500, 9000, 9500, 10000, or more nucleotides or amino acids, or any range in between, inclusive such as between 110 and 300 nucleotides;
3) a biologically active fragment of a nucleic acid or amino acid sequence of SEQ ID NO:1-22 having at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 400, 450, 500, 550, 600, 650, 700, 750, 800, 850, 900, 950, 1000, 1050, 1100, 1150, 1200, 1250, 1300, 1350, 1400, 1450, 1500, 1510, 1515, 1520, 1521, 1522, 1523, 1524, 1525, 1526, 1527, 1528, 1529, 1530, or more nucleotides or amino acids, or any range in between, inclusive such as between 110 and 300 nucleotides;
4) a biologically active fragment of a nucleic acid or amino acid sequence of SEQ ID NO:1-22 having 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 400, 450, 500, 550, 600, 650, 700, 750, 800, 850, 900, 950, 1000, 1050, 1100, 1150, 1200, 1250, 1300, 1350, 1400, 1450, 1500, 1510, 1515, 1520, 1521, 1522, 1523, 1524, 1525, 1526, 1527, 1528, 1529, 1530, or fewer nucleotides or amino acids, or any range in between, inclusive such as between 110 and 300 nucleotides;
5) one or more domains selected from the group consisting of an N-terminal signal peptide sequence (SS) domain, a leucine-rich repeat (LRR) domain, an EGF domain, a LamG domain, and a C-terminal cysteine knot domain, in any combination, inclusive such as an EGF domain and a C-terminal cysteine knot domain;
6) the ability to modulate one or more biological activities of a) brown fat and/or beige fat gene expression, such as expression of a marker selected from the group consisting of: cidea, adiponectin, adipsin, otopetrin, type II deiodinase, cig30, ppar gamma 2, pgc1α, ucp1, elovl3, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, dio2, fatty acid synthase (fas), leptin, resistin, and nuclear respiratory factor-1 (nrf1); b) thermogenesis in adipose cells; c) differentiation of adipose cells; d) insulin sensitivity of adipose cells; e) basal respiration or uncoupled respiration; f) whole body oxygen consumption; g) obesity or appetite; h) insulin secretion of pancreatic beta cells; i) glucose tolerance; j) modified phosphorylation of EGFR, ERK, AMPK, protein kinase A (PKA) substrates having an RRX(S/T) (SEQ ID NO: 127) motif, wherein the X is any amino acid and the (S/T) residue is a serine or threonine, HSL; and k) modified expression of UCP1 protein; and
7) any combination of 1) through 6), as well as those in the Examples and Figures and modified according to the descriptions provided herein, inclusive.

It will be appreciated that specific sequence identifiers (SEQ ID NOs) have been referenced throughout the specification for purposes of illustration and should therefore not be construed to be limiting. Any marker of the invention, including, but not limited to, the markers described in the specification and markers described herein (e.g., cidea, adiponectin (adipoq), adipsin, otopetrin, type II deiodinase, cig30, ppar gamma 2, pgc1α, ucp1, elovl3, cAMP, Prdml6, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, dio2, fatty acid synthase (fas), leptin, resistin, and nuclear respiratory factor-1 (nrf1)), are well known in the art and can be used in the embodiments of the invention.

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT |
| Arginine (Arg, R) | ACA, ACG, CGA, CCC, CGG, CGT |
| Asparaaine (Asn, N) | AAC, AAT |
| Aspartic acid (Asp, D) | GAC, GAT |
| Cysteine (Cys, C) | TGC, TGT |
| Glutamic acid (Glu, F) | GAA, GAG |
| Glutamine (Gln, Q) | CAA, CAG |
| Glycine (Gly, O) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Th-reonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end.) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA coding for a fusion protein or polypeptide of the present invention (or any portion thereof) can be used to derive the fusion protein or polypeptide amino acid sequence, using the genetic code to translate the DNA or RNA into an amino acid sequence. Likewise, for a fusion protein or polypeptide amino acid sequence, corresponding nucleotide sequences that can encode the fusion protein or polypeptide can be deduced from the genetic code (which, because of its redundancy, will produce multiple nucleic acid sequences for any given amino acid sequence). Thus, description and/or disclosure herein of a nucleotide sequence which encodes a fusion protein or polypeptide should be considered to also include description and/or disclosure of the amino acid sequence encoded by the nucleotide sequence. Similarly, description and/or disclosure of a fusion protein or polypeptide amino acid sequence herein should be considered to also include description and/or disclosure of all possible nucleotide sequences that can encode the amino acid sequence.

I. Isolated Nucleic Acids

One aspect of the invention pertains to methods utilizing isolated nucleic acid molecules that encode Slit2 or biologically active portions thereof. As used herein, the term "nucleic acid molecule" is intended to include DNA molecules (i.e., cDNA or genomic DNA) and RNA molecules (i.e., mRNA) and analogs of the DNA or RNA generated using nucleotide analogs. The nucleic acid molecule can be single-stranded or double-stranded, but preferably is double-stranded DNA. An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated Slit2 nucleic acid molecule can contain less than about 5 kb, 4kb, 3kb, 2kb, 1 kb, 0.5 kb or 0.1 kb of nucleotide sequences which naturally flank the nucleic acid molecule in genomic DNA of the cell from which the nucleic acid is derived (i.e., a brown adipocyte). Moreover, an "isolated" nucleic acid molecule, such as a cDNA molecule, can be substantially free of other cellular material, or culture medium when produced by recombinant techniques, or chemical precursors or other chemicals when chemically synthesized.

A nucleic acid molecule of the present invention, e.g., a nucleic acid molecule having the nucleotide sequence of a sequence described in Table 1 or a nucleotide sequence which is at least about 50%, preferably at least about 60%, more preferably at least about 70%, yet more preferably at least about 80%, still more preferably at least about 90%, and most preferably at least about 95% or more (e.g., about 98%) homologous or identical to a nucleotide sequence described in Table 1 or a portion thereof (i.e., 100, 200, 300, 400, 450, 500, or more nucleotides), can be isolated using standard molecular biology techniques and the sequence information provided herein. For example, a human Slit2 cDNA can be isolated from a human beige fat cell line (from Stratagene, LaJolla, CA, or Clontech, Palo Alto, CA) using all or portion of SEQ ID NOs: 1, 3, and 5, or fragment thereof, as a hybridization probe and standard hybridization techniques (i.e., as described in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, NY, 1989). Moreover, a nucleic acid molecule encompassing all or a portion of a sequence described in Table 1 or a nucleotide sequence which is at least about 50%, preferably at least about 60%, more preferably at least about 70%, yet more preferably at least about 80%, still more preferably at least about 90%, and most preferably at least about 95% or more homologous to a sequence described in Table 1, or fragment thereof, can be isolated by the polymerase chain reaction using oligonucleotide primers designed based upon the sequence described in Table 1, or fragment thereof, or the homologous nucleotide sequence. For example, mRNA can be isolated from muscle cells (i.e., by the guanidinium-thiocyanate extraction procedure of Chirgwin et al. (1979) *Biochemistry* 18: 5294-5299) and cDNA can be prepared using reverse transcriptase (i.e., Moloney MLV reverse transcriptase, available from Gibco/BRL, Bethesda, MD; or AMV reverse transcriptase, available from Seikagaku America, Inc., St. Petersburg, FL). Synthetic oligonucleotide primers for PCR amplification can be designed based upon a sequence described in Table 1, or fragment thereof, or to the homologous nucleotide sequence. A nucleic acid of the present invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to a Slit2 nucleotide sequence can be prepared by standard synthetic techniques, i.e., using an automated DNA synthesizer.

Probes based on the Slit2 nucleotide sequences can be used to detect transcripts or genomic sequences encoding the same or homologous proteins. In preferred embodiments, the probe further comprises a label group attached thereto, i.e., the label group can be a radioisotope, a fluorescent compound, an enzyme, or an enzyme co-factor. Such probes can be used as a part of a diagnostic test kit for identifying cells or tissue which express a Slit2 protein, such as by measuring a level of a Slit2-encoding nucleic acid in a sample of cells from a subject, i.e., detecting Slit2 mRNA levels.

Nucleic acid molecules encoding other Slit2 members and thus which have a nucleotide sequence which differs from the Slit2 sequences of SEQ ID NOs: 1, 3, 5, 7, 9, 11, 13, 15, 17, and 19, or fragment thereof, are contemplated. Moreover, nucleic acid molecules encoding Slit2 proteins from different species, and thus which have a nucleotide sequence which differs from the Slit2 sequences of SEQ ID NOs: 1, 3 5, 7, 9, 11, 13, 15, 17, and 19 are also intended to be within the scope of the present invention. For example, chimpanzee Slit2 cDNA can be identified based on the nucleotide sequence of a human and/or mouse Slit2.

In one embodiment, the nucleic acid molecule(s) of the invention encodes a protein or portion thereof which includes an amino acid sequence which is sufficiently homologous to an amino acid sequence of a sequence described in Table 1, or fragment thereof, such that the protein or portion thereof modulates (e.g., enhance), one or more of the following biological activities: a) brown fat and/or beige fat gene expression, such as expression of a marker selected from the group consisting of: cidea, adiponectin, adipsin, otopetrin, type II deiodinase, cig30, ppar gamma 2, pgc1α, ucp1, elovl3, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, dio2, fatty acid synthase (fas), leptin, resistin, and nuclear respiratory factor-1 (nrf1); b) thermogenesis in adipose cells; c) differentiation of adipose cells; d) insulin sensitivity of adipose cells; e) basal respiration or uncoupled respiration; f) whole body oxygen consumption; g) obesity or appetite; h) insulin secretion of pancreatic beta cells; i) glucose tolerance; j) modified phosphorylation of EGFR, ERK, AMPK, protein kinase A (PKA) substrates having an RRX(S/T) (SEQ ID NO: 127) motif, wherein the X is any amino acid and the (S/T) residue is a serine or threonine, HSL; k) modified expression of UCP1 protein; and 1) growth and effects of metabolic disorders, such as obesity-associated cancer, cachexia, anorexia, diabetes, and obesity.

As used herein, the language "sufficiently homologous" refers to proteins or portions thereof which have amino acid sequences which include a minimum number of identical or equivalent (e.g., an amino acid residue which has a similar side chain as an amino acid residue in an amino acid sequence described in Table 1, or fragment thereof) amino acid residues to an amino acid sequence of an amino acid sequence described in Table 1, or fragment thereof, such that the protein or portion thereof modulates (e.g., enhance) one or more of the following biological activities: a) brown fat and/or beige fat gene expression, such as expression of a marker selected from the group consisting of: cidea, adiponectin, adipsin, otopetrin, type II deiodinase, cig30, ppar gamma 2, pgc1α, ucp1, elovl3, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, dio2, fatty acid synthase (fas), leptin, resistin, and nuclear respiratory factor-1 (nrf1); b) thermogenesis in adipose cells; c) differentiation of adipose cells; d) insulin sensitivity of adipose cells; e) basal respiration or uncoupled respiration; f) whole body oxygen consumption; g) obesity or appetite; h) insulin secretion of pancreatic beta cells; i) glucose tolerance; j) modified phosphorylation of EGFR, ERK, AMPK, protein kinase A (PKA) substrates having an RRX(S/T) (SEQ ID NO: 127) motif, wherein the X is any amino acid and the (S/T) residue is a serine or threonine, HSL; k) modified expression of UCP1 protein; and 1) growth and effects of metabolic disorders, such as obesity-associated cancer, cachexia, anorexia, diabetes, and obesity.

In another embodiment, the protein is at least about 50%, preferably at least about 60%, more preferably at least about 70%, 75%, 80%, 85%, 90%, 91%, 92%, 93%, 94%, 95%, 96%, 97%, 98%, 99% or more homologous to the entire amino acid sequence of an amino acid sequence described in Table 1, or a fragment thereof.

Portions of proteins encoded by the Slit2 nucleic acid molecule of the invention are preferably biologically active portions of the Slit2 protein. As used herein, the term "biologically active portion of Slit2" is intended to include a portion, e.g., a domain/motif, of Slit2 that has one or more of the biological activities of the full-length Slit2 protein.

Standard binding assays, e.g., immunoprecipitations and yeast two-hybrid assays, as described herein, or functional assays, e.g., RNAi or overexpression experiments, can be performed to determine the ability of a Slit2 protein or a biologically active fragment thereof to maintain a biological activity of the full-length Slit2 protein.

The invention further encompasses nucleic acid molecules that differ from a sequence described in Table 1, or fragment thereof, due to degeneracy of the genetic code and thus encode the same Slit2 protein as that encoded by a nucleotide sequence described in Table 1, or a fragment thereof. In another embodiment, an isolated nucleic acid molecule of the invention has a nucleotide sequence encoding a protein having an amino acid sequence described in Table 1, or fragment thereof, or fragment thereof, or a protein having an amino acid sequence which is at least about 70%, 75%, 80%, 85%, 90%, 91%, 92%, 93%, 94%, 95%, 96%, 97%, 98%, 99% or more homologous to an amino acid sequence described in Table 1, or a fragment thereof, or differs by at least 1, 2, 3, 5 or 10 amino acids but not more than 30, 20, 15 amino acids from an amino acid sequence described in Table 1.

It will be appreciated by those skilled in the art that DNA sequence polymorphisms that lead to changes in the amino acid sequences of Slit2 may exist within a population (e.g., a mammalian population, e.g., a human population). Such genetic polymorphism in the Slit2 gene may exist among individuals within a population due to natural allelic variation. As used herein, the terms "gene" and "recombinant gene" refer to nucleic acid molecules comprising an open reading frame encoding a Slit2 protein, preferably a mammalian, e.g., human, Slit2 protein. Such natural allelic variations can typically result in 1-5% variance in the nucleotide sequence of the Slit2 gene. Any and all such nucleotide variations and resulting amino acid polymorphisms in Slit2 that are the result of natural allelic variation and that do not alter the functional activity of Slit2 are intended to be within the scope of the invention. Moreover, nucleic acid molecules encoding Slit2 proteins from other species, and thus which have a nucleotide sequence which differs from the human or mouse sequences of a sequence described in Table 1, are intended to be within the scope of the invention. Nucleic acid molecules corresponding to natural allelic variants and homologues of the human or mouse Slit2 cDNAs of the invention can be isolated based on their homology to the human or mouse Slit2 nucleic acid sequences disclosed herein using the human or mouse cDNA, or a portion thereof, as a hybridization probe according to standard hybridization techniques under stringent hybridization conditions (as described herein).

In addition to naturally-occurring allelic variants of the Slit2 sequence that may exist in the population, the skilled artisan will further appreciate that changes can be introduced by mutation into a sequence described in Table 1, or fragment thereof, thereby leading to changes in the amino acid sequence of the encoded Slit2 protein, without altering the functional ability of the Slit2 protein. For example, nucleotide substitutions leading to amino acid substitutions at "non-essential" amino acid residues can be made in a sequence described in Table 1, or fragment thereof. A "non-essential" amino acid residue is a residue that can be altered from the wild-type sequence of Slit2 (e.g., an amino acid sequence described in Table 1) without altering the activity of Slit2, whereas an "essential" amino acid residue is required for Slit2 activity. Other amino acid residues, however, (e.g., those that are not conserved or only semi-conserved between mouse and human) may not be essential for activity and thus are likely to be amenable to alteration without altering Slit2 activity. Furthermore, amino acid residues that are essential for Slit2 functions related to thermogenesis and/or adipogenesis, but not essential for Slit2 functions related to gluconeogenesis, are likely to be amenable to alteration.

Accordingly, another aspect of the invention pertains to nucleic acid molecules encoding Slit2 proteins that contain changes in amino acid residues that are not essential for Slit2 activity. Such Slit2 proteins differ in amino acid sequence from those amino acid sequences described in Table 1, or fragment thereof, yet retain at least one of the Slit2 activities described herein. In one embodiment, the isolated nucleic acid molecule comprises a nucleotide sequence encoding a protein, wherein the protein lacks one or more Slit2 domains.

"Sequence identity or homology", as used herein, refers to the sequence similarity between two polypeptide molecules or between two nucleic acid molecules. When a position in both of the two compared sequences is occupied by the same base or amino acid monomer subunit, e.g., if a position in each of two DNA molecules is occupied by adenine, then the molecules are homologous or sequence identical at that position. The percent of homology or sequence identity between two sequences is a function of the number of matching or homologous identical positions shared by the two sequences divided by the number of positions compared×100. For example, if 6 of 10, of the positions in two sequences are the same then the two sequences are 60% homologous or have 60% sequence identity. By way of example, the DNA sequences ATTGCC and TATGGC share 50% homology or sequence identity. Generally, a comparison is made when two sequences are aligned to give maximum homology. Unless otherwise specified "loop out regions", e.g., those arising from, from deletions or insertions in one of the sequences are counted as mismatches.

The comparison of sequences and determination of percent homology between two sequences can be accomplished using a mathematical algorithm. Preferably, the alignment can be performed using the Clustal Method. Multiple alignment parameters include GAP Penalty=10, Gap Length Penalty=10. For DNA alignments, the pairwise alignment parameters can be Htuple=2, Gap penalty=5, Window=4, and Diagonal saved=4. For protein alignments, the pairwise alignment parameters can be Ktuple=1, Gap penalty=3, Window=5, and Diagonals Saved=5.

In a preferred embodiment, the percent identity between two amino acid sequences is determined using the Needleman and Wunsch (*J. Mol. Biol.* (48):444-453 (1970)) algorithm which has been incorporated into the GAP program in the GCG software package (available online), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available online), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11-17 (1989)) which has been incorporated into the ALIGN program (version 2.0) (available online), using a PAM120 weight residue table, a gap length penalty of 12 and a gap penalty of 4.

An isolated nucleic acid molecule encoding a Slit2 protein homologous to an amino acid sequence described in Table 1, or fragment thereof, can be created by introducing one or more nucleotide substitutions, additions or deletions into a nucleotide sequence described in Table 1, or fragment thereof, or a homologous nucleotide sequence such that one or more amino acid substitutions, additions or deletions are introduced into the encoded protein. Mutations can be introduced into the sequence described in Table 1, or fragment thereof, or the homologous nucleotide sequence by standard techniques, such as site-directed mutagenesis and PCR-mediated mutagenesis. Preferably, conservative amino acid substitutions are made at one or more predicted nonessential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), branched side chains (e.g., threonine, valine, isoleucine) and aromatic side chains (e.g., tyrosine, phenylalanine, tryptophan, histidine). Thus, a predicted nonessential amino acid residue in Slit2 is preferably replaced with another amino acid residue from the same side chain family. Alternatively, in another embodiment, mutations can be introduced randomly along all or part of a Slit2 coding sequence, such as by saturation mutagenesis, and the resultant mutants can be screened for a Slit2 activity described herein to identify mutants that retain Slit2 activity. Following mutagenesis of a sequence described in Table 1, or fragment thereof, the encoded protein can be expressed recombinantly (as described herein) and the activity of the protein can be determined using, for example, assays described herein.

Slit2 levels may be assessed by any of a wide variety of well-known methods for detecting expression of a transcribed molecule or protein. Non-limiting examples of such methods include immunological methods for detection of proteins, protein purification methods, protein function or activity assays, nucleic acid hybridization methods, nucleic acid reverse transcription methods, and nucleic acid amplification methods.

In preferred embodiments, Slit2 levels are ascertained by measuring gene transcript (e.g., mRNA), by a measure of the quantity of translated protein, or by a measure of gene product activity. Expression levels can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In a particular embodiment, the Slit2 mRNA expression level can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from cells (see, e.g., Ausubel et al., ed., *Current Protocols in Molecular Biology*, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155).

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding Slit2. Other suitable probes for use in the diagnostic assays of the invention are described herein. Hybridization of an mRNA with the probe indicates that Slit2 is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in a gene chip array, e.g., an Affymetrix™ gene chip array. A skilled artisan can readily adapt known mRNA detection methods for use in detecting the level of the Slit2 mRNA expression levels.

An alternative method for determining the Slit2 mRNA expression level in a sample involves the process of nucleic acid amplification, e.g., by rtPCR (the experimental embodiment set forth in Mullis, 1987, U.S. Pat. No. 4,683,202), ligase chain reaction (Barany, 1991, *Proc. Natl. Acad. Sci. USA,* 88:189-193), self-sustained sequence replication (Guatelli et al., 1990, *Proc. Natl. Acad. Sci. USA* 87:1874-1878), transcriptional amplification system (Kwoh et al., 1989, *Proc. Natl. Acad. Sci. USA* 86:1173-1177), Q-Beta Replicase (Lizardi et al., 1988, *Bio/Technology* 6:1197), rolling circle replication (Lizardi et al., U.S. Pat. No. 5,854,033) or any other nucleic acid amplification method, followed by the detection of the amplified molecules using techniques well-known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the cells prior to detection. In such methods, a cell or tissue sample is prepared/processed using known histological methods. The sample is then immobilized on a support, typically a glass slide, and then contacted with a probe that can hybridize to the Slit2 mRNA.

As an alternative to making determinations based on the absolute Slit2 expression level, determinations may be based on the normalized Slit2 expression level. Expression levels are normalized by correcting the absolute Slit2 expression level by comparing its expression to the expression of a non-Slit2 gene, e.g., a housekeeping gene that is constitutively expressed. Suitable genes for normalization include housekeeping genes such as the actin gene, or epithelial cell-specific genes. This normalization allows the comparison of the expression level in one sample, e.g., a subject sample, to another sample, e.g., a normal sample, or between samples from different sources.

The level or activity of a Slit2 protein can also be detected and/or quantified by detecting or quantifying the expressed polypeptide. The Slit2 polypeptide can be detected and quantified by any of a number of means well known to those of skill in the art. These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, Western blotting, and the like. A skilled artisan can readily adapt known protein/antibody detection methods for use in determining whether cells express Slit2.

Also provided herein are compositions comprising one or more nucleic acids comprising or capable of expressing at least 1, 2, 3, 4, 5, 10, 20 or more small nucleic acids or antisense oligonucleotides or derivatives thereof, wherein said small nucleic acids or antisense oligonucleotides or derivatives thereof in a cell specifically hybridize (e.g., bind) under cellular conditions, with cellular nucleic acids (e.g., small non-coding RNAS such as miRNAs, pre-miRNAs, pri-miRNAs, miRNA*, piwiRNA, anti-miRNA, a miRNA binding site, a variant and/or functional variant thereof, cellular mRNAs or a fragments thereof). In one embodiment, expression of the small nucleic acids or antisense oligonucleotides or derivatives thereof in a cell can enhance or upregulate one or more biological activities associated with the corresponding wild-type, naturally occurring, or synthetic small nucleic acids. In another embodiment, expression of the small nucleic acids or antisense oligonucleotides or derivatives thereof in a cell can inhibit expression or biological activity of cellular nucleic acids and/or proteins, e.g., by inhibiting transcription, translation and/or small nucleic acid processing of, for example, one or more biomarkers of the present invention, including one or more biomarkers listed in Table 1, the Figures, and the Examples, or fragment(s) thereof. In one embodiment, the small nucleic acids or antisense oligonucleotides or derivatives thereof are small RNAs (e.g., microRNAs) or complements of small RNAs. In another embodiment, the small nucleic acids or antisense oligonucleotides or derivatives thereof can be single or double stranded and are at least six nucleotides in length and are less than about 1000, 900, 800, 700, 600, 500, 400, 300, 200, 100, 50, 40, 30, 25, 24, 23, 22, 21, 20, 19, 18, 17, 16, 15, or 10 nucleotides in length. In another embodiment, a composition may comprise a library of nucleic acids comprising or capable of expressing small nucleic acids or antisense oligonucleotides or derivatives thereof, or pools of said small nucleic acids or antisense oligonucleotides or derivatives thereof. A pool of nucleic acids may comprise about 2-5, 5-10, 10-20, 10-30 or more nucleic acids comprising or capable of expressing small nucleic acids or antisense oligonucleotides or derivatives thereof.

In one embodiment, binding may be by conventional base pair complementarity, or, for example, in the case of binding to DNA duplexes, through specific interactions in the major groove of the double helix. In general, “antisense” refers to the range of techniques generally employed in the art, and includes any process that relies on specific binding to oligonucleotide sequences.

It is well known in the art that modifications can be made to the sequence of a miRNA or a pre-miRNA without disrupting miRNA activity. As used herein, the term "functional variant" of a miRNA sequence refers to an oligonucleotide sequence that varies from the natural miRNA sequence, but retains one or more functional characteristics of the miRNA (e.g., cancer cell proliferation inhibition, induction of cancer cell apoptosis, enhancement of cancer cell susceptibility to chemotherapeutic agents, specific miRNA target inhibition). In some embodiments, a functional variant of a miRNA sequence retains all of the functional characteristics of the miRNA. In certain embodiments, a functional variant of a miRNA has a nucleobase sequence that is a least about 60%, 65%, 70%, 75%, 80%, 85%, 90%, 91%, 92%, 93%, 94%, 95%, 96%, 97%, 98% or 99% identical to the miRNA or precursor thereof over a region of about 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleobases, or that the functional variant hybridizes to the complement of the miRNA or precursor thereof under stringent hybridization conditions. Accordingly, in certain embodiments the nucleobase sequence of a functional variant is capable of hybridizing to one or more target sequences of the miRNA. miRNAs and their corresponding stem-loop sequences described herein may be found in miRBase, an online searchable database of miRNA sequences and annotation, found on the world wide web at microrna.sanger.ac.uk. Entries in the miRBase Sequence database represent a predicted hairpin portion of a miRNA transcript (the stem-loop), with information on the location and sequence of the mature miRNA sequence. The miRNA stem-loop sequences in the database are not strictly precursor miRNAs (pre-miRNAs), and may in some instances include the pre-miRNA and some flanking sequence from the presumed primary transcript. The miRNA nucleobase sequences described herein encompass any version of the miRNA, including the sequences described in Release 10.0 of the miRBase sequence database and sequences described in any earlier Release of the miRBase sequence database. A sequence database release may result in the re-naming of certain miRNAs. A sequence database release may result in a variation of a mature miRNA sequence.

In some embodiments, miRNA sequences of the present invention may be associated with a second RNA sequence that may be located on the same RNA molecule or on a separate RNA molecule as the miRNA sequence. In such cases, the miRNA sequence may be referred to as the active strand, while the second RNA sequence, which is at least partially complementary to the miRNA sequence, may be referred to as the complementary strand. The active and complementary strands are hybridized to create a double-stranded RNA that is similar to a naturally occurring miRNA precursor. The activity of a miRNA may be optimized by maximizing uptake of the active strand and minimizing uptake of the complementary strand by the miRNA protein complex that regulates gene translation. This can be done through modification and/or design of the complementary strand.

In some embodiments, the complementary strand is modified so that a chemical group other than a phosphate or hydroxyl at its 5' terminus. The presence of the 5' modification apparently eliminates uptake of the complementary strand and subsequently favors uptake of the active strand by the miRNA protein complex. The 5' modification can be any of a variety of molecules known in the art, including $NH_2$, $NHCOCH_3$, and biotin.

In another embodiment, the uptake of the complementary strand by the miRNA pathway is reduced by incorporating nucleotides with sugar modifications in the first 2-6 nucleotides of the complementary strand. It should be noted that such sugar modifications can be combined with the 5' terminal modifications described above to further enhance miRNA activities.

In some embodiments, the complementary strand is designed so that nucleotides in the 3' end of the complementary strand are not complementary to the active strand. This results in double-strand hybrid RNAs that are stable at the 3' end of the active strand but relatively unstable at the 5' end of the active strand. This difference in stability enhances the uptake of the active strand by the miRNA pathway, while reducing uptake of the complementary strand, thereby enhancing miRNA activity.

Small nucleic acid and/or antisense constructs of the methods and compositions presented herein can be delivered, for example, as an expression plasmid which, when transcribed in the cell, produces RNA which is complementary to at least a unique portion of cellular nucleic acids (e.g., small RNAs, mRNA, and/or genomic DNA). Alternatively, the small nucleic acid molecules can produce RNA which encodes mRNA, miRNA, pre-miRNA, pri-miRNA, miRNA*, piwiRNA, anti-miRNA, or a miRNA binding site, or a variant thereof. For example, selection of plasmids suitable for expressing the miRNAs, methods for inserting nucleic acid sequences into the plasmid, and methods of delivering the recombinant plasmid to the cells of interest are within the skill in the art. See, for example, Zeng et al. (2002), Molecular Cell 9:1327-1333; Tuschl (2002), Nat. Biotechnol, 20:446-448; Brummelkamp et al. (2002), Science 296:550-553; Miyagishi et al. (2002), Nat. Biotechnol. 20:497-500; Paddison et al. (2002), *Genes Dev.* 16:948-958; Lee et al. (2002), Nat. Biotechnol. 20:500-505; and Paul et al. (2002), Nat. Biotechnol. 20:505-508, the entire disclosures of which are herein incorporated by reference.

Alternatively, small nucleic acids and/or antisense constructs are oligonucleotide probes that are generated ex vivo and which, when introduced into the cell, results in hybridization with cellular nucleic acids. Such oligonucleotide probes are preferably modified oligonucleotides that are resistant to endogenous nucleases, e.g., exonucleases and/or endonucleases, and are therefore stable in vivo. Exemplary nucleic acid molecules for use as small nucleic acids and/or antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) BioTechniques 6:958-976; and Stein et al. (1988) Cancer Res 48:2659-2668.

Antisense approaches may involve the design of oligonucleotides (either DNA or RNA) that are complementary to cellular nucleic acids (e.g., complementary to biomarkers listed in Table 1, the Figures, and the Examples). Absolute complementarity is not required. In the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a nucleic acid (e.g., RNA) it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the mRNA, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well (Wagner, R. (1994) *Nature* 372:333). Therefore, oligonucleotides complementary to either the 5' or 3' untranslated, non-coding regions of genes could be used in an antisense approach to inhibit translation of endogenous mRNAs. Oligonucleotides complementary to the 5' untranslated region of the mRNA may include the complement of the AUG start codon. Antisense oligonucleotides complementary to mRNA coding regions are less efficient inhibitors of translation but could also be used in accordance with the methods and compositions presented herein. Whether designed to hybridize to the 5', 3' or coding region of cellular mRNAs, small nucleic acids and/or antisense nucleic acids should be at least six nucleotides in length, and can be less than about 1000, 900, 800, 700, 600, 500, 400, 300, 200, 100, 50, 40, 30, 25, 24, 23, 22, 21, 20, 19, 18, 17, 16, 15, or 10 nucleotides in length.

Regardless of the choice of target sequence, it is preferred that in vitro studies are first performed to quantitate the ability of the antisense oligonucleotide to inhibit gene expression. In one embodiment these studies utilize controls that distinguish between antisense gene inhibition and nonspecific biological effects of oligonucleotides. In another embodiment these studies compare levels of the target nucleic acid or protein with that of an internal control nucleic acid or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

Small nucleic acids and/or antisense oligonucleotides can be DNA or RNA or chimeric mixtures or derivatives or modified versions thereof, single-stranded or double-stranded. Small nucleic acids and/or antisense oligonucleotides can be modified at the base moiety, sugar moiety, or phosphate backbone, for example, to improve stability of the molecule, hybridization, etc., and may include other appended groups such as peptides (e.g., for targeting host cell receptors), or agents facilitating transport across the cell membrane (see, e.g., Letsinger et al. (1989) Proc. Natl. Acad. Sci. U.S.A. 86:6553-6556; Lemaitre et al. (1987) Proc. Natl. Acad. Sci. 84:648-652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al. (1988) BioTechniques 6:958-976) or intercalating agents. (See, e.g., Zon (1988), Pharm. Res. 5:539-549). To this end, small nucleic acids and/or antisense oligonucleotides may be conjugated to another molecule, e.g., a peptide, hybridization triggered cross-linking agent, transport agent, hybridization-triggered cleavage agent, etc.

Small nucleic acids and/or antisense oligonucleotides may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxytiethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Small nucleic acids and/or antisense oligonucleotides may also comprise at least one modified sugar moiety selected from the group including but not limited to arabinose, 2-fluoroarabinose, xylulose, and hexose.

In certain embodiments, a compound comprises an oligonucleotide (e.g., a miRNA or miRNA encoding oligonucleotide) conjugated to one or more moieties which enhance the activity, cellular distribution or cellular uptake of the resulting oligonucleotide. In certain such embodiments, the moiety is a cholesterol moiety (e.g., antagomirs) or a lipid moiety or liposome conjugate. Additional moieties for conjugation include carbohydrates, phospholipids, biotin, phenazine, folate, phenanthridine, anthraquinone, acridine, fluoresceins, rhodamines, coumarins, and dyes. In certain embodiments, a conjugate group is attached directly to the oligonucleotide. In certain embodiments, a conjugate group is attached to the oligonucleotide by a linking moiety selected from amino, hydroxyl, carboxylic acid, thiol, unsaturations (e.g., double or triple bonds), 8-amino-3,6-dioxaoctanoic acid (ADO), succinimidyl 4-(N-maleimidomethyl) cyclohexane-1-carboxylate (SMCC), 6-aminohexanoic acid (AHEX or AHA), substituted C1-C10 alkyl, substituted or unsubstituted C2-C10 alkenyl, and substituted or unsubstituted C2-C10 alkynyl. In certain such embodiments, a substituent group is selected from hydroxyl, amino, alkoxy, carboxy, benzyl, phenyl, nitro, thiol, thioalkoxy, halogen, alkyl, aryl, alkenyl and alkynyl.

In certain such embodiments, the compound comprises the oligonucleotide having one or more stabilizing groups that are attached to one or both termini of the oligonucleotide to enhance properties such as, for example, nuclease stability. Included in stabilizing groups are cap structures. These terminal modifications protect the oligonucleotide from exonuclease degradation, and can help in delivery and/or localization within a cell. The cap can be present at the 5'-terminus (5'-cap), or at the 3'-terminus (3'-cap), or can be present on both termini. Cap structures include, for example, inverted deoxy abasic caps.

Suitable cap structures include a 4',5'-methylene nucleotide, a 1-(beta-D-erythrofuranosyl) nucleotide, a 4'-thio nucleotide, a carbocyclic nucleotide, a 1,5-anhydrohexitol nucleotide, an L-nucleotide, an alpha-nucleotide, a modified base nucleotide, a phosphorodithioate linkage, a threo-pentofuranosyl nucleotide, an acyclic 3',4'-seco nucleotide, an acyclic 3,4-dihydroxybutyl nucleotide, an acyclic 3,5-dihydroxypentyl nucleotide, a 3'-3'-inverted nucleotide moiety, a 3'-3'-inverted abasic moiety, a 3'-2'-inverted nucleotide moiety, a 3'-2'-inverted abasic moiety, a 1,4-butanediol phosphate, a 3'-phosphoramidate, a hexylphosphate, an aminohexyl phosphate, a 3'-phosphate, a 3'-phosphorothioate, a phosphorodithioate, a bridging methylphosphonate moiety, and a non-bridging methylphosphonate moiety 5'-amino-alkyl phosphate, a 1,3-diamino-2-propyl phosphate, 3-aminopropyl phosphate, a 6-aminohexyl phosphate, a 1,2-aminododecyl phosphate, a hydroxypropyl phosphate, a 5'-5'-inverted nucleotide moiety, a 5'-5'-inverted abasic moiety, a 5'-phosphoramidate, a 5'-phosphorothioate, a 5'-amino, a bridging and/or non-bridging 5'-phosphoramidate, a phosphorothioate, and a 5'-mercapto moiety.

It is to be understood that additional well known nucleic acid architecture or chemistry can be applied. Different modifications can be placed at different positions to prevent the oligonucleotide from activating RNase H and/or being capable of recruiting the RNAi machinery. In another embodiment, they may be placed such as to allow RNase H activation and/or recruitment of the RNAi machinery. The modifications can be non-natural bases, e.g. universal bases. It may be modifications on the backbone sugar or phosphate, e.g., 2'-O-modifications including LNA or phosphorothioate linkages. As used herein, it makes no difference whether the modifications are present on the nucleotide before incorporation into the oligonucleotide or whether the oligonucleotide is modified after synthesis.

Preferred modifications are those that increase the affinity of the oligonucleotide for complementary sequences, i.e. increases the tm (melting temperature) of the oligonucleotide base paired to a complementary sequence. Such modifications include 2'-O-flouro, 2'-O-methyl, 2'-O-methoxyethyl. The use of LNA (locked nucleic acid) units, phosphoramidate, PNA (peptide nucleic acid) units or INA (intercalating nucleic acid) units is preferred. For shorter oligonucleotides, it is preferred that a higher percentage of affinity increasing modifications are present. If the oligonucleotide is less than 12 or 10 units long, it may be composed entirely of LNA units. A wide range of other non-natural units may also be build into the oligonucleotide, e.g., morpholino, 2'-deoxy-2'-fluoro-arabinonucleic acid (FANA) and arabinonucleic acid (ANA). In a preferred embodiment, the fraction of units modified at either the base or sugar relatively to the units not modified at either the base or sugar is selected from the group consisting of less than less than 99%, 95%, less than 90%, less than 85% or less than 75%, less than 70%, less than 65%, less than 60%, less than 50%, less than 45%, less than 40%, less than 35%, less than 30%, less than 25%, less than 20%, less than 15%, less than 10%, and less than 5%, less than 1%, more than 99%, more than 95%, more than 90%, more than 85% or more than 75%, more than 70%, more than 65%, more than 60%, more than 50%, more than 45%, more than 40%, more than 35%, more than 30%, more than 25%, more than 20%, more than 15%, more than 10%, and more than 5% and more than 1%.

Small nucleic acids and/or antisense oligonucleotides can also contain a neutral peptide-like backbone. Such molecules are termed peptide nucleic acid (PNA)-oligomers and are described, e.g., in Perry-O'Keefe et al. (1996) Proc. Natl. Acad. Sci. U.S.A. 93:14670 and in Eglom et al. (1993) Nature 365:566. One advantage of PNA oligomers is their capability to bind to complementary DNA essentially independently from the ionic strength of the medium due to the neutral backbone of the DNA. In yet another embodiment, small nucleic acids and/or antisense oligonucleotides comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In a further embodiment, small nucleic acids and/or antisense oligonucleotides are α-anomeric oligonucleotides. An α-anomeric oligonucleotide forms specific double-stranded hybrids with complementary RNA in which, contrary to the usual b-units, the strands run parallel to each other (Gautier et al. (1987) Nucl. Acids Res. 15:6625-6641). The oligonucleotide is a 2'-O-methylribonucleotide (Inoue et al. (1987) Nucl. Acids Res. 15:6131-6148), or a chimeric RNA-DNA analogue (Inoue et al. (1987) FEBS Lett. 215: 327-330).

Small nucleic acids and/or antisense oligonucleotides of the methods and compositions presented herein may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988) Nucl. Acids Res. 16:3209, methylphosphonate oligonucleotides can be prepared by use of controlled pore glass polymer supports (Sarin et al. (1988) Proc. Natl. Acad. Sci. U.S.A. 85:7448-7451), etc. For example, an isolated miRNA can be chemically synthesized or recombinantly produced using methods known in the art. In some instances, miRNA are chemically synthesized using appropriately protected ribonucleoside phosphoramidites and a conventional DNA/RNA synthesizer. Commercial suppliers of synthetic RNA molecules or synthesis reagents include, e.g., Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), Cruachem (Glasgow, UK), and Exiqon (Vedbaek, Denmark).

Small nucleic acids and/or antisense oligonucleotides can be delivered to cells in vivo. A number of methods have been developed for delivering small nucleic acids and/or antisense oligonucleotides DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

In one embodiment, small nucleic acids and/or antisense oligonucleotides may comprise or be generated from double stranded small interfering RNAs (siRNAs), in which sequences fully complementary to cellular nucleic acids (e.g., mRNAs) sequences mediate degradation or in which sequences incompletely complementary to cellular nucleic acids (e.g., mRNAs) mediate translational repression when expressed within cells. In another embodiment, double stranded siRNAs can be processed into single stranded antisense RNAs that bind single stranded cellular RNAs (e.g., microRNAs) and inhibit their expression. RNA interference (RNAi) is the process of sequence-specific, post-transcriptional gene silencing in animals and plants, initiated by double-stranded RNA (dsRNA) that is homologous in sequence to the silenced gene. in vivo, long dsRNA is cleaved by ribonuclease III to generate 21- and 22-nucleotide siRNAs. It has been shown that 21-nucleotide siRNA duplexes specifically suppress expression of endogenous and heterologous genes in different mammalian cell lines, including human embryonic kidney (293) and HeLa cells (Elbashir et al. (2001) *Nature* 411:494-498). Accordingly, translation of a gene in a cell can be inhibited by contacting the cell with short double stranded RNAs having a length of about 15 to 30 nucleotides or of about 18 to 21 nucleotides or of about 19 to 21 nucleotides. Alternatively, a vector encoding for such siRNAs or short hairpin RNAs (shRNAs)

that are metabolized into siRNAs can be introduced into a target cell (see, e.g., McManus et al. (2002) RNA 8:842; Xia et al. (2002) Nature Biotechnology 20:1006; and Brummelkamp et al. (2002) Science 296:550). Vectors that can be used are commercially available, e.g., from OligoEngine under the name pSuper RNAi System™.

Ribozyme molecules designed to catalytically cleave cellular mRNA transcripts can also be used to prevent translation of cellular mRNAs and expression of cellular polypeptides, or both (See, e.g., PCT International Publication WO90/11364, published Oct. 4, 1990; Sarver et al. (1990) Science 247:1222-1225 and U.S. Pat. No. 5,093,246). While ribozymes that cleave mRNA at site specific recognition sequences can be used to destroy cellular mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach (1988) Nature 334:585-591. The ribozyme may be engineered so that the cleavage recognition site is located near the 5' end of cellular mRNAs; i.e., to increase efficiency and minimize the intracellular accumulation of non-functional mRNA transcripts.

The ribozymes of the methods and compositions presented herein also include RNA endoribonucleases (hereinafter "Cech-type ribozymes") such as the one which occurs naturally in *Tetrahymena thermophila* (known as the IVS, or L-19 IVS RNA) and which has been extensively described by Thomas Cech and collaborators (Zaug, et al. (1984) Science 224:574-578; Zaug, et al. (1986) Science 231:470-475; Zaug, et al. (1986) Nature 324:429-433; published International patent application No. WO88/04300 by University Patents Inc.; Been, et al. (1986) Cell 47:207-216). The Cech-type ribozymes have an eight base pair active site which hybridizes to a target RNA sequence whereafter cleavage of the target RNA takes place. The methods and compositions presented herein encompasses those Cech-type ribozymes which target eight base-pair active site sequences that are present in cellular genes.

As in the antisense approach, the ribozymes can be composed of modified oligonucleotides (e.g., for improved stability, targeting, etc.). A preferred method of delivery involves using a DNA construct "encoding" the ribozyme under the control of a strong constitutive pol III or pol II promoter, so that transfected cells will produce sufficient quantities of the ribozyme to destroy endogenous cellular messages and inhibit translation. Because ribozymes unlike antisense molecules, are catalytic, a lower intracellular concentration is required for efficiency.

Nucleic acid molecules to be used in triple helix formation for the inhibition of transcription of cellular genes are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

Small nucleic acids (e.g., miRNAs, pre-miRNAs, pri-miRNAs, miRNA*, piwiRNA, anti-miRNA, or a miRNA binding site, or a variant thereof), antisense oligonucleotides, ribozymes, and triple helix molecules of the methods and compositions presented herein may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Moreover, various well-known modifications to nucleic acid molecules may be introduced as a means of increasing intracellular stability and half-life. One of skill in the art will readily understand that polypeptides, small nucleic acids, and antisense oligonucleotides can be further linked to another peptide or polypeptide (e.g., a heterologous peptide), e.g., that serves as a means of protein detection. Non-limiting examples of label peptide or polypeptide moieties useful for detection in the invention include, without limitation, suitable enzymes such as horseradish peroxidase, alkaline phosphatase, beta-galactosidase, or acetylcholinesterase; epitope tags, such as FLAG, MYC, HA, or HIS tags; fluorophores such as green fluorescent protein; dyes; radioisotopes; digoxygenin; biotin; antibodies; polymers; as well as others known in the art, for example, in Principles of Fluorescence Spectroscopy, Joseph R. Lakowicz (Editor), Plenum Pub Corp, 2nd edition (July 1999).

The modulatory agents described herein (e.g., antibodies, small molecules, peptides, fusion proteins, or small nucleic acids) can be incorporated into pharmaceutical compositions and administered to a subject in vivo. The compositions may contain a single such molecule or agent or any combination of agents described herein. Based on the genetic pathway analyses described herein, it is believed that such combinations of agents is especially effective in diagnosing, prognosing, preventing, and treating melanoma. Thus, "single active agents" described herein can be combined with other pharmacologically active compounds ("second active agents") known in the art according to the methods and compositions provided herein. It is believed that certain combinations work synergistically in the treatment of particular types of melanoma. Second active agents can be large molecules (e.g., proteins) or small molecules (e.g., synthetic inorganic, organometallic, or organic molecules).

II. Recombinant Expression Vectors and Host Cells

Another aspect of the invention pertains to the use of vectors, preferably expression vectors, containing a nucleic acid encoding Slit2 (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions. In one embodiment, adenoviral vectors comprising a Slit2 nucleic acid molecule are used.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, CA (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

The recombinant expression vectors of the invention can be designed for expression of Slit2 in prokaryotic or eukaryotic cells. For example, Slit2 can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, CA (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, MA) and pRIT5 (Pharmacia, Piscataway, NJ) which fuse glutathione S-transferase (GST), maltose E binding protein, or protein A, respectively, to the target recombinant protein. In one embodiment, the coding sequence of the Slit2 is cloned into a pGEX expression vector to create a vector encoding a fusion protein comprising, from the N-terminus to the C-terminus, and/or GST-thrombin cleavage site-Slit2. The fusion protein can be purified by affinity chromatography using glutathione-agarose resin. Recombinant Slit2 unfused to GST can be recovered by cleavage of the fusion protein with thrombin.

Examples of suitable inducible non-fusion *E. coli* expression vectors include pTrc (Amann et al., (1988) *Gene* 69:301-315) and pET 11d (Studier et al., *Gene Expression Technology: Methods in Enzymology* 185, Academic Press, San Diego, California (1990) 60-89). Target gene expression from the pTrc vector relies on host RNA polymerase transcription from a hybrid trp-lac fusion promoter. Target gene expression from the pET I1d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident X prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, California (1990) 119-128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res.* 20:2111-2118). Such alteration of nucleic acid sequences of the invention can be carried out by standard DNA synthesis techniques.

In another embodiment, the Slit2 expression vector is a yeast expression vector. Examples of vectors for expression in yeast S. cerivisae include pYepSecl (Baldari, et al., (1987) *EMBO J.* 6:229-234), pMFa (Kurjan and Herskowitz, (1982) *Cell* 30:933-943), pJRY88 (Schultz et al., (1987) *Gene* 54:113-123), and pYES2 (Invitrogen Corporation, San Diego, CA).

Alternatively, Slit2 can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156-2165) and the pVL series (Lucklow and Summers (1989) Virology 170:31-39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, NY, 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374-379) and the α-fetoprotein promoter (Campes and Tilghman (1989) *Genes Dev.* 3:537-546).

The invention further provides a recombinant expression vector comprising a nucleic acid molecule of the invention cloned into the expression vector in an antisense orientation. That is, the DNA molecule is operatively linked to a regulatory sequence in a manner which allows for expression (by transcription of the DNA molecule) of an RNA molecule which is antisense to Slit2 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, Slit2 protein can be expressed in bacterial cells such as *E. coli*, insect cells, yeast or mammalian cells (such as Fao hepatoma cells, primary hepatocytes, Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual. 2nd, ed., Cold Spring Harbor Laboratory*, Cold Spring Harbor Laboratory Press, Cold Spring Harbor, NY, 1989), and other laboratory manuals.

A cell culture includes host cells, media and other byproducts. Suitable media for cell culture are well known in the art. A Slit2 polypeptide or fragment thereof, may be secreted and isolated from a mixture of cells and medium containing the polypeptide. Alternatively, a Slit2 polypeptide or fragment thereof, may be retained cytoplasmically and the cells harvested, lysed and the protein or protein complex isolated. A Slit2 polypeptide or fragment thereof, may be isolated from cell culture medium, host cells, or both using techniques known in the art for purifying proteins, including ion-exchange chromatography, gel filtration chromatography, ultrafiltration, electrophoresis, and inmmunoaffinity purification with antibodies specific for particular epitopes of Slit2 or a fragment thereof. In other embodiments, heterologous tags can be used for purification purposes (e.g., epitope tags and FC fusion tags), according to standards methods known in the art.

Thus, a nucleotide sequence encoding all or a selected portion of a Slit2 polypeptide may be used to produce a recombinant form of the protein via microbial or eukaryotic cellular processes. Ligating the sequence into a polynucleotide construct, such as an expression vector, and transforming or transfecting into hosts, either eukaryotic (yeast, avian, insect or mammalian) or prokaryotic (bacterial cells), are standard procedures. Similar procedures, or modifications thereof, may be employed to prepare recombinant Slit2 polypeptides, or fragments thereof, by microbial means or tissue-culture technology in accord with the subject invention.

In another variation, protein production may be achieved using in vitro translation systems. In vitro translation systems are, generally, a translation system which is a cell-free extract containing at least the minimum elements necessary for translation of an RNA molecule into a protein. An in vitro translation system typically comprises at least ribosomes, tRNAs, initiator methionyl-tRNAMet, proteins or complexes involved in translation, e.g., eIF2, eIF3, the cap-binding (CB) complex, comprising the cap-binding protein (CBP) and eukaryotic initiation factor 4F (eIF4F). A variety of in vitro translation systems are well known in the art and include commercially available kits. Examples of in vitro translation systems include eukaryotic lysates, such as rabbit reticulocyte lysates, rabbit oocyte lysates, human cell lysates, insect cell lysates and wheat germ extracts. Lysates are commercially available from manufacturers such as Promega Corp., Madison, Wis.; Stratagene, La Jolla, Calif.; Amersham, Arlington Heights, Ill.; and GIBCO/BRL, Grand Island, N.Y. In vitro translation systems typically comprise macromolecules, such as enzymes, translation, initiation and elongation factors, chemical reagents, and ribosomes. In addition, an in vitro transcription system may be used. Such systems typically comprise at least an RNA polymerase holoenzyme, ribonucleotides and any necessary transcription initiation, elongation and termination factors. In vitro transcription and translation may be coupled in a one-pot reaction to produce proteins from one or more isolated DNAs.

In certain embodiments, the Slit2 polypeptide, or fragment thereof, may be synthesized chemically, ribosomally in a cell free system, or ribosomally within a cell. Chemical synthesis may be carried out using a variety of art recognized methods, including stepwise solid phase synthesis, semi-synthesis through the conformationally-assisted religation of peptide fragments, enzymatic ligation of cloned or synthetic peptide segments, and chemical ligation. Native chemical ligation employs a chemoselective reaction of two unprotected peptide segments to produce a transient thioester-linked intermediate. The transient thioester-linked intermediate then spontaneously undergoes a rearrangement to provide the full length ligation product having a native peptide bond at the ligation site. Full length ligation products are chemically identical to proteins produced by cell free synthesis. Full length ligation products may be refolded and/or oxidized, as allowed, to form native disulfide-containing protein molecules. (see e.g., U.S. Pat. Nos. 6,184,344 and 6,174,530; and T. W. Muir et al., Curr. Opin. Biotech. (1993): vol. 4, p 420; M. Miller, et al., Science (1989): vol. 246, p 1149; A. Wlodawer, et al., Science (1989): vol. 245, p 616; L. H. Huang, et al., Biochemistry (1991): vol. 30, p 7402; M. Sclmolzer, et al., Int. J. Pept. Prot. Res. (1992): vol. 40, p 180-193; K. Rajarathnam, et al., Science (1994): vol. 264, p 90; R. E. Offord, "Chemical Approaches to Protein Engineering", in Protein Design and the Development of New therapeutics and Vaccines, J. B. Hook, G. Poste, Eds., (Plenum Press, New York, 1990) pp. 253-282; C. J. A. Wallace, et al., J. Biol. Chem. (1992): vol. 267, p 3852; L. Abrahmsen, et al., Biochemistry (1991): vol. 30, p 4151; T. K. Chang, et al., Proc. Natl. Acad. Sci. USA (1994) 91: 12544-12548; M. Schnlzer, et al., Science (1992): vol., 3256, p 221; and K. Akaji, et al., Chem. Pharm. Bull. (Tokyo) (1985) 33: 184).

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding Slit2 or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) Slit2 protein. Accordingly, the invention further provides methods for producing Slit2 protein using the host cells of the invention. In one embodiment, the method comprises culturing the host cell of invention (into which a recombinant expression vector encoding Slit2 has been introduced) in a suitable medium until Slit2 is produced. In another embodiment, the method further comprises isolating Slit2 from the medium or the host cell.

The host cells of the invention can also be used to produce nonhuman transgenic animals. The nonhuman transgenic animals can be used in screening assays designed to identify agents or compounds, e.g., drugs, pharmaceuticals, etc., which are capable of ameliorating detrimental symptoms of selected disorders such as glucose homeostasis disorders, weight disorders or disorders associated with insufficient insulin activity. For example, in one embodiment, a host cell of the invention is a fertilized oocyte or an embryonic stem cell into which Slit2 encoding sequences, or fragments thereof, have been introduced. Such host cells can then be used to create non-human transgenic animals in which exogenous Slit2 sequences have been introduced into their genome or homologous recombinant animals in which endogenous Slit2 sequences have been altered. Such animals are useful for studying the function and/or activity of Slit2, or fragments thereof, and for identifying and/or evaluating modulators of Slit2 activity. As used herein, a "transgenic animal" is a nonhuman animal, preferably a mammal, more preferably a rodent such as a rat or mouse, in which one or more of the cells of the animal includes a transgene. Other examples of transgenic animals include nonhuman primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a nonhuman animal, preferably a mammal, more preferably a mouse, in which an endogenous Slit2 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing nucleic acids encoding Slit2, or a fragment thereof, into the male pronuclei of a fertilized oocyte, e.g., by microinjection, retroviral infection, and allowing the oocyte to develop in a pseudopregnant female foster animal. The huma Slit2 cDNA sequence can be introduced as a transgene into the genome of a nonhuman animal. Alternatively, a nonhuman homologue of the huma Slit2 gene can be used as a transgene. Intronic sequences and polyadenylation signals can also be included in the transgene to increase the efficiency of expression of the transgene. A tissue-specific regulatory sequence(s) can be operably linked to the Slit2 transgene to direct expression of Slit2 protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., Manipulating the Mouse Embryo, (Cold Spring Harbor Laboratory Press, Cold Spring Harbor, N.Y., 1986). Similar methods are used for production of other transgenic animals. A transgenic founder animal can be identified based upon the presence of the Slit2 transgene in its genome and/or expression of Slit2 mRNA in tissues or cells of the animals. A transgenic founder animal can then be used to breed additional animals carrying the transgene. Moreover, transgenic animals carrying a transgene encoding Slit2 can further be bred to other transgenic animals carrying other transgenes.

To create a homologous recombinant animal, a vector is prepared which contains at least a portion of a Slit2 gene into which a deletion, addition or substitution has been introduced to thereby alter, e.g., functionally disrupt, the Slit2 gene. The Slit2 gene can be a human gene, but more preferably, is a nonhuman homologue of a huma Slit2 gene. For example, a mouse Slit2 gene can be used to construct a homologous recombination vector suitable for altering an endogenous Slit2 gene, respectively, in the mouse genome. In a preferred embodiment, the vector is designed such that, upon homologous recombination, the endogenous Slit2 gene is functionally disrupted (i.e., no longer encodes a functional protein; also referred to as a "knock out" vector). Alternatively, the vector can be designed such that, upon homologous recombination, the endogenous Slit2 gene is mutated or otherwise altered but still encodes functional protein (e.g., the upstream regulatory region can be altered to thereby alter the expression of the endogenous Slit2 protein). In the homologous recombination vector, the altered portion of the Slit2 gene is flanked at its 5' and 3' ends by additional nucleic acid of the Slit2 gene to allow for homologous recombination to occur between the exogenous Slit2 gene carried by the vector and an endogenous Slit2 gene in an embryonic stem cell. The additional flanking Slit2 nucleic acid is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced Slit2 gene has homologously recombined with the endogenous Slit2 gene are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823-829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic nonhuman animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232-6236. Another example of a recombinase system is the FLP recombinase system of *Saccharomyces cerevisiae* (O'Gorman et al. (1991) *Science* 251:1351-1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the nonhuman transgenic animals described herein can also be produced according to the methods described in Wilmut, I. et al. (1997) *Nature* 385:810-813 and PCT International Publication Nos. WO 97/07668 and WO 97/07669. In brief, a cell, e.g., a somatic cell, from the transgenic animal can be isolated and induced to exit the growth cycle and enter $G_O$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring borne of this female foster animal will be a clone of the animal from which the cell, e.g., the somatic cell, is isolated.

III. Isolated Slit2 Polypeptides and Anti-Slit2 Antibodies

The present invention provides soluble, purified and/or isolated forms of Slit2 polypeptides, or fragments thereof, for use in the present methods or as compositions.

In one aspect, a Slit2 polypeptide may comprise a full-length Slit2 amino acid sequence or a full-length Slit2 amino acid sequence with 1 to about 20 conservative amino acid substitutions. Amino acid sequence of any Slit2 polypeptide described herein can also be at least 50, 55, 60, 65, 70, 75, 80, 85, 90, 91, 92, 93, 94, 95, 96, 97, 98, 99, or 99.5% identical to a Slit2 polypeptide sequence of interest, described herein, well known in the art, or a fragment thereof. In addition, any Slit2 polypeptide, or fragment thereof, described herein has modulates (e.g., enhance) one or more of the following biological activities: a) brown fat and/or beige fat gene expression, such as expression of a marker selected from the group consisting of: cidea, adiponectin, adipsin, otopetrin, type II deiodinase, cig30, ppar gamma 2, pgc1α, ucp1, elovl3, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, dio2, fatty acid synthase (fas), leptin, resistin, and nuclear respiratory factor-1 (nrf1); b) thermogenesis in adipose cells; c) differentiation of adipose cells; d) insulin sensitivity of adipose cells; e) basal respiration or uncoupled respiration; f) whole body oxygen consumption; g) obesity or appetite; h) insulin secretion of pancreatic beta cells; i) glucose tolerance; j) modified phosphorylation of EGFR, ERK, AMPK, protein kinase A (PKA) substrates having an RRX(S/T) (SEQ ID NO: 127) motif, wherein the X is any amino acid and the (S/T) residue is a serine or threonine, HSL; k) modified expression of UCP1 protein; and 1) growth and effects of metabolic disorders, such as obesity-associated cancer, cachexia, anorexia, diabetes, and obesity. In another aspect, the present invention contemplates a composition comprising an isolated Slit2 polypeptide and less than about 25%, or alternatively 15%, or alternatively 5%, contaminating biological macromolecules or polypeptides.

The present invention further provides compositions related to producing, detecting, or characterizing a Slit2 polypeptide, or fragment thereof, such as nucleic acids, vectors, host cells, and the like. Such compositions may serve as compounds that modulate a Slit2 polypeptide's expression and/or activity, such as antisense nucleic acids.

In certain embodiments, a Slit2 polypeptide of the invention may be a fusion protein containing a domain which increases its solubility and bioavilability and/or facilitates its purification, identification, detection, and/or structural characterization. Exemplary domains, include, for example, Fc, glutathione S-transferase (GST), protein A, protein G, calmodulin-binding peptide, thioredoxin, maltose binding protein, HA, myc, poly arginine, poly His, poly His-Asp or FLAG fusion proteins and tags. Additional exemplary domains include domains that alter protein localization in vivo, such as signal peptides, type III secretion system-targeting peptides, transcytosis domains, nuclear localization signals, etc. In various embodiments, a Slit2 polypeptide of the invention may comprise one or more heterologous fusions. Polypeptides may contain multiple copies of the same fusion domain or may contain fusions to two or more different domains. The fusions may occur at the N-terminus of the polypeptide, at the C-terminus of the polypeptide, or at both the N- and C-terminus of the polypeptide. It is also within the scope of the invention to include linker sequences between a polypeptide of the invention and the fusion domain in order to facilitate construction of the fusion protein or to optimize protein expression or structural constraints of the fusion protein. In one embodiment, the linker is a linker described herein, e.g., a linker of at least 8, 9, 10, 15, 20 amino acids. The linker can be, e.g., an unstructured recombinant polymer (URP), e.g., a URP that is 9, 10, 11, 12, 13, 14, 15, 20 amino acids in length, i.e., the linker has limited or lacks secondary structure, e.g., Chou-Fasman algorithm. An exemplary linker comprises (e.g., consists of) the amino acid sequence GGGGAGGGG (SEQ ID NO: 23). In another embodiment, the polypeptide may be constructed so as to contain protease cleavage sites between the fusion polypeptide and polypeptide of the invention in order to remove the tag after protein expression or thereafter. Examples of suitable endoproteases, include, for example, Factor Xa and TEV proteases.

In some embodiments, Slit2 polypeptides, or fragments thereof, are fused to an antibody (e.g., IgG 1, IgG2, IgG3, IgG4) fragment (e.g., Fc polypeptides). Techniques for preparing these fusion proteins are known, and are described, for example, in WO 99/31241 and in Cosman et.al., 2001 Immunity 14:123 133. Fusion to an Fc polypeptide offers the additional advantage of facilitating purification by affinity chromatography over Protein A or Protein G columns.

In still another embodiment, a Slit2 polypeptide may be labeled with a fluorescent label to facilitate their detection, purification, or structural characterization. In an exemplary embodiment, a Slit2 polypeptide of the invention may be fused to a heterologous polypeptide sequence which produces a detectable fluorescent signal, including, for example, green fluorescent protein (GFP), enhanced green fluorescent protein (EGFP), Renilla Reniformis green fluorescent protein, GFPmut2, GFPuv4, enhanced yellow fluorescent protein (EYFP), enhanced cyan fluorescent protein (ECFP), enhanced blue fluorescent protein (EBFP), citrine and red fluorescent protein from discosoma (dsRED).

Another aspect of the invention pertains to the use of isolated Slit2 proteins, and biologically active portions thereof, as well as peptide fragments suitable for use as immunogens to raise anti-Slit2 antibodies. An "isolated" or "purified" protein or biologically active portion thereof is substantially free of cellular material when produced by recombinant DNA techniques, or chemical precursors or other chemicals when chemically synthesized. The language "substantially free of cellular material" includes preparations of Slit2 protein in which the protein is separated from cellular components of the cells in which it is naturally or recombinantly produced. In one embodiment, the language "substantially free of cellular material" includes preparations of Slit2 protein having less than about 30% (by dry weight) of non-Slit2 protein (also referred to herein as a "contaminating protein"), more preferably less than about 20% of non-Slit2 protein, still more preferably less than about 10% of non-Slit2 protein, and most preferably less than about 5% non-Slit2 protein. When the Slit2 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations of Slit2 protein in which the protein is separated from chemical precursors or other chemicals which are involved in the synthesis of the protein. In one embodiment, the language "substantially free of chemical precursors or other chemicals" includes preparations of Slit2 protein having less than about 30% (by dry weight) of chemical precursors of non-Slit2 chemicals, more preferably less than about 20% chemical precursors of non-Slit2 chemicals, still more preferably less than about 10% chemical precursors of non-Slit2 chemicals, and most preferably less than about 5% chemical precursors of non-Slit2 chemicals. In preferred embodiments, isolated proteins or biologically active portions thereof lack contaminating proteins from the same animal from which the Slit2 protein is derived. Typically, such proteins are produced by recombinant expression of, for example, a huma Slit2 protein in a nonhuman cell.

In preferred embodiments, the protein or portion thereof comprises an amino acid sequence which is sufficiently homologous to an amino acid sequence described in Table 1, such that the protein or portion thereof maintains one or more of the following biological activities: a) brown fat and/or beige fat gene expression, such as expression of a marker selected from the group consisting of: cidea, adiponectin, adipsin, otopetrin, type II deiodinase, cig30, ppar gamma 2, pgc1α, ucp1, elovl3, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, dio2, fatty acid synthase (fas), leptin, resistin, and nuclear respiratory factor-1 (nrf1); b) thermogenesis in adipose cells; c) differentiation of adipose cells; d) insulin sensitivity of adipose cells; e) basal respiration or uncoupled respiration; f) whole body oxygen consumption; g) obesity or appetite; h) insulin secretion of pancreatic beta cells; i) glucose tolerance; j) modified phosphorylation of EGFR, ERK, AMPK, protein kinase A (PKA) substrates having an RRX(S/T) (SEQ ID NO: 127) motif, wherein the X is any amino acid and the (S/T) residue is a serine or threonine, HSL; k) modified expression of UCP1 protein; and 1) growth and effects of metabolic disorders, such as obesity-associated cancer, cachexia, anorexia, diabetes, and obesity. The portion of the protein is preferably a biologically active portion as described herein. In another preferred embodiment, the Slit2 protein has an amino acid sequence described in Table 1, or fragment thereof, respectively, or an amino acid sequence which is at least about 50%, 55%, 60%, 65%, 70%, 75%, 80%, 85%, 90%, 91%, 92%, 93%, 94%, 95%, 96%, 97%, 98%, 99% or more homologous to the amino acid sequence described in Table 1, or fragment thereof. In yet another preferred embodiment, the Slit2 protein has an amino acid sequence which is encoded by a nucleotide sequence which hybridizes, e.g., hybridizes under stringent conditions, to a nucleotide sequence described in Table 1, or fragment thereof, or a nucleotide sequence which is at least about 50%, preferably at least about 60%, more preferably at least about 70%, yet more preferably at least about 80%, still more preferably at least about 90%, and most preferably at least about 95% or more homologous to a nucleotide sequence described in Table 1, or fragment thereof. The preferred Slit2 proteins of the present invention also preferably possess at least one of the Slit2 biological activities, or activities associated with the complex, described herein. For example, a preferred Slit2 protein of the present invention includes an amino acid sequence encoded by a nucleotide sequence which hybridizes, e.g., hybridizes under stringent conditions, to a nucleotide sequence described in Table 1, or fragment thereof, and which can maintain one or more of the following biological activities or, in complex, modulates (e.g., enhance) one or more of the following biological activities: a) brown fat and/or beige fat gene expression, such as expression of a marker selected from the group consisting of: cidea, adiponectin, adipsin, otopetrin, type II deiodinase, cig30, ppar gamma 2, pgc1α, ucp1, elovl3, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, dio2, fatty acid synthase (fas), leptin, resistin, and nuclear respiratory factor-1 (nrf1); b) thermogenesis in adipose cells; c) differentiation of adipose cells; d) insulin sensitivity of adipose cells; e) basal respiration or uncoupled respiration; f) whole body oxygen consumption; g) obesity or appetite; h) insulin secretion of pancreatic beta cells; i) glucose tolerance; j) modified phosphorylation of EGFR, ERK, AMPK, protein kinase A (PKA) substrates having an RRX(S/T) (SEQ ID NO: 127) motif, wherein the X is any amino acid and the (S/T) residue is a serine or threonine, HSL; k) modified expression of UCP1 protein; and 1) growth and effects of metabolic disorders, such as obesity-associated cancer, cachexia, anorexia, diabetes, and obesity.

Biologically active portions of the Slit2 protein include peptides comprising amino acid sequences derived from the amino acid sequence of the Slit2 protein, e.g., an amino acid sequence described in Table 1, or fragment thereof, or the amino acid sequence of a protein homologous to the Slit2 protein, which include fewer amino acids than the full length Slit2 protein or the full length protein which is homologous to the Slit2 protein, and exhibit at least one activity of the Slit2 protein, or complex thereof. Typically, biologically active portions (peptides, e.g., peptides which are, for example, 50, 55, 60, 65, 70, 75, 80, 85, 90, 95, 100 or more amino acids in length) comprise a domain or motif, e.g., signal peptide, EGF repeat domain, C-terminal cysteine knot domain, etc.). In a preferred embodiment, the biologically active portion of the protein which includes one or more the domains/motifs described herein can modulate differentiation of adipocytes and/or thermogenesis in brown adipocytes. Moreover, other biologically active portions, in which other regions of the protein are deleted, can be prepared by recombinant techniques and evaluated for one or more of the activities described herein. Preferably, the biologically active portions of the Slit2 protein include one or more selected domains/motifs or portions thereof having biological activity. In an exemplary embodiment, a Slit2 fragment comprises and/or consists of about 408, 407, 406, 405, 404, 403, 402, 401, 400, 399, 398, 397, 396, 395, 394, 393, 392, 391, 390, 389, 388, 387, 386, 385, 384, 383, 382, 381, 380, 379, 378, 377, 376, 375, 374, 373, 372, 371, 370, 365, 360, 355, 350, 345, 340, 335, 330, 325, 320, 315, 310, 305, 300, 295, 290, 285, 280, 275, 270, 265, 260, 255, 250, 245, 240, 235, 230, 225, 220, 215, 210, 205, 200, or fewer residues of a sequence described in Table 1, or any range in between, inclusive, such as 275 to 408 amino acids in length.

Slit2 proteins can be produced by recombinant DNA techniques. For example, a nucleic acid molecule encoding the protein is cloned into an expression vector (as described above), the expression vector is introduced into a host cell (as described above) and the Slit2 protein is expressed in the host cell. The Slit2 protein can then be isolated from the cells by an appropriate purification scheme using standard protein purification techniques. Alternative to recombinant expression, a Slit2 protein, polypeptide, or peptide can be synthesized chemically using standard peptide synthesis techniques. Moreover, native Slit2 protein can be isolated from cells (e.g., brown adipocytes), for example using an anti-Slit2 antibody (described further below).

The invention also provides Slit2 chimeric or fusion proteins. As used herein, a Slit2 "chimeric protein" or "fusion protein" comprises a Slit2 polypeptide operatively linked to a non-Slit2 polypeptide. A "Slit2 polypeptide" refers to a polypeptide having an amino acid sequence corresponding to Slit2, whereas a "non-Slit2 polypeptide" refers to a polypeptide having an amino acid sequence corresponding to a protein which is not substantially homologous to the Slit2 protein, respectively, e.g., a protein which is different from the Slit2 protein and which is derived from the same or a different organism. Within the fusion protein, the term "operatively linked" is intended to indicate that the Slit2 polypeptide and the non-Slit2 polypeptide are fused in-frame to each other. The non-Slit2 polypeptide can be fused to the N-terminus or C-terminus of the Slit2 polypeptide, respectively. For example, in one embodiment the fusion protein is a Slit2-GST and/or Slit2-Fc fusion protein in which the Slit2 sequences, respectively, are fused to the N-terminus of the GST or Fc sequences. Such fusion proteins can facilitate the purification, expression, and/or bioavailbility of recombinant Slit2. In another embodiment, the fusion protein is a Slit2 protein containing a heterologous signal sequence at its C-terminus. In certain host cells (e.g., mammalian host cells), expression and/or secretion of Slit2 can be increased through use of a heterologous signal sequence.

Preferably, a Slit2 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A Slit2-encoding nucleic acid can be cloned into such an expression vector such that the fusion moiety is linked in-frame to the Slit2 protein.

The present invention also pertains to homologues of the Slit2 proteins which function as either a Slit2 agonist (mimetic) or a Slit2 antagonist. In a preferred embodiment, the Slit2 agonists and antagonists stimulate or inhibit, respectively, a subset of the biological activities of the naturally occurring form of the Slit2 protein. Thus, specific biological effects can be elicited by treatment with a homologue of limited function. In one embodiment, treatment of a subject with a homologue having a subset of the biological activities of the naturally occurring form of the protein has fewer side effects in a subject relative to treatment with the naturally occurring form of the Slit2 protein.

Homologues of the Slit2 protein can be generated by mutagenesis, e.g., discrete point mutation or truncation of the Slit2 protein. As used herein, the term "homologue" refers to a variant form of the Slit2 protein which acts as an agonist or antagonist of the activity of the Slit2 protein. An agonist of the Slit2 protein can retain substantially the same, or a subset, of the biological activities of the Slit2 protein. An antagonist of the Slit2 protein can inhibit one or more of the activities of the naturally occurring form of the Slit2 protein, by, for example, competitively binding to a downstream or upstream member of the Slit2 cascade which includes the Slit2 protein. Thus, the mammalia Slit2 protein and homologues thereof of the present invention can be, for example, either positive or negative regulators of adipocyte differentiation and/or thermogenesis in brown adipocytes.

In an alternative embodiment, homologues of the Slit2 protein can be identified by screening combinatorial libraries of mutants, e.g., truncation mutants, of the Slit2 protein for Slit2 protein agonist or antagonist activity. In one embodiment, a variegated library of Slit2 variants is generated by combinatorial mutagenesis at the nucleic acid level and is encoded by a variegated gene library. A variegated library of Slit2 variants can be produced by, for example, enzymatically ligating a mixture of synthetic oligonucleotides into gene sequences such that a degenerate set of potential Slit2 sequences is expressible as individual polypeptides, or alternatively, as a set of larger fusion proteins (e.g., for phage display) containing the set of Slit2 sequences therein. There are a variety of methods which can be used to produce libraries of potential Slit2 homologues from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential Slit2 sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of the Slit2 protein coding can be used to generate a variegated population of Slit2 fragments for screening and subsequent selection of homologues of a Slit2 protein. In one embodiment, a library of coding sequence fragments can be generated by treating a double stranded PCR fragment of a Slit2 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the Slit2 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of Slit2 homologues. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify Slit2 homologues (Arkin and Youvan (1992) *Proc. Natl. Acad. Sci. USA* 89:7811-7815; Delagrave et al. (1993) *Protein Engineering* 6(3):327-331).

In another aspect, an isolated Slit2 protein, or a fragment thereof, can be used as an immunogen to generate antibodies that bind Slit2, or the complex thereof, using standard techniques for polyclonal and monoclonal antibody preparation. The full-length Slit2 protein can be used or, alternatively, antigenic peptide fragments of Slit2, or peptides in complex, can be used as immunogens. A Slit2 immunogen typically is used to prepare antibodies by immunizing a suitable subject, (e.g., rabbit, goat, mouse or other mammal) with the immunogen. An appropriate immunogenic preparation can contain, for example, recombinantly expressed Slit2 protein or a chemically synthesized Slit2 peptide. The preparation can further include an adjuvant, such as Freund's complete or incomplete adjuvant, or similar immunostimulatory agent. Immunization of a suitable subject with an immunogenic Slit2 preparation induces a polyclonal anti-Slit2 antibody response.

Accordingly, another aspect of the invention pertains to the use of anti-Slit2 antibodies. The term "antibody" as used herein refers to immunoglobulin molecules and immunologically active portions of immunoglobulin molecules, i.e., molecules that contain an antigen binding site which specifically binds (immunoreacts with) an antigen, such as Slit2. Examples of immunologically active portions of immunoglobulin molecules include F(ab) and $F(ab')_2$ fragments which can be generated by treating the antibody with an enzyme such as pepsin. The invention provides polyclonal and monoclonal antibodies that bind Slit2. The term "monoclonal antibody" or "monoclonal antibody composition", as used herein, refers to a population of antibody molecules that contain only one species of an antigen binding site capable of immunoreacting with a particular epitope of Slit2. A monoclonal antibody composition thus typically displays a single binding affinity for a particular Slit2 protein with which it immunoreacts.

Polyclonal anti-Slit2 antibodies can be prepared as described above by immunizing a suitable subject with a Slit2 immunogen, or fragment thereof. The anti-Slit2 antibody titer in the immunized subject can be monitored over time by standard techniques, such as with an enzyme linked immunosorbent assay (ELISA) using immobilized Slit2. If desired, the antibody molecules directed against Slit2 can be isolated from the mammal (e.g., from the blood) and further purified by well known techniques, such as protein A chromatography to obtain the IgG fraction. At an appropriate time after immunization, i.e., when the anti-Slit2 antibody titers are highest, antibody-producing cells can be obtained from the subject and used to prepare monoclonal antibodies by standard techniques, such as the hybridoma technique originally described by Kohler and Milstein (1975) *Nature* 256:495-497) (see also, Brown et al. (1981) *J. Immunol.* 127:539-46; Brown et al. (1980) *J. Biol. Chem.* 255:4980-83; Yeh et al. (1976) *Proc. Natl. Acad. Sci. USA* 76:2927-31; and Yeh et al. (1982) *Int. J. Cancer* 29:269-75), the more recent human B cell hybridoma technique (Kozbor et al. (1983) *Immunol. Today* 4:72), the EBV-hybridoma technique (Cole et al. (1985), *Monoclonal Antibodies and Cancer Therapy*, Alan R. Liss, Inc., pp. 77-96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, New York (1980); E. A. Lerner (1981) *Yale J. Biol. Med.,* 54:387-402; M. L. Gefter et al. (1977) *Somatic Cell Genet.* 3:231-36). Briefly, an immortal cell line (typically a myeloma) is fused to lymphocytes (typically splenocytes) from a mammal immunized with a Slit2 immunogen as described above, and the culture supernatants of the resulting hybridoma cells are screened to identify a hybridoma producing a monoclonal antibody that binds Slit2.

Any of the many well-known protocols used for fusing lymphocytes and immortalized cell lines can be applied for the purpose of generating an anti-Slit2 monoclonal antibody (see, i.e., G. Galfre et al. (1977) *Nature* 266:550-52; Gefter et al. *Somatic Cell Genet*., cited supra; Lerner, *Yale J. Biol. Med*., cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, i.e., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind Slit2, i.e., using a standard ELISA assay.

As an alternative to preparing monoclonal antibody-secreting hybridomas, a monoclonal anti-Slit2 antibody can be identified and isolated by screening a recombinant combinatorial immunoglobulin library (e.g., an antibody phage display library) with Slit2 to thereby isolate immunoglobulin library members that bind Slit2. Kits for generating and screening phage display libraries are commercially available (e.g., the Pharmacia Recombinant Phage Antibody System, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1369-1372; Hay et al. (1992) *Hum. Antibod. Hybridomas* 3:81-85; Huse et al. (1989) *Science* 246:1275-1281; Griffiths et al. (1993) *EMBO J.* 12:725-734; Hawkins et al. (1992) *J. Mol. Biol.* 226:889-896; Clackson et al. (1991) *Nature* 352:624-628; Gram et al. (1992) *Proc. Natl. Acad. Sci. USA* 89:3576-3580; Garrard et al. (1991) *Bio/Technology* 9:1373-1377; Hoogenboom et al. (1991) *Nucleic Acids Res.* 19:4133-4137; Barbas et al. (1991) *Proc. Natl. Acad. Sci. USA* 88:7978-7982; and McCafferty et al. *Nature* (1990) 348:552-554.

Additionally, recombinant anti-Slit2 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) Canc. Res. 47:999-1005; Wood et al. (1985) *Nature* 314:446-449; and Shaw et al. (1988) *J. Natl. Cancer Inst.* 80:1553-1559); Morrison, S. L. (1985) *Science* 229:1202-1207; Oi et al. (1986) *BioTechniques* 4:214; Winter U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

An anti-Slit2 antibody (e.g., monoclonal antibody) can be used to isolate Slit2 by standard techniques, such as affinity chromatography or immunoprecipitation. An anti-Slit2 antibody can facilitate the purification of natural Slit2 from cells and of recombinantly produced Slit2 expressed in host cells. Moreover, an anti-Slit2 antibody can be used to detect Slit2 protein (e.g., in a cellular lysate or cell supernatant) in order to evaluate the abundance and pattern of expression of the Slit2 protein. Anti-Slit2 antibodies can be used to monitor protein levels in a cell or tissue, e.g., adipose cells or tissue, as part of a clinical testing procedure, e.g., in order to monitor a safe dosage of an uncoupling agent. Detection can be facilitated by coupling (e.g., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/ biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

In vivo techniques for detection of Slit2 protein include introducing into a subject a labeled antibody directed against the protein. For example, the antibody can be labeled with a radioactive marker whose presence and location in a subject can be detected by standard imaging techniques.

IV. Identification of Compounds that Modulate Slit2

The Slit2 nucleic acid and polypeptide molecules described herein may be used to design modulators of one or more of biological activities of the complex or complex polypeptides. In particular, information useful for the design of therapeutic and diagnostic molecules, including, for example, the protein domain, structural information, and the like for polypeptides of the invention is now available or attainable as a result of the ability to prepare, purify and characterize the complexes and complex polypeptides, and domains, fragments, variants and derivatives thereof.

In one aspect, modulators, inhibitors, or antagonists against the polypeptides of the invention, biological complexes containing them, or orthologues thereof, may be used to treat any disease or other treatable condition of a patient (including humans and animals), including, for example, metabolic disorders.

Modulators of Slit2 nucleic acid and polypeptide molecules, may be identified and developed as set forth below using techniques and methods known to those of skill in the art. The modulators of the invention may be employed, for instance, to inhibit and treat Slit2-mediated diseases or disorders. The modulators of the invention may elicit a change in one or more of the following activities: (a) a change in the level and/or rate of formation of a Slit2-receptor complex, (b) a change in the activity of a Slit2 nucleic acid and/or polypeptide, (c) a change in the stability of a Slit2 nucleic acid and/or polypeptide, (d) a change in the conformation of a Slit2 nucleic acid and/or polypeptide, or (e) a change in the activity of at least one polypeptide contained in a Slit2 complex. A number of methods for identifying a molecule which modulates a Slit2 nucleic acid and/or polypeptide are known in the art. For example, in one such method, a Slit2 nucleic acid and/or polypeptide, is contacted with a test compound, and the activity of the Slit2 nucleic acid and/or polypeptide is determined in the presence of the test compound, wherein a change in the activity of the Slit2 nucleic acid and/or polypeptide in the presence of the compound as compared to the activity in the absence of the compound (or in the presence of a control compound) indicates that the test compound modulates the activity of the Slit2 nucleic acid and/or polypeptide.

Compounds to be tested for their ability to act as modulators of Slit2 nucleic acids and/or polypeptides, can be produced, for example, by bacteria, yeast or other organisms (e.g. natural products), produced chemically (e.g. small molecules, including peptidomimetics), or produced recombinantly. Compounds for use with the above-described methods may be selected from the group of compounds consisting of lipids, carbohydrates, polypeptides, peptidomimetics, peptide-nucleic acids (PNAs), small molecules, natural products, aptamers and polynucleotides. In certain embodiments, the compound is a polynucleotide. In some embodiments, said polynucleotide is an antisense nucleic acid. In other embodiments, said polynucleotide is an siRNA. In certain embodiments, the compound comprises a biologically active fragment of a Slit2 polypeptide (e.g., a dominant negative form that binds to, but does not activate, a Slit2 receptor).

A variety of assay formats will suffice and, in light of the present disclosure, those not expressly described herein may nevertheless be comprehended by one of ordinary skill in the art based on the teachings herein. Assay formats for analyzing Slit2-receptor complex formation and/or activity of a Slit2 nucleic acid and/or polypeptide, may be generated in many different forms, and include assays based on cell-free systems, e.g. purified proteins or cell lysates, as well as cell-based assays which utilize intact cells. Simple binding assays can also be used to detect agents which modulate a Slit2, for example, by enhancing the formation of a Slit2, by enhancing the binding of a Slit2 to a substrate, and/or by enhancing the binding of a Slit2 polypeptide to a substrate. Another example of an assay useful for identifying a modulator of a Slit2 is a competitive assay that combines one or more Slit2 polypeptides with a potential modulator, such as, for example, polypeptides, nucleic acids, natural substrates or ligands, or substrate or ligand mimetics, under appropriate conditions for a competitive inhibition assay. Slit2 polypeptides can be labeled, such as by radioactivity or a colorimetric compound, such that Slit2-receptor complex formation and/or activity can be determined accurately to assess the effectiveness of the potential modulator.

Assays may employ kinetic or thermodynamic methodology using a wide variety of techniques including, but not limited to, microcalorimetry, circular dichroism, capillary zone electrophoresis, nuclear magnetic resonance spectroscopy, fluorescence spectroscopy, and combinations thereof. Assays may also employ any of the methods for isolating, preparing and detecting Slit2es, or complex polypeptides, as described above.

Complex formation between a Slit2 polypeptide, or fragment thereof, and a binding partner (e.g., Slit2 receptor) may be detected by a variety of methods. Modulation of the complex's formation may be quantified using, for example, detectably labeled proteins such as radiolabeled, fluorescently labeled, or enzymatically labeled polypeptides or binding partners, by immunoassay, or by chromatographic detection. Methods of isolating and identifying Slit2-receptor complexes described above may be incorporated into the detection methods.

In certain embodiments, it may be desirable to immobilize a Slit2 polypeptide to facilitate separation of Slit2 complexes from uncomplexed forms of one or both of the proteins, as well as to accommodate automation of the assay. Binding of a Slit2 polypeptide to a binding partner may be accomplished in any vessel suitable for containing the reactants. Examples include microtitre plates, test tubes, and micro-centrifuge tubes. In one embodiment, a fusion protein may be provided which adds a domain that allows the protein to be bound to a matrix. For example, glutathione-S-transferase/polypeptide (GST/polypeptide) fusion proteins may be adsorbed onto glutathione sepharose beads (Sigma Chemical, St. Louis, Mo.) or glutathione derivatized microtitre plates, which are then combined with the binding partner, e.g. an $^{35}S$-labeled binding partner, and the test compound, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintillant), or in the supernatant after the complexes are subsequently dissociated. Alternatively, the complexes may be dissociated from the matrix, separated by SDS-PAGE, and the level of Slit2 polypeptides found in the bead fraction quantified from the gel using standard electrophoretic techniques such as described in the appended examples.

Other techniques for immobilizing proteins on matrices are also available for use in the subject assay. For instance, a Slit2 polypeptide may be immobilized utilizing conjugation of biotin and streptavidin. For instance, biotinylated polypeptide molecules may be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with the polypeptide may be derivatized to the wells of the plate, and polypeptide trapped in the wells by antibody conjugation. As above, preparations of a binding partner and a test compound are incubated in the polypeptide presenting wells of the plate, and the amount of complex trapped in the well may be quantified. Exemplary methods for detecting such complexes, in addition to those described above for the GST-immobilized complexes, include immunodetection of complexes using antibodies reactive with the binding partner, or which are reactive with the Slit2 polypeptide and compete with the binding partner; as well as enzyme-linked assays which rely on detecting an enzymatic activity associated with the binding partner, either intrinsic or extrinsic activity. In the instance of the latter, the enzyme may be chemically conjugated or provided as a fusion protein with the binding partner. To illustrate, the binding partner may be chemically cross-linked or genetically fused with horseradish peroxidase, and the amount of Slit2 polypeptide trapped in the Slit2 complex may be assessed with a chromogenic substrate of the enzyme, e.g. 3,3'-diamino-benzadine terahydrochloride or 4-chloro-1-napthol. Likewise, a fusion protein comprising the Slit2 polypeptide and glutathione-S-transferase may be provided, and Slit2 complex formation quantified by detecting the GST activity using 1-chloro-2,4-dinitrobenzene (Habig et al (1974) J Biol Chem 249:7130).

Antibodies against the Slit2 polypeptide can be used for immunodetection purposes. Alternatively, the Slit2 polypeptide to be detected may be "epitope-tagged" in the form of a fusion protein that includes, in addition to the polypeptide sequence, a second polypeptide for which antibodies are readily available (e.g. from commercial sources). For instance, the GST fusion proteins described above may also be used for quantification of binding using antibodies against the GST moiety. Other useful epitope tags include myc-epitopes (e.g., see Ellison et al. (1991) J Biol Chem 266:21150-21157) which includes a 10-residue sequence from c-myc, as well as the pFLAG system (International Biotechnologies, Inc.) or the pEZZ-protein A system (Pharmacia, N.J.).

In certain in vitro embodiments of the present assay, the protein or the set of proteins engaged in a protein-protein, protein-substrate, or protein-nucleic acid interaction comprises a reconstituted protein mixture of at least semi-purified proteins. By semi-purified, it is meant that the proteins utilized in the reconstituted mixture have been previously separated from other cellular or viral proteins. For instance, in contrast to cell lysates, the proteins involved in a protein-substrate, protein-protein or nucleic acid-protein interaction are present in the mixture to at least 50% purity relative to all other proteins in the mixture, and more preferably are present at 90-95% purity. In certain embodiments of the subject method, the reconstituted protein mixture is derived by mixing highly purified proteins such that the reconstituted mixture substantially lacks other proteins (such as of cellular or viral origin) which might interfere with or otherwise alter the ability to measure activity resulting from the given protein-substrate, protein-protein interaction, or nucleic acid-protein interaction.

In one embodiment, the use of reconstituted protein mixtures allows more careful control of the protein-substrate, protein-protein, or nucleic acid-protein interaction conditions. Moreover, the system may be derived to favor discovery of modulators of particular intermediate states of the protein-protein interaction. For instance, a reconstituted protein assay may be carried out both in the presence and absence of a candidate agent, thereby allowing detection of a modulator of a given protein-substrate, protein-protein, or nucleic acid-protein interaction.

Assaying biological activity resulting from a given protein-substrate, protein-protein or nucleic acid-protein interaction, in the presence and absence of a candidate modulator, may be accomplished in any vessel suitable for containing the reactants. Examples include microtitre plates, test tubes, and micro-centrifuge tubes.

In yet another embodiment, a Slit2 polypeptide may be used to generate a two-hybrid or interaction trap assay (see also, U.S. Pat. No. 5,283,317; Zervos et al. (1993) Cell 72:223-232; Madura et al. (1993) J. Biol Chem 268:12046-12054; Bartel et al. (1993) Biotechniques 14:920-924; and Iwabuchi et al. (1993) Oncogene 8:1693-1696), for subsequently detecting agents which disrupt binding of the interaction components to one another.

In particular, the method makes use of chimeric genes which express hybrid proteins. To illustrate, a first hybrid gene comprises the coding sequence for a binding domain of a transcriptional activator may be fused in frame to the coding sequence for a "bait" protein, e.g., a Slit2 polypeptide of sufficient length to bind to a potential interacting protein. The second hybrid protein encodes a transcriptional activation domain fused in frame to a gene encoding a "fish" protein, e.g., a potential interacting protein of sufficient length to interact with the protein-protein interaction component polypeptide portion of the bait fusion protein. If the bait and fish proteins are able to interact, e.g., form a protein-protein interaction component complex, they bring into close proximity the two domains of the transcriptional activator. This proximity causes transcription of a reporter gene which is operably linked to a transcriptional regulatory site responsive to the transcriptional activator, and expression of the reporter gene may be detected and used to score for the interaction of the bait and fish proteins. The host cell also contains a first chimeric gene which is capable of being expressed in the host cell. The gene encodes a chimeric protein, which comprises (a) a binding domain that recognizes the responsive element on the reporter gene in the host cell, and (b) a bait protein (e.g., a Slit2 polypeptide). A second chimeric gene is also provided which is capable of being expressed in the host cell, and encodes the "fish" fusion protein. In one embodiment, both the first and the second chimeric genes are introduced into the host cell in the form of plasmids. Preferably, however, the first chimeric gene is present in a chromosome of the host cell and the second chimeric gene is introduced into the host cell as part of a plasmid.

The binding domain of the first hybrid protein and the transcriptional activation domain of the second hybrid protein may be derived from transcriptional activators having separable binding and transcriptional activation domains. For instance, these separate binding and transcriptional activation domains are known to be found in the yeast GAL4 protein, and are known to be found in the yeast GCN4 and ADR1 proteins. Many other proteins involved in transcription also have separable binding and transcriptional activation domains which make them useful for the present invention, and include, for example, the LexA and VP16 proteins. It will be understood that other (substantially) transcriptionally-inert binding domains may be used in the subject constructs; such as domains of ACE1, λcI, lac repressor, jun or fos. In another embodiment, the binding domain and the transcriptional activation domain may be from different proteins. The use of a LexA DNA binding domain provides certain advantages. For example, in yeast, the LexA moiety contains no activation function and has no known affect on transcription of yeast genes. In addition, use of LexA allows control over the sensitivity of the assay to the level of interaction (see, for example, the Brent et al. PCT publication WO94/10300).

In certain embodiments, any enzymatic activity associated with the bait or fish proteins is inactivated, e.g., dominant negative or other mutants of a protein-protein interaction component can be used.

Continuing with the illustrative example, formation of a complex between the bait and fish fusion proteins in the host cell, causes the activation domain to activate transcription of the reporter gene. The method is carried out by introducing the first chimeric gene and the second chimeric gene into the host cell, and subjecting that cell to conditions under which the bait and fish fusion proteins and are expressed in sufficient quantity for the reporter gene to be activated. The formation of a complex results in a detectable signal produced by the expression of the reporter gene.

In still further embodiments, the Slit2 polypeptide, or complex polypeptide, of interest may be generated in whole cells, taking advantage of cell culture techniques to support the subject assay. For example, the Slit2 polypeptide, or complex polypeptide, may be constituted in a prokaryotic or eukaryotic cell culture system. Advantages to generating the Slit2 polypeptide, or complex polypeptide, in an intact cell includes the ability to screen for modulators of the level and/or activity of the Slit2 polypeptide, or complex polypeptide, which are functional in an environment more closely approximating that which therapeutic use of the modulator would require, including the ability of the agent to gain entry into the cell. Furthermore, certain of the in vivo embodiments of the assay are amenable to high through-put analysis of candidate agents.

The Slit2 nucleic acids and/or polypeptide can be endogenous to the cell selected to support the assay. Alternatively, some or all of the components can be derived from exogenous sources. For instance, fusion proteins can be introduced into the cell by recombinant techniques (such as through the use of an expression vector), as well as by microinjecting the fusion protein itself or mRNA encoding the fusion protein. Moreover, in the whole cell embodiments of the subject assay, the reporter gene construct can provide, upon expression, a selectable marker. Such embodiments of the subject assay are particularly amenable to high through-put analysis in that proliferation of the cell can provide a simple measure of the protein-protein interaction.

The amount of transcription from the reporter gene may be measured using any method known to those of skill in the art to be suitable. For example, specific mRNA expression may be detected using Northern blots or specific protein product may be identified by a characteristic stain, western blots or an intrinsic activity. In certain embodiments, the product of the reporter gene is detected by an intrinsic activity associated with that product. For instance, the reporter gene may encode a gene product that, by enzymatic activity, gives rise to a detection signal based on color, fluorescence, or luminescence.

In many drug screening programs which test libraries of compounds and natural extracts, high throughput assays are desirable in order to maximize the number of compounds surveyed in a given period of time. Assays of the present invention which are performed in cell-free systems, such as may be derived with purified or semi-purified proteins or with lysates, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins or changes in enzymatic properties of the molecular target. Accordingly, potential modulators of Slit2 may be detected in a cell-free assay generated by constitution of a functional Slit2 in a cell lysate. In an alternate format, the assay can be derived as a reconstituted protein mixture which, as described below, offers a number of benefits over lysate-based assays.

The activity of a Slit2 or a Slit2 polypeptide may be identified and/or assayed using a variety of methods well known to the skilled artisan. For example, the activity of a Slit2 nucleic acid and/or polypeptide may be determined by assaying for the level of expression of RNA and/or protein molecules. Transcription levels may be determined, for example, using Northern blots, hybridization to an oligonucleotide array or by assaying for the level of a resulting protein product. Translation levels may be determined, for example, using Western blotting or by identifying a detectable signal produced by a protein product (e.g., fluorescence, luminescence, enzymatic activity, etc.). Depending on the particular situation, it may be desirable to detect the level of transcription and/or translation of a single gene or of multiple genes.

In other embodiments, the biological activity of a Slit2 nucleic acid and/or polypeptide may be assessed by monitoring changes in the phenotype of a targeted cell. For example, the detection means can include a reporter gene construct which includes a transcriptional regulatory element that is dependent in some form on the level and/or activity of a Slit2 nucleic acid and/or polypeptide. The Slit2 nucleic acid and/or polypeptide may be provided as a fusion protein with a domain that binds to a DNA element of a reporter gene construct. The added domain of the fusion protein can be one which, through its binding ability, increases or decreases transcription of the reporter gene. Whichever the case may be, its presence in the fusion protein renders it responsive to a Slit2 nucleic acid and/or polypeptide. Accordingly, the level of expression of the reporter gene will vary with the level of expression of a Slit2 nucleic acid and/or polypeptide.

Moreover, in the whole cell embodiments of the subject assay, the reporter gene construct can provide, upon expression, a selectable marker. A reporter gene includes any gene that expresses a detectable gene product, which may be RNA or protein. Preferred reporter genes are those that are readily detectable. The reporter gene may also be included in the construct in the form of a fusion gene with a gene that includes desired transcriptional regulatory sequences or exhibits other desirable properties. For instance, the product of the reporter gene can be an enzyme which confers resistance to an antibiotic or other drug, or an enzyme which complements a deficiency in the host cell (i.e. thymidine kinase or dihydrofolate reductase). To illustrate, the aminoglycoside phosphotransferase encoded by the bacterial transposon gene Tn5 neo can be placed under transcriptional control of a promoter element responsive to the level of a Slit2 nucleic acid and/or polypeptide present in the cell. Such embodiments of the subject assay are particularly amenable to high through-put analysis in that proliferation of the cell can provide a simple measure of inhibition of the Slit2 nucleic acid and/or polypeptide.

Similarly, individual cells or analyses of phenotypes in organisms can be formed to determine effects of test agents on the modulation (e.g., upregulation) of one or more of the following Slit2-mediated biological activities: a) brown fat and/or beige fat gene expression, such as expression of a marker selected from the group consisting of: cidea, adiponectin, adipsin, otopetrin, type II deiodinase, cig30, ppar gamma 2, pgc1α, ucp1, elovl3, cAMP, Prdml6, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, dio2, fatty acid synthase (fas), leptin, resistin, and nuclear respiratory factor-1 (nrf1); b) thermogenesis in adipose cells; c) differentiation of adipose cells; d) insulin sensitivity of adipose cells; e) basal respiration or uncoupled respiration; f) whole body oxygen consumption; g) obesity or appetite; h) insulin secretion of pancreatic beta cells; i) glucose tolerance; j) modified phosphorylation of EGFR, ERK, AMPK, protein kinase A (PKA) substrates having an RRX(S/T) (SEQ ID NO: 127) motif, wherein the X is any amino acid and the (S/T) residue is a serine or threonine, HSL; k) modified expression of UCP1 protein; and 1) growth and effects of metabolic disorders, such as obesity-associated cancer, cachexia, anorexia, diabetes, and obesity.

V. Methods of the Invention

One aspect of the present invention relates to methods of selecting agents (e.g., antibodies, fusion constructs, peptides, small molecules, and small nucleic acids) which bind to, upregulate, downregulate, or modulate one or more biomarkers of the present invention listed in Table 1, the Figures, and the Examples, and/or a metabolic disorder. Such methods can use screening assays, including cell-based and non-cell based assays.

In one embodiment, the invention relates to assays for screening candidate or test compounds which bind to or modulate the expression or activity level of, one or more biomarkers of the present invention, including one or more biomarkers listed in Table 1, the Figures, and the Examples, or a fragment or ortholog thereof. Such compounds include, without limitation, antibodies, proteins, fusion proteins, nucleic acid molecules, and small molecules.

In one embodiment, an assay is a cell-based assay, comprising contacting a cell expressing one or more biomarkers of the present invention, including one or more biomarkers listed in Table 1, the Figures, and the Examples, or a fragment thereof, with a test compound and determining the ability of the test compound to modulate (e.g., stimulate or inhibit) the level of interaction between the biomarker and its natural binding partners as measured by direct binding or by measuring a parameter of cancer.

For example, in a direct binding assay, the biomarker polypeptide, a binding partner polypeptide of the biomarker, or a fragment(s) thereof, can be coupled with a radioisotope or enzymatic label such that binding of the biomarker polypeptide or a fragment thereof to its natural binding partner(s) or a fragment(s) thereof can be determined by detecting the labeled molecule in a complex. For example, the biomarker polypeptide, a binding partner polypeptide of the biomarker, or a fragment(s) thereof, can be labeled with $^{125}I$ $^{35}S$, $^{14}C$, or $^{3}H$, either directly or indirectly, and the radioisotope detected by direct counting of radioemmission or by scintillation counting. Alternatively, the polypeptides of interest a can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound to modulate the interactions between one or more biomarkers of the present invention, including one or more biomarkers listed in Table 1, the Figures, and the Examples, or a fragment thereof, and its natural binding partner(s) or a fragment(s) thereof, without the labeling of any of the interactants (e.g., using a microphysiometer as described in McConnell, H. M. et al. (1992) *Science* 257:1906-1912). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between compound and receptor.

In a preferred embodiment, determining the ability of the blocking agents (e.g., antibodies, fusion proteins, peptides, nucleic acid molecules, or small molecules) to antagonize the interaction between a given set of nucleic acid molecules and/or polypeptides can be accomplished by determining the activity of one or more members of the set of interacting molecules. For example, the activity of one or more biomarkers of the present invention, including one or more biomarkers listed in Table 1, the Figures, and the Examples, or a fragment thereof, can be determined by detecting induction of cytokine or chemokine response, detecting catalytic/enzymatic activity of an appropriate substrate, detecting the induction of a reporter gene (comprising a target-responsive regulatory element operatively linked to a nucleic acid encoding a detectable marker, e.g., chloramphenicol acetyl transferase), or detecting a cellular response regulated by the biomarker or a fragment thereof (e.g., modulations of biological pathways identified herein, such as modulated proliferation, apoptosis, cell cycle, and/or ligand-receptor binding activity). Determining the ability of the blocking agent to bind to or interact with said polypeptide can be accomplished by measuring the ability of an agent to modulate immune responses, for example, by detecting changes in type and amount of cytokine secretion, changes in apoptosis or proliferation, changes in gene expression or activity associated with cellular identity, or by interfering with the ability of said polypeptide to bind to antibodies that recognize a portion thereof.

In yet another embodiment, an assay of the present invention is a cell-free assay in which one or more biomarkers of the present invention, including one or more biomarkers listed in Table 1, the Figures, and the Examples, or a fragment thereof, e.g., a biologically active fragment thereof, is contacted with a test compound, and the ability of the test compound to bind to the polypeptide, or biologically active portion thereof, is determined. Binding of the test compound to the biomarker or a fragment thereof, can be determined either directly or indirectly as described above. Determining the ability of the biomarker or a fragment thereof to bind to its natural binding partner(s) or a fragment(s) thereof can also be accomplished using a technology such as real-time Biomolecular Interaction Analysis (BIA) (Sjolander, S. and Urbaniczky, C. (1991) *Anal. Chem.* 63:2338-2345 and Szabo et al. (1995) *Curr. Opin. Struct. Biol.* 5:699-705). As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological polypeptides. One or more biomarkers polypeptide or a fragment thereof can be immobilized on a BIAcore chip and multiple agents, e.g., blocking antibodies, fusion proteins, peptides, or small molecules, can be tested for binding to the immobilized biomarker polypeptide or fragment thereof. An example of using the BIA technology is described by Fitz et al. (1997) Oncogene 15:613.

The cell-free assays of the present invention are amenable to use of both soluble and/or membrane-bound forms of proteins. In the case of cell-free assays in which a membrane-bound form protein is used it may be desirable to utilize a solubilizing agent such that the membrane-bound form of the protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)n, 3-[(3-cholamidopropyl) dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In one or more embodiments of the above described assay methods, it may be desirable to immobilize either the biomarker nucleic acid and/or polypeptide, the natural binding partner(s) of the biomarker, or fragments thereof, to facilitate separation of complexed from uncomplexed forms of the reactants, as well as to accommodate automation of the assay. Binding of a test compound in the assay can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase-base fusion proteins, can be adsorbed onto glutathione Sepharose® beads (Sigma Chemical, St. Louis, MO) or glutathione derivatized microtiter plates, which are then combined with the test compound, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of binding or activity determined using standard techniques.

In an alternative embodiment, determining the ability of the test compound to modulate the activity of one or more biomarkers of the present invention, including one or more biomarkers listed in Table 1, the Figures, and the Examples, or a fragment thereof, or of natural binding partner(s) thereof can be accomplished by determining the ability of the test compound to modulate the expression or activity of a gene, e.g., nucleic acid, or gene product, e.g., polypeptide, that functions downstream of the interaction. For example, cellular migration or invasion can be determined by monitoring cellular movement, matrigel assays, induction of invasion-related gene expression, and the like, as described further herein.

In another embodiment, modulators of one or more biomarkers of the present invention, including one or more biomarkers listed in Table 1, the Figures, and the Examples, or a fragment thereof, are identified in a method wherein a cell is contacted with a candidate compound and the expression or activity level of the biomarker is determined. The level of expression of biomarker RNA or polypeptide or fragments thereof in the presence of the candidate compound is compared to the level of expression of biomarker RNA or polypeptide or fragments thereof in the absence of the candidate compound. The candidate compound can then be identified as a modulator of biomarker expression based on this comparison. For example, when expression of biomarker RNA or polypeptide or fragments thereof is greater (statistically significantly greater) in the presence of the candidate compound than in its absence, the candidate compound is identified as a stimulator of biomarker expression. Alternatively, when expression of biomarker RNA or polypeptide or fragments thereof is reduced (statistically significantly less) in the presence of the candidate compound than in its absence, the candidate compound is identified as an inhibitor of biomarker expression. The expression level of biomarker RNA or polypeptide or fragments thereof in the cells can be determined by methods described herein for detecting biomarker mRNA or polypeptide or fragments thereof.

In yet another aspect of the present invention, a biomarker of the present invention, including one or more biomarkers listed in Table 1, the Figures, and the Examples, or a fragment thereof, can be used as "bait" in a two-hybrid assay or three-hybrid assay (see, e.g., U.S. Pat. No. 5,283,317; Zervos et al. (1993) Cell 72:223-232; Madura et al. (1993) J. Biol. Chem. 268:12046-12054; Bartel et al. (1993) Biotechniques 14:920-924; Iwabuchi et al. (1993) Oncogene 8:1693-1696; and Brent WO94/10300), to identify other nucleic acids and/or polypeptides which bind to or interact with the biomarker or fragments thereof and are involved in activity of the biomarkers. Such biomarker-binding proteins are also likely to be involved in the propagation of signals by the biomarker polypeptides or biomarker natural binding partner(s) as, for example, downstream elements of one or more biomarkers-mediated signaling pathway.

The two-hybrid system is based on the modular nature of most transcription factors, which consist of separable DNA-binding and activation domains. Briefly, the assay utilizes two different DNA constructs. In one construct, the gene that codes for one or more biomarkers polypeptide is fused to a gene encoding the DNA binding domain of a known transcription factor (e.g., GAL-4). In the other construct, a DNA sequence, from a library of DNA sequences, that encodes an unidentified polypeptide ("prey" or "sample") is fused to a gene that codes for the activation domain of the known transcription factor. If the "bait" and the "prey" polypeptides are able to interact, in vivo, forming one or more biomarkers-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the polypeptide which interacts with one or more biomarkers polypeptide of the present invention, including one or more biomarkers listed in Table 1, the Figures, and the Examples, or a fragment thereof.

In another aspect, the invention pertains to a combination of two or more of the assays described herein. For example, a modulating agent can be identified using a cell-based or a cell-free assay, and the ability of the agent to modulate the activity of one or more biomarkers polypeptide or a fragment thereof can be confirmed in vivo, e.g., in an animal such as an animal model for cellular transformation and/or tumorigenesis.

This invention further pertains to novel agents identified by the above-described screening assays. Accordingly, it is within the scope of this invention to further use an agent identified as described herein in an appropriate animal model. For example, an agent identified as described herein can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

In other aspects of the present invention, the biomarkers described herein, including the biomarkers listed in Table 1, the Figures, and the Examples, or fragments thereof, can be used in one or more of the following methods: a) screening assays; b) predictive medicine (e.g., diagnostic assays, prognostic assays, and monitoring of clinical trials); and c) methods of treatment (e.g., therapeutic and prophylactic, e.g., by up- or down-modulating the copy number, level of expression, and/or level of activity of the one or more biomarkers).

The biomarkers described herein or agents that modulate the expression and/or activity of such biomarkers can be used, for example, to (a) express one or more biomarkers of the present invention, including one or more biomarkers listed in Table 1, the Figures, and the Examples, or a fragment thereof (e.g., via a recombinant expression vector in a host cell in gene therapy applications or synthetic nucleic acid molecule), (b) detect biomarker RNA or a fragment thereof (e.g., in a biological sample) or a genetic alteration in one or more biomarkers gene, and/or (c) modulate biomarker activity, as described further below. The biomarkers or modulatory agents thereof can be used to treat conditions or disorders characterized by insufficient or excessive production of one or more biomarkers polypeptide or fragment thereof or production of biomarker polypeptide inhibitors. In addition, the biomarker polypeptides or fragments thereof can be used to screen for naturally occurring biomarker binding partner(s), to screen for drugs or compounds which modulate biomarker activity, as well as to treat conditions or disorders characterized by insufficient or excessive production of biomarker polypeptide or a fragment thereof or production of biomarker polypeptide forms which have decreased, aberrant or unwanted activity compared to biomarker wild-type polypeptides or fragments thereof (e.g., melanoma).

A. Screening Assays

In one aspect, the present invention relates to a method for preventing in a subject, a disease or condition associated with an unwanted, more than desirable, or less than desirable, expression and/or activity of one or more biomarkers described herein. Subjects at risk for a disease that would benefit from treatment with the claimed agents or methods can be identified, for example, by any one or combination of diagnostic or prognostic assays known in the art and described herein (see, for example, agents and assays described above in the section describing methods of selecting agents and compositions).

B. Predictive Medicine

The present invention also pertains to the field of predictive medicine in which diagnostic assays, prognostic assays, and monitoring of clinical trials are used for prognostic (predictive) purposes to thereby treat an individual prophylactically. Accordingly, one aspect of the present invention relates to diagnostic assays for determining the expression and/or activity level of biomarkers of the present invention, including biomarkers listed in Table 1, the Figures, and the Examples, or fragments thereof, in the context of a biological sample (e.g., blood, serum, cells, or tissue) to thereby determine whether an individual is afflicted with a disease or disorder, or is at risk of developing a disorder, associated with aberrant or unwanted biomarker expression or activity. The present invention also provides for prognostic (or predictive) assays for determining whether an individual is at risk of developing a disorder associated with biomarker polypeptide, nucleic acid expression or activity. For example, mutations in one or more biomarkers gene can be assayed in a biological sample.

Such assays can be used for prognostic or predictive purpose to thereby prophylactically treat an individual prior to the onset of a disorder characterized by or associated with biomarker polypeptide, nucleic acid expression or activity. For example, Slit2 expression and activity is associated with increased thermogenesis and metabolism such that overexpression of Slit2 predicts treatment of metabolic disorders, either alone or in combination with additional agents, including nuclear receptor inhibitors.

Another aspect of the present invention pertains to monitoring the influence of agents (e.g., drugs, compounds, and small nucleic acid-based molecules) on the expression or activity of biomarkers of the present invention, including biomarkers listed in Table 1, the Figures, and the Examples, or fragments thereof, in clinical trials. These and other agents are described in further detail in the following sections.

The term "altered amount" of a marker or "altered level" of a marker refers to increased or decreased copy number of the marker and/or increased or decreased expression level of a particular marker gene or genes in a cancer sample, as compared to the expression level or copy number of the marker in a control sample. The term "altered amount" of a marker also includes an increased or decreased protein level of a marker in a sample, e.g., a cancer sample, as compared to the protein level of the marker in a normal, control sample.

The "amount" of a marker, e.g., expression or copy number of a marker, or protein level of a marker, in a subject is "significantly" higher or lower than the normal amount of a marker, if the amount of the marker is greater or less, respectively, than the normal level by an amount greater than the standard error of the assay employed to assess amount, and preferably at least twice, and more preferably three, four, five, ten or more times that amount. Alternately, the amount of the marker in the subject can be considered "significantly" higher or lower than the normal amount if the amount is at least about two, and preferably at least about three, four, or five times, higher or lower, respectively, than the normal amount of the marker. In some embodiments, the amount of the marker in the subject can be considered "significantly" higher or lower than the normal amount if the amount is 10%, 15%, 20%, 25%, 30%, 35%, 40%, 45%, 50% or more, higher or lower, respectively, than the normal amount of the marker.

The term "altered level of expression" of a marker refers to an expression level or copy number of a marker in a test sample e.g., a sample derived from a subject suffering from cancer, that is greater or less than the standard error of the assay employed to assess expression or copy number, and is preferably at least twice, and more preferably three, four, five or ten or more times the expression level or copy number of the marker or chromosomal region in a control sample (e.g., sample from a healthy subject not having the associated disease) and preferably, the average expression level or copy number of the marker or chromosomal region in several control samples. The altered level of expression is greater or less than the standard error of the assay employed to assess expression or copy number, and is preferably at least twice, and more preferably three, four, five or ten or more times the expression level or copy number of the marker in a control sample (e.g., sample from a healthy subject not having the associated disease) and preferably, the average expression level or copy number of the marker in several control samples.

The term "altered activity" of a marker refers to an activity of a marker which is increased or decreased in a disease state, e.g., in a cancer sample, as compared to the activity of the marker in a normal, control sample. Altered activity of a marker may be the result of, for example, altered expression of the marker, altered protein level of the marker, altered structure of the marker, or, e.g., an altered interaction with other proteins involved in the same or different pathway as the marker, or altered interaction with transcriptional activators or inhibitors.

The term "altered structure" of a marker refers to the presence of mutations or allelic variants within the marker gene or maker protein, e.g., mutations which affect expression or activity of the marker, as compared to the normal or wild-type gene or protein. For example, mutations include, but are not limited to substitutions, deletions, or addition mutations. Mutations may be present in the coding or non-coding region of the marker.

The term "altered cellular localization" of a marker refers to the mislocalization of the marker within a cell relative to the normal localization within the cell e.g., within a healthy and/or wild-type cell. An indication of normal localization of the marker can be determined through an analysis of cellular localization motifs known in the field that are harbored by marker polypeptides. For example, SLNCR is a nuclear transcription factor coordinator and naturally functions to present combinations of nuclear transcription factors within the nucleus such that function is abrogated if nuclear import and/or export is inhibited.

The term "body fluid" refers to fluids that are excreted or secreted from the body as well as fluids that are normally not (e.g., amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, peritoneal fluid, pus, saliva, sebum, semen, serum, sweat, synovial fluid, tears, urine, vaginal lubrication, vitreous humor, vomit). In a preferred embodiment, body fluids are restricted to blood-related fluids, including whole blood, serum, plasma, and the like.

The term "classifying" includes "to associate" or "to categorize" a sample with a disease state. In certain instances, "classifying" is based on statistical evidence, empirical evidence, or both. In certain embodiments, the methods and systems of classifying use of a so-called training set of samples having known disease states. Once established, the training data set serves as a basis, model, or template against which the features of an unknown sample are compared, in order to classify the unknown disease state of the sample. In certain instances, classifying the sample is akin to diagnosing the disease state of the sample. In certain other instances, classifying the sample is akin to differentiating the disease state of the sample from another disease state.

The term "control" refers to any reference standard suitable to provide a comparison to the expression products in the test sample. In one embodiment, the control comprises obtaining a "control sample" from which expression product levels are detected and compared to the expression product levels from the test sample. Such a control sample may comprise any suitable sample, including but not limited to a sample from a control patient (can be stored sample or previous sample measurement) with a known outcome; normal tissue or cells isolated from a subject, such as a normal patient or the patient in need of metabolism modulation, cultured primary cells/tissues isolated from a subject such as a normal subject or the patient in need of metabolism modulation, adjacent normal cells/tissues obtained from the same organ or body location of the patient in need of metabolism modulation, a tissue or cell sample isolated from a normal subject, or a primary cells/tissues obtained from a depository. In another preferred embodiment, the control may comprise a reference standard expression product level from any suitable source, including but not limited to housekeeping genes, an expression product level range from normal tissue (or other previously analyzed control sample), a previously determined expression product level range within a test sample from a group of patients, or a set of patients with a certain outcome (for example, survival for one, two, three, four years, etc.) or receiving a certain treatment. It will be understood by those of skill in the art that such control samples and reference standard expression product levels can be used in combination as controls in the methods of the present invention. In one embodiment, the control may comprise normal or non-cancerous cell/tissue sample. In another preferred embodiment, the control may comprise an expression level for a set of patients, such as a set of cancer patients, or for a set of cancer patients receiving a certain treatment, or for a set of patients with one outcome versus another outcome. In the former case, the specific expression product level of each patient can be assigned to a percentile level of expression, or expressed as either higher or lower than the mean or average of the reference standard expression level. In another preferred embodiment, the control may comprise normal cells, cells from patients treated with a therapeutic and cells from patients having modulated metabolism. In another embodiment, the control may also comprise a measured value for example, average level of expression of a particular gene in a population compared to the level of expression of a housekeeping gene in the same population. Such a population may comprise normal subjects, cancer patients who have not undergone any treatment (i.e., treatment naive), cancer patients undergoing therapy, or patients having benign cancer. In another preferred embodiment, the control comprises a ratio transformation of expression product levels, including but not limited to determining a ratio of expression product levels of two genes in the test sample and comparing it to any suitable ratio of the same two genes in a reference standard; determining expression product levels of the two or more genes in the test sample and determining a difference in expression product levels in any suitable control; and determining expression product levels of the two or more genes in the test sample, normalizing their expression to expression of housekeeping genes in the test sample, and comparing to any suitable control. In particularly preferred embodiments, the control comprises a control sample which is of the same lineage and/or type as the test sample. In another embodiment, the control may comprise expression product levels grouped as percentiles within or based on a set of patient samples, such as all patients with cancer. In one embodiment a control expression product level is established wherein higher or lower levels of expression product relative to, for instance, a particular percentile, are used as the basis for predicting outcome. In another preferred embodiment, a control expression product level is established using expression product levels from cancer control patients with a known outcome, and the expression product levels from the test sample are compared to the control expression product level as the basis for predicting outcome. As demonstrated by the data below, the methods of the present invention are not limited to use of a specific cut-point in comparing the level of expression product in the test sample to the control.

The term "pre-determined" biomarker amount and/or activity measurement(s) may be a biomarker amount and/or activity measurement(s) used to, by way of example only, evaluate a subject that may be selected for a particular treatment, evaluate a response to a treatment such as an anti-immune checkpoint inhibitor therapy, and/or evaluate the disease state. A pre-determined biomarker amount and/or activity measurement(s) may be determined in populations of patients with or without cancer. The pre-determined biomarker amount and/or activity measurement(s) can be a single number, equally applicable to every patient, or the pre-determined biomarker amount and/or activity measurement(s) can vary according to specific subpopulations of patients. Age, weight, height, and other factors of a subject may affect the pre-determined biomarker amount and/or activity measurement(s) of the individual. Furthermore, the pre-determined biomarker amount and/or activity can be determined for each subject individually. In one embodiment, the amounts determined and/or compared in a method described herein are based on absolute measurements. In another embodiment, the amounts determined and/or compared in a method described herein are based on relative measurements, such as ratios (e.g., serum biomarker normalized to the expression of a housekeeping or otherwise generally constant biomarker). The pre-determined biomarker amount and/or activity measurement(s) can be any suitable standard. For example, the pre-determined biomarker amount and/or activity measurement(s) can be obtained from the same or a different human for whom a patient selection is being assessed. In one embodiment, the pre-determined biomarker amount and/or activity measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group.

Outcome measures, such as overall survival, increased thermogenesis, and weight loss can be monitored over a period of time for subjects following therapy for whom the measurement values are known. In certain embodiments, the same doses of therapeutic agents are administered to each subject. In related embodiments, the doses administered are standard doses known in the art for therapeutic agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months or longer. Biomarker threshold values that correlate to outcome of a therapy can be determined using methods such as those described in the Examples section. Outcomes can also be measured in terms of a "hazard ratio" (the ratio of death rates for one patient group to another; provides likelihood of death at a certain time point), "overall survival" (OS), and/or "progression free survival." In certain embodiments, the prognosis comprises likelihood of overall survival rate at 1 year, 2 years, 3 years, 4 years, or any other suitable time point. The significance associated with the prognosis of poor outcome in all aspects of the present invention is measured by techniques known in the art. For example, significance may be measured with calculation of odds ratio. In a further embodiment, the significance is measured by a percentage. In one embodiment, a significant risk of poor outcome is measured as odds ratio of 0.8 or less or at least about 1.2, including by not limited to: 0.1, 0.2, 0.3, 0.4, 0.5, 0.6, 0.7, 0.8, 1.2, 1.3, 1.4, 1.5, 1.6, 1.7, 1.8, 1.9, 2.0, 2.5, 3.0, 4.0, 5.0, 10.0, 15.0, 20.0, 25.0, 30.0 and 40.0. In a further embodiment, a significant increase or reduction in risk is at least about 20%, including but not limited to about 25%, 30%, 35%, 40%, 45%, 50%, 55%, 60%, 65%, 70%, 75%, 80%, 85%, 90%, 95% and 98%. In a further embodiment, a significant increase in risk is at least about 50%. Thus, the present invention further provides methods for making a treatment decision for a patient in need of modulated metabolism, comprising carrying out the methods for prognosing a patient according to the different aspects and embodiments of the present invention, and then weighing the results in light of other known clinical and pathological risk factors, in determining a course of treatment for the patient in need of modulated metabolism.

A "kit" is any manufacture (e.g., a package or container) comprising at least one reagent, e.g., a probe, for specifically detecting or modulating the expression of a marker of the present invention. The kit may be promoted, distributed, or sold as a unit for performing the methods of the present invention. Kits comprising compositions described herein are encompassed within the present invention.

1. Diagnostic Assays

The present invention provides, in part, methods, systems, and code for accurately classifying whether a biological sample is associated with a melanoma or a clinical subtype thereof. In some embodiments, the present invention is useful for classifying a sample (e.g., from a subject) as a sample that will respond to metabolic intervention using a statistical algorithm and/or empirical data (e.g., the presence or level of one or biomarkers described herein).

An exemplary method for detecting the level of expression or activity of one or more biomarkers of the present invention, including one or more biomarkers listed in Table 1, the Figures, and the Examples, or fragments thereof, and thus useful for classifying whether a sample is associated with melanoma or a clinical subtype thereof, involves obtaining a biological sample from a test subject and contacting the biological sample with a compound or an agent capable of detecting the biomarker (e.g., polypeptide or nucleic acid that encodes the biomarker or fragments thereof) such that the level of expression or activity of the biomarker is detected in the biological sample. In some embodiments, the presence or level of at least one, two, three, four, five, six, seven, eight, nine, ten, fifty, hundred, or more biomarkers of the present invention are determined in the individual's sample. In certain instances, the statistical algorithm is a single learning statistical classifier system. Exemplary statistical analyses are presented in the Examples and can be used in certain embodiments. In other embodiments, a single learning statistical classifier system can be used to classify a sample as a cancer sample, a cancer subtype sample, or a non-cancer sample based upon a prediction or probability value and the presence or level of one or more biomarkers described herein. The use of a single learning statistical classifier system typically classifies the sample as a cancer sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Other suitable statistical algorithms are well known to those of skill in the art. For example, learning statistical classifier systems include a machine learning algorithmic technique capable of adapting to complex data sets (e.g., panel of markers of interest) and making decisions based upon such data sets. In some embodiments, a single learning statistical classifier system such as a classification tree (e.g., random forest) is used. In other embodiments, a combination of 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (C&RT), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naive learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ). In certain embodiments, the method of the present invention further comprises sending the cancer classification results to a clinician, e.g., an oncologist or hematologist.

In another embodiment, the method of the present invention further provides a diagnosis in the form of a probability that the individual has a cancer, such as melanoma, or a clinical subtype thereof. For example, the individual can have about a 0%, 5%, 10%, 15%, 20%, 25%, 30%, 35%, 40%, 45%, 50%, 55%, 60%, 65%, 70%, 75%, 80%, 85%, 90%, 95%, or greater probability of having cancer or a clinical subtype thereof. In yet another embodiment, the method of the present invention further provides a prognosis of cancer in the individual. For example, the prognosis can be surgery, development of melanoma or a clinical subtype thereof, development of one or more symptoms, development of malignant cancer, or recovery from the disease. In some instances, the method of classifying a sample as a cancer sample is further based on the symptoms (e.g., clinical factors) of the individual from which the sample is obtained. The symptoms or group of symptoms can be, for example, those associated with the IPI. In some embodiments, the diagnosis of an individual as having melanoma or a clinical subtype thereof is followed by administering to the individual a therapeutically effective amount of a drug useful for treating one or more symptoms associated with melanoma or a clinical subtype thereof.

In some embodiments, an agent for detecting biomarker RNA, genomic DNA, or fragments thereof is a labeled nucleic acid probe capable of hybridizing to biomarker RNA, genomic DNA, or fragments thereof. The nucleic acid probe can be, for example, full-length biomarker nucleic acid, or a portion thereof, such as an oligonucleotide of at least 15, 30, 50, 100, 250 or 500 nucleotides in length and sufficient to specifically hybridize under stringent conditions well known to a skilled artisan to biomarker mRNA or genomic DNA. Other suitable probes for use in the diagnostic assays of the present invention are described herein. In some embodiments, the nucleic acid probe is designed to detect transcript variants (i.e., different splice forms) of a gene.

A preferred agent for detecting Slit2 bioimarkers in complex with biomarker proteins is an antibody capable of binding to the biomarker, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells, and biological fluids isolated from a subject, as well as tissues, cells, and fluids present within a subject. That is, the detection method of the present invention can be used to detect biomarker mRNA, polypeptide, genomic DNA, or fragments thereof, in a biological sample in vitro as well as in vivo. For example, in vitro techniques for detection of biomarker mRNA or a fragment thereof include Northern hybridizations and in situ hybridizations. In vitro techniques for detection of biomarker polypeptide include enzyme linked immunosorbent assays (ELISAs), Western blots, immunoprecipitations and immunofluorescence. In vitro techniques for detection of biomarker genomic DNA or a fragment thereof include Southern hybridizations. Furthermore, in vivo techniques for detection of one or more biomarkers polypeptide or a fragment thereof include introducing into a subject a labeled anti-biomarker antibody. For example, the antibody can be labeled with a radioactive marker whose presence and location in a subject can be detected by standard imaging techniques.

In one embodiment, the biological sample contains polypeptide molecules from the test subject. Alternatively, the biological sample can contain RNA molecules from the test subject or genomic DNA molecules from the test subject. A preferred biological sample is a hematological tissue (e.g., a sample comprising blood, plasma, B cell, bone marrow, etc.) sample isolated by conventional means from a subject.

In another embodiment, the methods further involve obtaining a control biological sample from a control subject, contacting the control sample with a compound or agent capable of detecting polypeptide, RNA, cDNA, small RNAs, mature miRNA, pre-miRNA, pri-miRNA, miRNA*, piwiRNA, anti-miRNA, or a miRNA binding site, or a variant thereof, genomic DNA, or fragments thereof of one or more biomarkers listed in Table 1, the Figures, and the Examples, such that the presence of biomarker polypeptide, RNA, genomic DNA, or fragments thereof, is detected in the biological sample, and comparing the presence of biomarker polypeptide, RNA, cDNA, small RNAs, mature miRNA, pre-miRNA, pri-miRNA, miRNA*, piwiRNA, anti-miRNA, or a miRNA binding site, or a variant thereof, genomic DNA, or fragments thereof in the control sample with the presence of biomarker polypeptide, RNA, cDNA, small RNAs, mature miRNA, pre-miRNA, pri-miRNA, miRNA*, piwiRNA, piwiRNA, anti-miRNA, or a miRNA binding site, or a variant thereof, genomic DNA, or fragments thereof in the test sample.

The invention also encompasses kits for detecting the presence of a polypeptide, RNA, cDNA, small RNAs, mature miRNA, pre-miRNA, pri-miRNA, miRNA*, piwiRNA, anti-miRNA, or a miRNA binding site, or a variant thereof, genomic DNA, or fragments thereof, of one or more biomarkers listed in Table 1, the Figures, and the Examples, in a biological sample. For example, the kit can comprise a labeled compound or agent capable of detecting one or more biomarkers polypeptide, RNA, cDNA, small RNAs, mature miRNA, pre-miRNA, pri-miRNA, miRNA*, piwiRNA, anti-miRNA, or a miRNA binding site, or a variant thereof, genomic DNA, or fragments thereof, in a biological sample; means for determining the amount of the biomarker polypeptide, RNA, cDNA, small RNAs, mature miRNA, pre-miRNA, pri-miRNA, miRNA*, piwiRNA, anti-miRNA, or a miRNA binding site, or a variant thereof, genomic DNA, or fragments thereof, in the sample; and means for comparing the amount of the biomarker polypeptide, RNA, cDNA, small RNAs, mature miRNA, pre-miRNA, pri-miRNA, miRNA*, piwiRNA, anti-miRNA, or a miRNA binding site, or a variant thereof, genomic DNA, or fragments thereof, in the sample with a standard. The compound or agent can be packaged in a suitable container. The kit can further comprise instructions for using the kit to detect the biomarker polypeptide, RNA, cDNA, small RNAs, mature miRNA, pre-miRNA, pri-miRNA, miRNA*, piwiRNA, anti-miRNA, or a miRNA binding site, or a variant thereof, genomic DNA, or fragments thereof.

In some embodiments, therapies tailored to treat stratified patient populations based on the described diagnostic assays are further administered, such as melanoma standards of treatment, immune therapy, and combinations thereof described herein.

2. Prognostic Assays

The diagnostic methods described herein can furthermore be utilized to identify subjects having or at risk of developing a disease or disorder associated with aberrant expression or activity of one or more biomarkers of the present invention, including one or more biomarkers listed in Table 1, the Figures, and the Examples, or a fragment thereof. As used herein, the term "aberrant" includes biomarker expression or activity levels which deviates from the normal expression or activity in a control.

The assays described herein, such as the preceding diagnostic assays or the following assays, can be used to identify a subject that would benefit from metabolic interventions (e.g., low levels of plasma Slit2 indicates that Slit2 administration would be differentially beneficial). Alternatively, the prognostic assays can be used to identify a subject having or at risk for developing a disorder associated with a misregulation of biomarker activity or expression. Thus, the present invention provides a method for identifying and/or classifying a disease associated with aberrant expression or activity of one or more biomarkers of the present invention, including one or more biomarkers listed in Table 1, the Figures, and the Examples, or a fragment thereof. Furthermore, the prognostic assays described herein can be used to determine whether a subject can be administered an agent (e.g., an agonist, antagonist, peptidomimetic, polypeptide, peptide, nucleic acid, small molecule, or other drug candidate) to treat a disease or disorder associated with aberrant biomarker expression or activity. For example, such methods can be used to determine whether a subject can be effectively treated with an agent for a melanoma. Thus, the present invention provides methods for determining whether a subject can be effectively treated with an agent for a disease associated with aberrant biomarker expression or activity in which a test sample is obtained and biomarker polypeptide or nucleic acid expression or activity is detected (e.g., wherein a significant increase or decrease in biomarker polypeptide or nucleic acid expression or activity relative to a control is diagnostic for a subject that can be administered the agent to treat a disorder associated with aberrant biomarker expression or activity). In some embodiments, significant increase or decrease in biomarker expression or activity comprises at least 1.1, 1.2, 1.3, 1.4, 1.5, 1.6, 1.7, 1.8, 1.9, 2.0, 2 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher or lower, respectively, than the expression activity or level of the marker in a control sample.

The methods of the present invention can also be used to detect genetic alterations in one or more biomarkers of the present invention, including one or more biomarkers listed in Table 1, the Figures, and the Examples, or a fragment thereof, thereby determining if a subject with the altered biomarker is at risk for melanoma characterized by aberrant biomarker activity or expression levels. In preferred embodiments, the methods include detecting, in a sample of cells from the subject, the presence or absence of a genetic alteration characterized by at least one alteration affecting the integrity of a gene encoding one or more biomarkers, or the mis-expression of the biomarker (e.g., mutations and/or splice variants). For example, such genetic alterations can be detected by ascertaining the existence of at least one of 1) a deletion of one or more nucleotides from one or more biomarkers gene, 2) an addition of one or more nucleotides to one or more biomarkers gene, 3) a substitution of one or more nucleotides of one or more biomarkers gene, 4) a chromosomal rearrangement of one or more biomarkers gene, 5) an alteration in the level of a messenger RNA transcript of one or more biomarkers gene, 6) aberrant modification of one or more biomarkers gene, such as of the methylation pattern of the genomic DNA, 7) the presence of a non-wild type splicing pattern of an RNA transcript of one or more biomarkers gene, 8) a non-wild type level of one or more biomarkers polypeptide, 9) allelic loss of one or more biomarkers gene, and 10) inappropriate post-translational modification of one or more biomarkers polypeptide. As described herein, there are a large number of assays known in the art which can be used for detecting alterations in one or more biomarkers gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. USA 91:360-364), the latter of which can be particularly useful for detecting point mutations in one or more biomarkers gene (see Abravaya et al. (1995) Nucleic Acids Res. 23:675-682). This method can include the steps of collecting a sample of cells from a subject, isolating nucleic acid (e.g., genomic DNA, mRNA, cDNA, small RNA, mature miRNA, pre-miRNA, pri-miRNA, miRNA*, piwiRNA, anti-miRNA, or a miRNA binding site, or a variant thereof) from the cells of the sample, contacting the nucleic acid sample with one or more primers which specifically hybridize to one or more biomarkers gene of the present invention, including the biomarker genes listed in Table 1, the Figures, and the Examples, or fragments thereof, under conditions such that hybridization and amplification of the biomarker gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self-sustained sequence replication (Guatelli, J. C. et al. (1990) Proc. Natl. Acad. Sci. USA 87:1874-1878), transcriptional amplification system (Kwoh, D. Y. et al. (1989) Proc. Natl. Acad. Sci. USA 86:1173-1177), Q-Beta Replicase (Lizardi, P. M. et al. (1988) Bio-Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in one or more biomarkers gene of the present invention, including one or more biomarkers listed in Table 1, the Figures, and the Examples, or a fragment thereof, from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in one or more biomarkers gene of the present invention, including a gene listed in Table 1, the Figures, and the Examples, or a fragment thereof, can be identified by hybridizing a sample and control nucleic acids, e.g., DNA, RNA, mRNA, small RNA, cDNA, mature miRNA, pre-miRNA, pri-miRNA, miRNA*, piwiRNA, anti-miRNA, or a miRNA binding site, or a variant thereof, to high density arrays containing hundreds or thousands of oligonucleotide probes (Cronin, M. T. et al. (1996) Hum. Mutat. 7:244-255; Kozal, M. J. et al. (1996) Nat. Med. 2:753-759). For example, genetic mutations in one or more biomarkers can be identified in two dimensional arrays containing light-generated DNA probes as described in Cronin et al. (1996) supra. Briefly, a first hybridization array of probes can be used to scan through long stretches of DNA in a sample and control to identify base changes between the sequences by making linear arrays of sequential, overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence one or more biomarkers gene of the present invention, including a gene listed in Table 1, the Figures, and the Examples, or a fragment thereof, and detect mutations by comparing the sequence of the sample biomarker gene with the corresponding wild-type (control) sequence. Examples of sequencing reactions include those based on techniques developed by Maxam and Gilbert (1977) Proc. Natl. Acad. Sci. USA 74:560 or Sanger (1977) Proc. Natl. Acad Sci. USA 74:5463. It is also contemplated that any of a variety of automated sequencing procedures can be utilized when performing the diagnostic assays (Naeve, C. W. (1995) Biotechniques 19:448-53), including sequencing by mass spectrometry (see, e.g., PCT International Publication No. WO 94/16101; Cohen et al. (1996) Adv. Chromatogr. 36:127-162; and Griffin et al. (1993) Appl. Biochem. Biotechnol. 38:147-159).

Other methods for detecting mutations in one or more biomarkers gene of the present invention, including a gene listed in Table 1, the Figures, and the Examples, or fragments thereof, include methods in which protection from cleavage agents is used to detect mismatched bases in RNA/RNA or RNA/DNA heteroduplexes (Myers et al. (1985) Science 230:1242). In general, the art technique of "mismatch cleavage" starts by providing heteroduplexes formed by hybridizing (labeled) RNA or DNA containing the wild-type sequence with potentially mutant RNA or DNA obtained from a tissue sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with SI nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) Proc. Natl. Acad. Sci. USA 85:4397 and Saleeba et al. (1992) Methods Enzymol. 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in biomarker genes of the present invention, including genes listed in Table 1, the Figures, and the Examples, or fragments thereof, obtained from samples of cells. For example, the mutY enzyme of *E. coli* cleaves A at G/A mismatches and the thymidine DNA glycosylase from HeLa cells cleaves T at G/T mismatches (Hsu et al. (1994) Carcinogenesis 15:1657-1662). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in biomarker genes of the present invention, including genes listed in Table 1, the Figures, and the Examples, or fragments thereof. For example, single strand conformation polymorphism (SSCP) may be used to detect differences in electrophoretic mobility between mutant and wild type nucleic acids (Orita et al. (1989) Proc Natl. Acad. Sci USA 86:2766; see also Cotton (1993) Mutat. Res. 285:125-144 and Hayashi (1992) Genet. Anal. Tech. Appl. 9:73-79). Single-stranded DNA fragments of sample and control nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet. 7:5).

In yet another embodiment the movement of mutant or wild-type fragments in polyacrylamide gels containing a gradient of denaturant is assayed using denaturing gradient gel electrophoresis (DGGE) (Myers et al. (1985) Nature 313:495). When DGGE is used as the method of analysis, DNA will be modified to ensure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) Biophys. Chem. 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) Nature 324:163; Saiki et al. (1989) *Proc. Natl. Acad. Sci. USA* 86:6230). Such allele specific oligonucleotides are hybridized to PCR amplified target DNA or a number of different mutations when the oligonucleotides are attached to the hybridizing membrane and hybridized with labeled target DNA. In some embodiments, the hybridization reactions can occur using biochips, microarrays, etc., or other array technology that are well known in the art.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) Nucleic Acids Res. 17:2437-2448) or at the extreme 3' end of one primer where, under appropriate conditions, mismatch can prevent, or reduce polymerase extension (Prossner (1993) Tibtech 11:238). In addition it may be desirable to introduce a novel restriction site in the region of the mutation to create cleavage-based detection (Gasparini et al. (1992) Mol. Cell Probes 6:1). It is anticipated that in certain embodiments amplification may also be performed using Taq ligase for amplification (Barany (1991) Proc. Natl. Acad. Sci USA 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving one or more biomarkers of the present invention, including one or more biomarkers listed in Table 1, the Figures, and the Examples, or fragments thereof.

3. Monitoring of Effects During Clinical Trials

Monitoring the influence of agents (e.g., drugs) on the expression or activity of one or more biomarkers of the present invention, including one or more biomarkers listed in Table 1, the Figures, and the Examples, or a fragment thereof (e.g., the modulation of a metabolic state) can be applied not only in basic drug screening, but also in clinical trials. For example, the effectiveness of an agent determined by a screening assay as described herein to increase expression and/or activity of one or more biomarkers of the present invention, including one or more biomarkers listed in Table 1, the Figures, and the Examples, or a fragment thereof, can be monitored in clinical trials of subjects exhibiting decreased expression and/or activity of one or more biomarkers of the present invention, including one or more biomarkers of the present invention, including one or more biomarkers listed in Table 1, the Figures, and the Examples, or a fragment thereof, relative to a control reference. Alternatively, the effectiveness of an agent determined by a screening assay to decrease expression and/or activity of one or more biomarkers of the present invention, including one or more biomarkers listed in Table 1, the Figures, and the Examples, or a fragment thereof, can be monitored in clinical trials of subjects exhibiting decreased expression and/or activity of the biomarker of the present invention, including one or more biomarkers listed in Table 1, the Figures, and the Examples, or a fragment thereof relative to a control reference. In such clinical trials, the expression and/or activity of the biomarker can be used as a “read out” or marker of the phenotype of a particular cell.

In some embodiments, the present invention provides a method for monitoring the effectiveness of treatment of a subject with an agent (e.g., an agonist, antagonist, peptidomimetic, polypeptide, peptide, nucleic acid, small molecule, or other drug candidate identified by the screening assays described herein) including the steps of (i) obtaining a pre-administration sample from a subject prior to administration of the agent; (ii) detecting the level of expression and/or activity of one or more biomarkers of the present invention, including one or more biomarkers listed in Table 1, the Figures, and the Examples, or fragments thereof in the preadministration sample; (iii) obtaining one or more post-administration samples from the subject; (iv) detecting the level of expression or activity of the biomarker in the post-administration samples; (v) comparing the level of expression or activity of the biomarker or fragments thereof in the pre-administration sample with the that of the biomarker in the post administration sample or samples; and (vi) altering the administration of the agent to the subject accordingly. For example, increased administration of the agent may be desirable to increase the expression or activity of one or more biomarkers to higher levels than detected (e.g., to increase the effectiveness of the agent.) Alternatively, decreased administration of the agent may be desirable to decrease expression or activity of the biomarker to lower levels than detected (e.g., to decrease the effectiveness of the agent). According to such an embodiment, biomarker expression or activity may be used as an indicator of the effectiveness of an agent, even in the absence of an observable phenotypic response.

C. Methods of Treatment

The present invention provides for both prophylactic and therapeutic methods of treating a subject at risk of (or susceptible to) a disorder characterized by insufficient or excessive production of biomarkers of the present invention, including biomarkers listed in Table 1, the Figures, and the Examples, or fragments thereof, which have aberrant expression or activity compared to a control. Moreover, agents of the present invention described herein can be used to detect and isolate the biomarkers or fragments thereof, regulate the bioavailability of the biomarkers or fragments thereof, and modulate biomarker expression levels or activity.

1. Prophylactic Methods

In one aspect, the present invention provides a method for preventing in a subject, a disease or condition associated with an aberrant expression or activity of one or more biomarkers of the present invention, including one or more biomarkers listed in Table 1, the Figures, and the Examples, or a fragment thereof, by administering to the subject an agent which modulates biomarker expression or at least one activity of the biomarker. Subjects at risk for a disease or disorder which is caused or contributed to by aberrant biomarker expression or activity can be identified by, for example, any or a combination of diagnostic or prognostic assays as described herein. Administration of a prophylactic agent can occur prior to the manifestation of symptoms characteristic of the biomarker expression or activity aberrancy, such that a disease or disorder is prevented or, alternatively, delayed in its progression.

2. Therapeutic Methods

Another aspect of the present invention pertains to methods of modulating the expression or activity or interaction with natural binding partner(s) of one or more biomarkers of the present invention, including one or more biomarkers listed in Table 1, the Figures, and the Examples, or fragments thereof, for therapeutic purposes. The biomarkers of the present invention have been demonstrated to correlate with adipose tissue thermogenesis and modulation of metabolism. Accordingly, the activity and/or expression of the biomarker, as well as the interaction between one or more biomarkers or a fragment thereof and its natural binding partner(s) or a fragment(s) thereof can be modulated in order to modulate the immune response.

Modulatory methods of the present invention involve contacting a cell with one or more biomarkers of the present invention, including one or more biomarkers of the present invention, including one or more biomarkers listed in Table 1, the Figures, and the Examples, or a fragment thereof or agent that modulates one or more of the activities of biomarker activity associated with the cell. An agent that modulates biomarker activity can be an agent as described herein, such as a nucleic acid or a polypeptide, a naturally-occurring binding partner of the biomarker, an antibody against the biomarker, a combination of antibodies against the biomarker and antibodies against other immune related targets, one or more biomarkers agonist or antagonist, a peptidomimetic of one or more biomarkers agonist or antagonist, one or more biomarkers peptidomimetic, other small molecule, or small RNA directed against or a mimic of one or more biomarkers nucleic acid gene expression product.

An agent that modulates the expression of one or more biomarkers of the present invention, including one or more biomarkers of the present invention, including one or more biomarkers listed in Table 1, the Figures, and the Examples, or a fragment thereof is a nucleic acid molecule described herein, e.g., an antisense nucleic acid molecule, RNAi molecule, shRNA, mature miRNA, pre-miRNA, pri-miRNA, miRNA*, piwiRNA, anti-miRNA, or a miRNA binding site, or a variant thereof, or other small RNA molecule, triplex oligonucleotide, ribozyme, or recombinant vector for expression of one or more biomarkers polypeptide. For example, an oligonucleotide complementary to the area around one or more biomarkers polypeptide translation initiation site can be synthesized. One or more antisense oligonucleotides can be added to cell media, typically at 200 μg/ml, or administered to a patient to prevent the synthesis of one or more biomarkers polypeptide. The antisense oligonucleotide is taken up by cells and hybridizes to one or more biomarkers mRNA to prevent translation. Alternatively, an oligonucleotide which binds double-stranded DNA to form a triplex construct to prevent DNA unwinding and transcription can be used. As a result of either, synthesis of biomarker polypeptide is blocked. When biomarker expression is modulated, preferably, such modulation occurs by a means other than by knocking out the biomarker gene.

Agents which modulate expression, by virtue of the fact that they control the amount of biomarker in a cell, also modulate the total amount of biomarker activity in a cell.

In one embodiment, the agent stimulates one or more activities of one or more biomarkers of the present invention, including one or more biomarkers listed in Table 1, the Figures, and the Examples, or a fragment thereof. Examples of such stimulatory agents include active biomarker polypeptides or a fragment thereof, such as Slit2 binding partners, and/or a nucleic acid molecule encoding the biomarker or a fragment thereof that has been introduced into the cell (e.g., cDNA, mRNA, shRNAs, siRNAs, small RNAs, mature miRNA, pre-miRNA, pri-miRNA, miRNA*, piwiRNA, anti-miRNA, or a miRNA binding site, or a variant thereof, or other functionally equivalent molecule known to a skilled artisan). In another embodiment, the agent inhibits one or more biomarker activities. In one embodiment, the agent inhibits or enhances the interaction of the biomarker with its natural binding partner(s). Examples of such inhibitory agents include antisense nucleic acid molecules, anti-biomarker antibodies, biomarker inhibitors, and compounds identified in the screening assays described herein.

These modulatory methods can be performed in vitro (e.g., by contacting the cell with the agent) or, alternatively, by contacting an agent with cells in vivo (e.g., by administering the agent to a subject). As such, the present invention provides methods of treating an individual afflicted with a condition or disorder that would benefit from up- or down-modulation of one or more biomarkers of the present invention listed in Table 1, the Figures, and the Examples, or a fragment thereof, e.g., a disorder characterized by unwanted, insufficient, or aberrant expression or activity of the biomarker or fragments thereof. In one embodiment, the method involves administering an agent (e.g., an agent identified by a screening assay described herein), or combination of agents that modulates (e.g., upregulates or downregulates) biomarker expression or activity. In another embodiment, the method involves administering one or more biomarkers polypeptide or nucleic acid molecule as therapy to compensate for reduced, aberrant, or unwanted biomarker expression or activity.

Stimulation of biomarker activity is desirable in situations in which the biomarker is abnormally downregulated and/or in which increased biomarker activity is likely to have a beneficial effect. Likewise, inhibition of biomarker activity is desirable in situations in which biomarker is abnormally upregulated and/or in which decreased biomarker activity is likely to have a beneficial effect.

In addition, these modulatory agents can also be administered in combination therapy with, e.g., metabolism enhancing agents, such as transplanted brown and/or beige fat cells, hormones, and the like. The preceding treatment methods can be administered in conjunction with other forms of conventional therapy (e.g., standard-of-care treatments for cancer well known to the skilled artisan), either consecutively with, pre- or post-conventional therapy. For example, these modulatory agents can be administered with a therapeutically effective dose of a metabolism modulatory agent.

The methods of the present invention relate to the expression and/or activity of Slit2 sufficient to modulate (e.g., induce or repress) brown and/or beige fat cell differentiation and/or activity, wherein increases in differentiated brown and/or beige fat cells or activity increase energy expenditure and favorably affect other metabolic processes and can therefore be used to treat metabolic disorders such as obesity, diabetes, decreased thermogenesis and subjects in need of more exercise; and, wherein decreases in differentiated brown and/or beige fat cells or activity decrease energy expenditure and can therefore be used to treat the effects of such conditions as cachexia, anorexia, and obesity-associated cancer.

The invention also relates to methods for increasing energy expenditure in a mammal comprising inducing expression and/or activity of Slit2 sufficient to activate brown and/or beige fat cell differentiation or activity in the mammal, wherein the differentiated and/or more active brown fat and/or beige fat cells promote energy expenditure thereby increasing energy expenditure in the mammal.

The term “sufficient to activate” is intended to encompass any increase in expression and/or activity of Slit2 that promotes, activates, stimulates, enhances, or results in brown fat and/or beige fat differentiation or activity.

In another aspect, the invention relates to methods for treating metabolic disorders in a subject comprising administering to the subject an agent that induces expression and/or activity of Slit2, wherein expression and/or activity of Slit2 increases respiration and energy expenditure to thereby treat the metabolic disorder. In one embodiment, total respiration is increased following the expression and/or activity of Slit2. In another embodiment, uncoupled respiration is increased following the expression and/or activity of Slit2. Uncoupled respiration dissipates heat and thereby increases energy expenditure in the subject.

As used herein, the term “agent” and “therapeutic agent” is defined broadly as anything that cells from a subject having a metabolic disorder may be exposed to in a therapeutic protocol. In one embodiment, the agent is a recombinant Slit2 protein, or fragment thereof, or nucleic acid molecule encoding such a polyptpide. In another embodiment, the agent is an anti-sense nucleic acid molecule having a sequence complementary to Slit2 (e.g., an RNAi, siRNA, or other RNA inhibiting nucleic acid molecule).

The term “administering” is intended to include routes of administration which allow the agent to perform its intended function of modulating (e.g., increasing or decreasing) expression and/or activity of Slit2. Examples of routes of administration which can be used include injection (subcutaneous, intravenous, parenterally, intraperitoneally, intrathecal, etc., such as in a subcutaneous injection into white fate depots), oral, inhalation, and transdermal. The injection can be bolus injections or can be continuous infusion. Depending on the route of administration, the agent can be coated with or disposed in a selected material to protect it from natural conditions which may detrimentally affect its ability to perform its intended function. The agent may be administered alone, or in conjunction with a pharmaceutically acceptable carrier. Further the agent may be coadministered with a pharmaceutically acceptable carrier. The agent also may be administered as a prodrug, which is converted to its active form in vivo. The agent may also be administered in combination with one or more additional therapeutic agent(s) (e.g., before, after or simultaneously therewith).

The term “effective amount” of an agent that induces expression and/or activity of Slit2 is that amount necessary or sufficient to modulate (e.g., increase or decrease) expression and/or activity of Slit2 in the subject or population of subjects. The effective amount can vary depending on such factors as the type of therapeutic agent(s) employed, the size of the subject, or the severity of the disorder.

It will be appreciated that individual dosages may be varied depending upon the requirements of the subject in the judgment of the attending clinician, the severity of the condition being treated and the particular compound being employed. In determining the therapeutically effective amount or dose, a number of additional factors may be considered by the attending clinician, including, but not limited to: the pharmacodynamic characteristics of the particular agent and its mode and route of administration; the desired time course of treatment; the species of mammal; its size, age, and general health; the specific disease involved; the degree of or involvement or the severity of the disease; the response of the individual subject; the particular compound administered; the mode of administration; the bioavailability characteristics of the preparation administered; the dose regimen selected; the kind of concurrent treatment; and other relevant circumstances.

Treatment can be initiated with smaller dosages which are less than the effective dose of the compound. Thereafter, in one embodiment, the dosage should be increased by small increments until the optimum effect under the circumstances is reached. For convenience, the total daily dosage may be divided and administered in portions during the day if desired.

The effectiveness of any particular agent to treat a metabolic disorder can be monitored by comparing two or more samples obtained from a subject undergoing anti-obesity or obesity-related disorder treatment. In general, it is preferable to obtain a first sample from the subject prior to beginning therapy and one or more samples during treatment. In such a use, a baseline of expression of cells from subjects with obesity or obesity-related disorders prior to therapy is determined and then changes in the baseline state of expression of cells from subjects with obesity or obesity-related disorders is monitored during the course of therapy. Alternatively, two or more successive samples obtained during treatment can be used without the need of a pre-treatment baseline sample. In such a use, the first sample obtained from the subject is used as a baseline for determining whether the expression of cells from subjects with obesity or obesity-related disorders is increasing or decreasing.

Another aspect of the invention relates to a method for inducing brown fat and/or beige fat cell differentiation and/or activity in a mammal comprising expressing Slit2 nucleic acid and/or polypeptide molecules in a mammal and, optionally, monitoring the differentiation of brown fat cells in the mammal. Increased brown and/or beige adipose tissue in the mammal will warm up the body and blood of the mammal resulting in an increased energy expenditure from the cells. The increased energy expenditure will increase the metabolic rate of the subject and may be used for the treatment and/or prevention of obesity and obesity related disorders. The induction of brown fat cells may be monitored by analyzing a) brown fat and/or beige fat gene expression, such as expression of a marker selected from the group consisting of: cidea, adiponectin, adipsin, otopetrin, type II deiodinase, cig30, ppar gamma 2, pgc1α, ucp1, elovl3, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, dio2, fatty acid synthase (fas), leptin, resistin, and nuclear respiratory factor-1 (nrf1); b) thermogenesis in adipose cells; c) differentiation of adipose cells; d) insulin sensitivity of adipose cells; e) basal respiration or uncoupled respiration; f) whole body oxygen consumption; g) obesity or appetite; h) insulin secretion of pancreatic beta cells; i) glucose tolerance; j) modified phosphorylation of EGFR, ERK, AMPK, protein kinase A (PKA) substrates having an RRX(S/T) (SEQ ID NO: 127) motif, wherein the X is any amino acid and the (S/T) residue is a serine or threonine, HSL; k) modified expression of UCP1 protein; and l) growth and effects of metabolic disorders, such as obesity-associated cancer, cachexia, anorexia, diabetes, and obesity.

In any method described herein, such as a diagnostic method, prognostic method, therapeutic method, or combination thereof, all steps of the method can be performed by a single actor or, alternatively, by more than one actor. For example, diagnosis can be performed directly by the actor providing therapeutic treatment. Alternatively, a person providing a therapeutic agent can request that a diagnostic assay be performed. The diagnostician and/or the therapeutic interventionist can interpret the diagnostic assay results to determine a therapeutic strategy. Similarly, such alternative processes can apply to other assays, such as prognostic assays.

Any means for the introduction of a polynucleotide into mammals, human or non-human, or cells thereof may be adapted to the practice of this invention for the delivery of the various constructs of the invention into the intended recipient. In one embodiment of the invention, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system of this invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Felgner, et al., Ann NY Acad Sci 126-139, 1995). Formulation of DNA, e.g. with various lipid or liposome materials, may then be effected using known methods and materials and delivered to the recipient mammal. See, e.g., Canonico et al, Am J Respir Cell Mol Biol 10:24-29, 1994; Tsan et al, Am J Physiol 268; Alton et al., Nat Genet. 5:135-142, 1993 and U.S. Pat. No. 5,679,647 by Carson et al.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites in a subject (see below).

Nucleic acids can be delivered in any desired vector. These include viral or non-viral vectors, including adenovirus vectors, adeno-associated virus vectors, retrovirus vectors, lentivirus vectors, and plasmid vectors. Exemplary types of viruses include HSV (herpes simplex virus), AAV (adeno associated virus), HIV (human immunodeficiency virus), BIV (bovine immunodeficiency virus), and MLV (murine leukemia virus). Nucleic acids can be administered in any desired format that provides sufficiently efficient delivery levels, including in virus particles, in liposomes, in nanoparticles, and complexed to polymers.

The nucleic acids encoding a protein or nucleic acid of interest may be in a plasmid or viral vector, or other vector as is known in the art. Such vectors are well known and any can be selected for a particular application. In one embodiment of the invention, the gene delivery vehicle comprises a promoter and a demethylase coding sequence. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter. A promoter may be constitutive or inducible.

In another embodiment, naked polynucleotide molecules are used as gene delivery vehicles, as described in WO 90/11092 and U.S. Pat. No. 5,580,859. Such gene delivery vehicles can be either growth factor DNA or RNA and, in certain embodiments, are linked to killed adenovirus. Curiel et al., Hum. Gene. Ther. 3:147-154, 1992. Other vehicles which can optionally be used include DNA-ligand (Wu et al., J. Biol. Chem. 264:16985-16987, 1989), lipid-DNA combinations (Felgner et al., Proc. Natl. Acad. Sci. USA 84:7413 7417, 1989), liposomes (Wang et al., Proc. Natl.

Acad. Sci. 84:7851-7855, 1987) and microprojectiles (Williams et al., Proc. Natl. Acad. Sci. 88:2726-2730, 1991).

A gene delivery vehicle can optionally comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the growth factor gene delivery vehicle is a recombinant retroviral vector. Recombinant retroviruses and various uses thereof have been described in numerous references including, for example, Mann et al., Cell 33:153, 1983, Cane and Mulligan, Proc. Nat'l. Acad. Sci. USA 81:6349, 1984, Miller et al., Human Gene Therapy 1:5-14, 1990, U.S. Pat. Nos. 4,405,712, 4,861,719, and 4,980,289, and PCT Application Nos. WO 89/02,468, WO 89/05,349, and WO 90/02,806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, Cancer Res. 53:3860-3864, 1993; Vile and Hart, Cancer Res. 53:962-967, 1993; Ram et al., Cancer Res. 53:83-88, 1993; Takamiya et al., J. Neurosci. Res. 33:493-503, 1992; Baba et al., J. Neurosurg. 79:729-735, 1993 (U.S. Pat. No. 4,777,127, GB 2,200,651, EP 0,345,242 and WO91/02805).

Other viral vector systems that can be used to deliver a polynucleotide of the invention have been derived from herpes virus, e.g., Herpes Simplex Virus (U.S. Pat. No. 5,631,236 by Woo et al., issued May 20, 1997 and WO 00/08191 by Neurovex), vaccinia virus (Ridgeway (1988) Ridgeway, "Mammalian expression vectors," In: Rodriguez R L, Denhardt D T, ed. Vectors: A survey of molecular cloning vectors and their uses. Stoneham: Butterworth; Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) Gene, 68:1-10), and several RNA viruses. Preferred viruses include an alphavirus, a poxivirus, an arena virus, a vaccinia virus, a polio virus, and the like. They offer several attractive features for various mammalian cells (Friedmann (1989) Science, 244:1275-1281; Ridgeway, 1988, supra; Baichwal and Sugden, 1986, supra; Coupar et al., 1988; Horwich et al. (1990) J. Virol., 64:642-650).

In other embodiments, target DNA in the genome can be manipulated using well-known methods in the art. For example, the target DNA in the genome can be manipulated by deletion, insertion, and/or mutation are retroviral insertion, artificial chromosome techniques, gene insertion, random insertion with tissue specific promoters, gene targeting, transposable elements and/or any other method for introducing foreign DNA or producing modified DNA/modified nuclear DNA. Other modification techniques include deleting DNA sequences from a genome and/or altering nuclear DNA sequences. Nuclear DNA sequences, for example, may be altered by site-directed mutagenesis.

In other embodiments, recombinant Slit2 polypeptides, and fragments thereof, can be administered to subjects. In some embodiments, fusion proteins can be constructed and administered which have enhanced biological properties (e.g., Fc fusion proteins discussed above). In addition, the Slit2 polypeptides, and fragment thereof, can be modified according to well known pharmacological methods in the art (e.g., pegylation, glycosylation, oligomerization, etc.) in order to further enhance desirable biological activities, such as increased bioavailability and decreased proteolytic degradation.

VI. Pharmaceutical Compositions

In another aspect, the present invention provides pharmaceutically acceptable compositions which comprise a therapeutically-effective amount of an agent that modulates (e.g., increases or decreases) Slit2 expression and/or activity, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "therapeutically-effective amount" as used herein means that amount of an agent that modulates (e.g., enhances) Slit2 expression and/or activity, or expression and/or activity of the complex, or composition comprising an agent that modulates (e.g., enhances) Slit2 expression and/or activity, or expression and/or activity of the complex, which is effective for producing some desired therapeutic effect, e.g., weight loss, at a reasonable benefit/risk ratio.

The phrase "pharmaceutically acceptable" is employed herein to refer to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of the agents that modulates (e.g., enhances) Slit2 expression and/or activity, or expression and/or activity of the complex encompassed by the invention. These salts can be prepared in situ during the final isolation and purification of the agents, or by separately reacting a purified agent in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (See, for example, Berge et al. (1977) "Pharmaceutical Salts", J. Pharm. Sci. 66:1-19).

In other cases, the agents useful in the methods of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of agents that modulates (e.g., enhances) Slit2 expression and/or activity, or expression and/or activity of the complex. These salts can likewise be prepared in situ during the final isolation and purification of the agents, or by separately reacting the purified agent in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an agent that modulates (e.g., increases or decreases) Slit2 expression and/or activity, with the carrier and, optionally, one or more accessory ingredients. In general, the formulations are prepared by uniformly and intimately bringing into association a agent with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a agent as an active ingredient. A compound may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions, which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions, which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active agent may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more agents with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of an agent that modulates (e.g., increases or decreases) Slit2 expression and/or activity include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to a agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an agent that modulates (e.g., increases or decreases) Slit2 expression and/or activity, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The agent that modulates (e.g., increases or decreases) Slit2 expression and/or activity, can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a agent to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more agents in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of an agent that modulates (e.g., increases or decreases) Slit2 expression and/or activity, in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

When the agents of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

Actual dosage levels of the active ingredients in the pharmaceutical compositions of this invention may be determined by the methods of the present invention so as to obtain an amount of the active ingredient, which is effective to achieve the desired therapeutic response for a particular subject, composition, and mode of administration, without being toxic to the subject.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054 3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

EXEMPLIFICATION

This invention is further illustrated by the following examples, which should not be construed as limiting.

Example 1: Materials and Methods for Examples 1-7

A. Animals

All animal experiments were approved by the Institutional Animal Care and Use Committee of the Beth Israel Deaconess Medical Center. Mice (*Mus musculus*) were obtained from Jackson Laboratories, maintained in 12 hour light-lark cycles (6 a.m.-6 p.m.) at 22° C., and fed a standard irradiated rodent chow diet or a high-fat diet (60% fat) for 12-20 weeks. AAV-8 viruses (Penn Vector Core) and adenoviruses (Vector Biolabs or constructed in-house) were injected at a titer of $10^{11}$ or $10^{10}$ per mouse, respectively. All experiments were done with male mice. The aP2-PRDM16 transgenic mice have been previously described in Seale et al. (2011) *J. Clin. Invest.* 121:96-105. PRDM16-floxed mice were crossed with adiponectin-Cre and were maintained on a pure C57BL/6 background (Cohen et al. (2014) *Cell* 156:304-316). The Slit2-floxed mice have been described previously in Rama et al. (2015) *Nat. Med.* 21:483-491. Lean C57BL/6 mice were obtained from Jackson Laboratories and were fed a high-fat diet (60% fat) for 12-20 weeks.

B. Metabolic Phenotyping

Glucose tolerance tests were performed on mice 7 days post-injection with adenovirus. No significant difference was seen in weight loss in any of the groups upon injection. Animals were fasted overnight and then received intraperitoneal glucose at 1 mg/kg. Energy expenditure was analyzed using a Comprehensive Lab Animal Monitoring System (Columbus Instruments). Cold exposure and thermoneutrality experiments were performed in Balb/c mice at 4° C. or 30° C., respectively. Total levels of cholesterol, free fatty acids, triglycerides and insulin were measured at the Core Facility at Joslin Diabetes Center.

C. Respiration

Tissue respiration was performed using a Clark electrode (Stathkelvin Instruments). Freshly isolated tissues were dissected from mice treated with LacZ or Slit2-C adenovirus for 7 days. Equally sized pieces of tissue were minced and placed in respiration buffer containing PBS supplemented with 2% (w/v) bovine serum albumin, 1% (w/v) glucose, and 1 mM Na pyruvate. Oxygen ($O_2$) consumption was normalized to tissue weight. Cellular oxygen consumption rates were determined using an XF24 Extracellular Flux Analyzer (Seahorse Biosciences). Primary brown fat adipocytes were seeded at 15,000 cells/well, differentiation was induced the following day as previously described, and the cells were analyzed on day 5. On the day of analysis, the cells were washed once with Seahorse respiration buffer (8.3 g/l DMEM, 1.8 g/l NaCl, 1 mM pyruvate, 20 mM glucose, pen/strep), placed in 0.5 ml Seahorse respiration buffer, and incubated in a C02-free incubator for 1 hr. Port injection solutions were prepared as follows: oligomycin (1 μM final concentration), norepinephrine (1 μM final concentration), FCCP (0.2 μM final concentration), and rotenone (3 μM final concentration). Each cycle consisted of the following: mix 4 min, wait 0 min, and measure 2 min. Data are presented as S.E.M.

D. Primary White and Brown Adipocyte Cultures

Inguinal and brown stromal-vascular fractions were obtained from 6 weeks old male or newborn mice (postnatal days 5-10) for white and brown fat cultures, respectively. Inguinal fat tissue was dissected and washed with PBS, minced and digested for 45 min at 37° C. in PBS containing 10 mM $CaCl_2$), 2.4 U/ml dispase II (Roche) and 10 mg/ml collagenase D (Roche). Brown fat tissue was dissected, washed with PBS, minced and digested for 45 min at 37° C. in PBS containing 1.3 mM $CaCl_2$, 123 mM NaCl, 5 mM KCl, 5.0 mM glucose, 100 mM HEPES, 4% BSA and 1.5 mg/ml collagenase B (Roche). Digested tissue was filtered through a 100-μm cell strainer and centrifuged at 600 g for 10 min. Pelleted inguinal stromal-vascular cells were grown to confluence and induced to differentiate by an adipogenic cocktail containing 0.02 μM insulin, 1 μM rosiglitazone, 5 μM dexamethasone, 0.5 μM isobuthylmethylxanthine. For differentiation of brown fat cells, 1 nM T3 and 125 μM indomethacin were also added to the adipogenic cocktail. Two days after induction, cells were maintained in adipocyte culture medium containing 0.02 μM insulin and 1 μM rosiglitazone. Where indicated, cells were treated with forskolin (10 μM), norepinephrine (100 nM) for 4 h or with recombinant proteins (1 μg/ml, R&D systems) for 24 h or for the indicated times. For adenoviral overexpression of Slit2-FL, Slit2-N, Slit2-C, LacZ or Cre, virus was added at day 2 of differentiation at a titer of $10^8$ particles/well and cells were analyzed at day 6-7. Where indicated, cells were treated with the drugs Erlotinib (SelleckChem), Lapatinib (Santa Cruz), PD0325901 (Santa Cruz), Propranolol (SelleckChem), H89 dihydrochloride (Santa Cruz), SQ-22536 (Santa Cruz) for indicated time points and concentrations.

E. Molecular Studies

RNA was extracted from cultured cells or frozen tissue samples using TRIzol®, purified with QIAGEN RNeasy® minicolumns. Normalized RNA was reversed transcribed using a high-capacity cDNA reverse transcription lot (Applied Biosystems) and cDNA was analyzed by qRT-CPR. Relative mRNA levels were calculated using the comparative CT method and normalized to cyclophilin miRNA. All primers used are listed with their sequences in Table 3 as follows:

TABLE 3

| | Forward primer (5' to 3') | Reverse primer (5' to 3') |
|---|---|---|
| Adiponectin | TGTTCCTCTTAATCCTGCCCA | CCAACCTGCACAAGTTCCCTT |
| Acsl1 | GATCTGGTGGAACGAGGCAA | CTTCGGGTTCTGGAGGCTTG |
| Acox | GCCCAACTGTGACTTCCATTAA | GTAGCACTCCCCTCGAGTGAT |
| Ap2 | AAGGTGAAGAGCATCATAACCCT | TCACGCCTTTCATAACACATTCC |
| Atgl | CAG CAC ATT TAT CCC GGT GTA C | AAA TGC CGC CAT CCA CAT AG |
| Atp5b | CACAATGCAGGAAAGGATCA | GGTCATCAGCAGGCACATAG |
| Atp6v0d2 | ACTTTTGGTGTTGTTCTGGGAA | GCATGAACAGGATCTCAGGC |
| Atp9b | TCTGGTAGTGTCCTGCTCACAG | TCGTAACGGCCAAAACAAAT |
| Cd31 | ACGCTGGTGCTCTATGCAAG | TCAGTTGCTGCCCATTCATCA |
| Cd34 | AAGGCTGGGTGAAGACCCTTA | TGAATGGCCGTTTCTGGAAGT |
| Cidea | TGC TCT TCT GTA TCG CCC AGT | GCC GTG TTA AGG AAT CTG CTG |
| Cox2 | GCCGACTAAATCAAGCAACA | CAATGGGCATAAAGCTATGG |
| Cox4 | GCACATGGGAGTGTTGTGA | CCTTCTCCTTCTCCTTCAGC |
| Cox5α | GGGTCACACGAGACAGATGA | GGAACCAGATCATAGCCAACA |
| Cox8 | GAACCATGAAGTCAACGACT | GCGAAGTTCACAGTGGTTCC |
| Cytb | CATTTATTATCGCGGCCCTA | TGTTGGGTTGTTTGATCCTG |
| Cyclophilin | GGAGATGGCACAGGAGGAA | GCCCGTAGTGCTTCAGCTT |
| Dio2 | CAGTGTGGTGCACGTCTCCAATC | TGAACCAAAGTTGACCACCAG |
| Ear2 | CCTGTAACCCCAGAACTCCA | CAGATGAGCAGGTGCAAA |
| Elovl3 | TCC GCG TTC TCA TGT AGG TCT | GGA CCT GAT GCA ACC CTA TGA |
| Err-α | GCAGGGCAGTGGGAAGCTA | CCTCTTGAAGGGCTTTGCA |
| Eva1 | CCACTTCTCCTGAGTTTACAGC | GCATTTTAACCGAACATCTGTCC |
| FasN | AGGTGGTGATAGCCGGTATGT | TGGGTAATCCATAGAGCCCAG |
| Gatm | GACCTGGTCTTGTGCTCTCC | GGGATGACTGGTGTTGGAGG |
| Glut1 | GGGCTGCCAGGTTCTAGTC | CCTCCGAGGTCCTTCTCA |
| Glut4 | AGAGTCTAAAGCGCCT | CCGAGACCAACGTGAA |
| Hsl | GCTGGAGGAGTGTTTTTTTGC | AGTTGAACCAAGCAGGTCACA3 |
| Leptin | GAGACCCCTGTGTCGGTTC | CTGCGTGTGTGAAATGTCATTG |
| Lxrα | AGGAGTGTCGACTTCGCAAA | CTCTTCTTGCCGCTTCAGTTT |
| Lxrβ | CTCCCACCCACGCTTACAC | GCCCTAACCTCTCTCCACTCA |
| Ng2 | GGGCTGTGCTGTCTGTTGA | TGATTCCCTTCAGGTAAGGCA |
| Nnmt | TTACAGCTTTGGGTCCAGACA | GGAGTTCTCCCTTTACAGCAC |
| Nrf1 | GAACTGCCAACCACAGTCAC | TTTGTTCCACCTCTCCATCA |
| Pepckm | GTGTGTACTGGGAAGGCATTGA | GCCACGAGGTTATGGTGACA |
| Pepckc | CAGGATCGAAAGCAAGACAGT | AAGTCCTCTTCCGACATCCAG |
| Pgc1α-total | TGATGTGAATGACTTGGATACAGACA | GCTCATTGTTGTACTGGTTGGATATG |

TABLE 3-continued

| | Forward primer (5' to 3') | Reverse primer (5' to 3') |
|---|---|---|
| Prdm16 | CAG CAC GGT GAA GCC ATT C | GCG TGC ATC CGC TTG TG |
| Ramp3 | GTGAGTGTGCCCAGGTATGC | CGACAGGTTGCACCACTTC |
| Resistin | CCAGAAGGCACAGCAGTCTT | CCGACATCAGGAAGCGACC |
| Slit1 | CTGGTCCCCGGATATGAACC | TAGCATGCACTCACACCTGG |
| Slit2 | GATTCTGGTGCACTTGTGCTG | TGTGTATTCCGGTGGGCAAA |
| Slit2-C | GCTGTGAACCATGCCACAAG | CACACATTTGTTTCCGAGGCA |
| Slit2-N | GCAACACCGAGAGACTGGATT | AGATCCTGGAATGCTCCCCT |
| Slit3 | CCACGCTGATCCTGAGCTAC | GCACTCGGAGGGATCTTAGC |
| Tgf-β | CCACCTGCAAGACCATCGAC | CTGGCGAGCCTTAGTTTGGAC |
| Tnf-α | CAGGCGGTGCCTATGTCTC | CGATCACCCCGAAGTTCAGTAG |
| Tyrosine Hydroxylase | GTCTCAGAGCAGGATACCAAGC | CTCTCCTCGAATACCACAGCC |
| VE cadherin | CACTGCTTGGGAGCCTTC | GGGGCAGCGATTCATTCATTTTTCT |
| Ucp1 | AAGCTGTGCGATGTCCATGT | AAGCCACAAACCCTTTGAAAA |
| Uqcrb | AGGGTTCCTGAGGACCTTTA | TCCTTAGGCAAGATCTGATGC |

For Western blotting, homogenized tissues, whole cell lysates, or concentrated serum free conditioned medium were lysed in RIPA buffer containing protease inhibitor cocktail (Thermo Scientific) and phosphatase inhibitor cocktail (Thermo Scientific), separated by SDS-PAGE and transferred to Immobilon-P® membranes (Millipore). For Western blotting of plasma samples, 1 μl of plasma was prepared containing 2× sample buffer (Invitrogen) with reducing agent, boiled and analyzed using Western blot against V5, FLAG, or the indicated antibody. V5-antibody was from Life Technologies and anti-Flag M2-HRP (A8592) from Sigma Aldrich. Anti-Slit2 antibody used was from Abcam (Abcam ab134166). Phospho-PKA Substrate, phospho-PKC Substrate, phospho-ERK1/2, total ERK, phospho-AKT, total AKT, phospho-AMPK, total AMPK, phospho-ATGL, ATGL, phospho-EGFR and EGFR were from Cell Signaling. Protein array was from R&D Systems (Proteome Profiler Mouse Phospho-RTK Array Kit, ARY014). Silverstain (SilverQuest™ Silver Staining Kit, LC6070) was purchased from Thermo Fisher.

F. Immunohistochemistry

Tissues were fixed in 4% paraformaldehyde. Paraffin embedding and sectioning were done by the Dana-Farber/Harvard Cancer Center Research Pathology core facility. For UCP1 immunohistochemistry, slides were deparaffinized in xylene, hydrated in descending 95%, 80% and 70% ethanol, and rinsed in water before heat-mediated antigen retrieval in 10 mM, pH 6.0 sodium citrate buffer. Quenching of endogenous peroxidases was performed using peroxidase quenching solution (Invitrogen). Slides were blocked in 10% goat serum and incubated with rabbit polyclonal UCP1 antibody (Abcam, ab10983) at 2 mg/ml in PBS-T/1% BSA overnight at 4° C. Slides were washed in PBS-T and incubated with 1:500 donkey anti-rabbit IgG HRP-linked antibody (GE healthcare) before developing using a SuperPicture™ 3rd Gen IHC Detection Kit (Invitrogen). Hematoxylin was used as counterstain. Immunohistochemical stainings of different fat depots were observed with a Nikon 80i upright light microscope using a 10× objective lens. Digital images were captured with a Nikon Digital Sight DS-Fil color camera and NIS-Elements acquisition software.

G. Construction of the Slit2 adenoviral expression plasmid, viral packaging, transduction, and Slit2-N and Slit2-C expression Slit2 full-length (untagged and Myc-DDK tagged) expression plasmids and corresponding LacZ control plasmids in adenovirus was purchased from Vector Biolabs. To construct the Slit2-N and Slit2-C ENTR clones, PCR primers were designed to amplify the signal peptide, N-terminal, and C-terminal Slit2 from mouse cDNA (OriGene MR227608). To construct the Slit2-N and Slit2-C ENTR clone, the Slit2N gene was amplified from mouse Slit2 cDNA to create PCR fragments corresponding to Slit2-signal peptide and Slit2-N that were ligated into the pENTR1a dual selection vector. The Slit2-C PCR fragment was sub-cloned into the pENTR1a vector containing the signal peptide. The Slit2-N and Slit2-C expression clones in which the fragments are fused to a C-terminal V5 tag were generated by performing the LR reaction between pENTR/D-TOPO-Slit2N or pENTR/D-TOPO-Slit2-C and pAD/CMV/V5-DEST (Life Technologies). The expression construct was cut with Pac and transfected into HEK-293A cells to produce crude adenoviral stock. Amplified virus was purified and concentrated using the Vivapure® adenopack 100 (Sartorius Stedim Biotech) and buffer exchanged to 10 mM Tris-Cl at pH 8.0, 2 mM MgCl2, 4% w/v sucrose. Adenovirus titer was calculated using an Adeno-X™ Rapid Titer kit (Clontech). For primary adipocytes a concentration of $10^8$ pfu/well was used and $10^{10}$ pfu/mouse were used for in vivo experiments. Expression levels of Slit2-N and Slit2-C were confirmed after 48 hours post infection by Western blot analysis using a V5 antibody (Life Technologies). Expression of Slit2-N and Slit2-C was performed by amplification from mouse Slit2 cDNA and ligated into the pENTR dual selection vector with a signal peptide sequence.

H. Cloning and Purification of Mammalian Recombinant Slit2-C

The pENTR/D-TOPO-Slit2-C were shuttled with LR Clonase (Thermo Fisher Scientific) into an in-house generated gateway compatible variant of pCLHCX-DEST, modified from pCLNCX (Novus), for mammalian expression with a C-terminal FLAG tag. Protein was purified from mammalian cell culture medium. HEK293A cells were infected with retrovirus expressing Slit2-C-FLAG in the presence of polybrene (8 μg/ml). After two days, cells were selected with hygromycin (150 μg/ml, Sigma Aldrich). The stable 293A cells were then grown in complete media. At confluence, the media was changed and harvested after 24 h. Media was centrifuged to remove debris (1000×g, 10 min, 4° C.) and the supernatant containing Slit2-C FLAG was transferred into a new tube. Slit2-C FLAG was immunoaffinity purified overnight at 4° C. using magnetic Flag-M2 beads (Sigma Aldrich). The beads were collected, washed three times in PBS, eluted with 3xFLAG peptide (0.1 μg/ml in PBS, Sigma Aldrich) and used for downstream applications. Purity and concentration was assessed using silverstain with an albumin standard as a reference.

I. Mass Spectrometry Analysis: Protein Extraction, Digestion, and Tandem Mass Tagging Labeling i. Sample Preparation, Protein Digestion, and TMT-Labeling Secreted proteins from primary inguinal cells from wild type or ap2-PRDM16tg mice (100 ml of serum free media, 24 hour (hr) incubation) were concentrated by methanol chloroform precipitation and analyzed by mass spectrometry analysis. Immunoprecipitation of Slit2-FLAG was performed using conditioned serum free medium from primary inguinal cells expressing Slit2-FL-FLAG using anti-FLAG M2 magnetic beads (Sigma Aldrich). Mass spectrometry for the detection of FLAG-reactive bands was performed by in-gel digestion of immunopurified Slit2-CTF separated on SDS-page and stained with SimplyBlue™ SafeStain (Invitrogen). Corresponding cell lysates were scraped down and snap frozen. Cultured adipocytes (biological duplicates for each condition) were lysed with a mechanical homogenizer, disulfide bonds were reduced with DTT and cysteine residues alkylated with iodoacetamide essentially as previously described in Huttlin et al. (2010) *Cell* 143:1174-1189. Protein from cultured medias was extracted by methanol-chloroform precipitation and protein pellets were solubilized in buffer composed of 50 mM HEPES pH 8.5, 50 mM O-glycerophosphate 2 mM sodium orthovanadate, 2 mM PMSF, and EDTA-free protease inhibitor cocktail (Promega) in 8 M Urea. Protein lysates were purified by methanol-chloroform precipitation and pellets were resuspended in 50 mM HEPES pH 8.5 in 8 M urea. Protein lysates were diluted to 4 M urea and digested with LysC (Wako) in a 1/200 enzyme/protein ratio overnight. Protein extracts were diluted further to a 1.0 M urea concentration and trypsin (Promega) was added to a final 1/200 enzyme/protein ratio for 6 hours at 37° C. Digests were acidified with 200 μL of 20% formic acid (FA) to a pH ~2 and subjected to 50 mg C18 solid-phase extraction (SPE) (Waters). Tryptic peptides were labeled with six-plex tandem mass tag (TMT) reagents (Thermo Scientific). Reagents (0.8 mg) were dissolved in 42 μl acetonitrile (ACN) and 20 μl of the solution was added to 150 μg of peptides dissolved in 100 μl of 50 mM HEPES, pH 8.5. After 1 hour, the reaction was quenched by adding 8 μl of 5% hydroxylamine for 15 minutes. Peptides were labeled with 4 reagents (126-129), combined and subjected to C18 SPE (50 mg).

ii. Basic pH Reversed-Phase HPLC (bpHrp)

TMT-labeled peptides were subjected to orthogonal bpHrp fractionation. TMT-labeled peptides were solubilized in 500 μl of buffer A (5% ACN 10 mM ammonium bicarbonate, pH 8.0) and separated by an Agilent 300 Extend C18 column (5 m particles, 4.6 mm ID and 220 mm in length). Using an Agilent 1100 binary pump equipped with a degasser and a photodiode array (PDA) detector (Thermo Scientific), a 45 minute linear gradient from 18% to 35% acetonitrile in 10 mM ammonium bicarbonate pH 8 (0.8 mL/min flowrate) separated the peptide mixtures into a total of 96 fractions. Fractions were consolidation into 24 samples in a checkerboard manner, acidified with 20% formic acid, and vacuum dried. Samples were dissolved in 5% acetonitrile/5% formic acid, desalted via StageTip, dried by vacuum centrifugation, and reconstituted for LC-MS/MS analysis.

iii. Liquid Chromatography Tandem Mass Spectrometry (LC-MS/MS)

All LC-MS/MS experiments were performed on a Velos-Orbitrap Elite™ hybrid mass spectrometer (Thermo Scientific) equipped with a FAMOS™ autosampler (LC Packings) and an Agilent 1200 binary HPLC pump (Agilent Technologies). Peptides were separated on a 100 μm I.D. microcapillary column packed first with approximately 1 cm of Magic C4 resin (5 μm, 100 Å, Michrom Bioresources) followed by 25 cm of Maccel C18AQ resin (3 μm, 200 Å, Nest Group). Peptides were separated by applying a gradient from 10 to 35% ACN in 0.125% FA over 170 min. at approximately 250 nl/min. Electrospray ionization was enabled through applying a voltage of 1.8 kV through a PEEK junction at the inlet of the microcapillary column.

The Velos-Orbitrap Elite™ hybrid mass spectrometer was operated in data-dependent mode for both $MS^2$ and $MS^3$ scans. For the $MS^2$ method, the survey scan was performed in the Orbitrap Elite™ in the range of 400-1400 m/z at a resolution of $3\times10^4$, followed by the selection of the ten most intense ions (TOP 10) for CID-$MS^2$ fragmentation using a precursor isolation width window of 2 m/z. The AGC settings were $3\times10^6$ and $2.5\times10^5$ ions for survey and $MS^2$ scans, respectively. Ions were selected for $MS^2$ when their intensity reached a threshold of 500 counts and an isotopic envelope was assigned. Maximum ion accumulation times were set to 1,000 ms for survey MS scans and to 150 ms for $MS^2$ scans. Singly charged ion species and ions for which a charge state could not be determined were not subjected to $MS^2$. Ions within a 10 ppm m/z window around ions selected for $MS^2$ were excluded from further selection for fragmentation for 60 s. In general, the survey $MS^2$ scan settings were identical for the $MS^3$ method, where the ten most intense ions were first isolated for ion trap CID-$MS^2$ at a precursor ion isolation width of 2 m/z, using an AGC setting of $2\times10^3$, a maximum ion accumulation time of 150 ms, and with wide band activation. Directly following each $MS^2$ experiment, ions were selected with an isolation width 2.5 m/z, the MS AGC was $2\times10^5$ and with a maximum ion time of 250 ms. Normalized collision energy was set to 35% and 60% at an activation time of 20 ms and 50 ms for $MS^2$ and $MS^3$ scans, respectively (McAlister et al. (2014) *Anal. Chem.* 86:7150-7158).

iv. Data Processing: MS2 Spectra Assignment, Data Filtering and Quantitative Data Analysis A suite of in-house developed software tools was used to convert mass spectrometric data from the RAW file to the mzXML format, as well as to correct inaccurate assignments of peptide ion charge state and monoisotopic m/z. The ReAdW.exe program was modified to include ion accumulation time in the output during conversion to the mzXML file format (available on the World Wide Web at sashimi.svn.sourceforge.net/viewvc/sashimi/) that had been modified to export ion accumulation times and FT peak noise. Assignment of $MS^2$ spectra was performed using the SEQUEST algorithm by searching the data against a protein sequence database containing all known translated proteins from the mouse UniProt database (downloaded on 08/2013) and known contaminants (porcine trypsin and human keratin). The forward (target) database component was followed by a decoy component including all listed protein sequences in reversed order. Searches were performed using a 25 ppm precursor ion tolerance, where both peptide termini were required to be consistent with trypsin specificity and allowing up to two missed cleavages. TMT tags on lysine residues and peptide N termini (+229.1629 Da) and carbamidomethylation of cysteine residues (+57.0214 Da) were set as static modifications, oxidation of methionine residues (+15.994 Da) as a variable modification. A $MS^2$ spectral assignment false discovery rate of less than 1% was achieved by applying the target-decoy database search strategy. Filtering was performed using a linear discrimination analysis method to create one combined filter parameter from the following peptide ion and $MS^2$ spectra properties: SEQUEST parameters XCorr and ΔCn, peptide ion mass accuracy, charge state and peptide length. Linear discrimination scores were used to assign probabilities to each $MS^2$ spectrum for being assigned correctly and these probabilities were used to filter the dataset with an $MS^2$ spectra assignment false discovery rate to obtain a protein identification false discovery rate of less than 1.0% (Huttlin et al. (2010) *Cell* 143:1174-1189). For quantification, a 0.03 m/z window centered on the theoretical m/z value of each reporter ion was monitored for ions, and the intensity of the signal closest to the theoretical m/z value was used. Reporter ion intensities were denormalized by multiplication with the ion accumulation time for each $MS^3$ spectrum and adjusted based on the overlap of isotopic envelopes of all reporter ions. Intensity distributions of isotopic envelopes were as provided by the manufacturer (Thermo Scientific). The total signal to noise (S/N) intensities across all peptides quantified were summed for each TMT channel, and all intensity values were normalized to account for potentially uneven TMT labeling (total minimum of 100 S/N). The intensities for all peptides of a given protein were summed to derive an overall protein abundance S/N value for each TMT signal (Ting et al. (2011) *Nat. Methods* 8:937-940). Proteins were filtered based on the criteria >1.3 fold enrichment in Prdml6tg conditioned medium (samples in duplicates), >1.3 fold enrichment in Prdml6tg BAT tissues and the presence of a signal peptide (see FIG. 1C for select genes). The values are expressed as fold change over control (wild type).

v. Mass Spectrometry from Slit2-CTF by in-Gel Digestion

In-gel protein tryptic digests were resuspended in 10 μL 1% formic acid, and 4 μL were analyzed by microcapillary liquid chromatography electrospray ionization tandem mass spectrometry (LC-MS/MS). Analyses were done on a LTQ Orbitrap Elite mass spectrometer (Thermo Scientific), an Agilent 1100 Series binary HPLC pump, and a Famos autosampler. Peptides were separated on a 100 μm×28 cm fused silica microcapillary column with an in-house made needle tip. The column was packed with MagicC18AQ $C_{18}$ reversed-phase resin (particle size, 3 μm; pore size, 200 Δ; Michrom Bioresources). Separation was achieved applying a 45 min gradient from 5 to 35% acetonitrile in 0.125% formic acid. The mass spectrometer was operated in a data dependent mode essentially as described previously (Villen and Gygi (2008) Nat. Protoc. 3:1630-1638) with a full MS scan acquired with the Orbitrap, followed by up to 20 LTQ MS/MS spectra on the most abundant ions detected in the MS scan. Mass spectrometer settings were: full MS (AGC, $1\times10^6$; resolution, $6\times10^4$; m/z range, 375-1800; maximum ion time, 1000 ms); MS/MS (AGC, $5\times10^3$; maximum ion time, 120 ms; minimum signal threshold, $4\times10^3$; isolation width, 2 Da; dynamic exclusion time setting, 30 sec). For peptide identification, RAW files were converted into mzXML format and processed using a suite of software tools developed in-house for analysis. All precursors selected for MS/MS fragmentation were confirmed using algorithms to detect and correct errors in monoisotopic peak assignment and refine precursor ion mass measurements. All MS/MS spectra were then exported as individual DTA files and searched using the Sequest algorithm (Eng et al. (1994) *J. Am. Soc. Mass. Spectrom.* 5:976-989). These spectra were then searched non-tryptically against a database containing sequence of mouse Slit2 in both forward and reversed orientations. The following parameters were selected to identify the sequence coverage of slit2: 20 ppm precursor mass tolerance, 0.8 Da product ion mass tolerance, fully tryptic digestion, and up to two missed cleavages. Variable modifications for oxidation of methionine (+15.994915) and a fixed modification for the carbamidomethylation for cysteine (+57.021464) was used as well.

J. Statistical Analysis

All values in graphs are presented as mean+/−s.e.m. The Student's t-test was used for single comparisons. Two-way ANOVA with repeated-measures was used for the GTT studies. The error bars (s.e.m.) shown for all results were derived from biological replicates, not technical replicates. Significant differences between two groups (* p>0.05, ** p >0.01, p >0.001) were evaluated using a two-tailed, unpaired t-test as the sample groups displayed a normal distribution and comparable variance.

K. Representative Brown and Beige Fat Markers

Table 2 below provides representative gene expression markers for brown and/or beige fat. In addition, assays for analyzing quantitative RT-PCR, mitochondrial biogenesis, oxygen consumption, glucose uptake, energy intake, energy expenditure, weight loss, multilocular lipid droplet morphology, mitochondrial content, and the like modulated by Slit2 and exhibited by brown and/or beige fat cells are well known in the art (see, at least Harms and Seale (2013) *Nat. Med.* 19:1252-1263 and U.S. Pat. Publ. 2013/0074199).

TABLE 2

| Gene Symbol | Gene Name | GenBank Gene Accession Number | GenBank Protein Accession Number | Gene ID |
|---|---|---|---|---|
| adipsin | complement factor D | e.g., NM_013459.2 and NM_001928.2 | e.g., NP_038487.1 and NP_001919.2 | e.g., 11537 and 1675 |
| fatty acid transporter cd 36 | fatty acid transporter/cd36 | e.g., NM_007643.3 and NM_000072.3 and NM_001001547.2 and NM_001001548.2 and NM_001127443.1 and NM_001127444.1 | e.g., NP_031669.2 and NP_000063.2 and NP_001001547.1 and NP_001001548.1 and NP_001120915.1 and NP_001120916.1 | e.g., 12491 and 948 |

TABLE 2-continued

| Gene Symbol | Gene Name | GenBank Gene Accession Number | GenBank Protein Accession Number | Gene ID |
|---|---|---|---|---|
| adiponectin | adiponectin | e.g., NM_009605.4 and NM_004797.2 | e.g., NP_0033735.3 and NP_004788.1 | e.g., 11450 and 9370 |
| UCP-1 | uncoupling protein 1 | e.g., NM_009463.3 and NM_021833.4 | e.g., NP_033489.1 and NP_068605.1 | e.g., 22227 and 7350 |
| cidea | cell death-inducing DFFA-like effector a | e.g., NM_007702.2 and NM_001279.3 and NM_198289.2 | e.g., NP_031728.1 and NP_001270. 1 and NP_938031.1 | e.g., 12683 and 1149 |
| PGC1a | Peroxisome proliferative activated receptor, gamma, coactivator 1 alpha | e.g., NM_008904.2 and NM_013261.3 | e.g., NP_032930.1 and NP_037393.1 | e.g., 19017 and 10891 |
| Elovl3 | elongation of very long chain fatty acids (FEN1/Elo2, SUR4/Elo3, yeast)-like 3 | e.g., NM_007703.2 and NM_152310.1 | e.g., NP_031729.1 and NP_689523.1 | e.g., 12686 and 83401 |
| C/EBPbeta | CCAAT/enhancer binding protein beta | e.g., NM_009883.3 and NM_005194.2 | e.g., NP_034013.1 and NP_005185.2 | e.g., 12608 and 1051 |
| Cox7a1 | cytochrome c oxidase subunit VIIa polypeptide 1 | e.g., NM_009944.3 and NM_001864.2 | e.g., NP_034074.1 and NP_001855.1 | e.g., 12865 and 1346 |
| Otopetrin | Otopetrin 1 | e.g., NM_172709.3 and NM_177998.1 | e.g., NP_766297.2 and NP_819056.1 | e.g., 21906 and 133060 |
| Type II deiodinase | Deiodinase, iodothyronine, type II | e.g., NM_010050.2 and NM_000793.4 and NM_001007023.2 and NM_013989.3 | e.g., NP_034180.1 and NP_000784.2 and NP_001007024.1 and NP_054644.1 | e.g., 13371 and 1734 |
| cytochrome C | cytochrome c | e.g., NM_009989.2 and NM_018947.4 | e.g., NP_034119.1 and NP_061820.1 | e.g., 13067 and 54205 |
| cox4i1 | cytochrome c oxidase subunit IV isoform I | e.g., NM_009941.2 and NM_001861.2 | e.g., NP_034071.1 and NP_001852.1 | e.g., 12857 and 1327 |
| coxIII | mitochondrially cencoded cytochrome c oxidase III | e.g., NC_005089.1 and ENST00000362079 | e.g., NP_904334.1 and ENSP00000354982 | e.g., 17705 and 4514 |
| cox5b | cytochrome c oxidase subunit Vb | e.g., NM_009942.2 and NM_001862.2 | e.g., NP_034072.2 and NP_001853.2 | e.g., 12859and 1329 |
| cox8b | cytochrome c oxidase subunit 8B, mitochondrial precursor | e.g., NM_007751.3 | e.g., NP_031777.1 | e.g., 12869 and 404544 |
| glut4 | solute carrier family 2 (facilitated glucose transporter), member 4 | e.g., NM_009204.2 and NM_001042.2 | e.g., NP_033230.2 and NP_001033.1 | e.g., 20528 and 6517 |
| atpase b2 | ATPase, H+ transportying, lysosomal 56/58kDa, V1 subunit B2 | e.g., NM_057213.2 and NM_001693.3 | e.g., NP_476561.1 and NP_001684.2 | e.g., 117596 and 526 |
| coxII | mitochondrially encoded cytochrome c oxidase II | e.g., NC_005089.1 and ENST00000361739 | e.g., NP_904331 and ENSP00000354876 | e.g., 17709 and 4513 |
| atp5o | ATP synthase, H+ transporting, mitochondrial F1 complex, O subunit | e.g., NM_138597.2 and NM_001697.2 | e.g., NP_613063.1 and NP_001688.1 | e.g., 28080 and 539 |
| ndufb5 | NADH dehydrogenase (ubiquinone) 1 beta subcomplex, 5, 16kDa | e.g., NM_025316.2 and NM_002492.2 | e.g., NP_079592.2 and NP_002483.1 | e.g., 66046 and 4711 |
| Rarres2 | retinoic acid receptor responder (tazarotene induced) 2 | e.g., NM_027852.2 and NM_002889.3 | e.g., NP_082128.1 and NP_002880.1 | e.g., 71660 and 5919 |
| Car3 | carbonic anhydrase 3 | e.g., NM_007606.3 and NM_005181.3 | e.g., NP_031632.2 and NP_005172.1 | e.g., 12350 and 761 |
| Peg10 | paternally expressed 10 | e.g., NM_001040611.1 and NM_001040152.1 and NM_001172437.1 and NM_001172438.1 and NM_015068.3 | e.g., NP_001035701.1 and NP_001035242.1 and NP_001165908.1 and NP_001165909.1 and NP_055883.2 | e.g., 170676 and 23089 |
| Cidec | Cidec cell death-inducing DFFA-like effector c | e.g., NM_178373.3 and NM_022094.2 | e.g., NP_848460.1 and NP_071377.2 | e.g., 14311 and 63924 |
| Cd24a | CD24a antigen | e.g., NM_009846.2 and NM_013230.2 | e.g.. NP_033976.1 and NP_037362.1 | e.g., 12484 and 100133941 |
| Nr1d2 | nuclear receptor subfamily 1, group D, member 2 | e.g., NM_011584.4 and NM_001145425.1 and NM_005126.4 | e.g., NP_035714.3 and NP_001138897.1 and NP_005117.3 | e.g., 353187 and 9975 |

TABLE 2-continued

| Gene Symbol | Gene Name | GenBank Gene Accession Number | GenBank Protein Accession Number | Gene ID |
|---|---|---|---|---|
| Ddx17 | DEAD (Asp-Glu-Ala-Asp) box polypeptide 17 | e.g., NM_001040187.1 and NM_001098504.1 and NM_001098505.1 and NM_006386.4 and NM_030881.3 | e.g., NP_001035277.1 and NP_001091974.1 and NP_001091975.1 and NP_006377.2 and NP_112020.1 | e.g., 67040 and 10521 |
| Aplp2 | amyloid beta (A4) precursor-like protein 2 | e.g., NM_001102455.1 and NM_901142276.1 and NM_001142277.1 and NM_001142278.1 and NM_001642.2 | e.g., NP_101095925.1 and NP_001135748.1 and NP_001135749.1 and NP_001135750.1 and NP_001633.1 | e.g., 11804 and 334 |
| Nr3c1 | nuclear receptor subfamily 3, group C, member 1 | e.g., NM_008173.3 and NM_000176.2 and NM_001018074.1 and NM_001018075.1 and NM_001018076.1 and NM_001018077.1 and NM_001020825.1 and NM_001024094.1 | e.g., NP_032199.3 and NP_0001167.1 and NP_001018084.1 and NP_001018085.1 and NP_001018086.1 and NP_001018087.1 and NP_001018661.1 and NP_001019265.1 | e.g., 14815 and 2908 |
| Rybp | RING1 and YY1 binding protein | e.g., NM_019743.3 and NM_012234.4 | e.g., NP_062717.2 arid NP_036366.3 | e.g., 56353 and 23429 |
| Txnip | thioredoxin interacting protein | e.g., NM_001009935.2 and NM_006472.3 | e.g., NP_001009935.1 and NP_006463.3 | e.g., 56338 and 10628 |
| Cig30 | Elongation of very long chain fatty acids-like 3 | e.g., NM_152310.1 and NM_007703.1[1] | e.g., NP_689523.1 and NP_031729.1[1] | e.g., 83401 and 12686 |
| Ppar gamma 2 | Peroxisome proliferator-activated receptor gamma 2 | e.g., NM_015869.4 and NM_011146.2[1] | e.g., NP_056953 and NP_035276.1[1] | e.g., 5468 and 19016 |
| Prdm16 | PR domain containing 16 protein | e.g., NM_022114.3 and NM_199454.2 and NM_027504.3 | e.g., NP_071397.3 and NP_955533.2 and NP_081780.3 | e.g., 63976 and 70673 |
| Ap2 | Fatty acid binding protein 4 | e.g., NM_001442.2 and NM_024406.1 | e.g., NP_001433.1 and NP_077717.1 | e.g., 2167 and 111770 |
| Ndufs2 | NADH dehydrogenase (ubiquinone) Fe—S protein 2, 49kDa (NADH-coenzyme Q reductase | e.g., NM_00166159.1 and NM_004550.4 and NM_153064.4 | e.g., NP_001159631.1 and NP_004541.1 and NP_694704.1 | e.g., 4720 and 226646 |
| Grp109A | Hydroxycarboxylic acid receptor 2 | e.g., NM_177551 and NM_030701.3 | e.g., NP_808219 and NP_109626.1 | e.g., 338442 and 80885 |
| Acy1CoA-thioesterase 4 | Acy1-coenzyme A thioesterase 4 | e.g., NM_152331 and NM_134247.3 | e.g., NP_689544 and NP_599008.3 | e.g., 122970 and 171282 |
| Claudin1 | Claudin1 | e.g., NM_021101.4 and NM_016674.4 | e.g., NP_066924.1 and NP_057883.1 | e.g., 9076 and 12737 |
| PEPCK | Phosphocnolpyruvate carboxykinase (mitochondrial) | e.g., NM_001018073.1 and NM_004563.2 and NM_028994.2 | e.g., NP_001018083.1 and NP_004554.2 and NP_083270.1 | e.g., 5106 and 74551 |
| Fgf21 | Fibroblast growth factor 21 | e.g., NM_0191113 and NM_020013.4 | e.g., NP_061986 and NP_064397.1 | e.g., 26291 and 56636 |
| AcyCoA-thioesterase 3 | Acy1-coenzyme A thioesterase 4 | e.g., NM_00103716.1 and NM_134246.3 | e.g., NP_001032238.1 and NP_599007.1 | e.g., 641371 and 171281 |
| Dio2 | Type II iodothyronine deiodinase | e.g., NM_00793.5 and NM_010050.2 | e.g., NP_000784.2 and NP_034180.1 | e.g., 1734 and 13371 |

L. Cell Surface Staining of Slit2-C Using Confocal Laser Scanning Microscopy

Live, primary differentiated adipocytes were incubated with recombinant Slit2-C FLAG-tagged protein for 1 h at 4° C. before fixation and staining with a fluorescent antibody for visualization of cell-surface bound proteins using a confocal laser scanning microscope.

Experiments were performed using a Nikon Ti w/A1R confocal inverted microscope equipped with a Nikon Plan Apo 60x/NA 1.4 oil immersion objective lens using excitation wavelengths of 405 and 561 nm. All experiments were performed under confocal imaging conditions (pinhole <1 airy unit) and images taken with the same laser settings. Image analysis was performed using the Nikon Elements acquisition software. Primary inguinal cells differentiated until day 5 was gently trypsinized and seeded onto poly-D-lysine-coated coverslips (Corning Biocoat 12 mm German Glass coverslips, #08-774-385) in a 6-well plate at a density of 10,000 cells per well in growth medium. On the next day, cell surface binding was performed by adding 1 μg/ml purified protein to cells or FLAG peptide in PBS in serum-containing medium for 1 h at 4° C. on ice. Cells were washed three times in PBS, fixed in 4% paraformaldehyde for 10 min at 4° C., and washed with PBS three times before blocking with 5% BSA in PBS for 1 h at room temperature. Cells treated with protein or FLAG peptide alone were stained using 1:200 anti-Flag M2-HRP overnight at 4° C. Cells were washed with 5% BSA in PBS three times 10 min and stained with Alexa Fluor 568 goat-anti-mouse (10 μg/ml, A-11031, Invitrogen) and 1 μg/ml of nuclear stain (Hoechst33342, Invitrogen) for 30 min at room temperature. Cells were washed three times in 5% BSA in PBS before being mounted on glass slides using a water-based fluorescent mounting medium.

Example 2: Slit2 is a Factor Secreted from Beige Adipose Cells

Figure 1B:
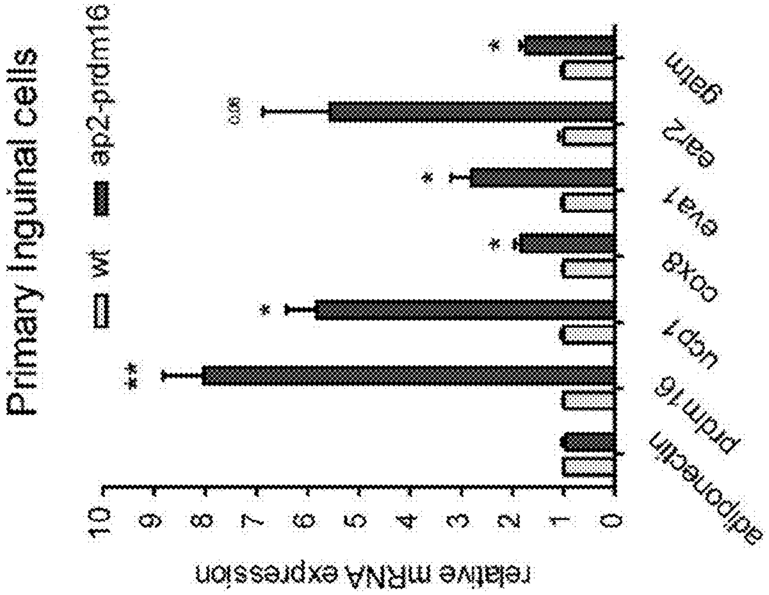
Figure 1C:
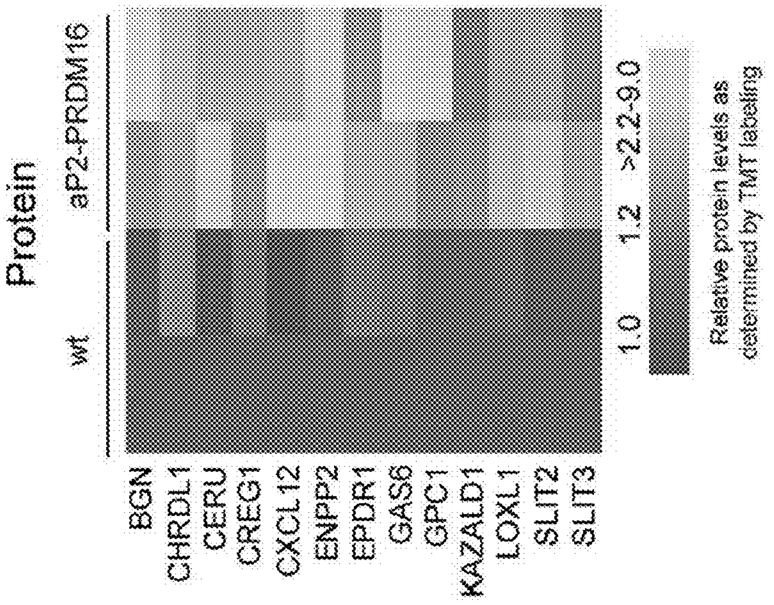
Figure 2C:
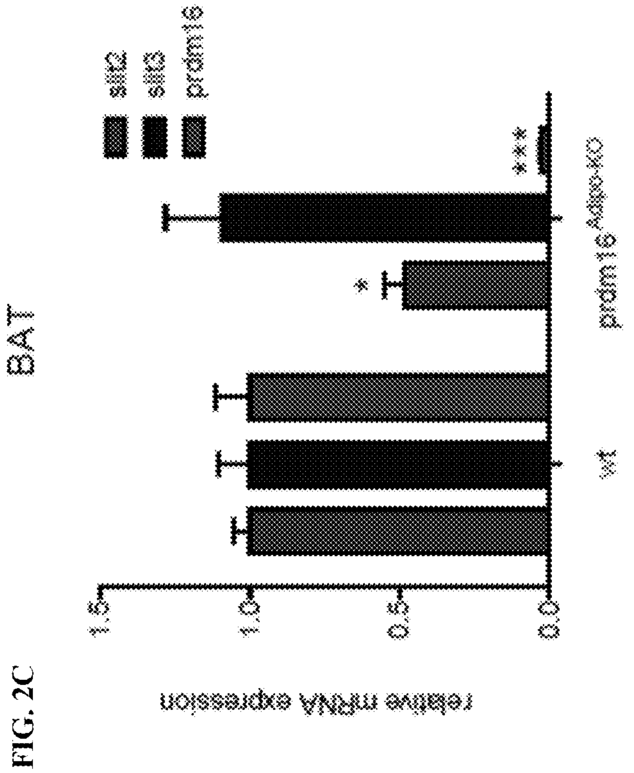
FIG. 2 includes 7 panels, identified as panels A, B, C, D, E, F, and G, which further show that Slit2 is a PRDM16-regulated secreted protein in adipose cells. Panel A shows peptides (bold text) corresponding to mouse Slit2 and Slit3 detected in conditioned medium from aP2-PRDM16 inguinal cells. Panels B and C show the normalized mRNA expression of Slit2, Slit3, and Prdm16 in brown fat tissue (BAT) from aP2-PRDM16 mice (Panel B) and adipocyte-specific deletion of PRDM16 ($prdm16^{adipo-KO}$) (Panel C). Panels D and E show tissue mRNA expression of Slit2 (Panel D) and Slit3 (Panel E) in 6 week old C57/b6 mice. Panel F shows normalized mRNA expression of Slit2 and Ucp1 in iWAT, eWAT and BAT after 3 days treatment with daily injections of CL 316,243 (1 mg/kg). Panel G shows normalized mRNA expression of Slit2 and Slit3 in BAT in lean mice or 16 weeks C57/b6 high fat diet mice.
Figure 2B:
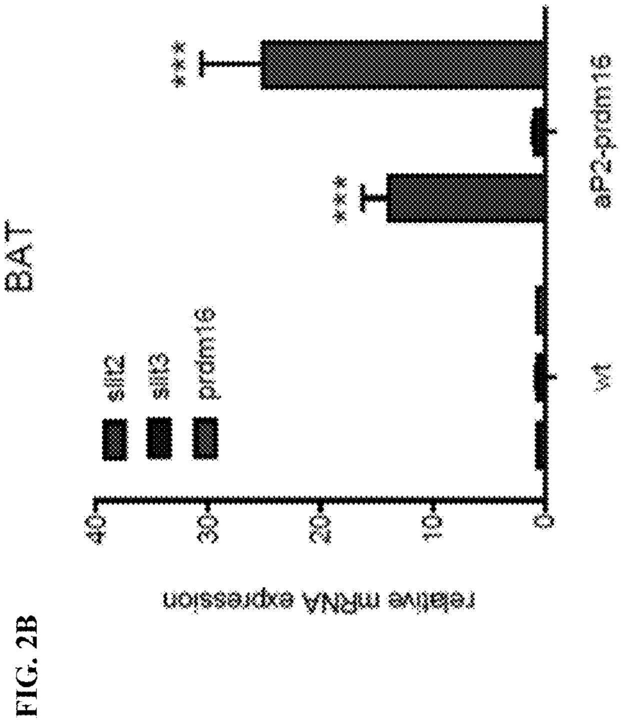

In order to identify factors secreted from beige adipocytes, the aP2-PRDM16 transgenic mouse model was used as a discovery tool. As reported previously in Seale et al. (2011) *J. Clin. Invest.* 121:96-105, aP2-PRDM16 mice have much more beige fat in vivo, as indicated by the increased number of multilocular, UCP1-positive cells in their inguinal fat pad (iWAT) (FIG. 1A). Primary cultures of inguinal adipocytes from aP2-PRDM16 mice also show much higher expression of thermogenic genes such as Prdm16, Ucp1 and Cox8. In addition, the previously identified beige and brown markers Eval, Ear2 (Wu et al. (2012) *Cell* 150:366-376) and the beige-enriched mitochondrial marker Gatm (Kazak et al. (2015) *Cell* 163:643-655) are elevated at the mRNA level compared to inguinal cultures from wild-type littermates (FIG. 1B). These data indicate that primary aP2-PRDM16 cultures are enriched in beige adipocytes. On day 6 of differentiation, when cultures were visibly differentiated more than 90%, serum-free conditioned media was collected for 24 h from aP2-PRDM16 and wild-type iWAT adipocytes. These supernatants were then analyzed by unbiased quantitative proteomics, using the TMT tagging method (see Example 1I). A total of 5,360 proteins were identified in this experiment, of which ~1260 were enriched in aP2-PRDM16 by more than >1.3 fold versus the wild-type adipocytes. Several criteria were established for prioritizing these candidates, including the presence of a signal peptide in the annotated gene and regulation by PRDM16 in tissues (see Example 1). This yielded a shortlist of 13 proteins of potential interest (FIG. 1C). Of these prioritized candidates, two belonged to the same family of *Drosophila* Slit homologs of extracellular proteins (Slit2 and Slit3). Multiple peptides from Slit2 and Slit3 were detected in conditioned medium from the beige cells (FIG. 2A) and tissues from aP2-PRDM16 and adipocyte-specific deletion of PRDM16 also indicated that Slit2 was a factor secreted from thermogenic adipocytes both in vitro and in vivo (FIGS. 2B-2C).

Figure 1D:
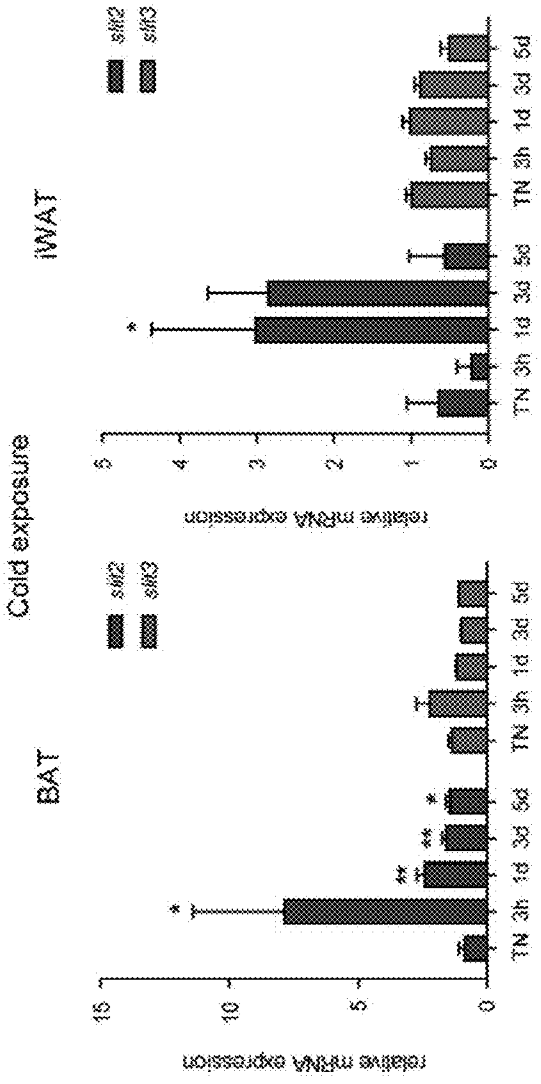
Figure 1E:
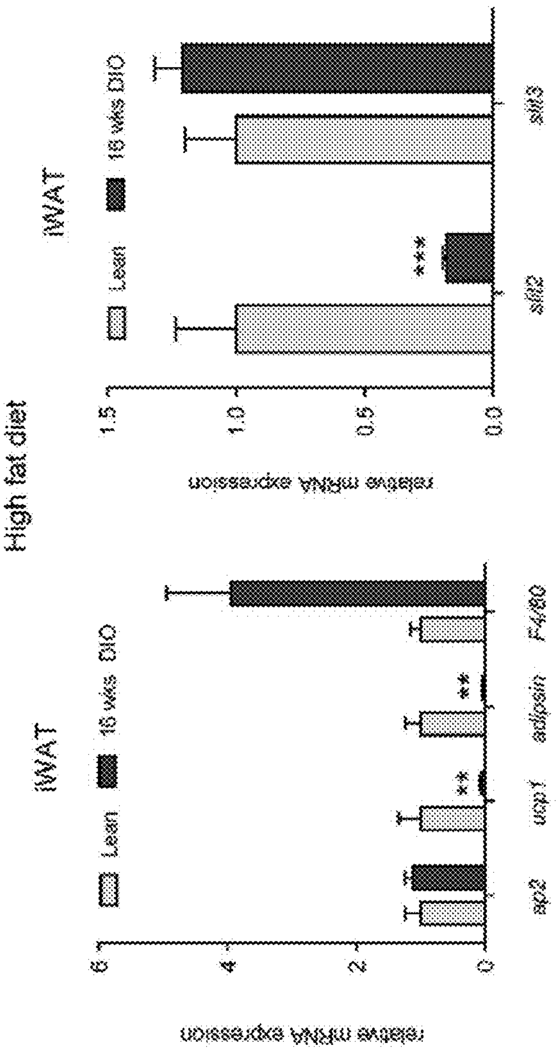
Figure 1G:
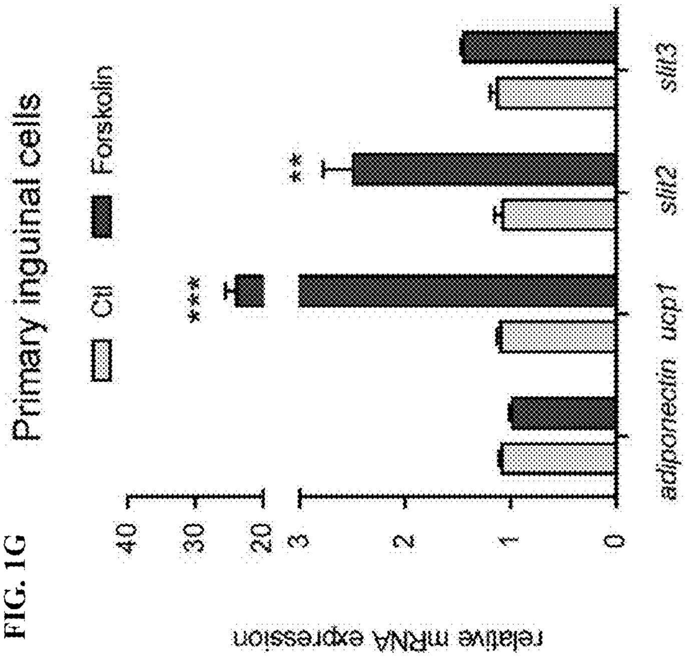
Figure 1F:
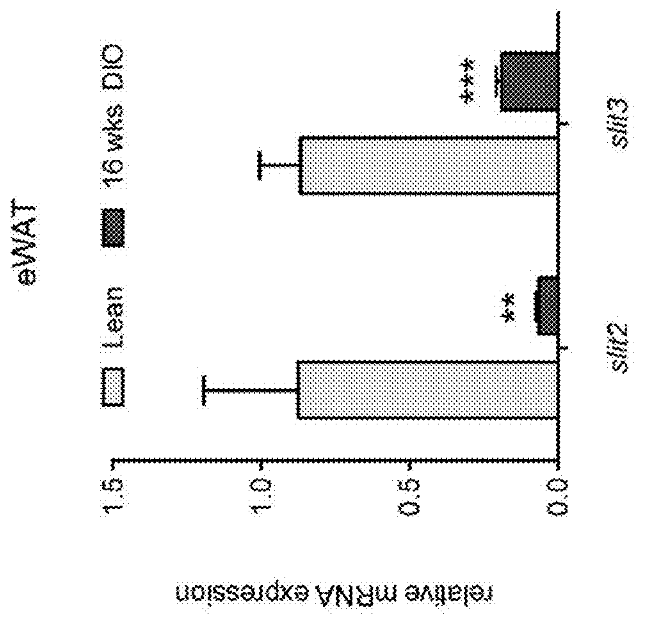
Figure 2D:
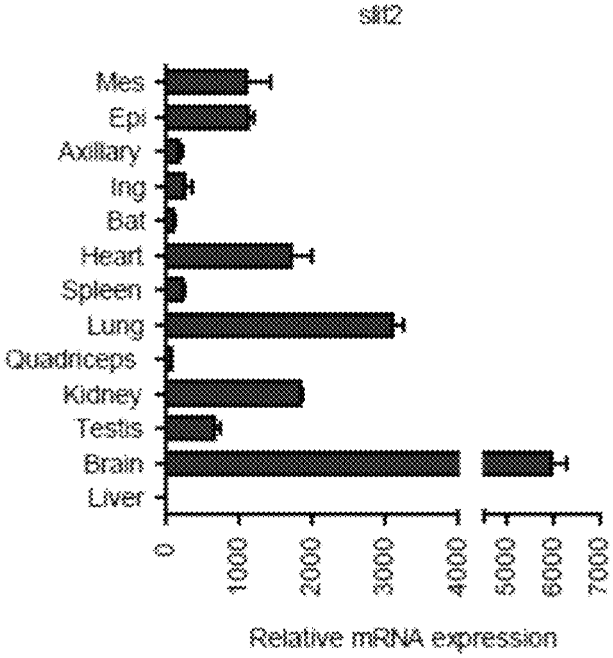
Figure 2E:
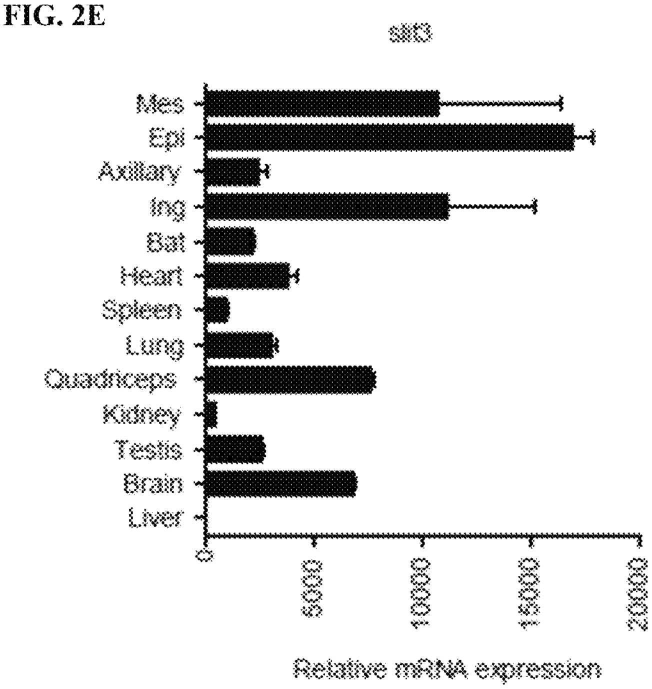
Figure 2G:
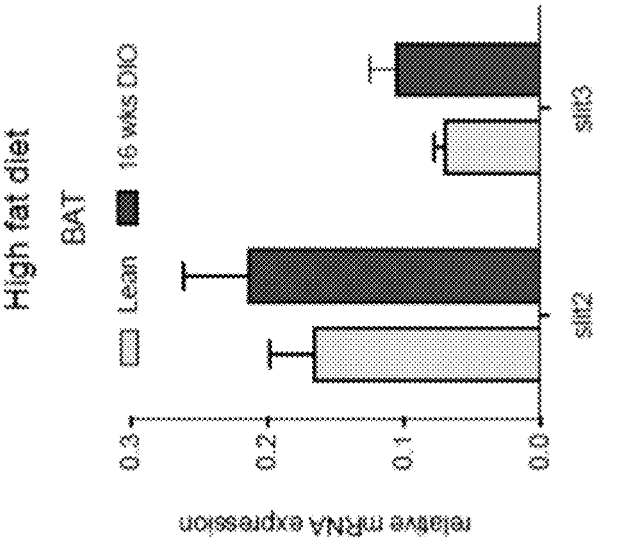
Figure 2F:
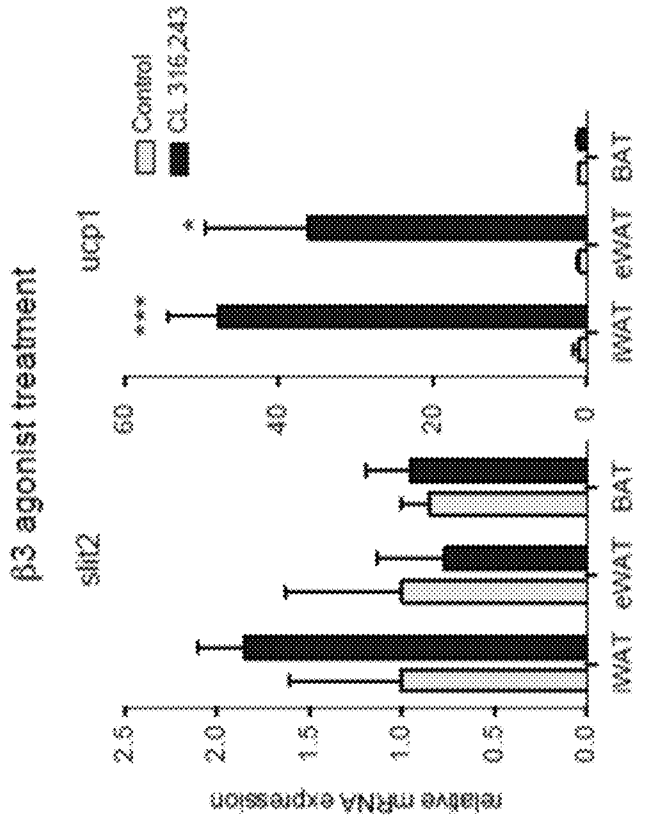

The Slit family in mouse and humans comprises three members—Slit1, Slit2 and Slit3. Slits are all extracellular matrix proteins of approximately 180 kDa with a 29 amino acid signal peptide for classical secretion. They have mainly been studied in the context of their important role in brain development (Brose et al. (1999) *Cell* 96:795-806; Nguyen et al. (1999) *Neuron* 22:463-473; Wang et al. (1999) *Cell* 96:771-784). Despite the broad tissue expression pattern of Slit2 and Slit3, none of the Slit proteins have been described to be present or functionally active in adult peripheral tissues. In order to investigate the function of the Slit members in the periphery, their expression and regulation in adipose tissues was analyzed. Slit2 and Slit3 mRNAs were present in all adipose tissues (FIGS. 1D and 2D-2E). Moreover, the mRNA expression of Slit2, but not Slit3, is also inducible in fat by actue but not long-term cold exposure in BAT and iWAT and suppressed by high fat diet (FIGS. 1D-1F). There was a trend to an increase in Slit2 gene expression in iWAT after 3 days treatment with the β-adrenergic agonist CL316, 243, but this did not reach statistical significance (FIG. 2F). This might be explained by a rapid desensitization mechanism upon long-term activation of cAMP, similar to the transient upregulation of Slit2 mRNA seen upon cold exposure (FIG. 1D). Interestingly, the expression of Slit2 is suppressed in iWAT in diet-induced obese mice that also presents very low Ucp1 and Adipsin mRNA levels (FIG. 1E). Slit2 mRNA is also downregulated in epididymal WAT (eWAT) (FIG. 1F) but not in classical BAT (FIG. 2G), suggesting distinct mechanisms of transcriptional regulation. In addition, Slit2 is induced in inguinal cells upon stimulation with the cyclic AMP-activator forskolin (FIG. 1G). These data point to a physiologic regulation of Slit2 in adipose cells and tissues and are suggestive of a link between Slit2 and thermogenic function.

Example 3: Slit2 Promotes a Thermogenic Program in Cells and in Mice

Figure 3A:
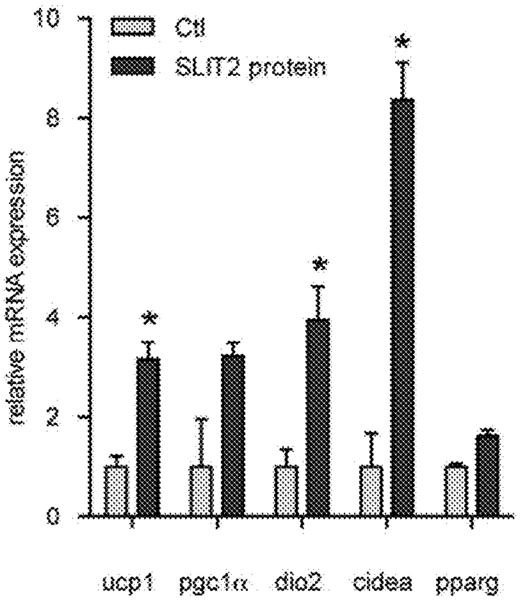
FIG. 3 includes 10 panels, identified as panels A, B, C, D, E, F, G, H, I, and J which show that Slit2 promotes a thermogenic program in cells and in mice. Panels A and B show thermogenic gene expression in primary inguinal cells treated for 24 h with 1 μg/ml of Slit2 (Panel A) or lysyl oxidase (LOX1), glypican1 (GPC1), chordin-like 1 (CHL1) or C-X-C motif chemokine 12 (CXCL12) recombinant proteins (Panel B) at day 6 of differentiation. Panel C shows the results of Western blotting against Slit2 in primary inguinal cells overexpressing full length Slit2 in adenoviral vectors. Panel D shows normalized thermogenic mRNA expression in primary inguinal cells overexpressing adenoviral full length Slit2 (Slit2-FL) or lacZ control. Panel E shows the results of C57/BL6 mice injected (i.v.) with adenoviral vectors Slit2-FL or LacZ (n=3) and Western blotting against Slit2 from plasma of these mice obtained at day 7 post-injection. Panel F shows normalized iWAT mRNA expression of thermogenesis genes and white fat selective genes at day 7 post-injection. Panel G shows representative images from UCP1 immunohistochemistry on sections of inguinal subcutaneous adipose tissue from mice injected with Slit2-FL or LacZ at day 7. Images are shown at 10× magnification. Scale bar, 100 μm. Panel H shows Western blotting against Slit2 in primary inguinal cells from $Slit2^{flox/flox}$ mice transduced with LacZ virus ($Slit2^{flox/flox}$) or Cre virus ($Slit2^{KO}$). Panel I shows gene expression in primary inguinal cells from $Slit2^{flox/flox}$ mice transduced with LacZ virus ($Slit2^{flox/flox}$) or CRE virus ($Slit2^{KO}$). Panel J shows gene expression in BAT tissue from Slit2flox/flox mice infected with GFP-AAV8 ($Slit2^{flox/flox}$-AAV8-GFP) or Cre virus ($Slit2^{flox/flox}$-AAV8-CRE).
Figure 3B:
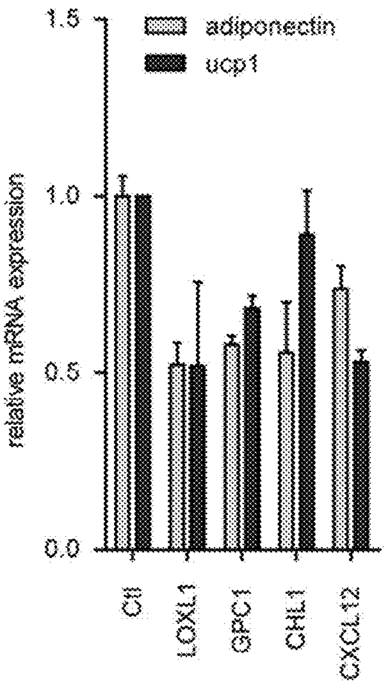
Figure 3C:
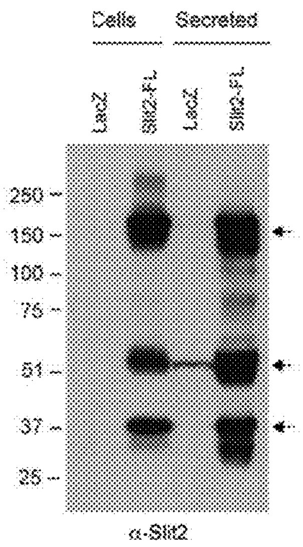
Figure 3D:
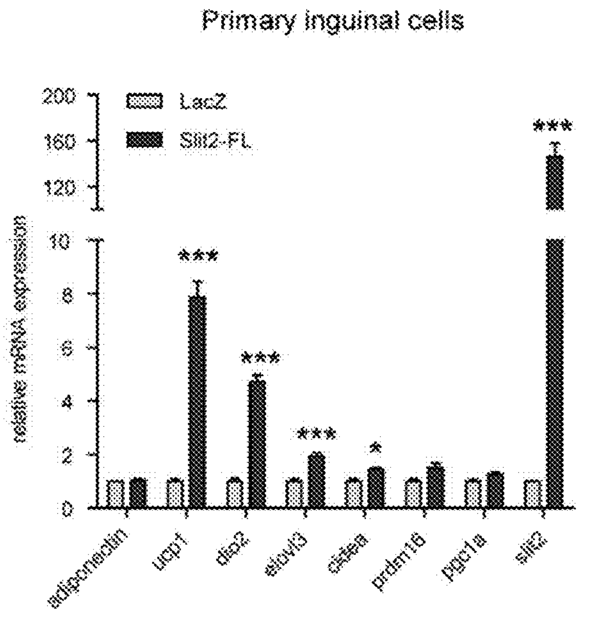

In order to assess whether Slit2 promotes thermogenesis in cultured cells, fully differentiated primary inguinal adipocytes were treated with recombinant Slit2 protein (1 μg/ml, 24 hours). Commercial recombinant Slit2 treatment induced an increase of ~3-fold in Ucp1 mRNA, as well as large increases in expression of other genes associated with thermogenesis, including Dio2 and Cidea (FIG. 3A). Importantly, recombinant protein treatment using several of the other 13 high-priority candidates (as commercially available recombinant proteins) did not produce a thermogenic response (FIG. 3B). As a complementary approach for Slit2, primary inguinal adipocytes were treated on day 2 of differentiation with adenoviruses expressing full-length Slit2 or lacZ control, and the cells were analyzed on day 7. Consistent with the recombinant protein treatment, ectopic expression of Slit2 robustly induced a thermogenic gene program leading to an 8-fold increase in Ucp1 mRNA and 2- to 5-fold elevations in Dio2, Elovl3, and cidea (FIG. 3D). Western blotting using an antibody against Slit2 revealed the expression of full-length Slit2 (180 kDa), but also several additional cleavage products, including prominent bands migrating at ~50 kDa and ~37 kDa (FIG. 3C).

Figure 3E:
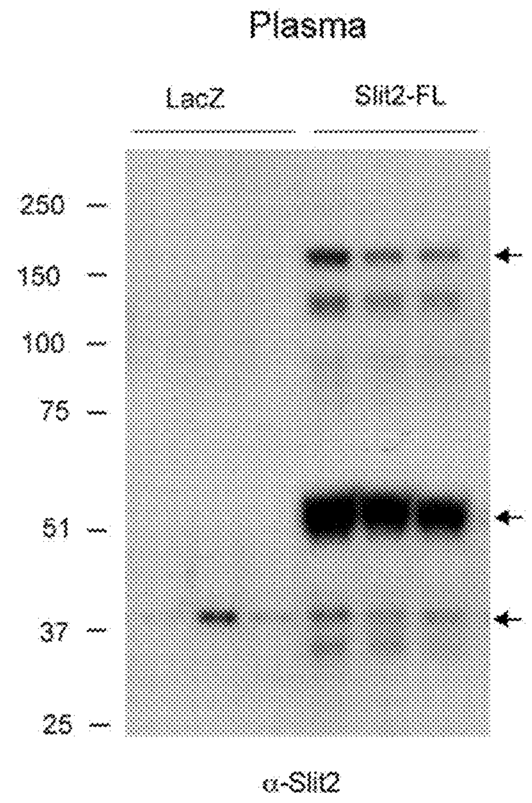
Figure 3F:
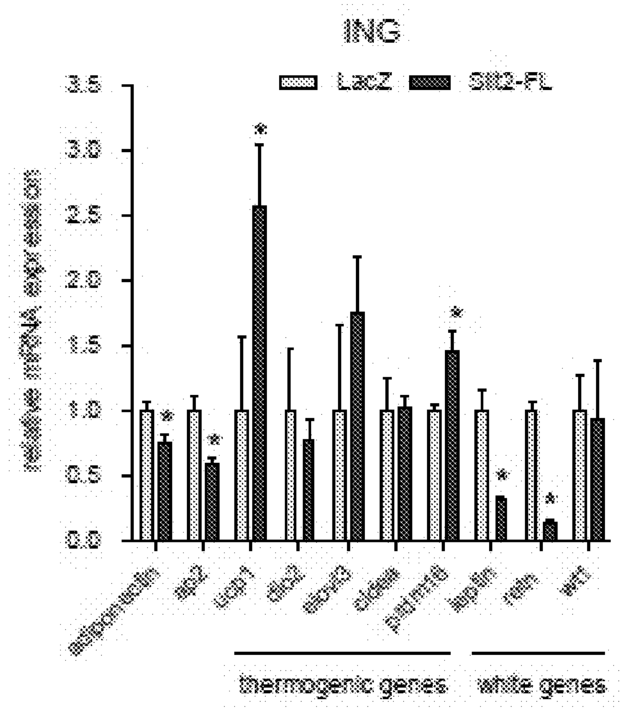
Figure 3G:
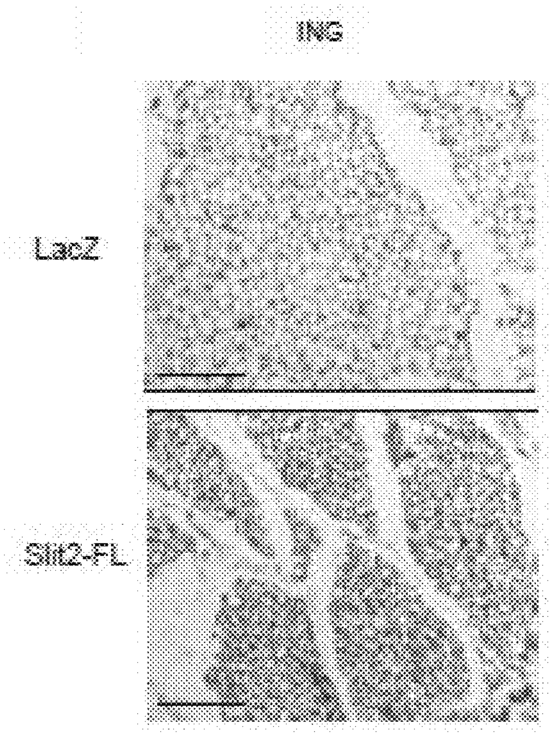
Figure 3H:
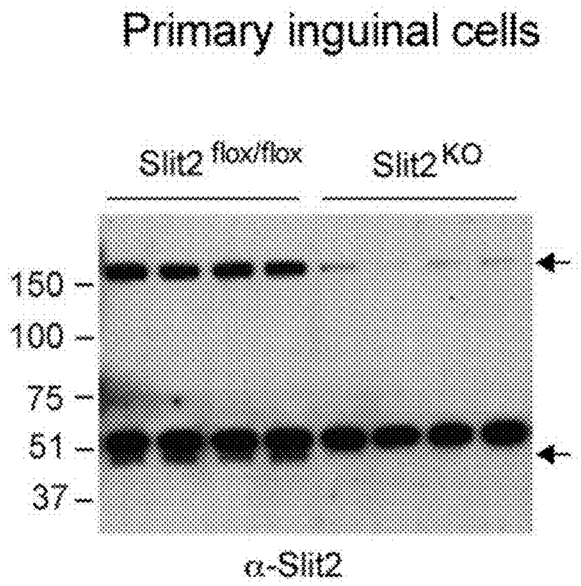
Figure 3I:
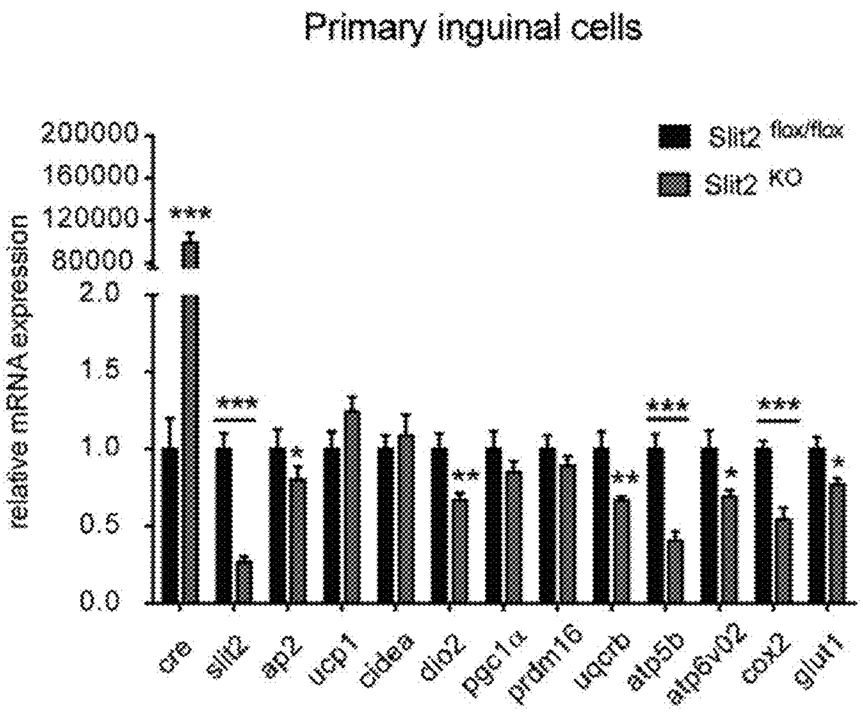
Figure 3J:
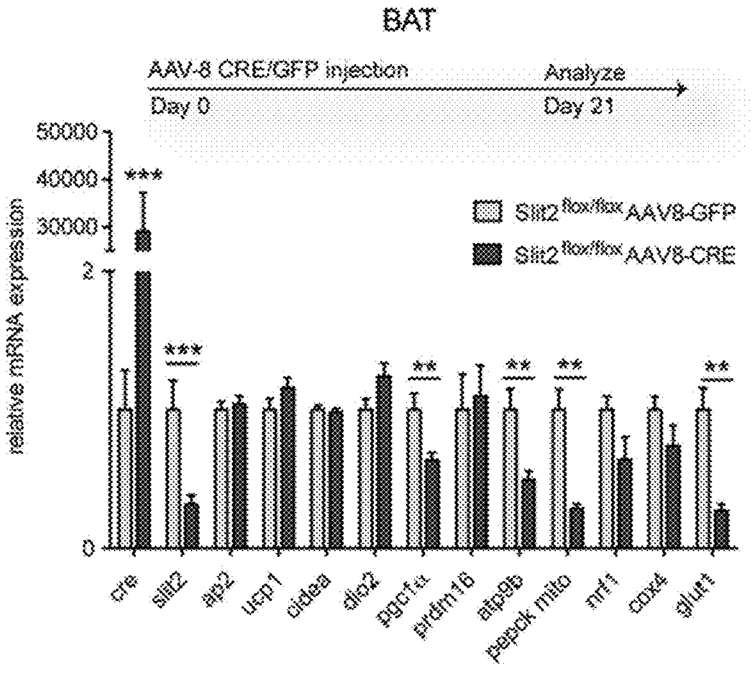
Figures 12A, 12B, 12C:
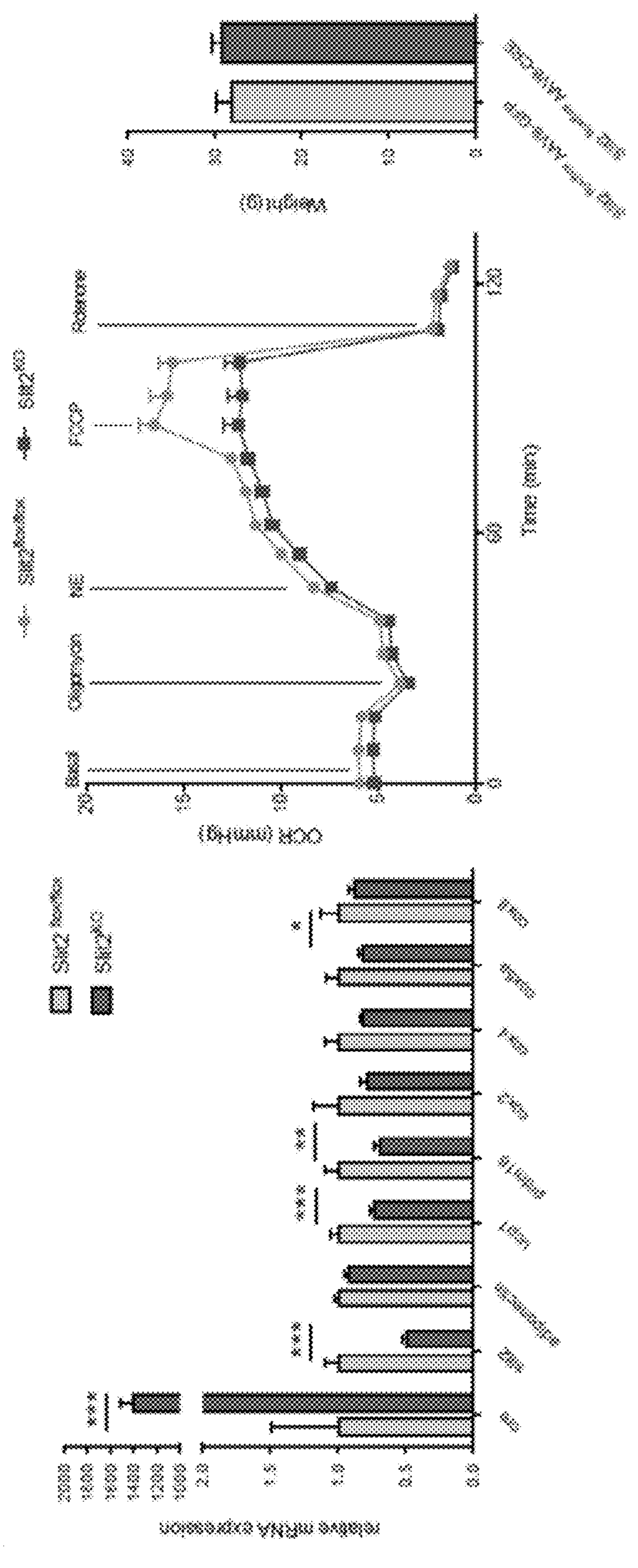

In order to determine whether Slit2 contributes to physiological browning, floxed SLIT2 mice were imported. These animals are on a mixed genetic background and hence are not suitable for metabolic analyses (Rama et al. (2015) *Nat. Med.* 21:483-491). Nevertheless, primary adipocytes from $Slit2^{flox/flox}$ mice were generated and both the full length and the cleaved 50 kDa form of Slit2 were deleted using adenovirus-mediated Cre expression (FIG. 3H). This resulted in a reduction in thermogenic gene expression and expression of mitochondrial genes in both primary inguinal fat cells and primary brown fat cells (FIG. 3I and FIG. 12A). In primary brown fat cells, loss of Slit2 results in reduced oxygen consumption (FIG. 12B). To understand the molecular relevance of Slit2 in vivo, injection of Cre recombinase driven by an AAV vector (AAV-8-CRE) was used for 3 weeks, which reduced endogenous Slit2 levels in the brown fat by 70%. This resulted in a significant reduction in Ucp1 expression and also reductions in expression of several other mitochondrial genes in this tissue (FIG. 3J) without any difference in weight loss between the groups (FIG. 12C). Together these experiments suggest that Slit2 is involved in regulation of thermogenic gene expression in vivo.

Figure 4A:
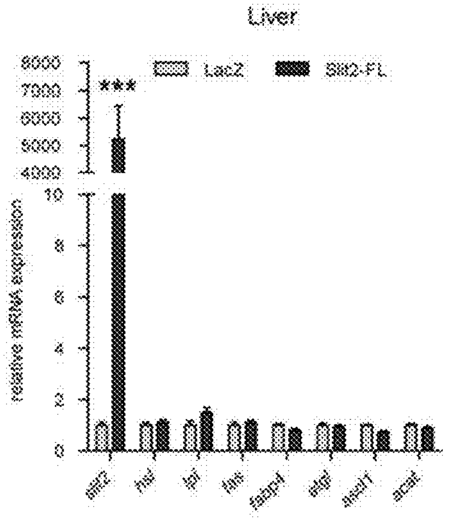
FIG. 4 includes 6 panels, identified as panels A, B, C, D, E and F, which further show that Slit2 promotes a thermogenic program in cells and in mice. Panels A-C show mRNA expression in liver (Panel A), quadriceps (Panel B) and brown fat (Panel C) in mice overexpressing LacZ or Slit2-FL. Panel D shows representative images from UCP1 immunohistochemistry on sections of BAT from mice injected with Slit2-FL or LacZ control at day 7. Images are shown at 10× magnification. Scale bar, 100 μm. Panel E shows normalized mRNA expression levels in iWAT (K) at day 7 postinjection. Panel F shows representative images from UCP1 immunohistochemistry of iWAT from C57/b6 mice injected with Slit2-FL or LacZ at day 7. Scale bar, 100 μm. Data are presented as mean±SEM. * $p<0.05$,  $p<0.01$, * $p<0.001$.
Figure 4B:
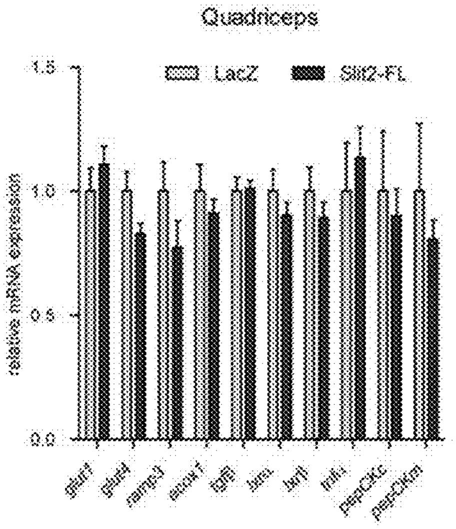
Figure 4C:
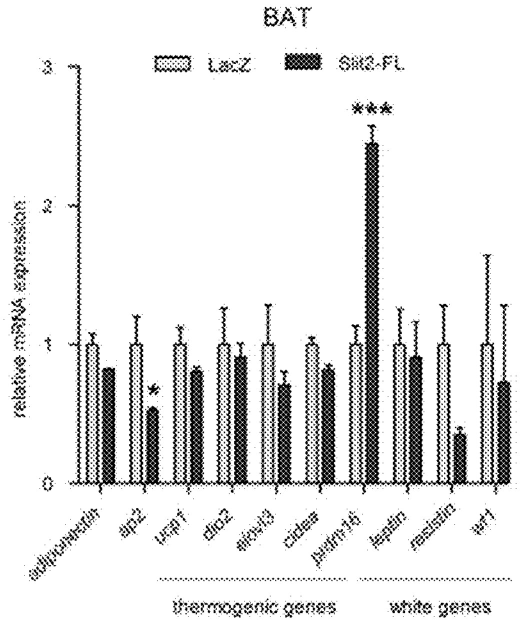
Figure 4D:
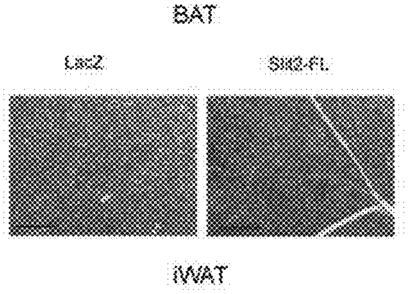
Figure 4E:
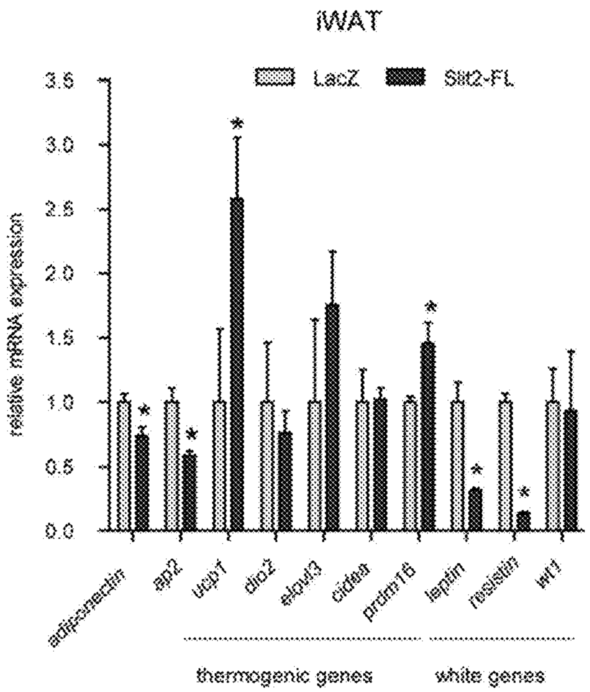
Figure 4F:
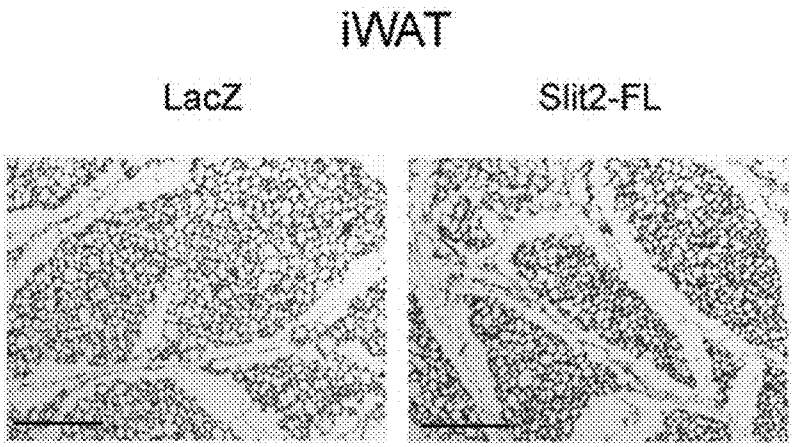
Figure 12F:
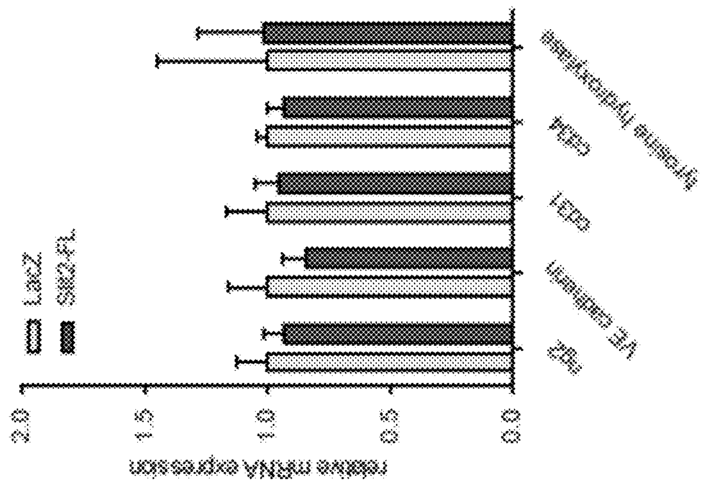
Figure 12E:
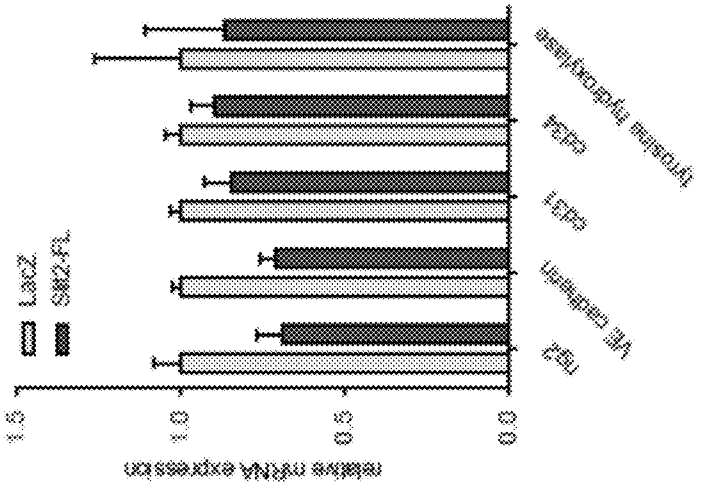
Figure 12D:
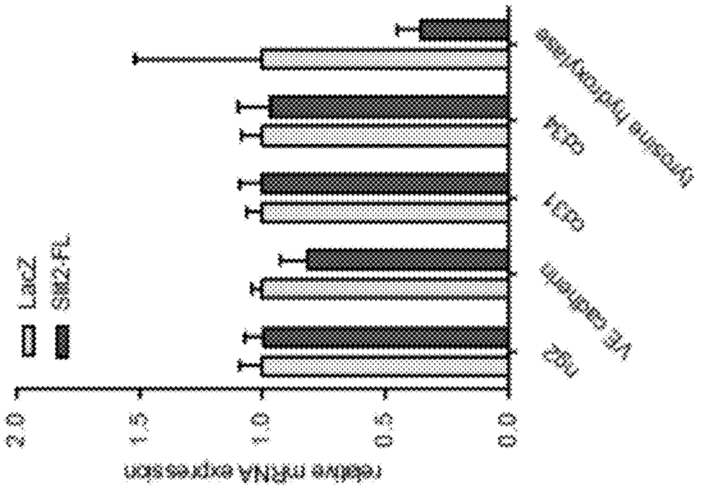

In order to investigate the capacity of pharmacological levels Slit2 to induce browning in vivo, either LacZ or Slit2 was overexpressed by intravenous delivery of adenovirus to lean mice. This protocol resulted in robust expression and secretion of Slit2 from the liver (FIGS. 3E and 4A). Western blotting of the plasma from LacZ- or Slit2-treated mice at 7-days post-injection demonstrated multiple Slit2 fragments secreted into the circulation, including a prominent ~50 kDa fragment similar or identical to the 50 kDa band also observed in cultured cells (FIG. 3E). No changes in lipolysis or lipogenesis gene expression were seen in the liver (FIG. 4A). In skeletal muscle, no gene expression changes in glucose transporters Glut1 and Glut4 or the inflammatory gene Tnfawere observed (FIG. 4B). In contrast, and consistent with the in vitro data, circulating Slit2 induced a thermogenic gene expression program in the iWAT, with a 2.5-fold induction of Ucp1 in iWAT and 1.5-fold induction of Prdm16 (FIG. 4E). Circulating Slit2 induced a thermogenic gene expression program with a 2-fold induction of Ucp1 and Elovl3 in inguinal adipose tissue (FIG. 3F). By contrast, white fat selective genes, including Leptin and Resistin, were strongly suppressed by circulating Slit2 (FIG. 4E). No obvious changes in hepatic lipolysis or lipogenesis gene expression was observed (FIG. 4A). In skeletal muscle, no gene expression changes in glucose transporters Glut1 and Glut4 or the inflammatory gene TNFα was seen (FIG. 4B). Consistent with the increase of Ucp1 mRNA, iWAT UCP1 protein was also increased as shown in histological sections stained with an antibody against UCP1 (FIGS. 3G, 4D, and 4F). Circulating Slit2 induced PRDM16 greater than 2-fold in brown fat without any changes in the other thermogenic genes or UCP1 protein (FIGS. 4D-4E); however the tissue had a more dense looking appearance (FIG. 4C, 4D, 4F). Circulating Slit2 did not change any of the vascular and neuronal markers in fat or in skeletal muscle (FIGS. 12D-12F). Taken together, these results demonstrate that ectopic expressed Slit2 in circulation promotes a thermogenic program in cultured adipocytes and adipose tissues.

Example 4: Identification and Characterization of a Slit2 Cleavage Fragment

Figures 5A, 5B, 5C, 5D, 5E, 5F:
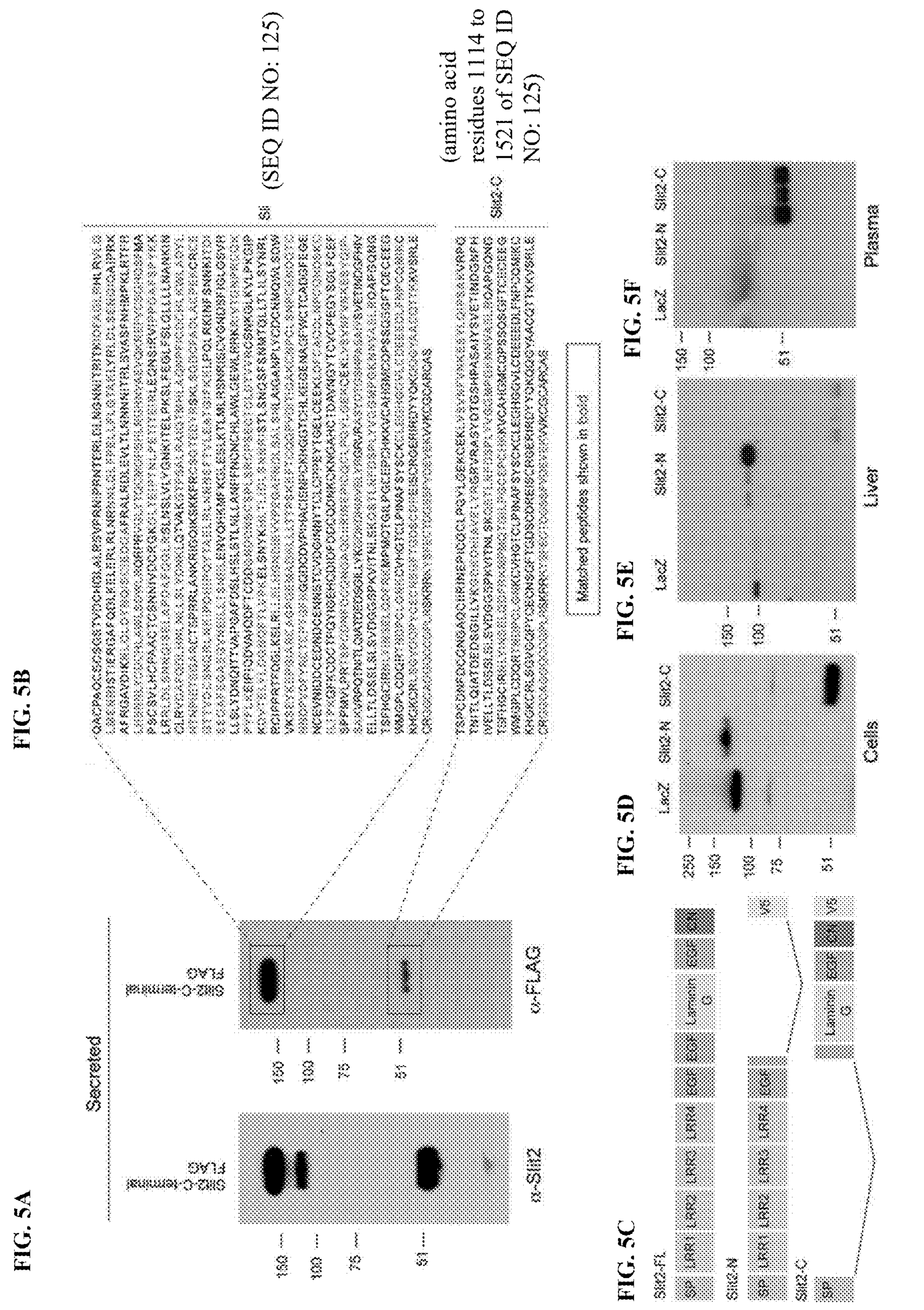
FIG. 5 includes 6 panels, identified as panels A, B, C, D, E, and F, which identify and characterize a Slit2 cleavage fragment. Panel A shows a Western blot of overexpressed full-length C-terminal FLAG-tagged Slit2 detected with a Slit2 antibody (left) and an anti-FLAG antibody (right).

It was believed that the ~50 kDa cleavage product observed from full-length Slit2 expression represented a bioactive, thermogenic fragment of full-length Slit2. It was sought to characterize its molecular identity in more detail. However, commercially available anti-Slit2 antibodies were not effective for immunoaffinity purification of Slit2 from the conditioned media. As an alternative strategy, adenoviruses that express full-length Slit2 with a FLAG-tagged at the C-terminus (Slit2-CTF) were generated. Primary inguinal cultures were transduced with Slit2-CTF on day 2 and serum-free conditioned media was collected between days 6 and 7. Western blotting of conditioned media from Slit2-CTF-transduced adipocytes showed secretion of full-length Slit2 (~180 kDa), as well as fragments corresponding to ~140 kDa and ~50 kDa when using an anti-Slit2 antibody (FIG. 5A, left panel). Notably, the ~50 kDa fragment was also detected by an anti-FLAG antibody indicating that this band represents a C-terminal Slit2 fragment (FIG. 5A, right panel).

In order to definitively establish the fragments' identity, immunoaffinity purified, FLAG-tagged Slit2-CTF bands were subjected to mass spectrometry analysis. Peptides identified from the 50 kDa fragment mapped exclusively to the C-terminus of Slit2 (FIG. 5B). In contrast, peptides identified from the ~180 kDa band mapped to all portions of the Slit2 protein. Taken together, these results demonstrate that the smaller 50 kDa fragment of Slit2 from fat cells contains the entire C-terminal region of Slit2. The same or a similar cleavage product has been observed previously (Brose et al. (1999) *Cell* 96:795-806; Nguyen et al. (2001) *J. Neurosci.* 21:4281-4289), but has no established function.

In order to examine the activity of the C-terminal fragment (hereinafter referred to as "Slit2-C"), adenoviral constructs containing Slit2-C, a signal peptide for secretion, and a C-terminal V5-tag, were generated (FIG. 5C). As the N-terminus of this C-terminal fragment, the sequence encoding amino acids immediately downstream of the putative cleavage site beginning at TSP (Brose et al. (1999) *Cell* 96:795-806; Nguyen et al. (2001) *J. Neurosci.* 21:4281-4289) was chosen. A similar construct containing the N-terminal portion of Slit2 immediately upstream of the Slit2-C sequence (hereinafter referred to as "Slit2-N"), was also generated (FIG. 5C). Primary inguinal adipocytes were transduced with lacZ, Slit2-N, and Slit2-C viruses on day 2, and the cells were harvested on day 6. Both Slit2-N and Slit2-C proteins were efficiently expressed in adipocytes at the predicted molecular sizes; ~140 kDa and ~50 kDa, respectively (FIG. 5D). Both were detected in both the cells and conditioned media, indicating that these fragments are efficiently secreted from adipocytes (FIG. 5D). Interestingly, only Slit2-C, but not Slit2-N, was efficiently secreted into the blood following intravenous delivery of adenoviruses into mice (FIG. 5F), despite efficient hepatic transduction for both constructs (FIG. 5E). Although the experiments described below focus on the biological effects of Slit2-C in subsequent experiments in vitro and in vivo, Slit2-N also exhibits similar qualitative, although quantitatively lower, biological activity as Slit-C. Based on this data, the biological effects of Slit2-C was focused upon in subsequent experiments in vitro and in vivo.

Example 5: Slit2-C is Sufficient to Recapitulate the Thermogenic Activity of Full-Length Slit2

Figure 6A:
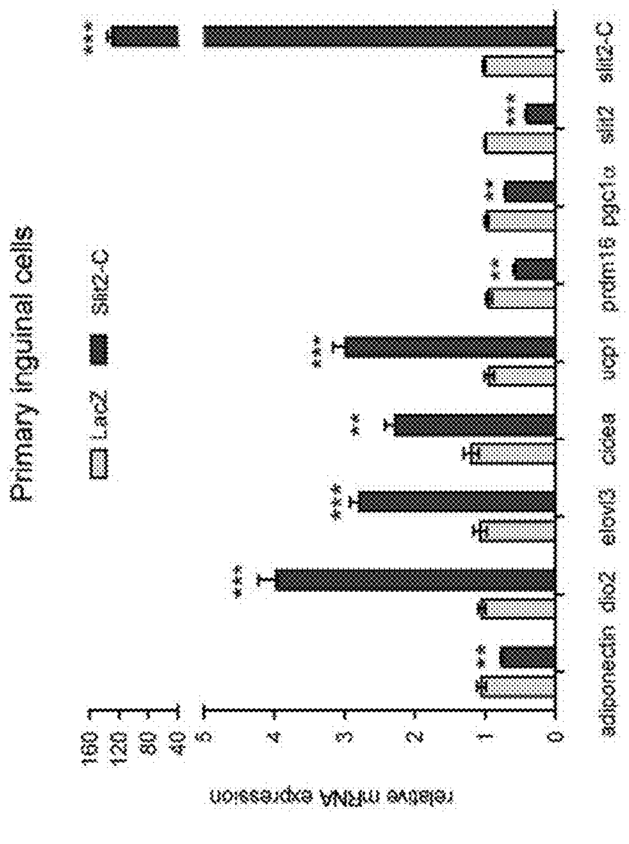
Figure 6B:
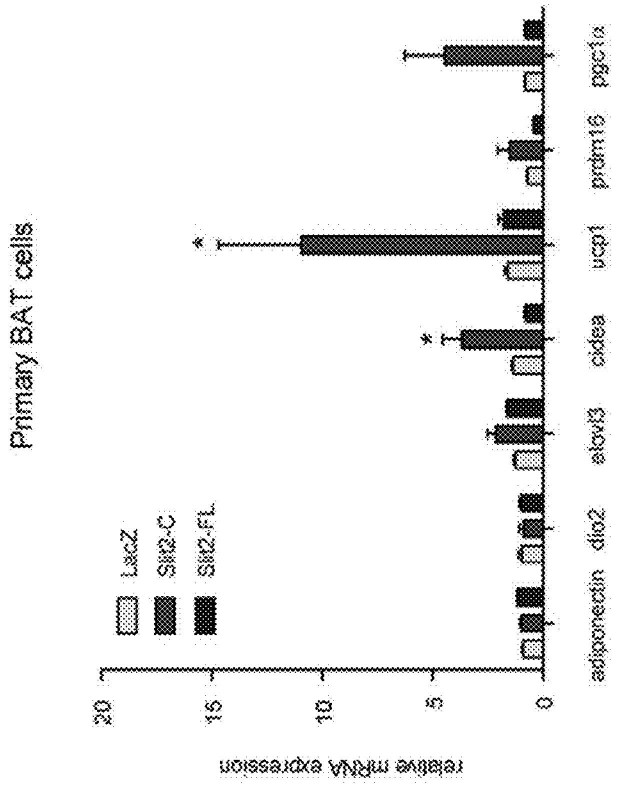
Figure 6D:
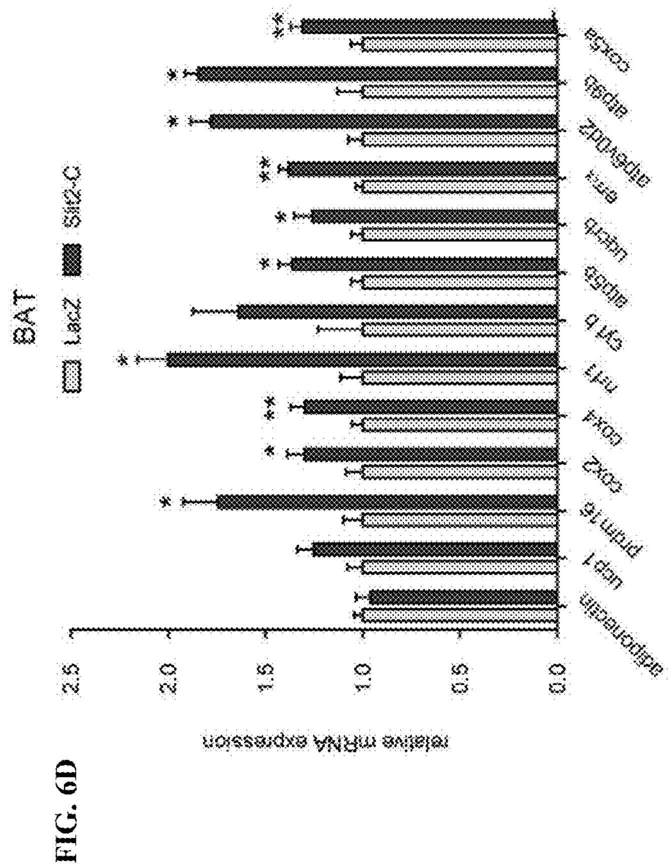
Figure 6C:
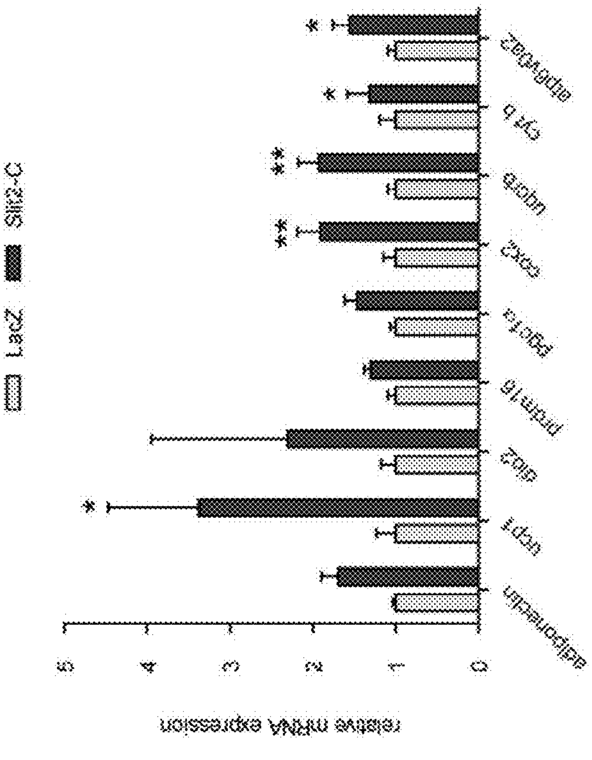
Figure 6E:
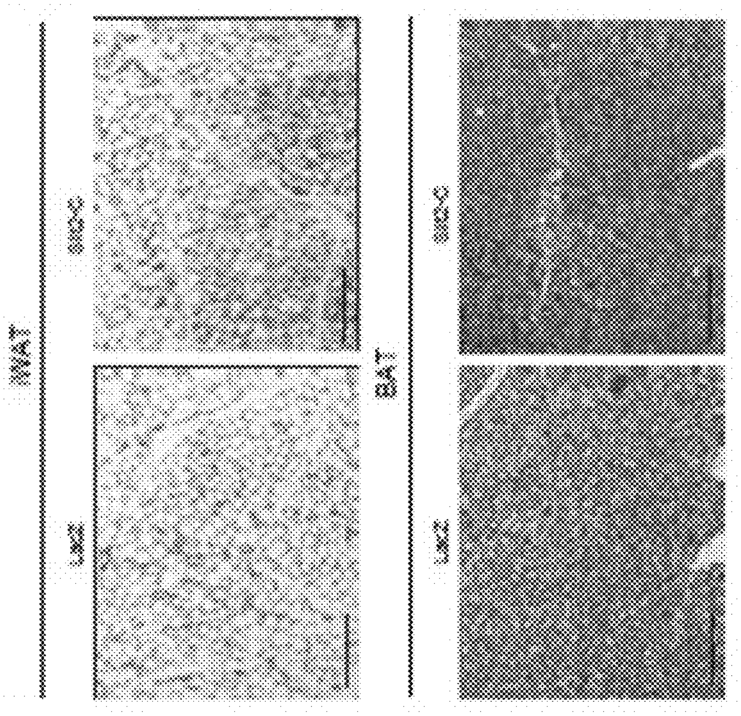
Figure 7C:
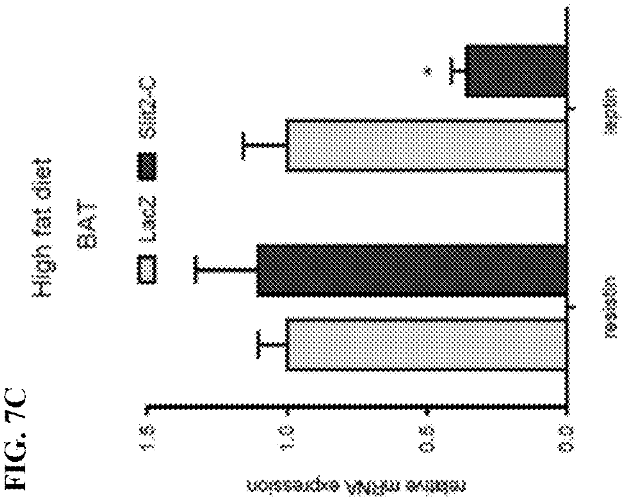
Figure 7B:
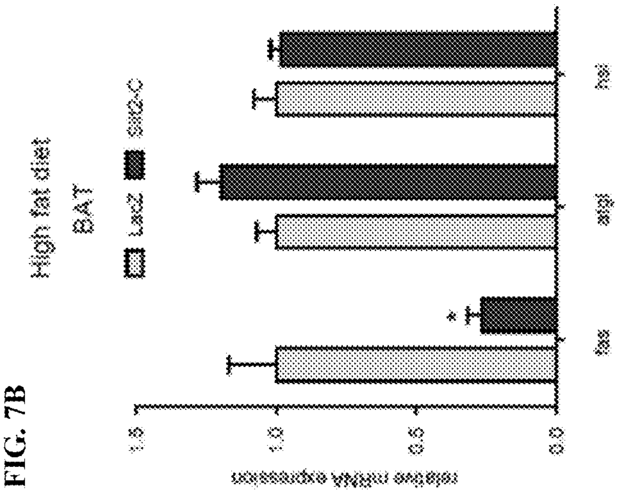
Figure 7A:
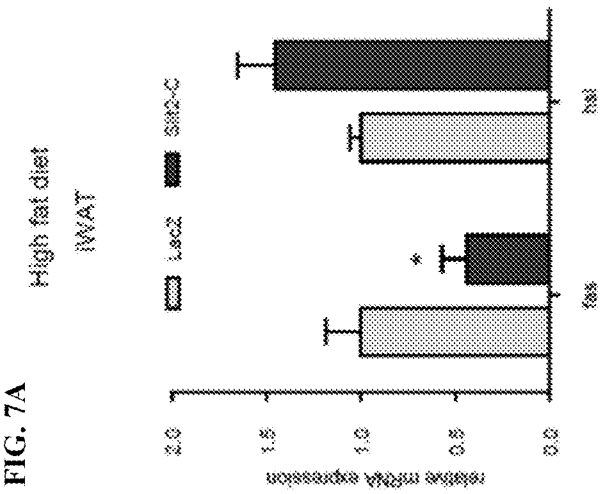
Figure 7D:
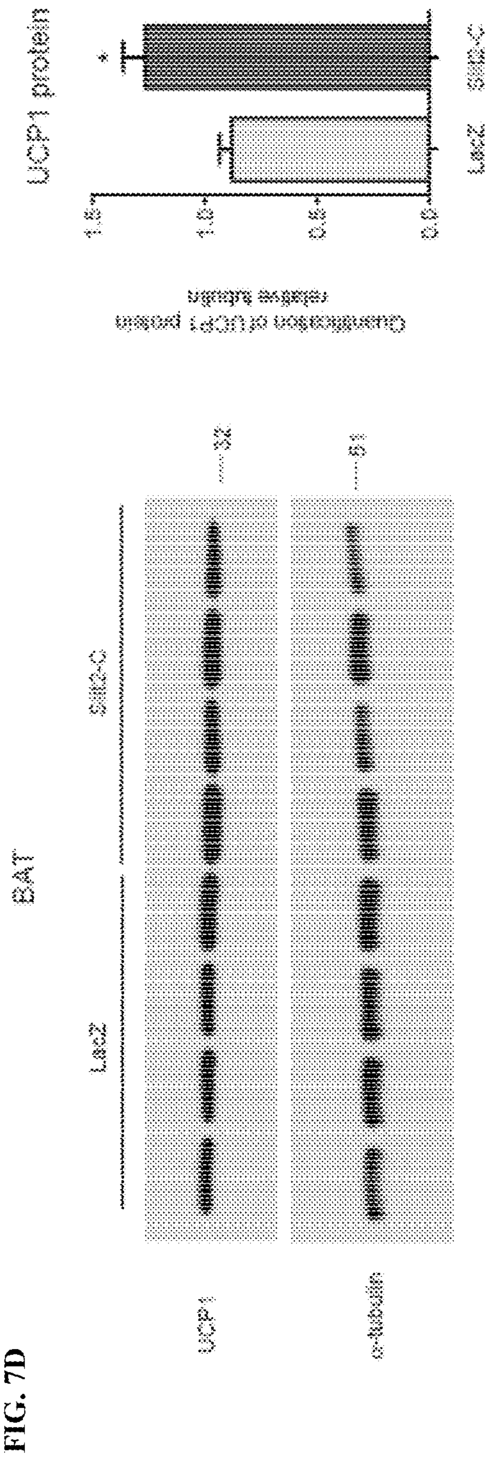

It was next determined whether Slit2-C possesses much or any of the thermogenic activity of full-length Slit2. Primary inguinal and brown fat cultures were transduced with the Slit2-C or LacZ control viruses, and thermogenic gene expression was analyzed at day 7. Under these conditions, Slit2-C induced a thermogenic gene expression comparable to full-length Slit2 in primary inguinal cells, while primary brown fat cells responded stronger to Slit2-C (FIGS. 6A-6B). Next, lean mice were injected with Slit2-C or control adenovirus and their adipose tissues were analyzed by gene expression methods. In the iWAT, Ucp1 mRNA was significantly induced 3-fold, and other mitochondrial genes also showed a modest, but significant, 1.5- to 2-fold increase (FIG. 6C). The classical brown fat showed significant changes in the transcriptional regulators, Prdm16, Nrf1, and Erra. In addition, there was also an upregulation of expression of several mitochondrial genes, such as Atp5b, Uqcrb, Atp6vOa2, Atp9b, and Cox5a, indicative of an activation of BAT (FIG. 6D). Similar experiments using 16-week diet-induced obese (DIO) mice showed a reduction in Fas in inguinal and brown fat, while Hsl and Atgl were unchanged (FIGS. 7A-7B). There was also a marked reduction in brown fat levels of Leptin upon Slit2-C treatment while another white-selective marker, Resistin, was unchanged (FIG. 7C). Consistent with this gene expression data, immunohistochemical analysis by UCP1 staining in the inguinal white fat depots showed multiple pockets of UCP1-positive cells in Slit2-C treated mice compared with control animals (FIGS. 6E, upper panel, and 6G). In the BAT, UCP1 staining in BAT was similar between the two groups. However, the tissue in Slit2-C treated animals had a more dense looking appearance with smaller lipid droplets (FIGS. 6E, lower panel, and 6G). Quantification of Ucp1 protein expression in BAT showed a 1.3-fold induction in BAT in Slit2-C treated animals (FIG. 7D).

Figure 6F:
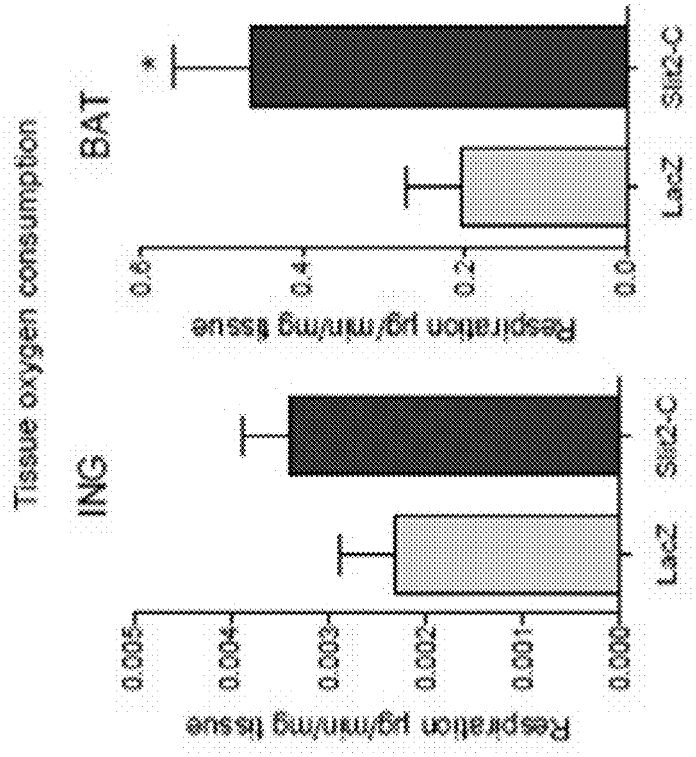
Figure 6H:
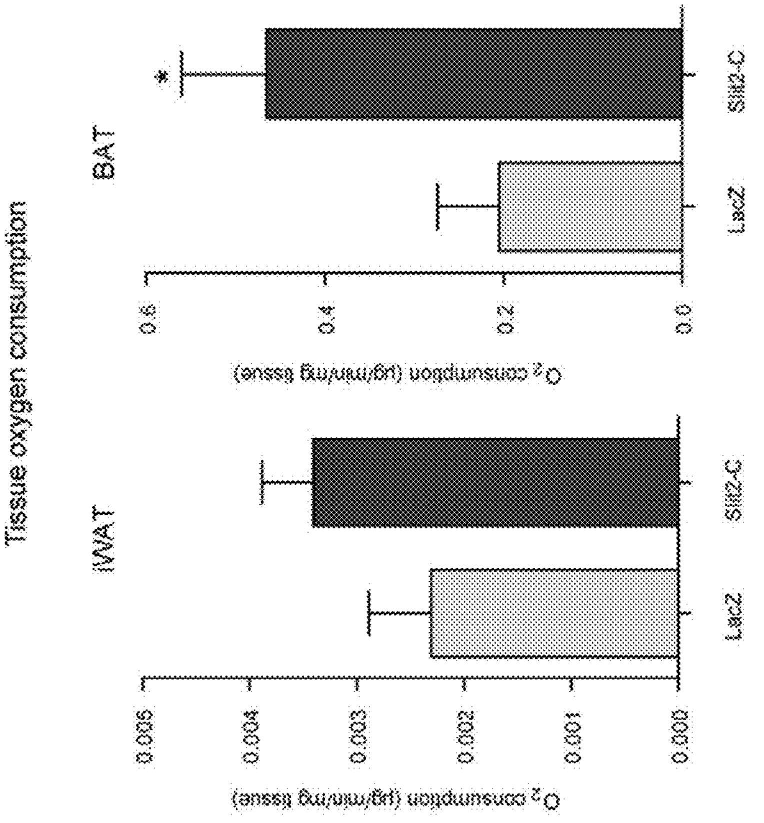
Figure 6G:
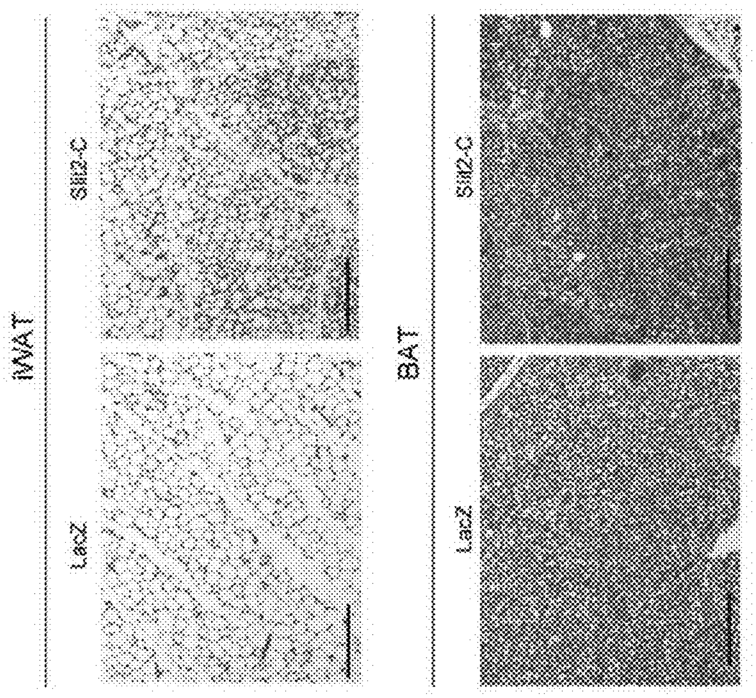

In order to assess the physiological effect of Slit2-C expression on tissue respiration, oxygen ($O_2$) consumption was analyzed as a readout. Brown and white adipose pads were dissected at day 7 after adenovirus injection and respiration of minced tissues was measured using a Clark electrode. 02 consumption was elevated in both inguinal and BAT receiving Slit2-C mice compared to tissues from mice receiving LacZ, although this only reached significance in the BAT (FIGS. 6F and 6H). The data are further described in FIG. 7. Qualitatively similar increases were observed in the inguinal pad (FIGS. 6F, left), though this only reached significance in the BAT (FIGS. 6F and 6H, right).

Figure 8B:
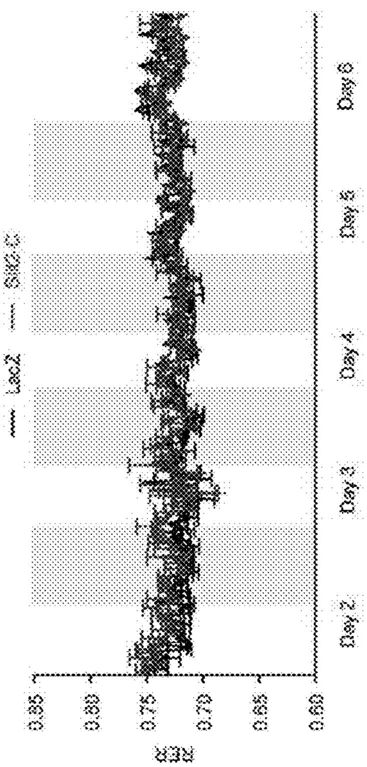
Figure 8A:
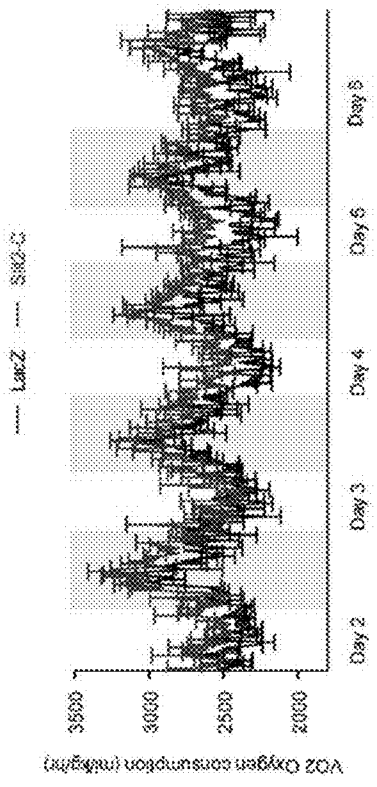
Figure 8D:
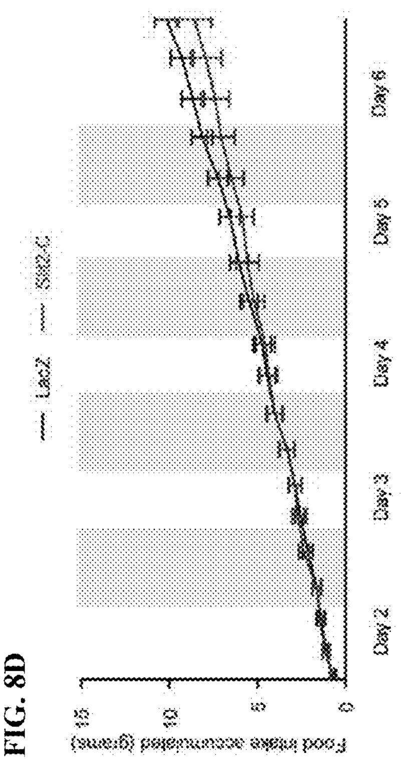
Figure 8C:
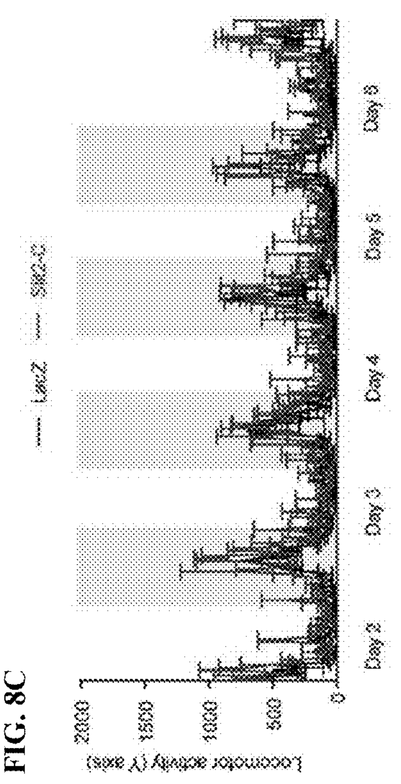
Figure 8E:
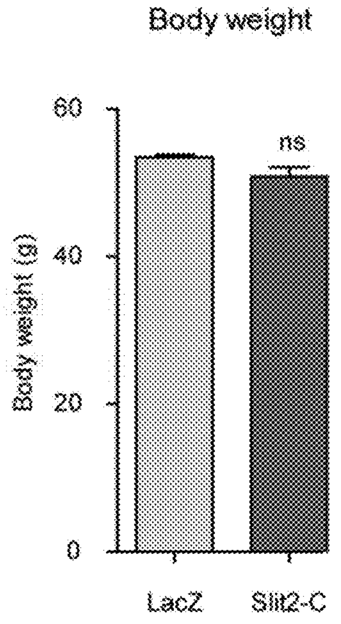
Figure 8F:
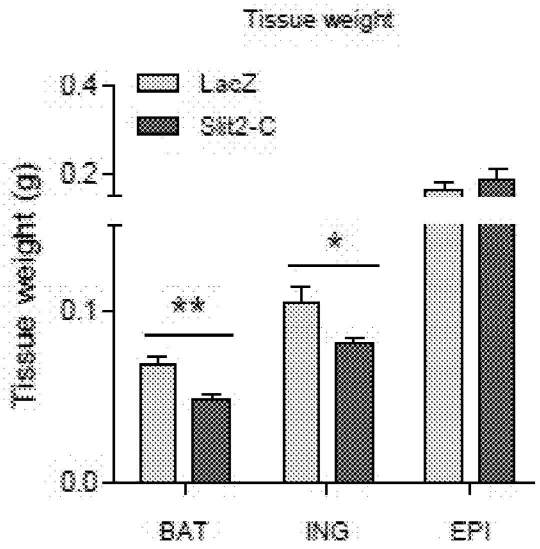
Figure 8G:
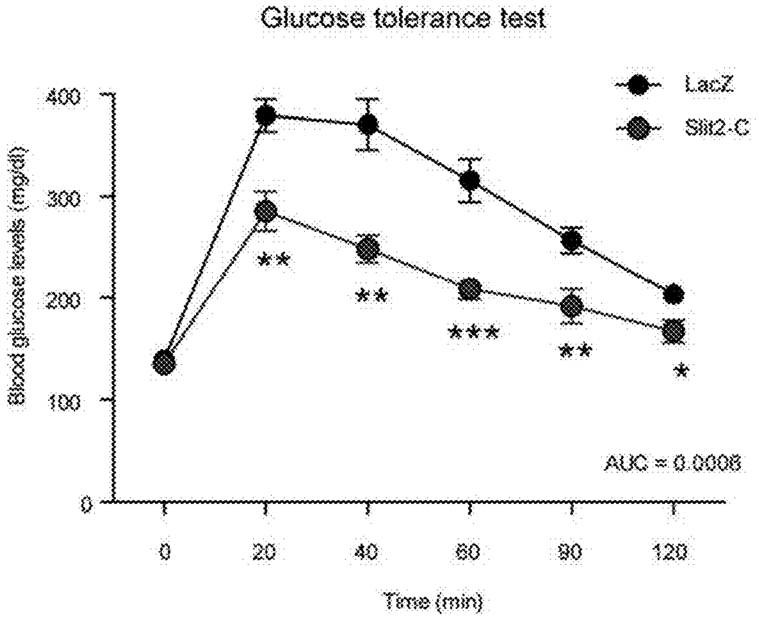
Figure 8H:
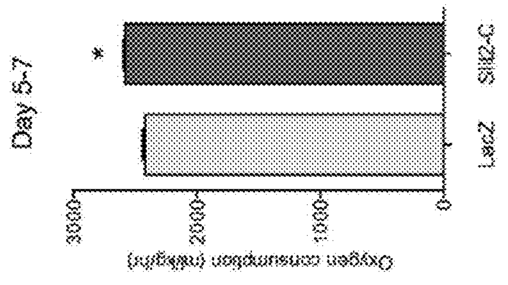
Figure 8I:
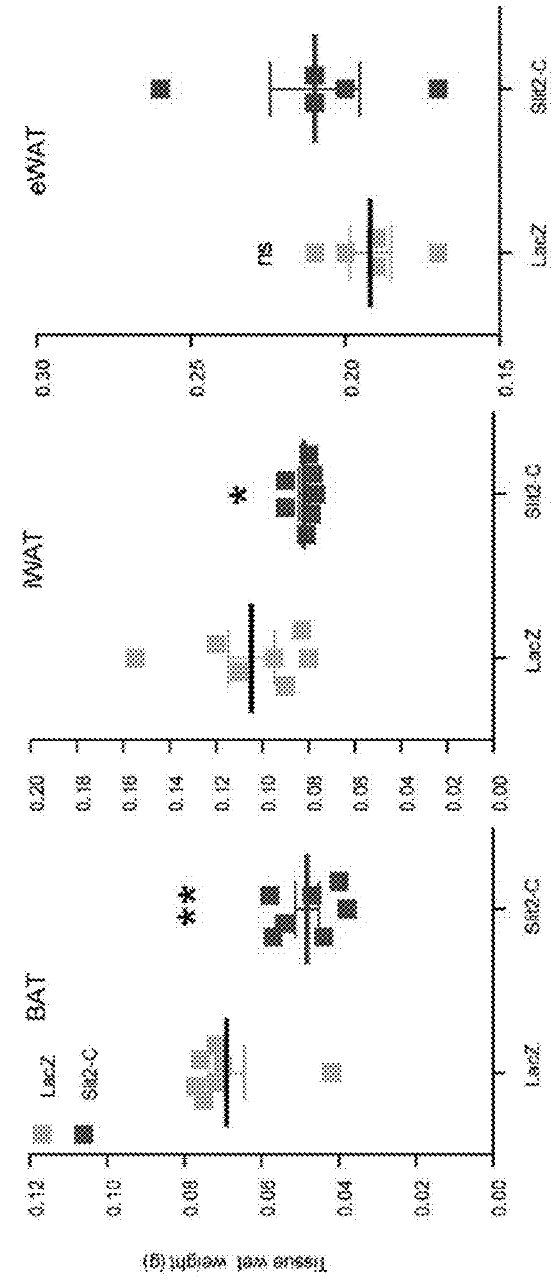
Figure 9A:
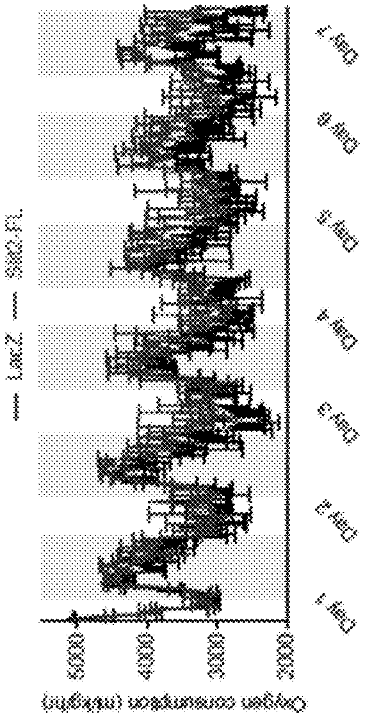
Figure 9B:
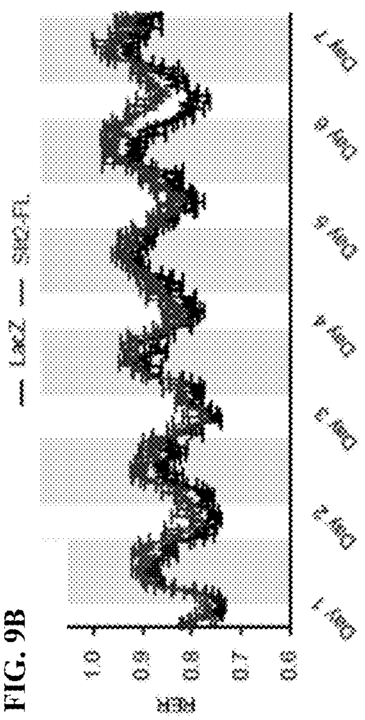
Figure 9C:
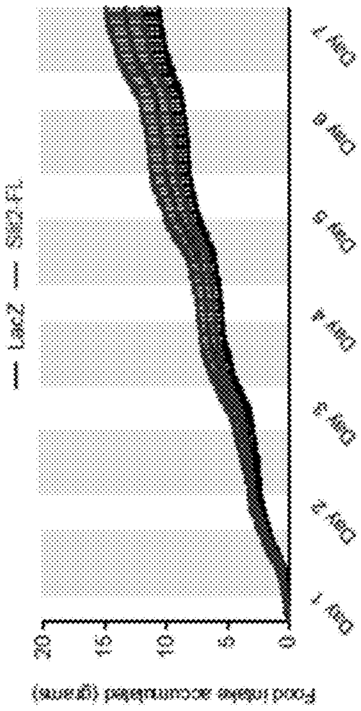
Figure 9D:
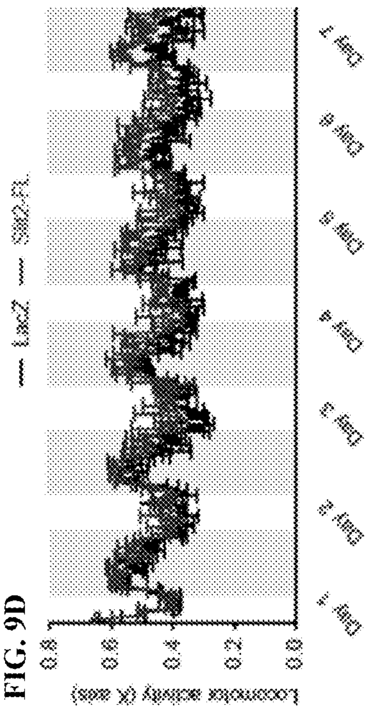
Figure 9E:
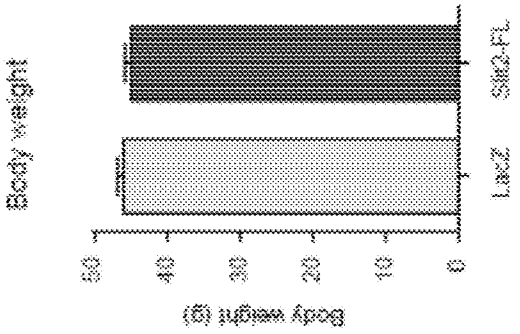
Figure 9F:
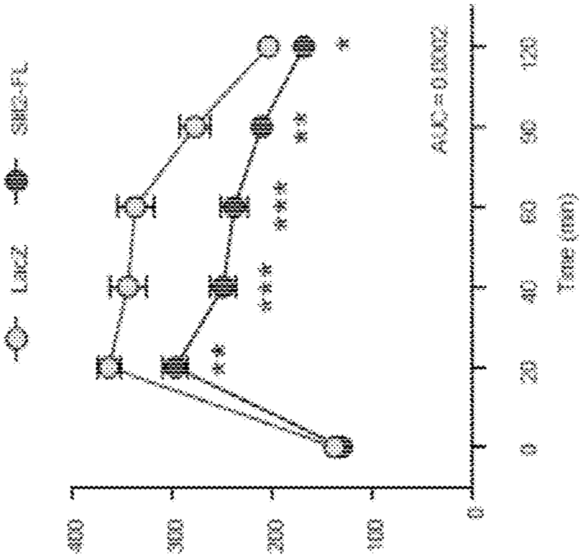
Figure 9G:
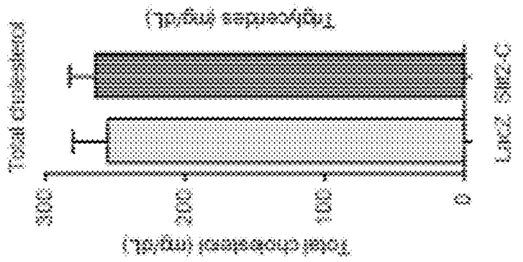
Figure 9H:
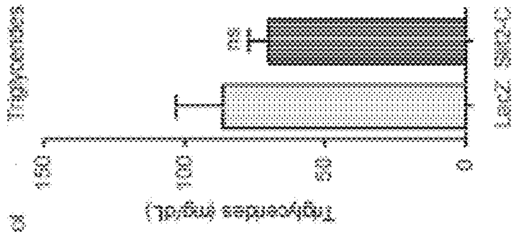
Figure 9I:
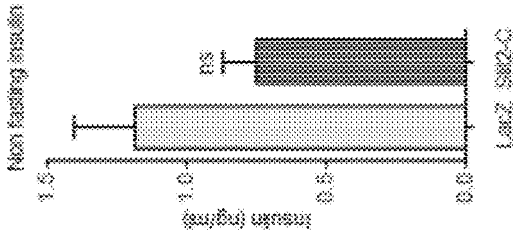

Example 6: Increased Circulating Slit2-C Augments Whole Body Energy Expenditure and Improves Glucose Homeostasis in Obese Mice In order to study the metabolic effects of increased circulating Slit2-C, 16-week high fat diet-fed mice were injected with adenoviral vectors expressing Slit2-C or a LacZ control. Whole body energy expenditure was analyzed over the following 7 days using a comprehensive laboratory animal monitoring system (CLAMS). Slit2-C induced whole-body oxygen consumption with no observable difference in respiratory exchange ratio (RER), locomotor activity, food intake, or body weight (FIGS. 8A-8E and 8H). These oxygen consumption data were normalized to total body weight. The elevated whole body oxygen consumption in the Slit2-C animals was accompanied by a reduction in the mass of the brown and inguinal, but not epididymal, depots (FIGS. 8F and 8I). Importantly, circulating Slit2-C was found to dramatically improve glucose tolerance in diet-induced obese mice (FIG. 8G). Similar experiments performed with full-length Slit2 had comparable results on energy expenditure and glucose tolerance (FIGS. 9A-9F). Total plasma cholesterol, plasma triglycerides and non-fasting insulin levels were not affected by Slit2-C treatment (FIGS. 9G-9I). These data demonstrate a new function for the C-terminal fragment of the Slit2 protein in augmenting whole body energy expenditure and improving metabolic health.

Figure 10A:
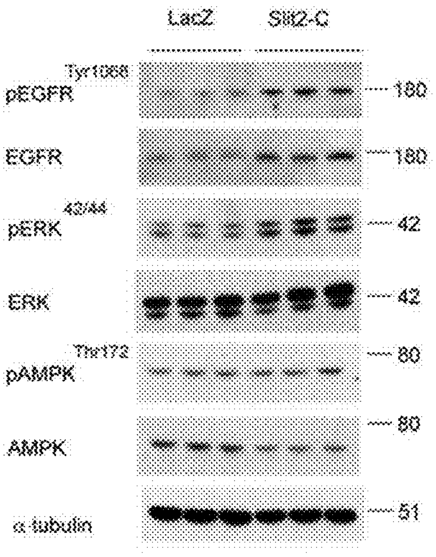
Figure 11A:
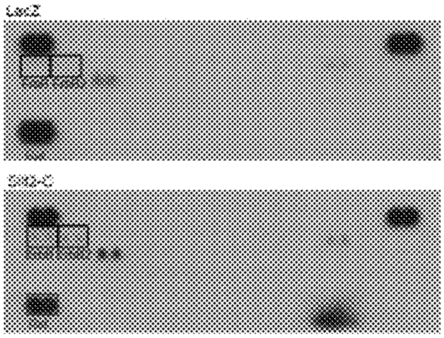
Figure 11B:
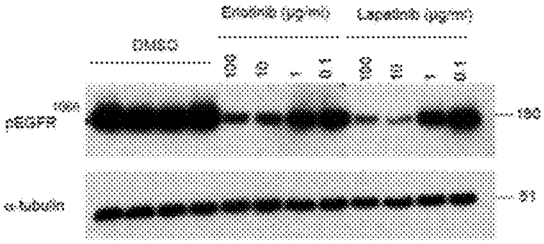
Figure 11C:
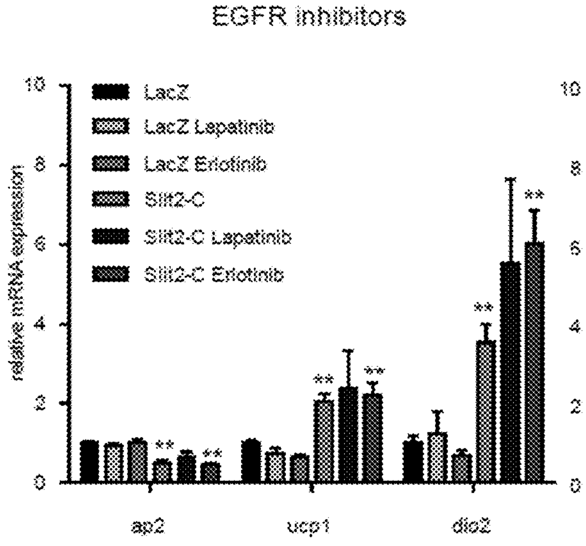
Figure 11D:
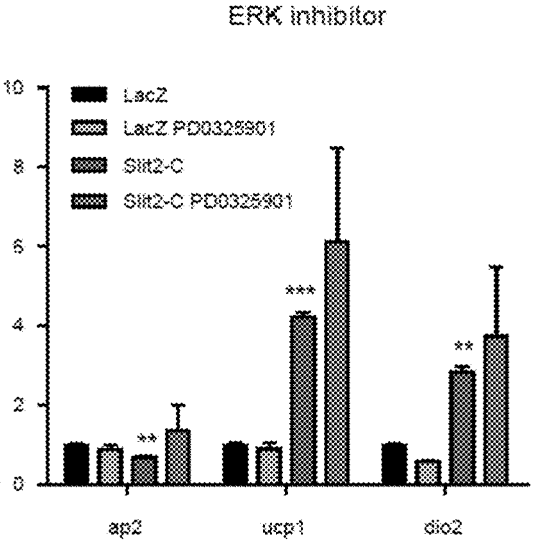

Example 7: Slit2-C Induces a Thermogenesis Program Through the PKA Signaling Pathway in Adipocytes Canonical Slit signaling in the central nervous system occurs by interaction of the N-terminus of Slit proteins with the Robo family of receptors, resulting in signaling through the small GTPase Cdc42 involved in neuronal migration (Wong et al. (2001) *Cell* 107:209-221). No in vivo function for the C-terminal region of Slit proteins has been described. The Slit2-C fragment as defined here completely lacks this ROBO interaction domain, suggesting that other receptors might be involved in signaling from this protein in adipocytes. In order to understand the possible receptors and signaling pathways by which Slit2-C exerts its thermogenic effects, phospho-arrays were used to identify the intracellular signaling pathways activated in primary inguinal adipocytes transduced with Slit2-C versus lacZ adenovirus (see Example 1). Of the 39 receptor tyrosine kinases and intracellular kinases tested in these initial assays, robust phosphorylation changes were observed in only two proteins, phospho-EGFR and phospho-ERK1/2, together with changes in total EGFR upon Slit2-C overexpression (FIGS. 10A and 11A). The EGFR and ERK pathways were antagonized with specific inhibitors, but the treatments failed to reverse Slit2-C-induced thermogenic gene expression effects (FIGS. 11A-IID). These data indicate that the EGFR and ERK pathways are activated by, but not required for, the thermogenic activity of Slit2-C activity.

Figure 10B:
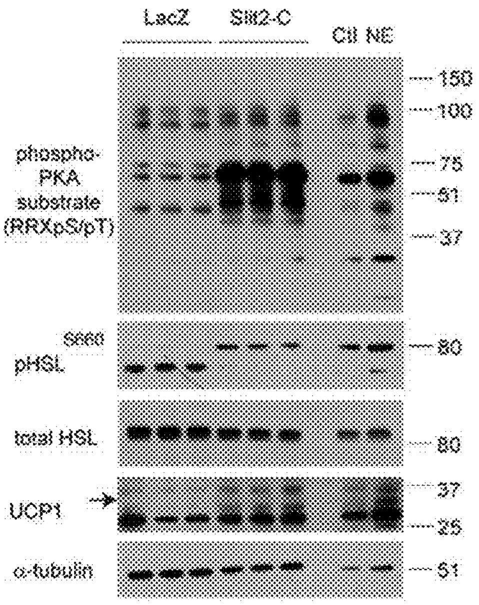
Figure 10C:
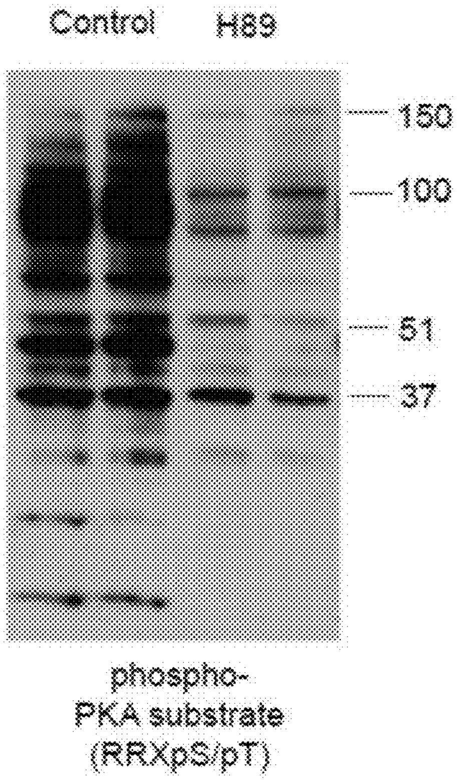
Figure 10D:
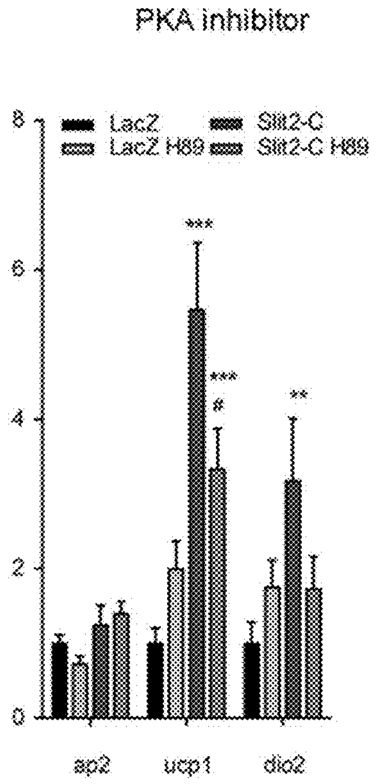
Figure 10E:
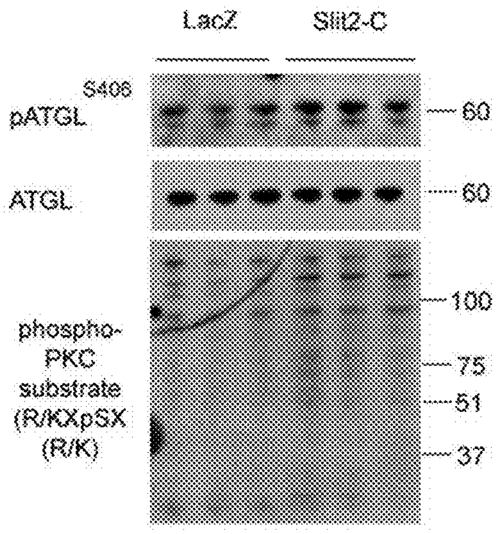
Figure 10F:
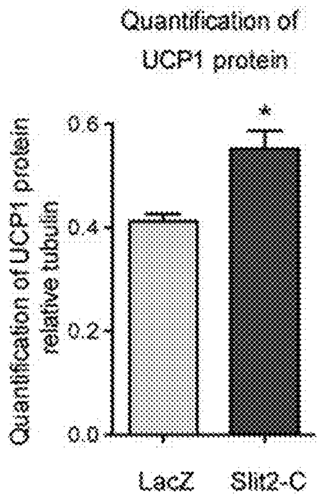

Analysis of PKA signaling was also performed since the PKA signaling pathway is known to be involved in the canonical thermogenic activation of fat cells. Slit2-C-transduced cells, but not lacZ-transduced cells, showed robust phosphorylation of PKA substrates (FIG. 10B). This Slit2-C-induced pattern is similar to the direct treatment of adipocytes with norepinephrine (NE). These observations indicate that Slit2-C activates an overlapping, but distinct, pathway from the canonical beta-adrenergic receptor-mediated signaling in adipocytes. Consistent with PKA activation, phosphorylation of hormone sensitive lipase ($HSL^{S660}$) was induced, while total HSL was unaffected (FIG. 10B). As a comparison, activation of protein kinase C (PKC) substrates and $ATGL^{S406}$ by Slit2-C was minimal (FIG. 10E). Under the same conditions, Slit2-C also increased the protein levels of UCP1, which result confirmed the gene expression levels upon Slit2-C overexpression (FIGS. 10B and 10F).

Figure 10G:
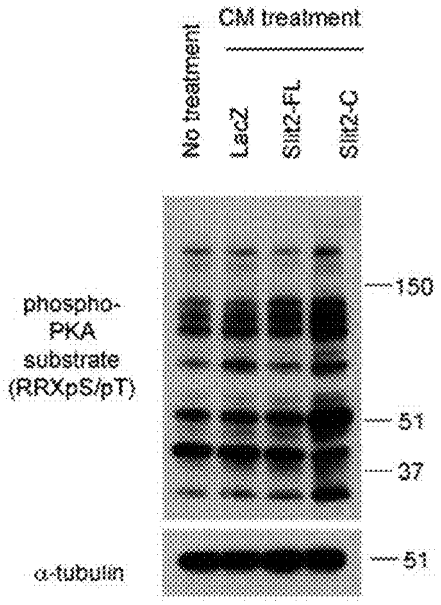

To exclude potential intracellular effects of adenoviral overexpression, serum-free conditioned media were generated from cells expressing LacZ, Slit2-FL, or Slit2-C. Treatment of primary inguinal cells with conditioned media also increased PKA signaling in a pattern similar to norepinephrine (FIG. 10G). These data demonstrate that extracellular Slit2-C activates the canonical β-adrenergic receptor-mediated signaling pathway in adipocytes through an unknown receptor. To more precisely map the mechanism of Slit2-C induced PKA signaling, Slit2-C transduced adipocytes were co-treated with various inhibitors. Propranolol, a pan-β-receptor antagonist did not inhibit Slit2-C induced thermogenesis (FIG. 10H), indicating that β-adrenergic signaling is not required for Slit2-C activity.

Figure 10H:
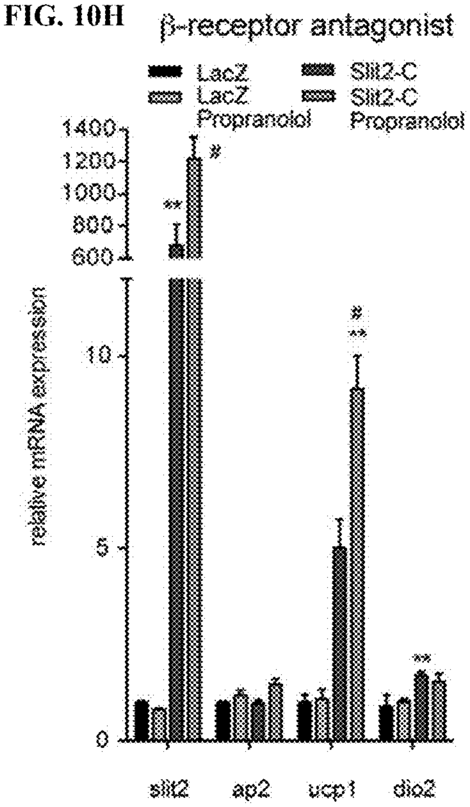
Figure 10I:
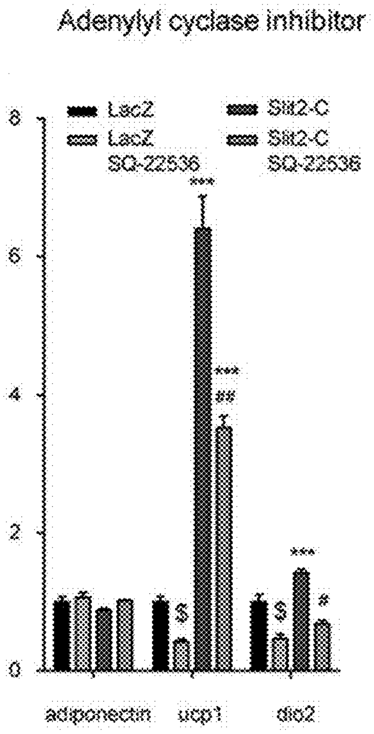

In addition, the PKA inhibitor, H89, was also used to inhibit this pathway in fat cells. At 30 μM concentration, H89 significantly reduced the phosphorylation of PKA substrates in primary inguinal cells (FIG. 10C). Under the same conditions, H89 significantly reduced Ucp1 mRNA by 50% and Dio2 down to baseline levels in cells receiving Slit2-C, indicating that the PKA pathway is responsible for the thermogenic response induced by Slit2-C overexpression (FIG. 10D). Similar effects were seen using the adenylyl cyclase inhibitor SQ-22536 that inhibits the formation of intracellular cAMP (FIG. 10I). Therefore, Slit2-C induces an activation of PKA signaling, which is required for its pro-thermogenesis activity. Together these data indicate that the generation of cAMP and activation of PKA signaling are important for the thermogenic activity of Slit2-C. Based on the foregoing, the data presented herein demonstrate a previously uncharacterized role for Slit2 and a C-terminal protein fragment of Slit2 in fat biology and glucose metabolism.

Figures 10J, 10K, 10L, 10M, 10N:
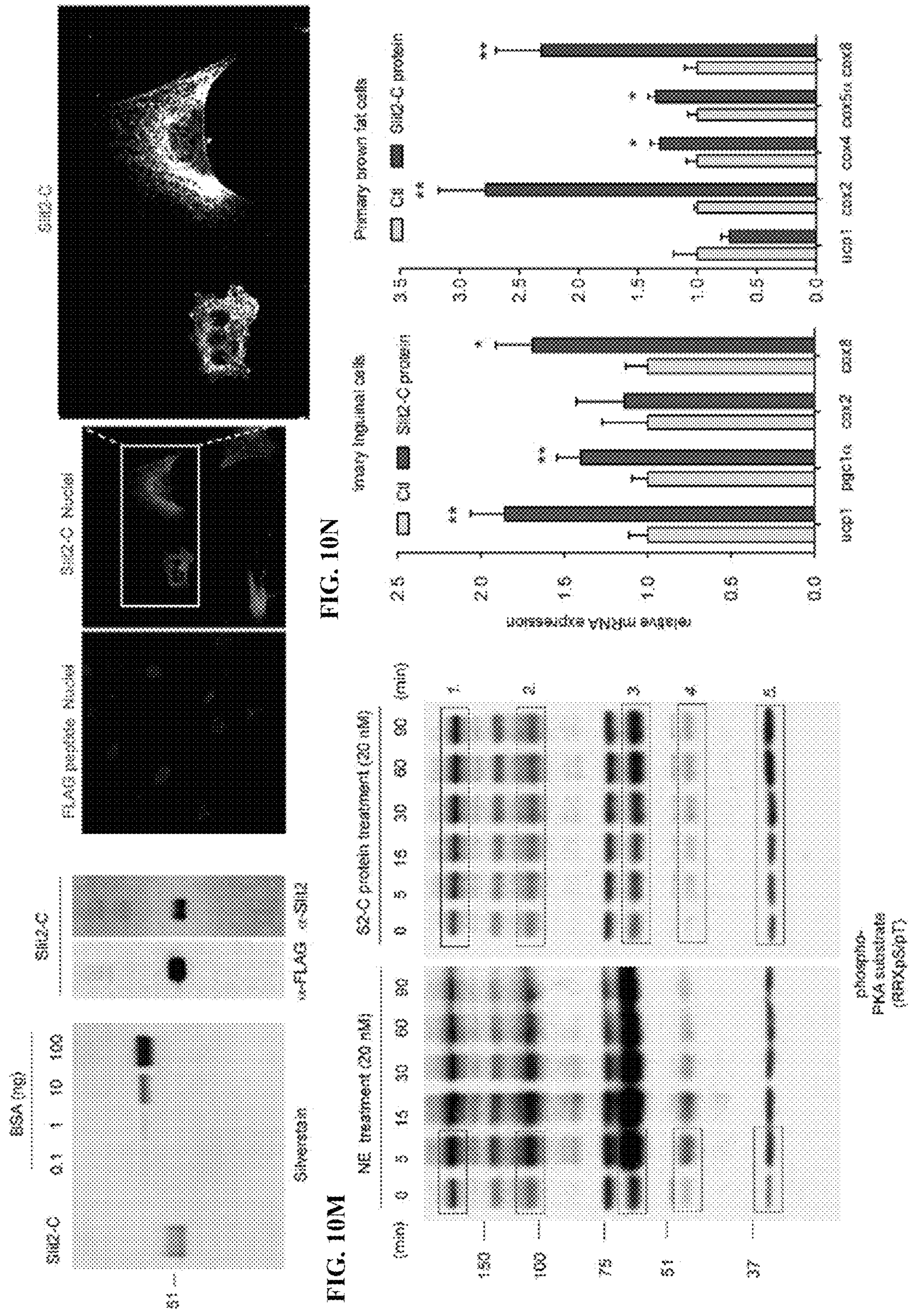
Figure 11G:
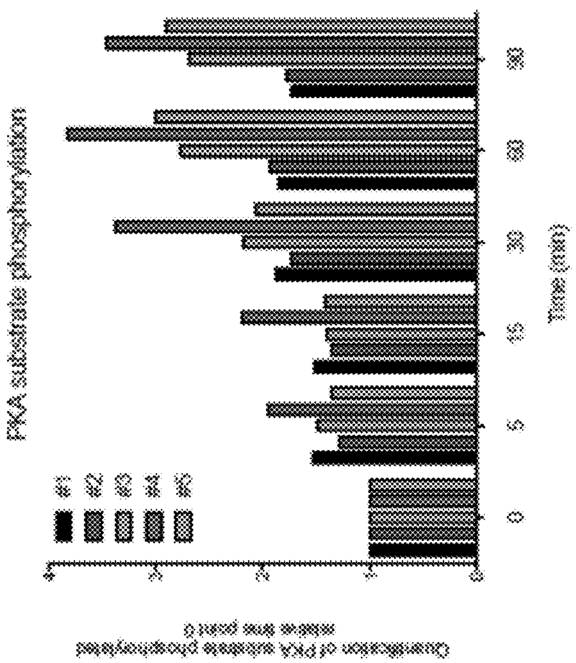
Figure 11F:
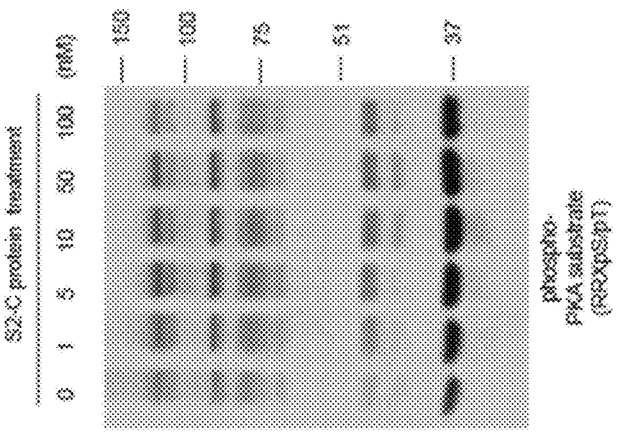
Figure 11E:
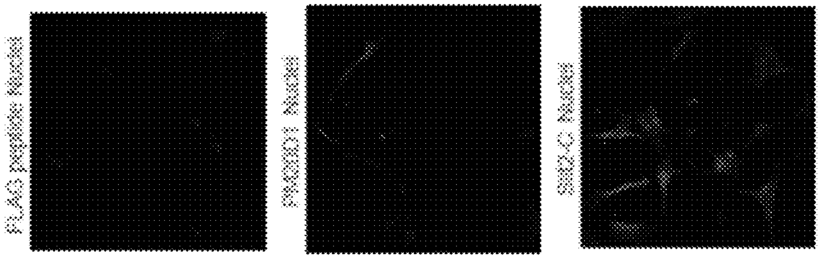

To provide direct evidence of a cell surface receptor for Slit2-C, small scale purified recombinant mammalian Slit2-C from HEK293 cells was generated. The purity and quantification of the protein content (compared with an albumin standard of known concentration) was verified by silver stained SDS gel electrophoresis (FIG. 10J). This shows a 50 kDa band as well as a single FLAG-reactive and Slit2-reactive band on a Western blot (FIG. 10K). Importantly, binding of nanomolar concentrations of purified Slit2-C to the cell surface on live adipocytes incubated at 4° C. was observed, suggesting the presence of a Slit2-C cell surface receptor on adipocytes (FIG. 10L). As a control for specific staining, side-by-side comparisons were performed using another FLAG-tagged protein secreted from thermogenic adipocytes, Pm20D1 (Long et al. (2014) *Cell metabolism* 19:810-820), demonstrating very limited binding to the cell surface of adipocytes compared with Slit2-C (FIG. 11E). Importantly, similarly to the virus overexpression experiments, a subset of PKA substrate phosphorylations was increased after Slit2-C protein treatment in a time-dependent (FIG. 10M) and dose-dependent (FIG. 11F) manner. In contrast with NE, which induces a full response by 5 minutes (min) of treatment, Slit2-C induces PKA phosphorylation at a slightly delayed time that peaks around 60 to 90 min (FIGS. 10M and 11G). The purified protein also induced subsequent changes in thermogenic gene expression in both white and brown adipocytes in culture 2 h after protein treatment (FIG. 10N). Taken together, these data suggests that Slit2-C is directly inducing the PKA pathway in adipocytes to induce thermogenesis by direct (and likely receptor-mediated) interaction with the target cell.

Human and rodent brown and beige fat have multiple shared characteristics, including a potent β-adrenergic receptor/PKA pathway that activates a thermogenic program. Recent studies in humans subjected to the 03-adrenergic receptor agonist mirabegron demonstrate an increased resting metabolic rate as well as an apparent activation of brown fat (Cypess et al. (2015) *Cell Metabolism* 21:33-38). These observations demonstrate that signaling through the β 3 adrenergic receptors, which drive cAMP synthesis, are functional in human BAT in vivo. However, β-adrenergic receptor agonists suffer from untoward effects, limiting their clinical use for the treatment of obesity and diabetes.

Based on the foreoing, it has been determined that the C-terminal fragment of Slit2, which is produced endogenously by adipose cells, has several properties that make it of translational interest. First, Slit2 expression is under the control of PRDM16, an important regulator of both brown and beige fat in rodents. PRDM16 is also selectively expressed in human brown fat cells and tissues (Jespersen et al. (2013) *Cell Metabolism* 17:798-805; Shinoda et al. (2015) *Nat. Med.* 21:389-394). Secondly, and importantly, the Slit2 C-terminal fragment appears to function largely through the cAMP/PKA signaling system. Although the magnitude of induction is may be lower and delayed in time compared with direct β-adrenergic receptor activation, it has the advantage of not working through the widely distributed β-adrenergic receptors. It is thus expected that this molecule may circumvent some or all of the existing side effects of direct β-adrenergic receptor agonism.

The transcriptional regulation of Slit2 suggests that cold exposure may control its expression in a manner not completely dependent on the β-adrenergic systems in iWAT and BAT. The mechanism of transcriptional regulation of Ucp1 is somewhat independent of the adrenergic receptors; hence, a parallel pathway of regulation may exist (FIG. 10H). Furthermore, Slit2 mRNA is reduced in iWAT after high fat diet. Similar reductions of Slit2 mRNA in eWAT, but not in BAT, were observed in mice fed a high fat diet, pointing towards interesting and distinct regulation mechanisms in the different adipose depots.

Moreover, the results reveal a functional specificity of Slit2 C-terminal fragment that is distinct from previous studies of Slit2. In brain, the actions of Slit2 are principally thought to occur via its N-terminal ROBO binding domain (Kidd et al. (1999) *Cell* 96:785-794; Wang et al. (1999) *Cell* 96:771-784). It has been determined herein that Slit2-C, which does not contain this ROBO binding motif, nevertheless possesses potent anti-diabetic effect in vivo. These data demonstrate that the biological effects of Slit2 extend well beyond its ROBO binding activity and N-terminal domain. It is worth considering that, Slit2-C may also be important in other areas of physiology. Even this 50 kDa Slit2-C fragment has multiple domains and may activate other pathways. BAT and iWAT responds slightly differently to Slit2-C overexpression in terms of downstream transcriptional targets. This may be explained by, for example, differences in baseline levels of thermogenic genes, the presence and abundance of the receptor(s) or co-receptor(s) and also by the fact that there are preferential signaling pathways in BAT and iWAT induced upon stimulation. It has been determined that PKA signaling is one mechanism that at least in part is responsible for the thermogenic effects. Studies evaluating the physiological relevance of circulating Slit2 in plasma are important for its significance as an endogenous endocrine protein. To date, because of lack of specific reagents for the detection of Slit2 protein in plasma, absolute quantifications of the circulating levels are to be determined. However, multiple unique peptides of Slit2 from both the N- and C-terminal Slit2 have been found in an independent plasma proteomic study (Liu et al. (2007) *J. Am. Soc. Mass. Spectrom.* 18:1249-1264). Thus, the 50 kDa fragment of Slit2 is believed to function, at least in part, in an endocrine fashion. Moreover, the Slit2-C pathway is believed to be promising for the treatment of obesity and related metabolic disorders.

Example 8: Cellular Oxygen Consumption Measured by Seahorse in Primary Inguinal Fat Cells after Treatment with Slit2-C As described above in Examples 5-7, in vitro and in vivo data on respiration using Slit2-C adenovirus overexpression models and loss-of-function analyses in Seahorse assays are described. In vitro confirmation of the results was determined using an alternative source of recombinant Slit2-C (FIG. 13). Briefly, primary white and brown adipocyte cultures were prepared as described in Example 1D, except that, where indicated in FIG. 13, cells were treated with norepinephrine (100 nM) or with recombinant proteins (1 ug/mL Slit2-C, Calico/AbbVie) for the indicated times. Cellular oxygen consumption rates were determined as described in Example 1 Statistical analysis was performed as described in Example 1C above. The data shown in FIG. 13 confirm the results described above in Examples 5-7.

INCORPORATION BY REFERENCE

The contents of all references, patent applications, patents, and published patent applications, as well as the Figures and the Sequence Listing, cited throughout this application are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed:

1. A method for detecting an agent that modulates Slit2 expression and/or activity for increasing a metabolic response in a subject, comprising detecting whether expression and/or activity of Slit2-C is significantly lower in a first sample from the subject prior to contact with the agent than for at least one subsequent sample from the subject after contact with the agent by contacting the first sample with an antibody that detects Slit2-C, and detecting association of Slit2-C and the antibody that detects Slit2-C.

2. The method of claim 1, further comprising detecting expression and/or activity of a marker selected from the group consisting of adipsin, fatty acid transporter cd36, adiponectin, UCP-1, cidea, PGC1a, Elovl3, C/EBPbeta, Cox7a1, otopetrin, type II deiodinase, cytochrome C, cox4i1, coxIII, cox5b, cox8b, glut4, atpase b2, coxII, atp5o, ndufb5, Rarres2, Car3, Peg10, Cidec, CD24a, Cr1d2, Ddx17, Aplp2, N43c1, Rybp, Txnip, Cig30, Ppar gamma 2, Prdm16, Ap2, Ndufs2, Grp109A, AcylCoA-thioesterase 4, Claudin1, PEPCK, Fgf21, AcylCoA-thioesterase 3, and Dio2 in a first sample from the subject prior to contact with the agent that is significantly lower than for at least one subsequent sample from the subject after contact with the agent.

3. The method of claim 1, wherein the first and/or at least one subsequent sample is selected from the group consisting of ex vivo and in vivo samples.

4. The method of claim 1, wherein the first and/or at least one subsequent sample is obtained from an animal model of a metabolic disorder.

5. The method of claim 1, wherein the first and/or at least one subsequent sample is selected from the group consisting of tissue, whole blood, serum, plasma, buccal scrape, saliva, cerebrospinal fluid, urine, stool, and bone marrow.

6. The method of claim 1, wherein the first and/or at least one subsequent sample is a portion of a single sample or pooled samples obtained from the subject.

7. The method of claim 1, wherein the agent is selected from the group consisting of a nucleic acid molecule encoding a Slit2 polypeptide or fragment thereof, a Slit2 polypeptide or fragment thereof, and a small molecule that binds to Slit2.

8. The method of claim 1, wherein between the time of the first sample and the at least one subsequent sample, the subject has undergone treatment for a metabolic disorder, has completed treatment for a metabolic disorder, and/or is in remission from a metabolic disorder.

9. The method of claim 1, wherein a significantly lower expression and/or activity of the marker is at least a 25% lower expression and/or activity.

10. The method of claim 1, wherein the metabolic response is selected from the group consisting of:

a) modified expression of a marker selected from the group consisting of: cidea, adiponectin, adipsin, otopetrin, type II deiodinase, cig30, ppar gamma 2, pgc1α, ucp1, elovl3, cAMP, Prdml6, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, dio2, fatty acid synthase (fas), leptin, resistin, and nuclear respiratory factor-1 (nrf1);

b) modified thermogenesis in adipose cells;

c) modified differentiation of adipose cells;

d) modified insulin sensitivity of adipose cells;

e) modified basal respiration or uncoupled respiration;
f) modified whole body oxygen consumption;
g) modified obesity or appetite;
h) modified insulin secretion of pancreatic beta cells;
i) modified glucose tolerance;
j) modified phosphorylation of EGFR, ERK, AMPK, protein kinase A (PKA) substrates having an RRX(S/T) motif, wherein the X is any amino acid and the (S/T) residue is a serine or threonine, or HSL; and
k) modified expression of UCP1 protein.

* * * * *